(12) United States Patent
DiCosimo et al.

(10) Patent No.: US 8,105,810 B2
(45) Date of Patent: Jan. 31, 2012

(54) METHOD FOR PRODUCING PEROXYCARBOXYLIC ACID

(75) Inventors: Robert DiCosimo, Chadds Ford, PA (US); William R. Cahill, Hockessin, DE (US); David George DiPietro, Mullica Hill, NJ (US); Eugenia Costa Hann, Carneys Point, NJ (US); Richard Alan Reynolds, Middletown, DE (US)

(73) Assignee: E. I. du Pont de Nemours and Company, Wilmington, DE (US)

(*) Notice: Subject to any disclaimer, the term of this patent is extended or adjusted under 35 U.S.C. 154(b) by 39 days.

(21) Appl. No.: 12/572,059

(22) Filed: Oct. 1, 2009

(65) Prior Publication Data

US 2010/0087528 A1 Apr. 8, 2010

Related U.S. Application Data

(60) Provisional application No. 61/102,505, filed on Oct. 3, 2008, provisional application No. 61/102,512, filed on Oct. 3, 2008, provisional application No. 61/102,514, filed on Oct. 3, 2008, provisional application No. 61/102,520, filed on Oct. 3, 2008, provisional application No. 61/102,531, filed on Oct. 3, 2008, provisional application No. 61/102,539, filed on Oct. 3, 2008.

(51) Int. Cl.
| | |
|---|---|
| C12P 7/40 | (2006.01) |
| C12N 9/00 | (2006.01) |
| D06L 1/02 | (2006.01) |
| C12S 11/00 | (2006.01) |
| C07H 21/04 | (2006.01) |

(52) U.S. Cl. ........ 435/136; 435/183; 510/281; 510/305; 536/23.2

(58) Field of Classification Search ........................ None
See application file for complete search history.

(56) References Cited

U.S. PATENT DOCUMENTS

| | | | |
|---|---|---|---|
| 3,974,082 A | 8/1976 | Weyn | |
| 4,444,886 A | 4/1984 | Esders et al. | |
| 4,585,150 A | 4/1986 | Beacham et al. | |
| 4,678,103 A | 7/1987 | Dirksing | |
| 5,116,575 A | 5/1992 | Badertscher et al. | |
| 5,152,461 A | 10/1992 | Proctor | |
| 5,281,525 A | 1/1994 | Mitsushima et al. | |
| 5,296,161 A | 3/1994 | Wiersema et al. | |
| 5,338,676 A | 8/1994 | Mitsushima et al. | |
| 5,364,554 A | 11/1994 | Stanislowski et al. | |
| 5,398,846 A | 3/1995 | Corba et al. | |
| 5,528,152 A | 6/1996 | Hinoshita et al. | |
| 5,532,157 A | 7/1996 | Fink | |
| 5,605,793 A | 2/1997 | Stemmer | |
| 5,624,634 A | 4/1997 | Brougham et al. | |
| 5,683,724 A | 11/1997 | Hei et al. | |
| 5,811,238 A | 9/1998 | Stemmer et al. | |
| 5,830,721 A | 11/1998 | Stemmer et al. | |
| 5,837,458 A | 11/1998 | Minshull et al. | |
| 5,862,949 A | 1/1999 | Markey et al. | |
| 5,932,532 A | 8/1999 | Ghosh et al. | |
| 5,954,213 A | 9/1999 | Gerhart et al. | |
| 6,183,807 B1 | 2/2001 | Gutzmann et al. | |
| 6,210,639 B1 | 4/2001 | Vlass et al. | |
| 6,223,942 B1 | 5/2001 | Markey et al. | |
| 6,319,888 B2 | 11/2001 | Wei et al. | |
| 6,391,840 B1 | 5/2002 | Thompson et al. | |
| 6,465,233 B1 | 10/2002 | Knauseder et al. | |
| 6,518,307 B2 | 2/2003 | McKenzie et al. | |
| 6,545,047 B2 | 4/2003 | Gutzmann et al. | |
| 6,635,286 B2 | 10/2003 | Hei et al. | |
| 6,645,233 B1 | 11/2003 | Ayers et al. | |
| 6,758,411 B2 | 7/2004 | Conway et al. | |
| 6,995,125 B2 | 2/2006 | Dasque et al. | |
| 7,448,556 B2 | 11/2008 | Muehlhausen et al. | |
| 2002/0030063 A1 | 3/2002 | Leray et al. | |
| 2004/0127381 A1 | 7/2004 | Scialla et al. | |
| 2005/0008526 A1 | 1/2005 | Bianchetti et al. | |
| 2008/0176299 A1 | 7/2008 | Dicosimo et al. | |
| 2008/0176783 A1 | 7/2008 | DiCosimo et al. | |
| 2009/0005590 A1 | 1/2009 | DiCosimo et al. | |

FOREIGN PATENT DOCUMENTS

| | | |
|---|---|---|
| EP | 0807156 B1 | 11/1997 |
| WO | WO96/32149 | 10/1996 |
| WO | WO97/41833 | 11/1997 |
| WO | WO99/03984 | 1/1999 |
| WO | WO00/61713 | 10/2000 |
| WO | WO02/22467 | 3/2002 |
| WO | WO2005/035705 A2 | 4/2005 |
| WO | WO2007/070609 A2 | 6/2007 |
| WO | WO2007/106293 A1 | 9/2007 |
| WO | WO2008/073139 A1 | 6/2008 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Justus Liebigs Annalen der Chemie; 105:206 (1858).
Wurtz, Annales de Chimie; 55:443 (1859).
Seelig, Univ. of Berlin Laboratory; 24: 3466 (1891).
Stöchiometrie und Verwandtschaftslehre vol. 183, [K. Loskit, On the Knowledge of Triglycerides, p. 135-155], vol. 134, Nos. 1 and 2, May 1928.
Abbott et al., Physical Properties and Kinetic Behavior of a Cephalosporin . . . , Appl. Microbiol. 30(3):413-419 (1975).

(Continued)

*Primary Examiner* — Christian Fronda

(57) ABSTRACT

Disclosed herein are two-component enzymatic peracid generation systems and methods of using such systems wherein the first component comprises a formulation of at least one enzyme catalyst having perhydrolysis activity, a carboxylic acid ester substrate, and a cosolvent and wherein the second component comprises a source of peroxygen in water. The two components are combined to produce an aqueous peracid formulation useful as, e.g., a disinfecting or bleaching agent. Specifically, organic cosolvents are used to control the viscosity of a substrate-containing component and to enhance the solubility of the substrate in an aqueous reaction formulation without causing substantial loss of perhydrolytic activity of the enzyme catalyst.

22 Claims, 6 Drawing Sheets

OTHER PUBLICATIONS

Funasaki, N. et al., Intramolecular Hydrophobic Association of Two Alkyl Chains of Oligoethylene Glycol Diethers and Diesters in Water, J. Phys. Chem. 88:5786-5790 (1984).
C. Laane et al., Rules for Optimization of Biocatalysis in Organic Solvents, Biotechnol. Bioeng. 30:81-87 (1987).
Cowan et al., Biocatalysis in Organic Phase Media., Ch. 7 in Biocatalysis at Extreme Temperatures . . . , Amer. Chem. Soc. Symposium Series 498, pp. 86-107 (1992).
Lee, Y.E. et al., Genetic Organization, Sequence and Biochemical Characterization of Recombinant . . . , J Gen Microbiol. (1993), 139:1235-1243.
Mitsushima et al Gene Cloning, Nucleotide Sequence, and Expression . . . , Appl. Env. Microbiol. 61(6):2224-2229, (1995).
Fromant et al., Direct Random Mutagenesis of Gene-Sized DNA Fragments Using Polymerase Chain Reaction, Analytical Biochemistry 224, 347-353 (1995).
Kobayashi et al., Purification and Properties of an Alkaline Protease from Alkalophilic Bacillus sp. KSM-K16, Appl. Microbiol. Biotechnol. 43 (3), 473-481 (1995).
Kuo, S-J. et al., Solvent Polarity Influences Product Selectivity of Lipase-Mediated Esterification Reactions in Microaqueous Media, J. Am. Oil Chem. Soc. 73:1427-1433 (1996).
Pinkernell, U. et al., Simultaneous HPLC Determination of Peroxyacetic Acid and Hydrogen Peroxide, Anal. Chem., 69(17):3623-3627 (1997).
Kunst et al., The Complete Genome Sequence of the Gram-Positive Bacterium Bacillus Subtilis, Nature 390:249-256 (1997).
Lin-Goerke et al., PCR-based Random Mutagenesis Using Manganese and Reduced dNTP Concentration, Biotechniques, 23(3):409-12 (1997).
Nixon et al., Assembly of an Active Enzyme by the Linkage of Two Protein Modules, PNAS, 94:1069-1073 (1997).
Lorenz et al., Isolation, Analysis and Expresion of Two Genes from Thermoanaerobacterium . . . , J. Bacteriol 179:5436-5441 (1997).
Politino et al., Purification and Characterization of a Cephalosporin Esterase . . . , Appl. Environ. Microbiol., 63(12):4807-4811 (1997).
Sakai et al., Purification and Properties of Cephalosporing-C Deacetylase from the Yeast . . . , J. Ferment. Bioeng. 85:53-57 (1998).
Gilbert et al., Recent Advances in Carbohydrate Bioengineering, The Royal Society of Chemistry, Cambridge, pp. 3-12. (1999).
Nelson et al., Evidence for Lateral Gene Transfer Between Archaea and Bacteria From Genome Sequence of Thermotoga Maritime, Nature, 399:323-329 (1999).
Melnikov et al., Random Mutagenesis by Recombinational Capture of PCR Products in Bacillus Subtilis and Acinetobacter Calcoaceticus, Nucleic Acids Res. 27(4):1056-62 (1999).
Cardoza et al., A Cephalosporin C Acetylhydrolase is Present in the Cultures of Nocardia Lactamdurans, Appl. Microbiol. Biotechnol., 54(3):406-412 (2000).
Berman, H.M. et al., The Protein Data Bank. Nucleic Acids Research, 28 pp. 235-242 (2000).
Degrassi et al., The Acetyl Xyland Esterase of Bacillus Pumilus Belongs to a Family . . . , Microbiology., 146:1585-1591 (2000).
Takami et al., Complete Genome Sequences of the Alkaliphilic Bacterium Bacillus Halodurans and . . . , NAR, 28(21):4317-4331 (2000).
Gunning, Y. M. et al., Phase Behavior and Component Partitioning in Low Water Content Amorphous Carbohydrates . . . , J. Agric. Food Chem. 48:395-399 (2000).
Vincent et al., Multifunctional Xylooligosaccharide/Cephalosporin C Deacetylase . . . , J. Mol. Biol., 330:593-606 (2003).
Ru et al, On the Salt-Induced Activation of Lyophilized Enzyme in Organic Solvents, J. Am. Chem. Soc. vol. 122, No. 8, pp. 1465-1571, Feb. 9, 2000.
Ikeda et al., Complete Genome Sequence and Comparative Analysis of the Industrial Microorganism Streptomyces Avermitilis, Nat. Biotechnol. 21 (5), 526-531 (2003).
H.M. Berman, Announcing the Worldwide Protein Data Bank, Nature Structural Biology 10 (12), p. 980 (2003).
Rey et al., Complete Genome Sequence of the Industrial Bacterium Bacillus Licheniformis and . . . , Genome Biol., 5(10): article 77, R77.1-R77-12, (2004).
Braeken, L. et al , Modeling of the Adsorption of Organic Compounds on Polymeric Nanofiltration Membranes in Solutions Containing . . . , Chem Phys Chem, 6:1606-1612 (2005).
Castillo et al., On the Activity Loss of Hydrolases in Organic Solvents . . . , J. Mol. Catalysis Elsevier, vol. 35, Nos. 4-6, pp. 147-153, Sep. 1, 2005.
Krastanova et al., Heterologous Expression, Purificaiton, Crystallization, X-Ray Analysis and . . . , Biochimica ET Biophysica Acta, vol. 1748, No. 2, May 2005, pp. 222-230.
Serdakowski et al., Enzyme Activation for Organic Solvents Made Easy, Treads in Biotechnology, Trends in Biotechnology, Review, vol. 26, No. 1, pp. 48-54, Nov. 26, 2007.
Siezen et al., Genome-Scale Genotype-Phenotype Matching of Two Lactococcus lactis Isolates from Plants Identifies . . . , Appl. Environ. Microbiol. (2008) 74(2): 424-436).
Yoshii et al., Effects of protein on Retention of ADH enzyme Activity Encapsulated . . . , Journal of Food Engr., vol. 87, No. 1, pp. 34-39, Feb. 23, 2008.
DiCosimo, Thermophilic Perhydrolases for Peracetic Acid Production, Sim Annual Meeting and Exhibition, XP0002557717, Jul. 30, 2009.
Copending U.S. Appl. No. 11/638,635, filed Dec. 12, 2006.
Copending U.S. Appl. No. 12/143,375, filed Jun. 20, 2008.
Copending U.S. Appl. No. 12/539,025, filed Aug. 11, 2009.
Copending U.S. Appl. No. 12/571,702, filed Oct. 1, 2009.
Copending U.S. Appl. No. 12/572,115, filed Oct. 1, 2009.
Copending U.S. Appl. No. 12/572,070, filed Oct. 1, 2009.
Copending U.S. Appl. No. 12/572,107, filed Oct. 1, 2009.
Copending U.S. Appl. No. 12/572,086, filed Oct. 1, 2009.
Copending U.S. Appl. No. 12/572,094, filed Oct. 1, 2009.
Belghith, Stabilization of Penicillium Occitanis Cellulases by Sray Drying in Presence .., Enzyme and Microbial Tech., 28 (2001) 253-258, XP-002558791.
International Search Report and Written Opinion of the International Searching Authority in PCT/US2009/059233, issued Feb. 8, 2010.

* cited by examiner

| | |
|---|---|
| SEQ ID NO:2 | -MQLFDLPLDQLQTYKPEKTAPKDFSEFWKLSLEELAKVQAEPDLQPVDYPADGVKVYRL |
| SEQ ID NO:4 | -MQLFDLPLDQLQTYKPEKTAPKDFSEFWKLSLEELAKVQAEPDLQPVDYPADGVKVYRL |
| SEQ ID NO:6 | -MQLFDLPLDQLQTYKPEKTTPNDFSEFWKSSLDELAKVKAAPDLQLVDYPADGVKVYRL |
| SEQ ID NO:8 | MQQPYDMPLEQLYQYKPERTAPADFKEFWKGSLEELANEKAGPQLEPHEYPADGVKVYWL |
| SEQ ID NO:10 | -MQLFDLSLEELKKKYPKKTARPDFSDFWKKSLEELRQVEAEPTLESYDYPVKGVKVYRL |
| SEQ ID NO:12 | MAQLYDMPLEELKKYYKPALTKQKDFDEFWEKSLKELAEIPLKYQLIPYDFPARRVKVFRV |
| SEQ ID NO:14 | -MAFFDMPLEELKKYRPERYEEKDFDEFWRETLKESEGFPLDPVFEKVDFHLKTVETYDV |
| SEQ ID NO:16 | -MAFFDLPLEELKKYRPERYEEKDFDEFWEETLAESEKFPLDPVFERMESHLKTVEAYDV |
| SEQ ID NO:18 | -MGLFDMPLQKLREYTGTNPCPEDFDEYWNRALDEMRSVDPKIELKESSFQVSFAECYDL |
| SEQ ID NO:20 | -MNLFDMPLEELQHYKPAQTRQDDFESFWKKRIEENSQYPLNIEVMERVYPVPGVRVYDI |
| SEQ ID NO:22 | -MPLIDMPLTELKEYMGRNPKPDDFTEYWDRALQEMRKVNPNVELIPSDFQTTYAECFHL |
| SEQ ID NO:24 | -MPLVDMPLRELLAYEGINPKPADFDQYWNRAKTEIEAIDPEVTLVESSFQCSFANCYHF |
| SEQ ID NO:26 | -MQLFDLPLDQLQTYKPEKTAPKDFSEFWKLSLEELAKVQAEPDLQPVDYPADGVKVYRL |
| SEQ ID NO:54 | -MGLFDMPLQKLREYTGTNPCPEDFDEYWDRALDEMRSVDPKIKMKKSFQVPFAECYDL |
| SEQ ID NO:60 | -MVYFDMPLEDLRKYLPQRYEEKDFDFWKQTIHETRGYFQEPILKKVDFYLQNVETFDV |
| SEQ ID NO:64 | -MAFFDLPLEELKKYRPERYEEKDFDEFWEGTLAENEKFPLDPVFERMESHLKTVEAYDV |
| SEQ ID NO:68 | -MAFFDLPLEELKKYRPERYEEKDFDEFWKETLAESEKFPLDPVFERMESHLKTVEVYDV |
| SEQ ID NO:72 | -MALFDMPLEELKKLRSYLPDRYEEEDFDLFWKETLEESRKFPLDPIFERVDYLLENVEVYDV |
| SEQ ID NO:73 | -MAFFDMPLEELKKYRPERYEEKDFDEFWRETLKESEGFPLDPVFEKVDFHLKTVETYDV |
| SEQ ID NO:74 | -MAFFDLPLEELKKYRPERYEEKDFDEFWEETLAESEKFPLDPVFERMESHLKTVEAYDV |

FIG. 1A

| SEQ ID NO: 2  | TYKSFGNARITGWYAVPDKQ---GPHPAIVKYHGYNASYDGEIHEMVNWALHGYAAFGMLV |
| SEQ ID NO: 4  | TYKSFGNARITGWYAVPDKE---GPHPAIVKYHGYNASYDGEIHEMVNWALHGYATFGMLV |
| SEQ ID NO: 6  | TYKSFGNARITGWYAVPDKE---GPHPAIVKYHGYNASYDGEIHEMVNWALHGYAAFGMLV |
| SEQ ID NO: 8  | TYRSIGGARIKGWYAVPDRQ---GPHPAIVKYHGYNASYDGDIHDIVNWALHGYAAFGMLV |
| SEQ ID NO: 10 | TYQSFGHSKIEGFYAVPDQT---GPHPALVRFHGYNASYDGGIHDIVNWALHGYATFGMLV |
| SEQ ID NO: 12 | EYLGFKGANIEGWLAVPEGE---GLYPGLVQFHGYNWAMDGCVPDVVNWALNGYAAFLMLV |
| SEQ ID NO: 14 | TFSGYRGQRIKGWLLVPKLA-EEKLPCVVQYIGYNGG-RGFPHDWLFWPSMGYICFVMDT |
| SEQ ID NO: 16 | TFSGYRGQRIKGWLLVPKLE-EEKLPCVVQYIGYNGG-RGFPHDWLFWPSMGYICFVMDT |
| SEQ ID NO: 18 | YFTGVRGARIHAKYIKP---KTEGKHPALIRFHGYSSN-SGDWNDKLNYVAAGFTVVAMDV |
| SEQ ID NO: 20 | YFDGFRNSRIHGVYVTPETP-GADTPAAVIFHGYNWN-TLQPHYSFKHVIQGIPVLMVEV |
| SEQ ID NO: 22 | YFTGVRGARIHAKYVRPR-HTSGTHPAVIHFHGYTMN-AGEWTGLLHYAALGYSVLAMDV |
| SEQ ID NO: 24 | YYRSAGNAKIHAKYVQP---KAGEKTPAVFMHGYGGR-SAEWSSLLNYVAAGESVFYMDV |
| SEQ ID NO: 26 | TYKSFGNARITGWYAVPDKQ---GPHPAIVKYHGYNASYDGEIHEMVNWALHGYAAFGMLV |
| SEQ ID NO: 54 | YFTGVRGARIHAKYIRP--KTEGKHPALIRFHGYSSN-SGDWNDKLNYVAAGFTVVAMDA |
| SEQ ID NO: 60 | TFSGYMGQRIKGWLILPKFR-NGKLPCVVEFVGYGGG-RGFPYDWLLWSAAGYAHFIMDT |
| SEQ ID NO: 64 | TFSGYRGQRIKGWLLVPKLE-EEKLPCVVQYIGYNGG-RGFPYDWLFWPSMGYICFVMDT |
| SEQ ID NO: 68 | TFSGYRGQRIKGWLLVPKLE-EEKLPCVVQYIGYNGG-RGFPHDWLFWPSMGYICFVMDT |
| SEQ ID NO: 72 | TFSGYRGQRIKAWLILPVVKKEERLPCIVEFIGYRGG-RGFPFDWLFWSSAGYAHFVMDT |
| SEQ ID NO: 73 | TFSGYRGQRIKGWLLVPKLA-EEKLPCVVQYIGYNGG-RGFPHDWLFWPSMGYICFVMDT |
| SEQ ID NO: 74 | TFSGYRGQRIKGWLLVPKLE-EEKLPCVVQYIGYNGG-RGFPHDWLFWPSMGYICFVMDT |

FIG. 1B

| | |
|---|---|
| SEQ ID NO: 2  | RGQQS----SEDTSISLHG------HALGWMTKGILD--KDTYYYRGVYLDAVRALEVISSFDE |
| SEQ ID NO: 4  | RGQQS----SEDTSISPHG------HALGWMTKGILD--KDTYYYRGVYLDAVRALEVISSFDE |
| SEQ ID NO: 6  | RGQQS----SEDTSISPHG------HALGWMTKGILD--KDTYYYRGVYLDAVRALEVISSFDE |
| SEQ ID NO: 8  | RGQNS----SEDTEISHHG------HVPGWMTKGILD--PKTYYYRGVYLDAVRAVEVVSGFAE |
| SEQ ID NO:10  | RGQGG----SEDTSVTPGG------HALGWMTKGILS--KDTYYYRGVYLDAVRALEVIQSFPE |
| SEQ ID NO:12  | RGQQGR---SVDNIVPGSG------HALGWMSKGILS--PEEYYYRGVYMDAVRAVEILASLPC |
| SEQ ID NO:14  | RGQGSGWMKGDTPDYPEGPVDPQYPGFMTRGILD--PGTYYYRRVFVDAVRAVEAAISFPR |
| SEQ ID NO:16  | RGQGSGWLKGDTPDYPEGPVDPQYPGFMTRGILD--PRTYYYRRVFTDAVRAVEAAASFPQ |
| SEQ ID NO:18  | RGQGGQ---SQDVGGVTGN------TLNGHIIRGLDDDADNMLFRHIFLDTAQLAGIVMNMPE |
| SEQ ID NO:20  | RGQNL----LSPDRNHYGNG-----GPGGWMTLGVMD--PDQYYSLVYMDCFRSIDAVRELSR |
| SEQ ID NO:22  | RGQGGL---SEDTGGVKGN------THSGHIIRGLDDNADQLLFRHVFLDTAQLANIVMNLPE |
| SEQ ID NO:24  | RGQGGT---SEDPGGVRGN------TYRGHIIRGLDAGPDALFYRSVFLDTVQLVRAAKTLPH |
| SEQ ID NO:26  | RGQQS----SEDTSISPHG------HALGWMTKGILD--KDTYYYRGVYLDAVRALEVISSFDE |
| SEQ ID NO:54  | RGQGGQ---SQDVGGVNGN------TLNGHIIRGLDDDADNMLFRHIFLDTAQLAGIVMNMPE |
| SEQ ID NO:60  | RGQGSNWMKGDTPDYEDNPSDPQYPGFLTKGVLN--PETYYYRRVFMDAFMAVETISQLEQ |
| SEQ ID NO:64  | RGQGSGWMKGDTPDYPEDPVDPQYPGFMTRGILD--PRTYYYRRVFTDAVRAVEAAASFPR |
| SEQ ID NO:68  | RGQGSGWMKGDTPDYPEDPVDPQYPGFMTRGILD--PRTYYYRRVFTDAVRAVEAAASFPR |
| SEQ ID NO:72  | RGQGTSRVKGDTPDYCDEPINPQFPGFMTRGILD--PRTYYYRRVFTDAVRAVETASSFPG |
| SEQ ID NO:73  | RGQGSGWMKGDTPDYPEGPVDPQYPGFMTRGILD--PGTYYYRRVFVDAVRAVEAAISFPR |
| SEQ ID NO:74  | RGQGSGWLKGDTPDYPEGPVDPQYPGFMTRGILD--PRTYYYRRVFTDAVRAVEAAASFPQ |

FIG. 1C

| | | |
|---|---|---|
| SEQ ID NO:2 | VDETRIGVTGGSQGGGLTIAAAALSDIPKAAVADYPYLSNFERAIDVALEQ-PYLEINSF |
| SEQ ID NO:4 | VDETRIGVTGGSQGGGLTIAAAALSDIPKAAVADYPYLSNFERAIDVALEQ-PYLEINSF |
| SEQ ID NO:6 | VDETRIGVTGGSQGGGLTIAAAALSDIPKAAVADYPYLSNFERAIDVALEQ-PYLEINSF |
| SEQ ID NO:8 | VDEKRIGVIGASQGGGLAVAVSALSDIPKAAVSEYPYLSNFQRAIDTAIDQ-PYLEINSF |
| SEQ ID NO:10 | VDEHRIGVIGGSQGGALAIAAAALSDIPKVVVADYPYLSNFERAVDVALEQ-PYLEINSY |
| SEQ ID NO:12 | VDESRIGVTGGSQGGGLALAVAALSGIPKVAAVHYPFLAHFERAIDVAPDG-PYLEINEY |
| SEQ ID NO:14 | VDSRKVVVAGGSQGGIALAVSALSNRVKALLCDVPFLCHFRRAVQLVDTH-PYVEITNF |
| SEQ ID NO:16 | VDQERIVIAGGSQGGIALAVSALSKKAKALLCDVPFLCHFRRAVQLVDTH-PYAEITNF |
| SEQ ID NO:18 | VDEDRVGVMGPSQGGGLSLACAALEPRVRKVVSEYPFLSDYKRVWDLDLAKNAYQEITDY |
| SEQ ID NO:20 | K---RSVFVEGGSQGGALAIAAAALQDDILLALADIPFLTHFKRSVELSSDG-PYQEISHY |
| SEQ ID NO:22 | VDEERVAVTGWSQGGALAIACAALEPKIKKVAPVYPFLSDYQRVWEMDLAEKAYDELQTY |
| SEQ ID NO:24 | IDKTRLMATGWSQGGALTLACAALVPEIKRLAPVYPFLSDYKRVWQMDLAVRSYKELADY |
| SEQ ID NO:26 | VDETRIGVTGGSQGGGLTIAAAALSDIPKAAVADYPYLSNFERAIDVALEQ-PYLEINSF |
| SEQ ID NO:54 | IDEDRVAVMGPSQGGGLSLACAALEPKIRKVVSEYPFLSDYKRVWDLDLAKNAYQEITDY |
| SEQ ID NO:60 | IDSQTIILSGASQGGIALAVSALSSKVMALLCDVPFLCHYKRAVQITDSM-PYAEITRY |
| SEQ ID NO:64 | VDHERIVIAGGSQGGIALAVSALSKKAKALLCDVPFLCHFRRAVQLVDTH-PYAEITNF |
| SEQ ID NO:68 | VDHERIVIAGGSQGGIALAVSALSKKAKALLCDVPFLCHFRRAVQLVDTH-PYAEITNF |
| SEQ ID NO:72 | IDPERIAVVGTSQGGIALAVAALSEIPKALVSNVPFLCHFRRAVQITDNA-PYSEIVNY |
| SEQ ID NO:73 | VDSRKVVVAGGSQGGIALAVSALSNRVKALLCDVPFLCHFRRAVQLVDTH-PYVEITNF |
| SEQ ID NO:74 | VDQERIVIAGGSQGGIALAVSALSKKAKALLCDVPFLCHFRRAVQLVDTH-PYAEITNF |

FIG. 1D

```
SEQ ID NO:2   FRRNGSP-ETEVQAMKTLSYFDIMNLADRVKVPVLMSIGLIDKVTPPSTVFAAYNHLETE
SEQ ID NO:4   FRRNGSP-ETEVQAMKTLSYFDIMNLADRVKVPVLMSIGLIDKVTPPSTVFAAYNHLETK
SEQ ID NO:6   FRRNGSP-ETEEKAMKTLSYFDIMNLADRVKVPVLMSIGLIDKVTPPSTVFAAYNHLETE
SEQ ID NO:8   FRRNTSP-DIEQAAMHTLSYFDVMNLAQLVKATVLMSIGLVDTITPPSTVFAAYNHLETD
SEQ ID NO:10  FRRNSDP-KVEEKAFETLSYFDLINLAGWVKQPTLMAIGLIDKITPPSTVFAAYNHLETD
SEQ ID NO:12  LRRNSGE-EIERQVKKTLSYFDIMNLAPRIKCRTWICTGLVDEITPPSTVFAVYNHLKCP
SEQ ID NO:14  LKTHR----DKEEIVFRTLSYFDGVNFAARAKVPALFSVGLMDTICPPSTVFAAYNHYAGP
SEQ ID NO:16  LKTHR----DKEEIVFRTLSYFDGVNFAARAKIPALFSVGLMDNICPPSTVFAAYNYYAGP
SEQ ID NO:18  FRLFDPRHERENEVFTKLGYIDVKNLAKRIKGDVLMCVGLMDQVCPPSTVFAAYNNIQSK
SEQ ID NO:20  FKVHDPLHQTEEQVYQTLSYVDCMNMASMVECPVLLSAGLEDIVCPPSSAFALFNHLGGP
SEQ ID NO:22  FRRFDPQHRREAEIFTKLGYIDIQHLAPLVKGEVLLAVGLMDTVCPPSTQFAMYNKLTTT
SEQ ID NO:24  FRSYDPQHKRHGEIFERLGYIDVQHLADRIQGDVLMGVGLMDTECPPSTQFAAYNKIKAK
SEQ ID NO:26  FRRNGSP-ETEVQAMKTLSYFDIMNLADRVKVPVLMSIGLIDKVTPPSTVFAAYNHLETE
SEQ ID NO:54  FRLFDPRHERENEVFTKLGYIDVKNLAKRIKGDVLMCVGLMDQVCPPSTVFAAYNNIQSK
SEQ ID NO:60  CKTHI----DKIQTVFRTLSYFDGVNFAARAKCPALFSVGLMDDICPPSTVFAAYNYYAGE
SEQ ID NO:64  LKTHR----DKEEIVFRTLSYFDGVNFAVRAKIPALFSVGLMDNICPPSTVFAAYNHYAGP
SEQ ID NO:68  LKTHR----DKEEIVFRTLSYFDGVNFAVRAKIPALFSVGLMDNICPPSTVFAAYNHYAGP
SEQ ID NO:72  LKVHR----DKEEIVFRTLSYFDGVNFAARAKVPALFSVGLMDTIXPPSTVFAAYNHYAGP
SEQ ID NO:73  LKTHR----DKEEIVFRTLSYFDGVNFAARAKIPALFSVALMDKTCPPSTVFAAYNHYAGP
SEQ ID NO:74  LKTHR----DKEEIVFRTLSYFDGVNFAARAKIPALFSVGLMDNIXPPSTVFAAYNYYAGP
```

FIG. 1E

| | |
|---|---|
| SEQ ID NO: 2 | KELKVYRYFGHEYIPAFQT-EKLAFFKQHLKG---------- |
| SEQ ID NO: 4 | KELKVYRYFGHEYIPAFQT-EKLAFFKQHLKG---------- |
| SEQ ID NO: 6 | KELKVYRYFGHEYIPAFQT-EKLAFFKQHLKG---------- |
| SEQ ID NO: 8 | KELKVYRYFGHEYTPPFQT-EKLAFLRKHLK----------- |
| SEQ ID NO: 10 | KDLKVYRYFGHEFIPAFQT-EKLSFLQKHLLLST-------- |
| SEQ ID NO: 12 | KEISVFRYFGHEHMPGSVE-IKLRILMDELNP---------- |
| SEQ ID NO: 14 | KEIRIYPYNNHEGGGSFQAIEQVKFLKRLFEEG--------- |
| SEQ ID NO: 16 | KEIRIYPYNNHEGGSFQAVEQVKFLKKLFEKG---------- |
| SEQ ID NO: 18 | KDIKVYPDYGHEPMRGFGD-LAMQFMLELYS----------- |
| SEQ ID NO: 20 | KEIRAYPEYAHEVPAVHEE-EKLKFISSRLKNREKRCRP    |
| SEQ ID NO: 22 | KSIELYPDFAHEDLPGHRD-RIFQFLSDL------------- |
| SEQ ID NO: 24 | KSYELYPDFGHERLPGMND-HIFRFFTS-------------- |
| SEQ ID NO: 26 | KELKVYRYFGHEYIPAFQT-EKLAFFKQHLKG---------- |
| SEQ ID NO: 54 | KDIKVYPDYGHEPMRGFGD-LAMQFMLELYS----------- |
| SEQ ID NO: 60 | KDIRIYPYNNHEGGGSFHTLEKLKFVKKTISMRE-------- |
| SEQ ID NO: 64 | KEIRIYPYNNHEGGGSFQAIEQVKFLKRLFEKG--------- |
| SEQ ID NO: 68 | KEIKVYPFNEHEGGESFQRMEELRFMKRILKGEFKA------ |
| SEQ ID NO: 72 | KEIRIYPYNNHEGGESFQAIEQVKFLKRLFEEG--------- |
| SEQ ID NO: 73 | KEIKVYPFNEHEGGESFQRMEELRFMKRILKGEFKA------ |
| SEQ ID NO: 74 | KEIRIYPYNNHEGGGSFQAVEQVKFLKKLFEKG--------- |

FIG. 1F

SEQUENCE LISTING

```
<160> NUMBER OF SEQ ID NOS: 74

<210> SEQ ID NO 1
<211> LENGTH: 960
<212> TYPE: DNA
<213> ORGANISM: Bacillus subtilis
<220> FEATURE:
<221> NAME/KEY: CDS
<222> LOCATION: (1)..(960)

<400> SEQUENCE: 1 atg caa cta ttc gat ctg ccg ctc gac caa ttg caa aca tat aag cct    48
Met Gln Leu Phe Asp Leu Pro Leu Asp Gln Leu Gln Thr Tyr Lys Pro
1               5                   10                  15 gaa aaa aca gca ccg aaa gat ttt tct gag ttt tgg aaa ttg tct ttg    96
Glu Lys Thr Ala Pro Lys Asp Phe Ser Glu Phe Trp Lys Leu Ser Leu
            20                  25                  30 gag gaa ctt gca aaa gtc caa gca gaa cct gat tta cag ccg gtt gac   144
Glu Glu Leu Ala Lys Val Gln Ala Glu Pro Asp Leu Gln Pro Val Asp
        35                  40                  45 tat cct gct gac gga gta aaa gtg tac cgt ctc aca tat aaa agc ttc   192
Tyr Pro Ala Asp Gly Val Lys Val Tyr Arg Leu Thr Tyr Lys Ser Phe
    50                  55                  60 gga aac gcc cgc att acc gga tgg tac gcg gtg cct gac aag caa ggc   240
Gly Asn Ala Arg Ile Thr Gly Trp Tyr Ala Val Pro Asp Lys Gln Gly
65                  70                  75                  80 ccg cat ccg gcg atc gtg aaa tat cat ggc tac aat gca agc tat gat   288
Pro His Pro Ala Ile Val Lys Tyr His Gly Tyr Asn Ala Ser Tyr Asp
                85                  90                  95
```

```
ggt gag att cat gaa atg gta aac tgg gca ctc cat ggc tac gcc gca      336
Gly Glu Ile His Glu Met Val Asn Trp Ala Leu His Gly Tyr Ala Ala
            100                 105                 110 ttc ggc atg ctt gtc cgc ggc cag cag agc agc gag gat acg agt att      384
Phe Gly Met Leu Val Arg Gly Gln Gln Ser Ser Glu Asp Thr Ser Ile
        115                 120                 125 tca ctg cac ggt cac gct ttg ggc tgg atg acg aaa gga att ctt gat      432
Ser Leu His Gly His Ala Leu Gly Trp Met Thr Lys Gly Ile Leu Asp
    130                 135                 140 aaa gat aca tac tat tac cgc ggt gtt tat ttg gac gcc gtc cgc gcg      480
Lys Asp Thr Tyr Tyr Tyr Arg Gly Val Tyr Leu Asp Ala Val Arg Ala
145                 150                 155                 160 ctt gag gtc atc agc agc ttc gac gag gtt gac gaa aca agg atc ggt      528
Leu Glu Val Ile Ser Ser Phe Asp Glu Val Asp Glu Thr Arg Ile Gly
                165                 170                 175 gtg aca gga gga agc caa ggc gga ggt tta acc att gcc gca gca gcg      576
Val Thr Gly Gly Ser Gln Gly Gly Gly Leu Thr Ile Ala Ala Ala Ala
            180                 185                 190 ctg tca gac att cca aaa gcc gcg gtt gcc gat tat cct tat tta agc      624
Leu Ser Asp Ile Pro Lys Ala Ala Val Ala Asp Tyr Pro Tyr Leu Ser
        195                 200                 205 aac ttc gaa cgg gcc att gat gtg gcg ctt gaa cag ccg tac ctt gaa      672
Asn Phe Glu Arg Ala Ile Asp Val Ala Leu Glu Gln Pro Tyr Leu Glu
    210                 215                 220 atc aat tcc ttc ttc aga aga aat ggc agc ccg gaa aca gaa gtg cag      720
Ile Asn Ser Phe Phe Arg Arg Asn Gly Ser Pro Glu Thr Glu Val Gln
225                 230                 235                 240 gcg atg aag aca ctt tca tat ttc gat att atg aat ctc gct gac cga      768
Ala Met Lys Thr Leu Ser Tyr Phe Asp Ile Met Asn Leu Ala Asp Arg
                245                 250                 255 gtg aag gtg cct gtc ctg atg tca atc ggc ctg att gac aag gtc acg      816
Val Lys Val Pro Val Leu Met Ser Ile Gly Leu Ile Asp Lys Val Thr
            260                 265                 270 ccg ccg tcc acc gtg ttt gcc gcc tac aat cat ttg gaa aca gag aaa      864
Pro Pro Ser Thr Val Phe Ala Ala Tyr Asn His Leu Glu Thr Glu Lys
        275                 280                 285 gag ctg aag gtg tac cgc tac ttc gga cat gag tat atc cct gct ttt      912
Glu Leu Lys Val Tyr Arg Tyr Phe Gly His Glu Tyr Ile Pro Ala Phe
    290                 295                 300 caa acg gaa aaa ctt gct ttc ttt aag cag cat ctt aaa ggc tga taa      960
Gln Thr Glu Lys Leu Ala Phe Phe Lys Gln His Leu Lys Gly
305                 310                 315

<210> SEQ ID NO 2
<211> LENGTH: 318
<212> TYPE: PRT
<213> ORGANISM: Bacillus subtilis

<400> SEQUENCE: 2

Met Gln Leu Phe Asp Leu Pro Leu Asp Gln Leu Gln Thr Tyr Lys Pro
1               5                   10                  15

Glu Lys Thr Ala Pro Lys Asp Phe Ser Glu Phe Trp Lys Leu Ser Leu
            20                  25                  30

Glu Glu Leu Ala Lys Val Gln Ala Glu Pro Asp Leu Gln Pro Val Asp
        35                  40                  45

Tyr Pro Ala Asp Gly Val Lys Val Tyr Arg Leu Thr Tyr Lys Ser Phe
    50                  55                  60

Gly Asn Ala Arg Ile Thr Gly Trp Tyr Ala Val Pro Asp Lys Gln Gly
65                  70                  75                  80
```

```
Pro His Pro Ala Ile Val Lys Tyr His Gly Tyr Asn Ala Ser Tyr Asp
                85                   90                  95

Gly Glu Ile His Glu Met Val Asn Trp Ala Leu His Gly Tyr Ala Ala
            100                 105                 110

Phe Gly Met Leu Val Arg Gly Gln Gln Ser Ser Glu Asp Thr Ser Ile
        115                 120                 125

Ser Leu His Gly His Ala Leu Gly Trp Met Thr Lys Gly Ile Leu Asp
    130                 135                 140

Lys Asp Thr Tyr Tyr Tyr Arg Gly Val Tyr Leu Asp Ala Val Arg Ala
145                 150                 155                 160

Leu Glu Val Ile Ser Ser Phe Asp Glu Val Asp Glu Thr Arg Ile Gly
                165                 170                 175

Val Thr Gly Gly Ser Gln Gly Gly Gly Leu Thr Ile Ala Ala Ala Ala
            180                 185                 190

Leu Ser Asp Ile Pro Lys Ala Ala Val Ala Asp Tyr Pro Tyr Leu Ser
        195                 200                 205

Asn Phe Glu Arg Ala Ile Asp Val Ala Leu Glu Gln Pro Tyr Leu Glu
    210                 215                 220

Ile Asn Ser Phe Phe Arg Arg Asn Gly Ser Pro Glu Thr Glu Val Gln
225                 230                 235                 240

Ala Met Lys Thr Leu Ser Tyr Phe Asp Ile Met Asn Leu Ala Asp Arg
                245                 250                 255

Val Lys Val Pro Val Leu Met Ser Ile Gly Leu Ile Asp Lys Val Thr
            260                 265                 270

Pro Pro Ser Thr Val Phe Ala Ala Tyr Asn His Leu Glu Thr Glu Lys
        275                 280                 285

Glu Leu Lys Val Tyr Arg Tyr Phe Gly His Glu Tyr Ile Pro Ala Phe
    290                 295                 300

Gln Thr Glu Lys Leu Ala Phe Phe Lys Gln His Leu Lys Gly
305                 310                 315

<210> SEQ ID NO 3
<211> LENGTH: 957
<212> TYPE: DNA
<213> ORGANISM: Bacillus subtilis

<400> SEQUENCE: 3
atgcaactat tcgatctgcc gctcgaccaa ttgcaaacat ataagcctga aaaacagca      60 ccgaaagatt tttctgagtt ttggaaattg tctttggagg aacttgcaaa agtccaagca    120
gaacctgatt tacagccggt tgactatcct gctgacggag taaaagtgta ccgtctcaca    180
tataaaagct tcggaaacgc ccgcattacc ggatggtacg cggtgcctga caaggaaggc    240
ccgcatccgg cgatcgtgaa atatcatggc tacaatgcaa gctatgatgg tgagattcat    300
gaaatggtaa actgggcact ccatggctac gccacattcg gcatgcttgt ccgcggccag    360
cagagcagcg aggatacgag tatttcaccg cacggtcacg ctttgggctg gatgacgaaa    420
ggaattcttg ataaagatac atactattac cgcggtgttt atttggacgc cgtccgcgcg    480
cttgaggtca tcagcagctt cgacgaggtt gacgaaacaa ggatcggtgt gacaggagga    540
agccaaggcg gaggtttaac cattgccgca gcagcgctgt cagacattcc aaaagccgcg    600
gttgccgatt atccttattt aagcaacttc gaacgggcca ttgatgtggc cttgaacag    660 ccgtaccttg aaatcaattc cttcttcaga agaaatggca gcccggaaac agaagtgcag    720
gcgatgaaga cactttcata tttcgatatt atgaatctcg ctgaccgagt gaaggtgcct    780
gtcctgatgt caatcggcct gattgacaag gtcacgccgc cgtccaccgt gtttgccgcc    840
```

```
tacaatcatt tggaaacaaa gaaagagctg aaggtgtacc gctacttcgg acatgagtat    900
atccctgctt ttcaaactga aaaacttgct ttctttaagc agcatcttaa aggctga      957
```

<210> SEQ ID NO 4
<211> LENGTH: 318
<212> TYPE: PRT
<213> ORGANISM: Bacillus subtilis

<400> SEQUENCE: 4

```
Met Gln Leu Phe Asp Leu Pro Leu Asp Gln Leu Gln Thr Tyr Lys Pro
1               5                   10                  15

Glu Lys Thr Ala Pro Lys Asp Phe Ser Glu Phe Trp Lys Leu Ser Leu
            20                  25                  30

Glu Glu Leu Ala Lys Val Gln Ala Glu Pro Asp Leu Gln Pro Val Asp
        35                  40                  45

Tyr Pro Ala Asp Gly Val Lys Val Tyr Arg Leu Thr Tyr Lys Ser Phe
    50                  55                  60

Gly Asn Ala Arg Ile Thr Gly Trp Tyr Ala Val Pro Asp Lys Glu Gly
65                  70                  75                  80

Pro His Pro Ala Ile Val Lys Tyr His Gly Tyr Asn Ala Ser Tyr Asp
                85                  90                  95

Gly Glu Ile His Glu Met Val Asn Trp Ala Leu His Gly Tyr Ala Thr
            100                 105                 110

Phe Gly Met Leu Val Arg Gly Gln Gln Ser Ser Glu Asp Thr Ser Ile
        115                 120                 125

Ser Pro His Gly His Ala Leu Gly Trp Met Thr Lys Gly Ile Leu Asp
    130                 135                 140

Lys Asp Thr Tyr Tyr Tyr Arg Gly Val Tyr Leu Asp Ala Val Arg Ala
145                 150                 155                 160

Leu Glu Val Ile Ser Ser Phe Asp Glu Val Asp Glu Thr Arg Ile Gly
                165                 170                 175

Val Thr Gly Gly Ser Gln Gly Gly Gly Leu Thr Ile Ala Ala Ala Ala
            180                 185                 190

Leu Ser Asp Ile Pro Lys Ala Ala Val Ala Asp Tyr Pro Tyr Leu Ser
        195                 200                 205

Asn Phe Glu Arg Ala Ile Asp Val Ala Leu Glu Gln Pro Tyr Leu Glu
    210                 215                 220

Ile Asn Ser Phe Phe Arg Arg Asn Gly Ser Pro Glu Thr Glu Val Gln
225                 230                 235                 240

Ala Met Lys Thr Leu Ser Tyr Phe Asp Ile Met Asn Leu Ala Asp Arg
                245                 250                 255

Val Lys Val Pro Val Leu Met Ser Ile Gly Leu Ile Asp Lys Val Thr
            260                 265                 270

Pro Pro Ser Thr Val Phe Ala Ala Tyr Asn His Leu Glu Thr Lys Lys
        275                 280                 285

Glu Leu Lys Val Tyr Arg Tyr Phe Gly His Glu Tyr Ile Pro Ala Phe
    290                 295                 300

Gln Thr Glu Lys Leu Ala Phe Phe Lys Gln His Leu Lys Gly
305                 310                 315
```

<210> SEQ ID NO 5
<211> LENGTH: 957
<212> TYPE: DNA
<213> ORGANISM: Bacillus subtilis

<400> SEQUENCE: 5

```
atgcaactat tcgatctgcc gctcgaccaa ttgcaaacgt ataagcctga aaaaacaaca    60
ccgaacgatt tttctgagtt ttggaaatcg tctttggacg aacttgcgaa agtcaaagca   120
gcacctgatt tacagctggt tgattatcct gctgatggag tcaaggtgta ccgcctcaca   180
tataaaagct tcggaaacgc ccgcattacc ggatggtacg cagtgcctga caaggaagga   240
ccgcatccgg cgatcgtcaa atatcatggc tacaacgcta gctatgacgg tgagattcat   300
gaaatggtaa actgggcgct ccacggttac gccgcattcg gcatgctagt ccgcggccag   360
cagagcagcg aggatacgag tatttctcca catggccatg ctttgggctg atgacgaaa    420
ggaatccttg ataaagatac atactattac cggggcgttt atttggacgc tgtccgcgcg   480
cttgaggtca tcagcagctt tgacgaagtt gacgaaacaa gaatcggtgt gacaggcgga   540
agccaaggag gcggcttaac cattgccgca gccgctctgt cagacattcc aaaagccgcg   600
gttgccgatt atccttattt aagcaacttt gaacgggcca ttgatgtggc gcttgaacag   660
ccgtaccttg aaatcaattc cttctttaga agaaatggaa gcccggaaac ggaagagaag   720
gcgatgaaga cactttcata tttcgatatt atgaatctcg ctgaccgagt gaaggtccct   780
gtcctgatgt cgatcggtct gattgacaag gtcacgccgc cgtccaccgt gtttgccgca   840
tacaaccact tggagacaga gaaagagctc aaagtgtacc gctacttcgg catgagtat    900
atccctgcct tcaaacaga aaacttgct ttctttaagc agcatcttaa aggctga        957
```

<210> SEQ ID NO 6
<211> LENGTH: 318
<212> TYPE: PRT
<213> ORGANISM: Bacillus subtilis

<400> SEQUENCE: 6

```
Met Gln Leu Phe Asp Leu Pro Leu Asp Gln Leu Gln Thr Tyr Lys Pro
1               5                   10                  15

Glu Lys Thr Thr Pro Asn Asp Phe Ser Glu Phe Trp Lys Ser Ser Leu
            20                  25                  30

Asp Glu Leu Ala Lys Val Lys Ala Ala Pro Asp Leu Gln Leu Val Asp
        35                  40                  45

Tyr Pro Ala Asp Gly Val Lys Val Tyr Arg Leu Thr Tyr Lys Ser Phe
    50                  55                  60

Gly Asn Ala Arg Ile Thr Gly Trp Tyr Ala Val Pro Asp Lys Glu Gly
65                  70                  75                  80

Pro His Pro Ala Ile Val Lys Tyr His Gly Tyr Asn Ala Ser Tyr Asp
                85                  90                  95

Gly Glu Ile His Glu Met Val Asn Trp Ala Leu His Gly Tyr Ala Ala
            100                 105                 110

Phe Gly Met Leu Val Arg Gly Gln Gln Ser Ser Glu Asp Thr Ser Ile
        115                 120                 125

Ser Pro His Gly His Ala Leu Gly Trp Met Thr Lys Gly Ile Leu Asp
    130                 135                 140

Lys Asp Thr Tyr Tyr Arg Gly Val Tyr Leu Asp Ala Val Arg Ala
145                 150                 155                 160

Leu Glu Val Ile Ser Ser Phe Asp Glu Val Asp Glu Thr Arg Ile Gly
                165                 170                 175

Val Thr Gly Gly Ser Gln Gly Gly Leu Thr Ile Ala Ala Ala Ala
            180                 185                 190

Leu Ser Asp Ile Pro Lys Ala Ala Val Ala Asp Tyr Pro Tyr Leu Ser
        195                 200                 205
```

| | | | | | | | | | | | |
|---|---|---|---|---|---|---|---|---|---|---|---|
|Asn|Phe|Glu|Arg|Ala|Ile|Asp|Val|Ala|Leu|Glu|Gln|Pro|Tyr|Leu|Glu|
| |210| | | |215| | | |220| | |

Asn Phe Glu Arg Ala Ile Asp Val Ala Leu Glu Gln Pro Tyr Leu Glu
            210                 215                 220

Ile Asn Ser Phe Phe Arg Arg Asn Gly Ser Pro Glu Thr Glu Glu Lys
225                 230                 235                 240

Ala Met Lys Thr Leu Ser Tyr Phe Asp Ile Met Asn Leu Ala Asp Arg
                245                 250                 255

Val Lys Val Pro Val Leu Met Ser Ile Gly Leu Ile Asp Lys Val Thr
            260                 265                 270

Pro Pro Ser Thr Val Phe Ala Ala Tyr Asn His Leu Glu Thr Glu Lys
        275                 280                 285

Glu Leu Lys Val Tyr Arg Tyr Phe Gly His Glu Tyr Ile Pro Ala Phe
    290                 295                 300

Gln Thr Glu Lys Leu Ala Phe Phe Lys Gln His Leu Lys Gly
305                 310                 315

<210> SEQ ID NO 7
<211> LENGTH: 957
<212> TYPE: DNA
<213> ORGANISM: Bacillus licheniformis

<400> SEQUENCE: 7

```
atgcagcagc cttatgatat gccgcttgaa cagctttatc agtataaacc tgaacggacg      60
gcaccggccg attttaaaga gttctggaag ggttcattgg aggaattggc aaatgaaaaa     120
gcgggaccgc agcttgaacc gcatgaatat ccggctgacg gggtaaaagt ctactggctt     180
acatacagaa gcatcggggg agcgcgaatt aaaggctggt acgcagtacc cgaccgccaa     240
gggcctcatc ctgcgatcgt caaataccac ggctataacg caagctatga cggagacatt     300
cacgatattg tcaattgggc tcttcacggc tatgcggcat tcggtatgct ggtccgcgga     360
cagaacagca gtgaagatac agagatctct catcacggac atgtacccgg ctggatgaca     420
aaaggaatcc tcgatccgaa acatattac tacagagggg tctatttaga tgccgtacga     480
gcagtcgaag tggtcagcgg ttttgctgaa gtcgatgaaa gcggatcgg ggtgatcggg     540
gcaagccaag gaggcgggct ggccgtcgcg gtttcggcgc tgtccgatat tccaaaagca     600
gccgtgtcag aatacccta tttaagcaat tttcaacgag cgatcgatac agcgatcgac     660
cagccatatc tcgaaatcaa ctccttttc agaagaaaca ccagtccgga tattgagcag     720
gcggccatgc atacctgtc ttatttcgat gtcatgaacc ttgcccaatt ggtcaaagcg     780
accgtactca tgtcgatcgg actggttgac accatcactc cgccatccac cgtctttgcg     840
gcttacaatc acttggaaac ggataaagaa ataaagtgt accgttattt tggacacgaa     900
tacatcccgc cgttccaaac cgaaaagctg gcgtttctga aaagcatct gaaataa       957
```

<210> SEQ ID NO 8
<211> LENGTH: 318
<212> TYPE: PRT
<213> ORGANISM: Bacillus licheniformis

<400> SEQUENCE: 8

Met Gln Gln Pro Tyr Asp Met Pro Leu Glu Gln Leu Tyr Gln Tyr Lys
1               5                   10                  15

Pro Glu Arg Thr Ala Pro Ala Asp Phe Lys Glu Phe Trp Lys Gly Ser
            20                  25                  30

Leu Glu Glu Leu Ala Asn Glu Lys Ala Gly Pro Gln Leu Glu Pro His
        35                  40                  45

Glu Tyr Pro Ala Asp Gly Val Lys Val Tyr Trp Leu Thr Tyr Arg Ser
    50                  55                  60

```
Ile Gly Gly Ala Arg Ile Lys Gly Trp Tyr Ala Val Pro Asp Arg Gln
 65                  70                  75                  80

Gly Pro His Pro Ala Ile Val Lys Tyr His Gly Tyr Asn Ala Ser Tyr
                 85                  90                  95

Asp Gly Asp Ile His Asp Ile Val Asn Trp Ala Leu His Gly Tyr Ala
            100                 105                 110

Ala Phe Gly Met Leu Val Arg Gly Gln Asn Ser Ser Glu Asp Thr Glu
        115                 120                 125

Ile Ser His His Gly His Val Pro Gly Trp Met Thr Lys Gly Ile Leu
    130                 135                 140

Asp Pro Lys Thr Tyr Tyr Arg Gly Val Tyr Leu Asp Ala Val Arg
145                 150                 155                 160

Ala Val Glu Val Val Ser Gly Phe Ala Glu Val Asp Glu Lys Arg Ile
                165                 170                 175

Gly Val Ile Gly Ala Ser Gln Gly Gly Leu Ala Val Ala Val Ser
            180                 185                 190

Ala Leu Ser Asp Ile Pro Lys Ala Ala Val Ser Glu Tyr Pro Tyr Leu
        195                 200                 205

Ser Asn Phe Gln Arg Ala Ile Asp Thr Ala Ile Asp Gln Pro Tyr Leu
    210                 215                 220

Glu Ile Asn Ser Phe Phe Arg Arg Asn Thr Ser Pro Asp Ile Glu Gln
225                 230                 235                 240

Ala Ala Met His Thr Leu Ser Tyr Phe Asp Val Met Asn Leu Ala Gln
                245                 250                 255

Leu Val Lys Ala Thr Val Leu Met Ser Ile Gly Leu Val Asp Thr Ile
            260                 265                 270

Thr Pro Pro Ser Thr Val Phe Ala Ala Tyr Asn His Leu Glu Thr Asp
        275                 280                 285

Lys Glu Ile Lys Val Tyr Arg Tyr Phe Gly His Glu Tyr Ile Pro Pro
    290                 295                 300

Phe Gln Thr Glu Lys Leu Ala Phe Leu Arg Lys His Leu Lys
305                 310                 315

<210> SEQ ID NO 9
<211> LENGTH: 963
<212> TYPE: DNA
<213> ORGANISM: Bacillus pumilus

<400> SEQUENCE: 9
atgcaattgt tcgatttatc actagaagag ctaaaaaaat ataaaccaaa gaaaacagca      60
cgtcctgatt tctcagactt ttggaagaaa tcgctcgaag aactgcgcca agtggaggca     120
gagccaacac ttgaatctta tgactatcca gtgaaaggcg tcaaggtgta ccgcctgacg     180
tatcaaagct ttggacattc taaaattgaa ggcttttatg ctgtgcctga tcaaactggt     240
ccgcatccag cgctcgttcg ttttcatggc tataatgcca gctatgacgg cggcattcac     300
gacatcgtca actgggcgct gcacggctat gcaacatttg gtatgctcgt ccgcggtcaa     360
ggtggcagtg aagacacatc agtgacacca ggcgggcatg cattagggtg tgatgacaaaa    420 ggcattttat cgaaagatac gtactattat cgaggcgttt atctagatgc tgttcgtgca     480
cttgaagtca ttcagtcttt ccccgaagta gatgaacacc gtatcggcgt gatcggtgga     540
agtcaggggg gtgcgttagc gattgcggcc gcagcccttt cagacattcc aaaagtcgtt     600
gtggcagact atccttactt atcaaatttt gagcgtgcag ttgatgttgc cttggagcag     660
ccttatttag aaatcaattc atactttcgc agaaacagtg atccgaaagt ggaggaaaag     720
```

```
gcatttgaga cattaagcta ttttgattta atcaatttag ctggatgggt gaaacagcca    780
acattgatgg cgatcggtct gattgacaaa ataaccccac catctactgt gtttgcggca    840
tacaaccatt tagaaacaga taaagacctg aaagtatatc gctattttgg acacgagttt    900
atccctgctt ttcaaacaga gaagctgtcc tttttacaaa agcatttgct tctatcaaca    960
taa                                                                  963
```

```
<210> SEQ ID NO 10
<211> LENGTH: 320
<212> TYPE: PRT
<213> ORGANISM: Bacillus pumilus

<400> SEQUENCE: 10
```

| | | | | | | | | | | | | | | | |
|---|---|---|---|---|---|---|---|---|---|---|---|---|---|---|---|
| Met | Gln | Leu | Phe | Asp | Leu | Ser | Leu | Glu | Glu | Leu | Lys | Lys | Tyr | Lys | Pro |
| 1 | | | | 5 | | | | | 10 | | | | | 15 | |
| Lys | Lys | Thr | Ala | Arg | Pro | Asp | Phe | Ser | Asp | Phe | Trp | Lys | Lys | Ser | Leu |
| | | | 20 | | | | | 25 | | | | | 30 | | |
| Glu | Glu | Leu | Arg | Gln | Val | Glu | Ala | Glu | Pro | Thr | Leu | Glu | Ser | Tyr | Asp |
| | | | | 35 | | | | | 40 | | | | | 45 | |
| Tyr | Pro | Val | Lys | Gly | Val | Lys | Val | Tyr | Arg | Leu | Thr | Tyr | Gln | Ser | Phe |
| | 50 | | | | | 55 | | | | | 60 | | | | |
| Gly | His | Ser | Lys | Ile | Glu | Gly | Phe | Tyr | Ala | Val | Pro | Asp | Gln | Thr | Gly |
| 65 | | | | | 70 | | | | | 75 | | | | | 80 |
| Pro | His | Pro | Ala | Leu | Val | Arg | Phe | His | Gly | Tyr | Asn | Ala | Ser | Tyr | Asp |
| | | | | 85 | | | | | 90 | | | | | 95 | |
| Gly | Gly | Ile | His | Asp | Ile | Val | Asn | Trp | Ala | Leu | His | Gly | Tyr | Ala | Thr |
| | | | 100 | | | | | 105 | | | | | 110 | | |
| Phe | Gly | Met | Leu | Val | Arg | Gly | Gln | Gly | Gly | Ser | Glu | Asp | Thr | Ser | Val |
| | | | | 115 | | | | | 120 | | | | | 125 | |
| Thr | Pro | Gly | Gly | His | Ala | Leu | Gly | Trp | Met | Thr | Lys | Gly | Ile | Leu | Ser |
| | | | 130 | | | | | 135 | | | | | 140 | | |
| Lys | Asp | Thr | Tyr | Tyr | Tyr | Arg | Gly | Val | Tyr | Leu | Asp | Ala | Val | Arg | Ala |
| 145 | | | | | 150 | | | | | 155 | | | | | 160 |
| Leu | Glu | Val | Ile | Gln | Ser | Phe | Pro | Glu | Val | Asp | Glu | His | Arg | Ile | Gly |
| | | | | 165 | | | | | 170 | | | | | 175 | |
| Val | Ile | Gly | Gly | Ser | Gln | Gly | Gly | Ala | Leu | Ala | Ile | Ala | Ala | Ala | Ala |
| | | | 180 | | | | | 185 | | | | | 190 | | |
| Leu | Ser | Asp | Ile | Pro | Lys | Val | Val | Ala | Asp | Tyr | Pro | Tyr | Leu | Ser |
| | | | 195 | | | | | 200 | | | | | 205 | | |
| Asn | Phe | Glu | Arg | Ala | Val | Asp | Val | Ala | Leu | Glu | Gln | Pro | Tyr | Leu | Glu |
| | | | 210 | | | | | 215 | | | | | 220 | | |
| Ile | Asn | Ser | Tyr | Phe | Arg | Arg | Asn | Ser | Asp | Pro | Lys | Val | Glu | Glu | Lys |
| 225 | | | | | 230 | | | | | 235 | | | | | 240 |
| Ala | Phe | Glu | Thr | Leu | Ser | Tyr | Phe | Asp | Leu | Ile | Asn | Leu | Ala | Gly | Trp |
| | | | | 245 | | | | | 250 | | | | | 255 | |
| Val | Lys | Gln | Pro | Thr | Leu | Met | Ala | Ile | Gly | Leu | Ile | Asp | Lys | Ile | Thr |
| | | | 260 | | | | | 265 | | | | | 270 | | |
| Pro | Pro | Ser | Thr | Val | Phe | Ala | Ala | Tyr | Asn | His | Leu | Glu | Thr | Asp | Lys |
| | | | 275 | | | | | 280 | | | | | 285 | | |
| Asp | Leu | Lys | Val | Tyr | Arg | Tyr | Phe | Gly | His | Glu | Phe | Ile | Pro | Ala | Phe |
| | | 290 | | | | | 295 | | | | | 300 | | | |
| Gln | Thr | Glu | Lys | Leu | Ser | Phe | Leu | Gln | Lys | His | Leu | Leu | Ser | Thr |
| 305 | | | | | 310 | | | | | 315 | | | | | 320 |

```
<210> SEQ ID NO 11
<211> LENGTH: 963
<212> TYPE: DNA
<213> ORGANISM: Clostridium thermocellum

<400> SEQUENCE: 11
atggcacaat tatatgatat gcctttggag gaattaaaaa aatataagcc tgcgcttaca      60
aaacagaaag attttgatga gttttgggaa aaagcctta aagagctggc tgaaattcct      120
ttaaaatatc aacttatacc ttatgattt ccggcccgga gggtaaaagt tttcagagtt      180
gaatatcttg ttttaaagg tgcaaatat gaagggtggc ttgccgttcc cgagggagaa      240
gggttgtatc ccgggcttgt acagtttcac ggatacaact gggcgatgga tggatgtgtt      300
cccgatgtgg taaattgggc tttgaatgga tatgccgcat tcttatgct tgttcgggga      360 cagcagggaa gaagcgtgga caatattgtg cccggcagcg gtcatgcttt gggatggatg      420
tcgaaaggta ttttgtcacc ggaggaatat tattatagag gagtatatat ggatgcggtt      480
cgtgctgttg aaattttggc ttcgcttcct tgtgtggatg aatcgagaat aggagtgaca      540
gggggcagcc agggtggagg acttgcactg gcggtggctg ctctgtccgg cataccgaaa      600
gttgcagccg tgcattatcc gtttctggca cattttgagc gtgccattga cgttgcgccg      660 gacggcccctt atcttgaaat taacgaatat ttaagaagaa acagcggtga agaaatagaa      720
agacaggtaa agaaaaccct ttcctatttt gatatcatga tcttgctcc ccgtataaaa      780 tgccgtactt ggatttgcac tggtcttgtg gatgagatta ctcctccgtc aacggttttt      840
gcagtgtaca atcaccctcaa atgcccaaag gaaatttcgg tattcagata ttttgggcat      900
gaacatatgc aggaagcgt tgaaatcaag ctgaggatac ttatggatga gctgaatccg      960
taa                                                                  963

<210> SEQ ID NO 12
<211> LENGTH: 320
<212> TYPE: PRT
<213> ORGANISM: Clostridium thermocellum

<400> SEQUENCE: 12

Met Ala Gln Leu Tyr Asp Met Pro Leu Glu Glu Leu Lys Lys Tyr Lys
1               5                   10                  15

Pro Ala Leu Thr Lys Gln Lys Asp Phe Asp Glu Phe Trp Glu Lys Ser
            20                  25                  30

Leu Lys Glu Leu Ala Glu Ile Pro Leu Lys Tyr Gln Leu Ile Pro Tyr
        35                  40                  45

Asp Phe Pro Ala Arg Arg Val Lys Val Phe Arg Val Glu Tyr Leu Gly
    50                  55                  60

Phe Lys Gly Ala Asn Ile Glu Gly Trp Leu Ala Val Pro Glu Gly Glu
65                  70                  75                  80

Gly Leu Tyr Pro Gly Leu Val Gln Phe His Gly Tyr Asn Trp Ala Met
                85                  90                  95

Asp Gly Cys Val Pro Asp Val Val Asn Trp Ala Leu Asn Gly Tyr Ala
            100                 105                 110

Ala Phe Leu Met Leu Val Arg Gly Gln Gln Gly Arg Ser Val Asp Asn
        115                 120                 125

Ile Val Pro Gly Ser Gly His Ala Leu Gly Trp Met Ser Lys Gly Ile
    130                 135                 140

Leu Ser Pro Glu Glu Tyr Tyr Tyr Arg Gly Val Tyr Met Asp Ala Val
145                 150                 155                 160

Arg Ala Val Glu Ile Leu Ala Ser Leu Pro Cys Val Asp Glu Ser Arg
```

```
                165                 170                 175
Ile Gly Val Thr Gly Ser Gln Gly Gly Leu Ala Leu Ala Val
            180                 185                 190

Ala Ala Leu Ser Gly Ile Pro Lys Val Ala Ala Val His Tyr Pro Phe
                195                 200                 205

Leu Ala His Phe Glu Arg Ala Ile Asp Val Ala Pro Asp Gly Pro Tyr
            210                 215                 220

Leu Glu Ile Asn Glu Tyr Leu Arg Arg Asn Ser Gly Glu Glu Ile Glu
225                 230                 235                 240

Arg Gln Val Lys Lys Thr Leu Ser Tyr Phe Asp Ile Met Asn Leu Ala
                245                 250                 255

Pro Arg Ile Lys Cys Arg Thr Trp Ile Cys Thr Gly Leu Val Asp Glu
            260                 265                 270

Ile Thr Pro Pro Ser Thr Val Phe Ala Val Tyr Asn His Leu Lys Cys
            275                 280                 285

Pro Lys Glu Ile Ser Val Phe Arg Tyr Phe Gly His Glu His Met Pro
            290                 295                 300

Gly Ser Val Glu Ile Lys Leu Arg Ile Leu Met Asp Glu Leu Asn Pro
305                 310                 315                 320

<210> SEQ ID NO 13
<211> LENGTH: 978
<212> TYPE: DNA
<213> ORGANISM: Thermotoga neapolitana

<400> SEQUENCE: 13
atggccttct tcgatatgcc ccttgaggaa ctgaaaaagt accggcctga aaggtacgag    60
gagaaagatt tcgatgagtt ctggagggaa acacttaaag aaagcgaagg attccctctg   120
gatcccgtct ttgaaaaggt ggactttcat ctcaaaacgg ttgaaacgta cgatgttact   180
ttctctggat acaggggca gagaataaag ggctggcttc ttgttccgaa gttggcggaa   240
gaaaagcttc catgcgtcgt gcagtacata ggttacaatg gtggaagggg ttttccacac   300
gactggctgt tctggccgtc aatgggttac atctgttttg tcatggacac caggggcag   360 ggaagcggct ggatgaaggg agacacaccg gattaccctg agggtccagt cgatccacag   420
taccccggat tcatgacgag gggcattctg gatccgggaa cctattacta caggcgagtc   480
ttcgtggatg cggtcagggc ggtggaagca gccatttcct cccgagagt ggattccagg   540 aaggtggtgg tggccggagg cagtcagggt gggggaatcg cccttgcggt gagtgccctg   600
tcgaacaggg tgaaggctct gctctgcgat gtgccgtttc tgtgccactt cagaagggcc   660
gtgcaacttg tcgacacaca cccatacgtg gagatcacca acttcctcaa aacccacagg   720
gacaaagagg agattgtttt cagaacactt tcctacttcg atggtgtgaa ctttgcagca   780
agggcaaagg tgcccgccct gttttccgtt gggctcatgg acaccatctg tcctccctcg   840
acggtcttcg ccgcttacaa ccactacgcc ggtccaaagg agatcagaat ctatccgtac   900
aacaaccacg aaggtggagg ttctttccag gcaattgagc aggtgaaatt cttgaagaga   960
ctatttgagg aaggctag                                                  978

<210> SEQ ID NO 14
<211> LENGTH: 325
<212> TYPE: PRT
<213> ORGANISM: Thermotoga neapolitana

<400> SEQUENCE: 14

Met Ala Phe Phe Asp Met Pro Leu Glu Glu Leu Lys Lys Tyr Arg Pro
```

```
  1               5                  10                 15
Glu Arg Tyr Glu Glu Lys Asp Phe Asp Glu Phe Trp Arg Glu Thr Leu
            20                  25                 30

Lys Glu Ser Glu Gly Phe Pro Leu Asp Pro Val Phe Glu Lys Val Asp
            35                  40                 45

Phe His Leu Lys Thr Val Glu Thr Tyr Asp Val Thr Phe Ser Gly Tyr
            50                  55                 60

Arg Gly Gln Arg Ile Lys Gly Trp Leu Leu Val Pro Lys Leu Ala Glu
65                  70                  75                 80

Glu Lys Leu Pro Cys Val Val Gln Tyr Ile Gly Tyr Asn Gly Gly Arg
                85                  90                 95

Gly Phe Pro His Asp Trp Leu Phe Trp Pro Ser Met Gly Tyr Ile Cys
                100                 105                110

Phe Val Met Asp Thr Arg Gly Gln Gly Ser Gly Trp Met Lys Gly Asp
                115                 120                125

Thr Pro Asp Tyr Pro Glu Gly Pro Val Asp Pro Gln Tyr Pro Gly Phe
            130                 135                140

Met Thr Arg Gly Ile Leu Asp Pro Gly Thr Tyr Tyr Arg Val
145                 150                 155                160

Phe Val Asp Ala Val Arg Ala Val Glu Ala Ala Ile Ser Phe Pro Arg
                165                 170                175

Val Asp Ser Arg Lys Val Val Ala Gly Ser Gln Gly Gly Gly
            180                 185                190

Ile Ala Leu Ala Val Ser Ala Leu Ser Asn Arg Val Lys Ala Leu Leu
            195                 200                205

Cys Asp Val Pro Phe Leu Cys His Phe Arg Arg Ala Val Gln Leu Val
            210                 215                220

Asp Thr His Pro Tyr Val Glu Ile Thr Asn Phe Leu Lys Thr His Arg
225                 230                 235                240

Asp Lys Glu Glu Ile Val Phe Arg Thr Leu Ser Tyr Phe Asp Gly Val
                245                 250                255

Asn Phe Ala Ala Arg Ala Lys Val Pro Ala Leu Phe Ser Val Gly Leu
            260                 265                270

Met Asp Thr Ile Cys Pro Pro Ser Thr Val Phe Ala Ala Tyr Asn His
            275                 280                285

Tyr Ala Gly Pro Lys Glu Ile Arg Ile Tyr Pro Tyr Asn Asn His Glu
            290                 295                300

Gly Gly Gly Ser Phe Gln Ala Ile Glu Gln Val Lys Phe Leu Lys Arg
305                 310                 315                320

Leu Phe Glu Glu Gly
                325

<210> SEQ ID NO 15
<211> LENGTH: 978
<212> TYPE: DNA
<213> ORGANISM: Thermotoga maritima

<400> SEQUENCE: 15
atggccttct tcgatttacc actcgaagaa ctgaagaaat atcgtccaga gcggtacgaa    60
gagaaagact tcgatgagtt ctgggaagag acactcgcag agagcgaaaa gttcccctta   120
gaccccgtct tcgagaggat ggagtctcac ctcaaaacag tcgaagcgta cgatgtcacc   180
ttctccggat acaggggaca gaggatcaaa gggtggctcc ttgttccaaa actgaagaa    240 gaaaaacttc cctgcgttgt gcagtacata ggatacaacg gtggaagagg attccctcac   300
```

```
gactggctgt tctggccttc tatgggttac atatgtttcg tcatggatac tcgaggtcag    360
ggaagcggct ggctgaaagg agacacaccg gattaccctg agggtcccgt tgaccctcag    420
tatccaggat tcatgacaag aggaatactg gatcccagaa cttactacta cagacgagtc    480
ttcacggacg ctgtcagagc cgttgaagct gctgcttctt ttcctcaggt agatcaagaa    540
agaatcgtga tagctggagg cagtcagggt ggcggaatag cccttgcggt gagcgctctc    600
tcaaagaaag caaaggctct tctgtgcgat gtgccgtttc tgtgtcactt cagaagagca    660
gtacagcttg tggatacgca tccatacgcg gagatcacga actttctaaa gacccacaga    720
gacaaggaag aaatcgtgtt caggactctt tcctatttcg atggagtgaa cttcgcagcc    780
agagcgaaga tccctgcgct gttttctgtg ggtctcatgg acaacatttg tcctccttca    840
acggttttcg ctgcctacaa ttactacgct ggaccgaagg aaatcagaat ctatccgtac    900
aacaaccacg agggaggagg ctctttccaa gcggttgaac aggtgaaatt cttgaaaaaa    960
ctatttgaga aaggctaa                                                  978
```

<210> SEQ ID NO 16
<211> LENGTH: 325
<212> TYPE: PRT
<213> ORGANISM: Thermotoga maritima

<400> SEQUENCE: 16

```
Met Ala Phe Phe Asp Leu Pro Leu Glu Glu Leu Lys Lys Tyr Arg Pro
1               5                   10                  15
Glu Arg Tyr Glu Glu Lys Asp Phe Asp Glu Phe Trp Glu Glu Thr Leu
            20                  25                  30
Ala Glu Ser Glu Lys Phe Pro Leu Asp Pro Val Phe Glu Arg Met Glu
        35                  40                  45
Ser His Leu Lys Thr Val Glu Ala Tyr Asp Val Thr Phe Ser Gly Tyr
    50                  55                  60
Arg Gly Gln Arg Ile Lys Gly Trp Leu Val Pro Lys Leu Glu Glu
65                  70                  75                  80
Glu Lys Leu Pro Cys Val Val Gln Tyr Ile Gly Tyr Asn Gly Gly Arg
                85                  90                  95
Gly Phe Pro His Asp Trp Leu Phe Trp Pro Ser Met Gly Tyr Ile Cys
            100                 105                 110
Phe Val Met Asp Thr Arg Gly Gln Gly Ser Gly Trp Leu Lys Gly Asp
        115                 120                 125
Thr Pro Asp Tyr Pro Glu Gly Pro Val Asp Pro Gln Tyr Pro Gly Phe
    130                 135                 140
Met Thr Arg Gly Ile Leu Asp Pro Arg Thr Tyr Tyr Tyr Arg Arg Val
145                 150                 155                 160
Phe Thr Asp Ala Val Arg Ala Val Glu Ala Ala Ser Phe Pro Gln
                165                 170                 175
Val Asp Gln Glu Arg Ile Val Ile Ala Gly Gly Ser Gln Gly Gly Gly
            180                 185                 190
Ile Ala Leu Ala Val Ser Ala Leu Ser Lys Lys Ala Lys Ala Leu Leu
        195                 200                 205
Cys Asp Val Pro Phe Leu Cys His Phe Arg Arg Ala Val Gln Leu Val
    210                 215                 220
Asp Thr His Pro Tyr Ala Glu Ile Thr Asn Phe Leu Lys Thr His Arg
225                 230                 235                 240
Asp Lys Glu Glu Ile Val Phe Arg Thr Leu Ser Tyr Phe Asp Gly Val
                245                 250                 255
```

```
Asn Phe Ala Ala Arg Ala Lys Ile Pro Ala Leu Phe Ser Val Gly Leu
                260                 265                 270

Met Asp Asn Ile Cys Pro Pro Ser Thr Val Phe Ala Ala Tyr Asn Tyr
            275                 280                 285

Tyr Ala Gly Pro Lys Glu Ile Arg Ile Tyr Pro Tyr Asn Asn His Glu
        290                 295                 300

Gly Gly Gly Ser Phe Gln Ala Val Glu Gln Val Lys Phe Leu Lys Lys
305                 310                 315                 320

Leu Phe Glu Lys Gly
                325

<210> SEQ ID NO 17
<211> LENGTH: 963
<212> TYPE: DNA
<213> ORGANISM: Thermoanaerobacterium sp.

<400> SEQUENCE: 17
atgggacttt tcgacatgcc attacaaaaa cttagagaat acactggtac aaatccatgc      60
cctgaagatt tcgatgagta ttggaatagg gctttagatg agatgaggtc agttgatcct     120
aaaattgaat tgaaagaaag tagctttcaa gtatcctttg cagaatgcta tgacttgtac     180
tttacaggtg ttcgtggtgc cagaattcat gcaaagtata taaaacctaa gacagaaggg     240
aaacatccag cgttgataag atttcatgga tattcgtcaa attcaggcga ctggaacgac     300
aaattaaatt acgtggcggc aggcttcacc gttgtggcta tggatgtaag aggtcaagga     360 ggcagtctc aagatgttgg cggtgtaact gggaatactt aaatgggca tattataaga     420 gggctagacg atgatgctga taatatgctt tcaggcata ttttcttaga cactgcccaa     480
ttggctggaa tagttatgaa catgccagaa gttgatgaag atagagtggg agtcatggga     540
ccttctcaag gcggagggct gtcgttggcg tgtgctgcat ggagccaag ggtacgcaaa     600 gtagtatctg aatatccttt tttatctgac acaagagag tttgggactt agaccttgca     660
aaaaacgcct atcaagagat tacggactat ttcaggcttt ttgacccaag gcatgaaagg     720
gagaatgagg tatttacaaa gcttggatat atagacgtta aaaaccttgc gaaaaggata     780
aaaggcgatg tcttaatgtg cgttgggctt atggaccaag tatgtccgcc atcaactgtt     840
tttgcagcct acaacaacat acagtcaaaa aaagatataa agtgtatcc tgattatgga     900 catgaaccta tgagaggatt tggagattta gcgatgcagt ttatgttgga actatattca     960
taa                                                                   963

<210> SEQ ID NO 18
<211> LENGTH: 320
<212> TYPE: PRT
<213> ORGANISM: Thermoanaerobacterium sp.

<400> SEQUENCE: 18

Met Gly Leu Phe Asp Met Pro Leu Gln Lys Leu Arg Glu Tyr Thr Gly
1               5                   10                  15

Thr Asn Pro Cys Pro Glu Asp Phe Asp Glu Tyr Trp Asn Arg Ala Leu
            20                  25                  30

Asp Glu Met Arg Ser Val Asp Pro Lys Ile Glu Leu Lys Glu Ser Ser
        35                  40                  45

Phe Gln Val Ser Phe Ala Glu Cys Tyr Asp Leu Tyr Phe Thr Gly Val
    50                  55                  60

Arg Gly Ala Arg Ile His Ala Lys Tyr Ile Lys Pro Lys Thr Glu Gly
65                  70                  75                  80
```

```
Lys His Pro Ala Leu Ile Arg Phe His Gly Tyr Ser Ser Asn Ser Gly
                85                  90                  95
Asp Trp Asn Asp Lys Leu Asn Tyr Val Ala Ala Gly Phe Thr Val Val
            100                 105                 110
Ala Met Asp Val Arg Gly Gln Gly Gln Ser Gln Asp Val Gly Gly
        115                 120                 125
Val Thr Gly Asn Thr Leu Asn Gly His Ile Ile Arg Gly Leu Asp Asp
    130                 135                 140
Asp Ala Asp Asn Met Leu Phe Arg His Ile Phe Leu Asp Thr Ala Gln
145                 150                 155                 160
Leu Ala Gly Ile Val Met Asn Met Pro Glu Val Asp Glu Asp Arg Val
                165                 170                 175
Gly Val Met Gly Pro Ser Gln Gly Gly Leu Ser Leu Ala Cys Ala
                180                 185                 190
Ala Leu Glu Pro Arg Val Arg Lys Val Val Ser Glu Tyr Pro Phe Leu
            195                 200                 205
Ser Asp Tyr Lys Arg Val Trp Asp Leu Asp Leu Ala Lys Asn Ala Tyr
        210                 215                 220
Gln Glu Ile Thr Asp Tyr Phe Arg Leu Phe Asp Pro Arg His Glu Arg
225                 230                 235                 240
Glu Asn Glu Val Phe Thr Lys Leu Gly Tyr Ile Asp Val Lys Asn Leu
                245                 250                 255
Ala Lys Arg Ile Lys Gly Asp Val Leu Met Cys Val Gly Leu Met Asp
                260                 265                 270
Gln Val Cys Pro Pro Ser Thr Val Phe Ala Ala Tyr Asn Asn Ile Gln
            275                 280                 285
Ser Lys Lys Asp Ile Lys Val Tyr Pro Asp Tyr Gly His Glu Pro Met
        290                 295                 300
Arg Gly Phe Gly Asp Leu Ala Met Gln Phe Met Leu Glu Leu Tyr Ser
305                 310                 315                 320

<210> SEQ ID NO 19
<211> LENGTH: 1023
<212> TYPE: DNA
<213> ORGANISM: Bacillus sp.

<400> SEQUENCE: 19
atgaggacgg ttcctgctcc tgttttttg gagaggagtg gggagatgaa ccttttgat      60
atgccccttg aggagctgca gcattacaag cctgcccaga ccaggcagga tgattttgag    120
tcattctgga aaaagcggat tgaggagaac agtcaatatc cgctgaatat agaagtaatg    180
gagcgggttt atccggttcc gggagtgaga gtatatgata tttattttga cgggttccgg    240
aattcccgca tccatggggt gtatgttact ccagaaactc cggagcggga cactcctgcg    300
gcagtgattt tcacggcta taactggaac acgctgcagc cgcattacag cttcaagcac    360
gtgattcagg ggattcctgt actgatggtg gaggtgcggg gacaaaatct cttgtctcca    420
gatagaaatc attatgggaa tggaggtccg ggaggctgga tgacactcgg cgtgatggat    480
cccgatcaat attattacag cctggtatat atggactgct ccgcagcat tgatgctgtc    540
agggaactgt cgaggaagag aagtgtgttt gtggaaggcg gaagccaggg aggtgcactg    600
gcgattgccg cagccgccct gcaggatgac atcctgcttg cactcgccga catccctttt    660
ctcacccatt tcaagcgttc cgtggagctt cctcggatg gaccgtatca ggagatttcc    720
cactacttca agttcatga tcctcttcat caaacggaag agcaggtata tcagacgctc    780
agctatgtgg actgcatgaa catggccagc atggttgaat gtccagtcct tctttcagcc    840
```

```
ggtctggaag acatcgtttg tcccccgtcc agtgcatttg cactgttcaa ccatctcggc      900
gggccaaaag aaatacgggc ctatccggaa tacgcccatg aagtaccggc tgtccatgaa      960
gaggaaaagc tgaagtttat atcttcaagg ctaaaaaata gagaaaagag gtgccggcca     1020
tga                                                                  1023
```

<210> SEQ ID NO 20
<211> LENGTH: 325
<212> TYPE: PRT
<213> ORGANISM: Bacillus sp.

<400> SEQUENCE: 20

```
Met Asn Leu Phe Asp Met Pro Leu Glu Glu Leu Gln His Tyr Lys Pro
1               5                   10                  15

Ala Gln Thr Arg Gln Asp Asp Phe Glu Ser Phe Trp Lys Lys Arg Ile
            20                  25                  30

Glu Glu Asn Ser Gln Tyr Pro Leu Asn Ile Glu Val Met Glu Arg Val
        35                  40                  45

Tyr Pro Val Pro Gly Val Arg Val Tyr Asp Ile Tyr Phe Asp Gly Phe
    50                  55                  60

Arg Asn Ser Arg Ile His Gly Val Tyr Val Thr Pro Glu Thr Pro Gly
65                  70                  75                  80

Ala Asp Thr Pro Ala Ala Val Ile Phe His Gly Tyr Asn Trp Asn Thr
                85                  90                  95

Leu Gln Pro His Tyr Ser Phe Lys His Val Ile Gln Gly Ile Pro Val
            100                 105                 110

Leu Met Val Glu Val Arg Gly Gln Asn Leu Leu Ser Pro Asp Arg Asn
        115                 120                 125

His Tyr Gly Asn Gly Gly Pro Gly Gly Trp Met Thr Leu Gly Val Met
    130                 135                 140

Asp Pro Asp Gln Tyr Tyr Tyr Ser Leu Val Tyr Met Asp Cys Phe Arg
145                 150                 155                 160

Ser Ile Asp Ala Val Arg Glu Leu Ser Arg Lys Arg Ser Val Phe Val
                165                 170                 175

Glu Gly Gly Ser Gln Gly Gly Ala Leu Ala Ile Ala Ala Ala Ala Leu
            180                 185                 190

Gln Asp Asp Ile Leu Leu Ala Leu Ala Asp Ile Pro Phe Leu Thr His
        195                 200                 205

Phe Lys Arg Ser Val Gly Leu Ser Ser Asp Gly Pro Tyr Gln Glu Ile
    210                 215                 220

Ser His Tyr Phe Lys Val His Asp Pro Leu His Gln Thr Glu Gln
225                 230                 235                 240

Val Tyr Gln Thr Leu Ser Tyr Val Asp Cys Met Asn Met Ala Ser Met
                245                 250                 255

Val Glu Cys Pro Val Leu Leu Ser Ala Gly Leu Glu Asp Ile Val Cys
            260                 265                 270

Pro Pro Ser Ser Ala Phe Ala Leu Phe Asn His Leu Gly Gly Pro Lys
        275                 280                 285

Glu Ile Arg Ala Tyr Pro Glu Tyr Ala His Glu Val Pro Ala Val His
    290                 295                 300

Glu Glu Glu Lys Leu Lys Phe Ile Ser Ser Arg Leu Lys Asn Arg Glu
305                 310                 315                 320

Lys Arg Cys Arg Pro
                325
```

```
<210> SEQ ID NO 21
<211> LENGTH: 960
<212> TYPE: DNA
<213> ORGANISM: Bacillus halodurans

<400> SEQUENCE: 21
ttagagatca gataaaaatt gaaaaatccg atcacgatgg cctggcaaat cttcgtgagc      60
aaagtctgga tataactcga tacttttgt cgtcgtgagt ttgttataca tggcaaattg     120
tgtagacggc gggcaaaccg tatccattaa cccaacagca agtaagactt ctcccttac     180 gagtggagca agatgctgaa tatcaatata gcctagcttc gtaaagattt cagcctcacg     240
tcggtgctgt ggatcaaagc gacgaaaata cgtttgcaat tcgtcataag ctttctcggc     300
taaatccatc tcccatacgc gttggtaatc gctaaggaaa ggataaacag gagctacctt     360 tttaatttc ggttccaaag ccgcacaagc aatcgctaag gcccctcctt gtgaccaacc     420
tgtcactgcc acgcgctctt catcgacttc aggaaggttc atcacaatgt tggcaagctg     480
agccgtatca agaaacacat gacggaacaa taattgatca gcattatcat cgagtccgcg     540
tattatatga ccggaatgag tattcccctt cacgcctcct gtgtcttcag acaagcctcc     600
ttgcccgcga acgtccattg caagaacaga atatccgagg gctgcgtaat gaagtaaacc     660
cgtccattcc cccgcattca tcgtatatcc gtgaaaatga ataaccgccg ggtgtgtccc     720
gctcgtgtgt cttgggcgca cgtattttgc gtgaattcta gcaccctaa ccctgtaaa     780 atataggtgg aagcattctg catacgtggt ttgaaaatca ctcggtatga gctctacgtt     840
tggatttacc tttctcatct cttgtaaagc acgatcccaa tactcagtaa agtcatctgg     900
ctttggatta cgtcccatgt actcttttaa ttcggttaac ggcatgtcta ttagtggcat     960

<210> SEQ ID NO 22
<211> LENGTH: 319
<212> TYPE: PRT
<213> ORGANISM: Bacillus halodurans

<400> SEQUENCE: 22

Met Pro Leu Ile Asp Met Pro Leu Thr Glu Leu Lys Glu Tyr Met Gly
1               5                   10                  15

Arg Asn Pro Lys Pro Asp Asp Phe Thr Glu Tyr Trp Asp Arg Ala Leu
            20                  25                  30

Gln Glu Met Arg Lys Val Asn Pro Asn Val Glu Leu Ile Pro Ser Asp
        35                  40                  45

Phe Gln Thr Thr Tyr Ala Glu Cys Phe His Leu Tyr Phe Thr Gly Val
    50                  55                  60

Arg Gly Ala Arg Ile His Ala Lys Tyr Val Arg Pro Arg His Thr Ser
65                  70                  75                  80

Gly Thr His Pro Ala Val Ile His Phe His Gly Tyr Thr Met Asn Ala
                85                  90                  95

Gly Glu Trp Thr Gly Leu Leu His Tyr Ala Ala Leu Gly Tyr Ser Val
            100                 105                 110

Leu Ala Met Asp Val Arg Gly Gln Gly Leu Ser Glu Asp Thr Gly
        115                 120                 125

Gly Val Lys Gly Asn Thr His Ser Gly His Ile Ile Arg Gly Leu Asp
    130                 135                 140

Asp Asn Ala Asp Gln Leu Leu Phe Arg His Val Phe Leu Asp Thr Ala
145                 150                 155                 160

Gln Leu Ala Asn Ile Val Met Asn Leu Pro Glu Val Asp Glu Glu Arg
                165                 170                 175
```

```
Val Ala Val Thr Gly Trp Ser Gln Gly Gly Ala Leu Ala Ile Ala Cys
            180                 185                 190

Ala Ala Leu Glu Pro Lys Ile Lys Lys Val Ala Pro Val Tyr Pro Phe
        195                 200                 205

Leu Ser Asp Tyr Gln Arg Val Trp Glu Met Asp Leu Ala Glu Lys Ala
210                 215                 220

Tyr Asp Glu Leu Gln Thr Tyr Phe Arg Arg Phe Asp Pro Gln His Arg
225                 230                 235                 240

Arg Glu Ala Glu Ile Phe Thr Lys Leu Gly Tyr Ile Asp Ile Gln His
                245                 250                 255

Leu Ala Pro Leu Val Lys Gly Glu Val Leu Ala Val Gly Leu Met
            260                 265                 270

Asp Thr Val Cys Pro Pro Ser Thr Gln Phe Ala Met Tyr Asn Lys Leu
        275                 280                 285

Thr Thr Thr Lys Ser Ile Glu Leu Tyr Pro Asp Phe Ala His Glu Asp
        290                 295                 300

Leu Pro Gly His Arg Asp Arg Ile Phe Gln Phe Leu Ser Asp Leu
305                 310                 315

<210> SEQ ID NO 23
<211> LENGTH: 954
<212> TYPE: DNA
<213> ORGANISM: Bacillus clausii

<400> SEQUENCE: 23
atgccattag tcgatatgcc gttgcgcgag ttgttagctt atgaaggaat aaaccctaaa      60
ccagcagatt ttgaccaata ctggaaccgg gccaaaacgg aaattgaagc gattgatccc     120
gaagtcactc tagtcgaatc ttctttccag tgttcgtttg caaactgtta ccatttctat     180
tatcgaagcg ctggaaatgc aaaaatccat gcgaaatacg tacagccaaa agcaggggag     240
aagacgccag cagttttttat gttccatggg tatgggggc gttcagccga atggagcagc     300
ttgttaaatt atgtagcggc gggttttttct gttttctata tggacgtgcg tggacaaggt     360
ggaacttcag aggatcctgg gggcgtaagg gggaatacat aggggcca cattattcgc      420 ggcctcgatg ccgggccaga cgcactttt taccgcagcg ttttcttgga caccgtccaa      480
ttggttcgtg ctgctaaaac attgcctcac atcgataaaa cacggcttat ggccacaggg     540
tggtcgcaag ggggcgcctt aacgcttgcc tgtgctgccc ttgttcctga atcaagcgt      600 cttgctccag tataccgtt tttaagcgat tacaagcgag tgtggcaaat ggatttagcg      660
gttcgttcgt ataaagaatt ggctgattat ttccgttcat acgatccgca acataaacgc     720
catggcgaaa tttttgaacg ccttggctac atcgatgtcc agcatcttgc tgaccggatt     780
caaggagatg tcctaatggg agttggtta atggatacag aatgcccgcc gtctacccaa      840
tttgctgctt ataataaaat aaaggctaaa aaatcgtatg agctctatcc tgattttggc     900
catgagcacc ttccaggaat gaacgatcat atttttcgct ttttcactag ttga          954

<210> SEQ ID NO 24
<211> LENGTH: 317
<212> TYPE: PRT
<213> ORGANISM: Bacillus clausii

<400> SEQUENCE: 24

Met Pro Leu Val Asp Met Pro Leu Arg Glu Leu Leu Ala Tyr Glu Gly
1               5                   10                  15

Ile Asn Pro Lys Pro Ala Asp Phe Asp Gln Tyr Trp Asn Arg Ala Lys
```

```
                    20                  25                  30
Thr Glu Ile Glu Ala Ile Asp Pro Glu Val Thr Leu Val Glu Ser Ser
                35                  40                  45

Phe Gln Cys Ser Phe Ala Asn Cys Tyr His Phe Tyr Arg Ser Ala
            50                  55                  60

Gly Asn Ala Lys Ile His Ala Lys Tyr Val Gln Pro Lys Ala Gly Glu
65                  70                  75                  80

Lys Thr Pro Ala Val Phe Met Phe His Gly Tyr Gly Arg Ser Ala
                85                  90                  95

Glu Trp Ser Ser Leu Leu Asn Tyr Val Ala Ala Gly Phe Ser Val Phe
                100                 105                 110

Tyr Met Asp Val Arg Gly Gln Gly Gly Thr Ser Glu Asp Pro Gly Gly
                115                 120                 125

Val Arg Gly Asn Thr Tyr Arg Gly His Ile Ile Arg Gly Leu Asp Ala
            130                 135                 140

Gly Pro Asp Ala Leu Phe Tyr Arg Ser Val Phe Leu Asp Thr Val Gln
145                 150                 155                 160

Leu Val Arg Ala Ala Lys Thr Leu Pro His Ile Asp Lys Thr Arg Leu
                165                 170                 175

Met Ala Thr Gly Trp Ser Gln Gly Gly Ala Leu Thr Leu Ala Cys Ala
                180                 185                 190

Ala Leu Val Pro Glu Ile Lys Arg Leu Ala Pro Val Tyr Pro Phe Leu
                195                 200                 205

Ser Asp Tyr Lys Arg Val Trp Gln Met Asp Leu Ala Val Arg Ser Tyr
            210                 215                 220

Lys Glu Leu Ala Asp Tyr Phe Arg Ser Tyr Asp Pro Gln His Lys Arg
225                 230                 235                 240

His Gly Glu Ile Phe Glu Arg Leu Gly Tyr Ile Asp Val Gln His Leu
                245                 250                 255

Ala Asp Arg Ile Gln Gly Asp Val Leu Met Gly Val Gly Leu Met Asp
                260                 265                 270

Thr Glu Cys Pro Pro Ser Thr Gln Phe Ala Ala Tyr Asn Lys Ile Lys
            275                 280                 285

Ala Lys Lys Ser Tyr Glu Leu Tyr Pro Asp Phe Gly His Glu His Leu
            290                 295                 300

Pro Gly Met Asn Asp His Ile Phe Arg Phe Phe Thr Ser
305                 310                 315

<210> SEQ ID NO 25
<211> LENGTH: 960
<212> TYPE: DNA
<213> ORGANISM: Bacillus subtilis
<220> FEATURE:
<221> NAME/KEY: CDS
<222> LOCATION: (1)..(960)

<400> SEQUENCE: 25 atg caa cta ttc gat ctg ccg ctc gac caa ttg caa aca tat aag cct    48
Met Gln Leu Phe Asp Leu Pro Leu Asp Gln Leu Gln Thr Tyr Lys Pro
1               5                   10                  15 gaa aaa aca gca ccg aaa gat ttt tct gag ttt tgg aaa ttg tct ttg    96
Glu Lys Thr Ala Pro Lys Asp Phe Ser Glu Phe Trp Lys Leu Ser Leu
                20                  25                  30 gag gaa ctt gca aaa gtc caa gca gaa cct gat cta cag ccg gtt gac   144
Glu Glu Leu Ala Lys Val Gln Ala Glu Pro Asp Leu Gln Pro Val Asp
            35                  40                  45 tat cct gct gac gga gta aaa gtg tac cgt ctc aca tat aaa agc ttc   192
```

| | | | | | | | | | | | | | | |
|---|---|---|---|---|---|---|---|---|---|---|---|---|---|---|
| Tyr | Pro | Ala | Asp | Gly | Val | Lys | Val | Tyr | Arg | Leu | Thr | Tyr | Lys | Ser | Phe |
| | 50 | | | | 55 | | | | 60 | | | | | | |

```
gga aac gcc cgc att acc gga tgg tac gcg gtg cct gac aag caa ggc    240
Gly Asn Ala Arg Ile Thr Gly Trp Tyr Ala Val Pro Asp Lys Gln Gly
 65          70              75              80 ccg cat ccg gcg atc gtg aaa tat cat ggc tac aat gca agc tat gat    288
Pro His Pro Ala Ile Val Lys Tyr His Gly Tyr Asn Ala Ser Tyr Asp
             85              90              95 ggt gag att cat gaa atg gta aac tgg gca ctc cat ggc tac gcc gca    336
Gly Glu Ile His Glu Met Val Asn Trp Ala Leu His Gly Tyr Ala Ala
                100             105             110 ttc ggc atg ctt gtc cgc ggc cag cag agc agc gag gat acg agt att    384
Phe Gly Met Leu Val Arg Gly Gln Gln Ser Ser Glu Asp Thr Ser Ile
            115             120             125 tca ccg cac ggt cac gct ttg ggc tgg atg acg aaa gga att ctt gat    432
Ser Pro His Gly His Ala Leu Gly Trp Met Thr Lys Gly Ile Leu Asp
    130             135             140 aaa gat aca tac tat tac cgc ggt gtt tat ttg gac gcc gtc cgc gcg    480
Lys Asp Thr Tyr Tyr Tyr Arg Gly Val Tyr Leu Asp Ala Val Arg Ala
145             150             155             160 ctt gag gtc atc agc agc ttc gac gag gtt gac gaa aca agg atc ggt    528
Leu Glu Val Ile Ser Ser Phe Asp Glu Val Asp Glu Thr Arg Ile Gly
                165             170             175 gtg aca gga gga agc caa ggc gga ggt tta acc att gcc gca gca gcg    576
Val Thr Gly Gly Ser Gln Gly Gly Gly Leu Thr Ile Ala Ala Ala Ala
            180             185             190 ctg tca gac att cca aaa gcc gcg gtt gcc gat tat cct tat tta agc    624
Leu Ser Asp Ile Pro Lys Ala Ala Val Ala Asp Tyr Pro Tyr Leu Ser
    195             200             205 aac ttc gaa cgg gcc att gat gtg gcg ctt gaa cag ccg tac ctt gaa    672
Asn Phe Glu Arg Ala Ile Asp Val Ala Leu Glu Gln Pro Tyr Leu Glu
210             215             220 atc aat tcc ttc ttc aga aga aat ggc agc ccg gaa aca gaa gtg cag    720
Ile Asn Ser Phe Phe Arg Arg Asn Gly Ser Pro Glu Thr Glu Val Gln
225             230             235             240 gcg atg aag aca ctt tca tat ttc gat att atg aat ctc gct gac cga    768
Ala Met Lys Thr Leu Ser Tyr Phe Asp Ile Met Asn Leu Ala Asp Arg
            245             250             255 gtg aag gtg cct gtc ctg atg tca atc ggc ctg att gac aag gtc acg    816
Val Lys Val Pro Val Leu Met Ser Ile Gly Leu Ile Asp Lys Val Thr
        260             265             270 ccg cca tcc acc gtg ttt gcc gcc tac aat cat ttg gaa aca gag aaa    864
Pro Pro Ser Thr Val Phe Ala Ala Tyr Asn His Leu Glu Thr Glu Lys
    275             280             285 gag ctg aag gtg tac cgc tac ttc gga cat gag tat atc cct gct ttt    912
Glu Leu Lys Val Tyr Arg Tyr Phe Gly His Glu Tyr Ile Pro Ala Phe
290             295             300 caa acg gaa aaa ctt gct ttc ttt aag cag cat ctt aaa ggc tga taa    960
Gln Thr Glu Lys Leu Ala Phe Phe Lys Gln His Leu Lys Gly
305             310             315
```

<210> SEQ ID NO 26
<211> LENGTH: 318
<212> TYPE: PRT
<213> ORGANISM: Bacillus subtilis

<400> SEQUENCE: 26

```
Met Gln Leu Phe Asp Leu Pro Leu Asp Gln Leu Gln Thr Tyr Lys Pro
1               5                   10                  15

Glu Lys Thr Ala Pro Lys Asp Phe Ser Glu Phe Trp Lys Leu Ser Leu
            20                  25                  30
```

Glu Glu Leu Ala Lys Val Gln Ala Glu Pro Asp Leu Gln Pro Val Asp
             35                  40                  45

Tyr Pro Ala Asp Gly Val Lys Val Tyr Arg Leu Thr Tyr Lys Ser Phe
 50                  55                  60

Gly Asn Ala Arg Ile Thr Gly Trp Tyr Ala Val Pro Asp Lys Gln Gly
 65                  70                  75                  80

Pro His Pro Ala Ile Val Lys Tyr His Gly Tyr Asn Ala Ser Tyr Asp
                 85                  90                  95

Gly Glu Ile His Glu Met Val Asn Trp Ala Leu His Gly Tyr Ala Ala
            100                 105                 110

Phe Gly Met Leu Val Arg Gly Gln Gln Ser Ser Glu Asp Thr Ser Ile
            115                 120                 125

Ser Pro His Gly His Ala Leu Gly Trp Met Thr Lys Gly Ile Leu Asp
            130                 135                 140

Lys Asp Thr Tyr Tyr Arg Gly Val Tyr Leu Asp Ala Val Arg Ala
145                 150                 155                 160

Leu Glu Val Ile Ser Ser Phe Asp Glu Val Asp Glu Thr Arg Ile Gly
                165                 170                 175

Val Thr Gly Gly Ser Gln Gly Gly Gly Leu Thr Ile Ala Ala Ala Ala
            180                 185                 190

Leu Ser Asp Ile Pro Lys Ala Ala Val Ala Asp Tyr Pro Tyr Leu Ser
            195                 200                 205

Asn Phe Glu Arg Ala Ile Asp Val Ala Leu Glu Gln Pro Tyr Leu Glu
            210                 215                 220

Ile Asn Ser Phe Phe Arg Arg Asn Gly Ser Pro Glu Thr Glu Val Gln
225                 230                 235                 240

Ala Met Lys Thr Leu Ser Tyr Phe Asp Ile Met Asn Leu Ala Asp Arg
                245                 250                 255

Val Lys Val Pro Val Leu Met Ser Ile Gly Leu Ile Asp Lys Val Thr
                260                 265                 270

Pro Pro Ser Thr Val Phe Ala Ala Tyr Asn His Leu Glu Thr Glu Lys
            275                 280                 285

Glu Leu Lys Val Tyr Arg Tyr Phe Gly His Glu Tyr Ile Pro Ala Phe
            290                 295                 300

Gln Thr Glu Lys Leu Ala Phe Phe Lys Gln His Leu Lys Gly
305                 310                 315

<210> SEQ ID NO 27
<211> LENGTH: 24
<212> TYPE: DNA
<213> ORGANISM: Artificial Sequence
<220> FEATURE:
<223> OTHER INFORMATION: Primer

<400> SEQUENCE: 27
atggctttct ttgacatgcc gctg                                              24

<210> SEQ ID NO 28
<211> LENGTH: 27
<212> TYPE: DNA
<213> ORGANISM: Artificial Sequence
<220> FEATURE:
<223> OTHER INFORMATION: Primer

<400> SEQUENCE: 28
ttagccttct tcgaacaggc gtttcag                                           27

<210> SEQ ID NO 29
<211> LENGTH: 978
<212> TYPE: DNA
<213> ORGANISM: Artificial Sequence
<220> FEATURE:
<223> OTHER INFORMATION: Synthetic construct

<400> SEQUENCE: 29

| | | | | | |
|---|---|---|---|---|---|
| atggctttct | ttgacatgcc | gctggaagaa | ctgaaaaagt | accgtccgga | acgttacgag | 60 |
| gaaaaagact | ttgacgaatt | tggcgcgaa | accctgaaag | aatccgaggg | tttcccactg | 120 |
| gacccggtat | ttgaaaaagt | tgacttccac | ctgaagaccg | tcgaaactta | cgacgtcacc | 180 |
| ttcagcggtt | atcgtggcca | gcgtatcaaa | ggttggctgc | tggtaccgaa | actggcggaa | 240 |
| gagaaactgc | cgtgtgttgt | tcagtacatt | ggttacaacg | gtggccgtgg | tttcccgcac | 300 |
| gactggctgt | tctggccgtc | tatgggttac | atctgcttcg | ttatggacac | ccgtggtcag | 360 |
| ggtagcggtt | ggatgaaggg | tgatactccg | gactacccgg | aaggtccggt | ggacccgcag | 420 |
| tacccgggct | tcatgacgcg | cggcatcctg | atcctggca | cctattacta | ccgtcgtgtg | 480 |
| tttgtcgatg | ccgtgcgcgc | cgttgaagcc | gctatcagct | cccacgcgt | cgattctcgt | 540 |
| aaagtggtag | ttgctggtgg | ctctcaaggt | ggcggcattg | cactggcagt | ttccgcgctg | 600 |
| tccaaccgtg | ttaaagccct | gctgtgcgat | gttccgttcc | tgtgccactt | ccgtcgtgcg | 660 |
| gtacagctgg | tggacaccca | cccgtacgta | gaaattacga | acttcctgaa | acccatcgt | 720 |
| gataagaag | agatcgtatt | ccgtaccctg | tcttactttg | atggcgttaa | ttttgcggct | 780 |
| cgtgcaaaag | taccggcgct | gttcagcgta | ggtctgatgg | acactatttg | tccgccgtct | 840 |
| accgtattcg | cagcctacaa | ccactacgct | ggtccgaaag | aaatccgcat | ctacccgtac | 900 |
| aacaaccacg | aaggtggtgg | ttcttccag | gcaatcgaac | aggttaaatt | cctgaaacgc | 960 |
| ctgttcgaag | aaggctaa | | | | | 978 |

<210> SEQ ID NO 30
<211> LENGTH: 795
<212> TYPE: DNA
<213> ORGANISM: Artificial Sequence
<220> FEATURE:
<223> OTHER INFORMATION: Primer

<400> SEQUENCE: 30

| | | | | | |
|---|---|---|---|---|---|
| atgattgaac | aagatggatt | gcacgcaggt | tctccggccg | cttgggtgga | gaggctattc | 60 |
| ggctatgact | gggcacaaca | gacaatcggc | tgctctgatg | ccgccgtgtt | ccggctgtca | 120 |
| gcgcagggc | gcccggttct | ttttgtcaag | accgacctgt | ccggtgccct | gaatgaactg | 180 |
| caggacgagg | cagcgcggct | atcgtggctg | gccacgacgg | gcgttccttg | cgcagctgtg | 240 |
| ctcgacgttg | tcactgaagc | gggaagggac | tggctgctat | gggcgaagt | gccggggcag | 300 |
| gatctcctgt | catctcacct | tgctcctgcc | gagaaagtat | ccatcatggc | tgatgcaatg | 360 |
| cggcggctgc | atacgcttga | tccggctacc | tgcccattcg | accaccaagc | gaaacatcgc | 420 |
| atcgagcgag | cacgtactcg | gatggaagcc | ggtcttgtcg | atcaggatga | tctggacgaa | 480 |
| gagcatcagg | ggctcgcgcc | agccgaactg | ttcgccaggc | tcaaggcgcg | catgcccgac | 540 |
| ggcgaggatc | tcgtcgtgac | ccatggcgat | gcctgcttgc | cgaatatcat | ggtggaaaat | 600 |
| ggccgctttt | ctggattcat | cgactgtggc | cggctgggtg | tggcggaccg | ctatcaggac | 660 |
| atagcgttgg | ctacccgtga | tattgctgaa | gagcttggcg | gcgaatgggc | tgaccgcttc | 720 |
| ctcgtgcttt | acggtatcgc | cgctcccgat | tcgcagcgca | tcgccttcta | tcgccttctt | 780 |
| gacgagttct | tctaa | | | | | 795 |

<210> SEQ ID NO 31
<211> LENGTH: 3434
<212> TYPE: DNA
<213> ORGANISM: Artificial Sequence
<220> FEATURE:
<223> OTHER INFORMATION: Plasmid pKD13

<400> SEQUENCE: 31

| | | | | | |
|---|---|---|---|---|---|
| agattgcagc | attacacgtc | ttgagcgatt | gtgtaggctg | gagctgcttc | gaagttccta | 60 |
| tactttctag | agaataggaa | cttcggaata | ggaacttcaa | gatcccctta | ttagaagaac | 120 |
| tcgtcaagaa | ggcgatagaa | ggcgatgcgc | tgcgaatcgg | gagcggcgat | accgtaaagc | 180 |
| acgaggaagc | ggtcagccca | ttcgccgcca | agctcttcag | caatatcacg | ggtagccaac | 240 |
| gctatgtcct | gatagcggtc | cgccacaccc | agccggccac | agtcgatgaa | tccagaaaag | 300 |
| cggccatttt | ccaccatgat | attcggcaag | caggcatcgc | catgggtcac | gacgagatcc | 360 |
| tcgccgtcgg | catgcgcgc | cttgagcctg | gcgaacagtt | cggctggcgc | gagccccctga | 420 |
| tgctcttcgt | ccagatcatc | ctgatcgaca | agaccggctt | ccatccgagt | acgtgctcgc | 480 |
| tcgatgcgat | gtttcgcttg | gtggtcgaat | gggcaggtag | ccggatcaag | cgtatgcagc | 540 |
| cgccgcattg | catcagccat | gatggatact | ttctcggcag | gagcaaggtg | agatgacagg | 600 |
| agatcctgcc | ccggcacttc | gcccaatagc | agccagtccc | ttcccgcttc | agtgacaacg | 660 |
| tcgagcacag | ctgcgcaagg | aacgcccgtc | gtggccagcc | acgatagccg | cgctgcctcg | 720 |
| tcctgcagtt | cattcagggc | accggacagg | tcggtcttga | caaaaagaac | cgggcgcccc | 780 |
| tgcgctgaca | gccggaacac | ggcggcatca | gagcagccga | ttgtctgttg | tgcccagtca | 840 |
| tagccgaata | gcctctccac | ccaagcggcc | ggagaacctg | cgtgcaatcc | atcttgttca | 900 |
| atcatgcgaa | acgatcctca | tcctgtctct | tgatcagatc | ttgatcccct | gcgccatcag | 960 |
| atccttggcg | gcaagaaagc | catccagttt | actttgcagg | gcttcccaac | cttaccagag | 1020 |
| ggcgccccag | ctggcaattc | cggttcgctt | gctgtccata | aaaccgccca | gtctagctat | 1080 |
| cgccatgtaa | gcccactgca | agctacctgc | tttctctttg | cgcttgcgtt | ttcccttgtc | 1140 |
| cagatagccc | agtagctgac | attcatccgg | ggtcagcacc | gtttctgcgg | actggctttc | 1200 |
| tacgtgttcc | gcttccttta | gcagcccttg | cgccctgagt | gcttgcggca | gcgtgagctt | 1260 |
| caaaagcgct | ctgaagttcc | tatactttct | agagaatagg | aacttcgaac | tgcaggtcga | 1320 |
| cggatccccg | gaattaattc | tcatgtttga | cagcttatca | ctgatcagtg | aattaatggc | 1380 |
| gatgacgcat | cctcacgata | atatccgggt | aggcgcaatc | actttcgtct | ctactccgtt | 1440 |
| acaaagcgag | gctgggtatt | ccccggcctt | tctgttatcc | gaaatccact | gaaagcacag | 1500 |
| cggctggctg | aggagataaa | taataaacga | ggggctgtat | gcacaaagca | tcttctgttg | 1560 |
| agttaagaac | gagtatcgag | atggcacata | gccttgctca | aattggaatc | aggtttgtgc | 1620 |
| caataccagt | agaaacagac | gaagaagcta | gctttgcact | ggattgcgag | gctttgccat | 1680 |
| ggctaattcc | catgtcagcc | gttaagtgtt | cctgtgtcac | tgaaaattgc | tttgagaggc | 1740 |
| tctaagggct | tctcagtgcg | ttacatccct | ggcttgttgt | ccacaaccgt | taaaccttaa | 1800 |
| aagctttaaa | agccttatat | attcttttt | ttcttataaa | acttaaaacc | ttagaggcta | 1860 |
| tttaagttgc | tgatttatat | taattttatt | gttcaaacat | gagagcttag | tacgtgaaac | 1920 |
| atgagagctt | agtacgttag | ccatgagagc | ttagtacgtt | agccatgagg | gtttagttcg | 1980 |
| ttaaacatga | gagcttagta | cgttaaacat | gagagcttag | tacgtgaaac | atgagagctt | 2040 |
| agtacgtact | atcaacaggt | tgaactgcgg | atcttgcggc | cgcaaaaatt | aaaaatgaag | 2100 |

```
ttttaaatca atctaaagta tatatgagta aacttggtct gacagttacc aatgcttaat    2160
cagtgaggca cctatctcag cgatctgtct atttcgttca tccatagttg cctgactccc    2220
cgtcgtgtag ataactacga tacgggaggg cttaccatct ggccccagtg ctgcaatgat    2280
accgcgagac ccacgctcac cggctccaga tttatcagca ataaaccagc cagccggaag    2340
ggccgagcgc agaagtggtc ctgcaacttt atccgcctcc atccagtcta ttaattgttg    2400
ccgggaagct agagtaagta gttcgccagt taatagtttg cgcaacgttg ttgccattgc    2460
tacaggcatc gtggtgtcac gctcgtcgtt tggtatggct tcattcagct ccggttccca    2520
acgatcaagg cgagttacat gatcccccat gttgtgcaaa aaagcggtta gctccttcgg    2580
tcctccgatc gttgtcagaa gtaagttggc cgcagtgtta tcactcatgg ttatggcagc    2640
actgcataat tctcttactg tcatgccatc cgtaagatgc ttttctgtga ctggtgagta    2700
ctcaaccaag tcattctgag aatagtgtat gcggcgaccg agttgctctt gcccggcgtc    2760
aatacgggat aataccgcgc cacatagcag aactttaaaa gtgctcatca ttggaaaacg    2820
ttcttcgggg cgaaaactct caaggatctt accgctgttg agatccagtt cgatgtaacc    2880
cactcgtgca cccaactgat cttcagcatc ttttactttc accagcgttt ctgggtgagc    2940
aaaaacagga aggcaaaatg ccgcaaaaaa gggaataagg gcgacacgga aatgttgaat    3000
actcatactc ttcctttttc aatattattg aagcatttat cagggttatt gtctcatgag    3060
cggatacata tttgaatgta tttagaaaaa taaacaaata ggggttccgc gcacatttcc    3120
ccgaaaagtg ccacctgcat cgatggcccc ccgatgtag  tgtggggtct ccccatgcga    3180
gagtagggaa ctgccaggca tcaaataaaa cgaaaggctc agtcgaaaga ctgggccttt    3240
cgttttatct gttgtttgtc ggtgaacgct ctcctgagta ggacaaatcc gccgggagcg    3300
gatttgaacg ttgcgaagca acggcccgga gggtggcggg caggacgccc gccataaact    3360
gccaggcatc aaattaagca gaaggccatc ctgacggatg cctttttgc  gtggccagtg    3420 ccaagcttgc atgc                                                      3434
```

<210> SEQ ID NO 32
<211> LENGTH: 80
<212> TYPE: DNA
<213> ORGANISM: Artificial Sequence
<220> FEATURE:
<223> OTHER INFORMATION: Primer

<400> SEQUENCE: 32

```
atgagcacgt cagacgatat ccataacacc acagccactg gcaaatgccc gttccatcag    60
gtgtaggctg gagctgcttc                                                80
```

<210> SEQ ID NO 33
<211> LENGTH: 82
<212> TYPE: DNA
<213> ORGANISM: Artificial Sequence
<220> FEATURE:
<223> OTHER INFORMATION: Primer

<400> SEQUENCE: 33

```
taacagcagg tcgaaacggt cgaggttcat cactttcacc catgccgcca cgaagtcttt    60
attccgggga tccgtcgacc tg                                             82
```

<210> SEQ ID NO 34
<211> LENGTH: 1424
<212> TYPE: DNA
<213> ORGANISM: Artificial Sequence -continued

```
<220> FEATURE:
<223> OTHER INFORMATION: Primer

<400> SEQUENCE: 34
taacagcagg tcgaaacggt cgaggttcat cactttcacc catgccgcca cgaagtcttt        60 attccggga tccgtcgacc tgcagttcga agttcctatt ctctagaaag tataggaact       120
tcagagcgct tttgaagctc acgctgccgc aagcactcag ggcgcaaggg ctgctaaagg       180
aagcggaaca cgtagaaagc cagtccgcag aaacggtgct gaccccggat gaatgtcagc       240
tactgggcta tctggacaag ggaaaacgca agcgcaaaga gaaagcaggt agcttgcagt       300
gggcttacat ggcgatagct agactgggcg gtttatgga cagcaagcga accggaattg       360
ccagctgggg cgccctctgg taaggttggg aagccctgca agtaaactg gatggctttc       420 ttgccgccaa ggatctgatg gcgcagggga tcaagatctg atcaagagac aggatgagga       480
tcgtttcgca tgattgaaca agatggattg cacgcaggtt ctccggccgc ttgggtggag       540
aggctattcg gctatgactg gcacaacag acaatcggct gctctgatgc cgccgtgttc       600
cggctgtcag cgcaggggcg cccggttctt tttgtcaaga ccgacctgtc cggtgccctg       660
aatgaactgc aggacgaggc agcgcggcta tcgtggctgg ccacgacggg cgttccttgc       720
gcagctgtgc tcgacgttgt cactgaagcg ggaagggact ggctgctatt gggcgaagtg       780
ccggggcagg atctcctgtc atctcacctt gctcctgccg agaaagtatc catcatggct       840
gatgcaatgc ggcggctgca tacgcttgat ccggctacct gcccattcga ccaccaagcg       900
aaacatcgca tcgagcgagc acgtactcgg atggaagccg tcttgtcga tcaggatgat       960 ctggacgaag agcatcaggg gctcgcgcca gccgaactgt tcgccaggct caaggcgcgc      1020
atgcccgacg gcgaggatct cgtcgtgacc catggcgatg cctgcttgcc gaatatcatg      1080
gtggaaaatg gccgcttttc tggattcatc gactgtggcc ggctgggtgt ggcggaccgc      1140
tatcaggaca tagcgttggc tacccgtgat attgctgaag agcttggcgg cgaatgggct      1200
gaccgcttcc tcgtgcttta cggtatcgcc gctcccgatt cgcagcgcat cgccttctat      1260
cgccttcttg acgagttctt ctaataaggg gatcttgaag ttcctattcc gaagttccta      1320
ttctctagaa agtataggaa cttcgaagca gctccagcct acacctgatg gaacgggcat      1380
ttgccagtgg ctgtggtgtt atggatatcg tctgacgtgc tcat                       1424

<210> SEQ ID NO 35
<211> LENGTH: 2181
<212> TYPE: DNA
<213> ORGANISM: Escherichia coli
<220> FEATURE:
<221> NAME/KEY: CDS
<222> LOCATION: (1)..(2181)

<400> SEQUENCE: 35 atg agc acg tca gac gat atc cat aac acc aca gcc act ggc aaa tgc         48
Met Ser Thr Ser Asp Asp Ile His Asn Thr Thr Ala Thr Gly Lys Cys
 1               5                  10                  15 ccg ttc cat cag ggc ggt cac gac cag agt gcg ggg gcg ggc aca acc         96
Pro Phe His Gln Gly Gly His Asp Gln Ser Ala Gly Ala Gly Thr Thr
             20                  25                  30 act cgc gac tgg tgg cca aat caa ctt cgt gtt gac ctg tta aac caa        144
Thr Arg Asp Trp Trp Pro Asn Gln Leu Arg Val Asp Leu Leu Asn Gln
         35                  40                  45 cat tct aat cgt tct aac cca ctg ggt gag gac ttt gac tac cgc aaa        192
His Ser Asn Arg Ser Asn Pro Leu Gly Glu Asp Phe Asp Tyr Arg Lys
     50                  55                  60
```

-continued

| | | |
|---|---|---|
| gaa ttc agc aaa tta gat tac tac ggc ctg aaa aaa gat ctg aaa gcc<br>Glu Phe Ser Lys Leu Asp Tyr Tyr Gly Leu Lys Lys Asp Leu Lys Ala<br>65                            70                           75                      80 | 240 |
| ctg ttg aca gaa tct caa ccg tgg tgg cca gcc gac tgg ggc agt tac<br>Leu Leu Thr Glu Ser Gln Pro Trp Trp Pro Ala Asp Trp Gly Ser Tyr<br>                       85                           90                           95 | 288 |
| gcc ggt ctg ttt att cgt atg gcc tgg cac ggc gcg ggg act tac cgt<br>Ala Gly Leu Phe Ile Arg Met Ala Trp His Gly Ala Gly Thr Tyr Arg<br>                    100                          105                           110 | 336 |
| tca atc gat gga cgc ggt ggc gcg ggt cgt ggt cag caa cgt ttt gca<br>Ser Ile Asp Gly Arg Gly Gly Ala Gly Arg Gly Gln Gln Arg Phe Ala<br>          115                           120                           125 | 384 |
| ccg ctg aac tcc tgg ccg gat aac gta agc ctc gat aaa gcg cgt cgc<br>Pro Leu Asn Ser Trp Pro Asp Asn Val Ser Leu Asp Lys Ala Arg Arg<br>130                            135                           140 | 432 |
| ctg ttg tgg cca atc aaa cag aaa tat ggt cag aaa atc tcc tgg gcc<br>Leu Leu Trp Pro Ile Lys Gln Lys Tyr Gly Gln Lys Ile Ser Trp Ala<br>145                            150                           155                           160 | 480 |
| gac ctg ttt atc ctc gcg ggt aac gtg gcg cta gaa aac tcc ggc ttc<br>Asp Leu Phe Ile Leu Ala Gly Asn Val Ala Leu Glu Asn Ser Gly Phe<br>                    165                          170                           175 | 528 |
| cgt acc ttc ggt ttt ggt gcc ggt cgt gaa gac gtc tgg gaa ccg gat<br>Arg Thr Phe Gly Phe Gly Ala Gly Arg Glu Asp Val Trp Glu Pro Asp<br>                    180                          185                           190 | 576 |
| ctg gat gtt aac tgg ggt gat gaa aaa gcc tgg ctg act cac cgt cat<br>Leu Asp Val Asn Trp Gly Asp Glu Lys Ala Trp Leu Thr His Arg His<br>         195                           200                           205 | 624 |
| ccg gaa gcg ctg gcg aaa gca ccg ctg ggt gca acc gag atg ggt ctg<br>Pro Glu Ala Leu Ala Lys Ala Pro Leu Gly Ala Thr Glu Met Gly Leu<br>210                            215                           220 | 672 |
| att tac gtt aac ccg gaa ggc ccg gat cac agc ggc gaa ccg ctt tct<br>Ile Tyr Val Asn Pro Glu Gly Pro Asp His Ser Gly Glu Pro Leu Ser<br>225                            230                           235                           240 | 720 |
| gcg gca gca gct atc cgc gcg acc ttc ggc aac atg ggc atg aac gac<br>Ala Ala Ala Ala Ile Arg Ala Thr Phe Gly Asn Met Gly Met Asn Asp<br>                    245                          250                           255 | 768 |
| gaa gaa acc gtg gcg ctg att gcg ggt ggt cat acg ctg ggt aaa acc<br>Glu Glu Thr Val Ala Leu Ile Ala Gly Gly His Thr Leu Gly Lys Thr<br>                    260                          265                           270 | 816 |
| cac ggt gcc ggt ccg aca tca aat gta ggt cct gat cca gaa gct gca<br>His Gly Ala Gly Pro Thr Ser Asn Val Gly Pro Asp Pro Glu Ala Ala<br>         275                           280                           285 | 864 |
| ccg att gaa gaa caa ggt tta ggt tgg gcg agc act tac ggc agc ggc<br>Pro Ile Glu Glu Gln Gly Leu Gly Trp Ala Ser Thr Tyr Gly Ser Gly<br>290                            295                           300 | 912 |
| gtt ggc gca gat gcc att acc tct ggt ctg gaa gta gtc tgg acc cag<br>Val Gly Ala Asp Ala Ile Thr Ser Gly Leu Glu Val Val Trp Thr Gln<br>305                            310                           315                           320 | 960 |
| acg ccg acc cag tgg agc aac tat ttc ttc gag aac ctg ttc aag tat<br>Thr Pro Thr Gln Trp Ser Asn Tyr Phe Phe Glu Asn Leu Phe Lys Tyr<br>                    325                          330                           335 | 1008 |
| gag tgg gta cag acc cgc agc ccg gct ggc gca atc cag ttc gaa gcg<br>Glu Trp Val Gln Thr Arg Ser Pro Ala Gly Ala Ile Gln Phe Glu Ala<br>                    340                          345                           350 | 1056 |
| gta gac gca ccg gaa att atc ccg gat ccg ttt gat ccg tcg aag aaa<br>Val Asp Ala Pro Glu Ile Ile Pro Asp Pro Phe Asp Pro Ser Lys Lys<br>         355                           360                           365 | 1104 |
| cgt aaa ccg aca atg ctg gtg acc gac ctg acg ctg cgt ttt gat cct<br>Arg Lys Pro Thr Met Leu Val Thr Asp Leu Thr Leu Arg Phe Asp Pro<br>370                            375                           380 | 1152 |

```
gag ttc gag aag atc tct cgt cgt ttc ctc aac gat ccg cag gcg ttc     1200
Glu Phe Glu Lys Ile Ser Arg Arg Phe Leu Asn Asp Pro Gln Ala Phe
385                 390                 395                 400 aac gaa gcc ttt gcc cgt gcc tgg ttc aaa ctg acg cac agg gat atg     1248
Asn Glu Ala Phe Ala Arg Ala Trp Phe Lys Leu Thr His Arg Asp Met
                405                 410                 415 ggg ccg aaa tct cgc tac atc ggg ccg gaa gtg ccg aaa gaa gat ctg     1296
Gly Pro Lys Ser Arg Tyr Ile Gly Pro Glu Val Pro Lys Glu Asp Leu
            420                 425                 430 atc tgg caa gat ccg ctg ccg cag ccg atc tac aac ccg acc gag cag     1344
Ile Trp Gln Asp Pro Leu Pro Gln Pro Ile Tyr Asn Pro Thr Glu Gln
        435                 440                 445 gac att atc gat ctg aaa ttc gcg att gcg gat tct ggt ctg tct gtt     1392
Asp Ile Ile Asp Leu Lys Phe Ala Ile Ala Asp Ser Gly Leu Ser Val
450                 455                 460 agt gag ctg gta tcg gtg gcc tgg gca tct gct tct acc ttc cgt ggt     1440
Ser Glu Leu Val Ser Val Ala Trp Ala Ser Ala Ser Thr Phe Arg Gly
465                 470                 475                 480 ggc gac aaa cgc ggt ggt gcc aac ggt gcg cgt ctg gca tta atg ccg     1488
Gly Asp Lys Arg Gly Gly Ala Asn Gly Ala Arg Leu Ala Leu Met Pro
                485                 490                 495 cag cgc gac tgg gat gtg aac gcc gca gcc gtt cgt gct ctg cct gtt     1536
Gln Arg Asp Trp Asp Val Asn Ala Ala Ala Val Arg Ala Leu Pro Val
            500                 505                 510 ctg gag aaa atc cag aaa gag tct ggt aaa gcc tcg ctg gcg gat atc     1584
Leu Glu Lys Ile Gln Lys Glu Ser Gly Lys Ala Ser Leu Ala Asp Ile
        515                 520                 525 ata gtg ctg gct ggt gtg gtt ggt gtt gag aaa gcc gca agc gcc gca     1632
Ile Val Leu Ala Gly Val Val Gly Val Glu Lys Ala Ala Ser Ala Ala
530                 535                 540 ggt ttg agc att cat gta ccg ttt gcg ccg ggt cgc gtt gat gcg cgt     1680
Gly Leu Ser Ile His Val Pro Phe Ala Pro Gly Arg Val Asp Ala Arg
545                 550                 555                 560 cag gat cag act gac att gag atg ttt gag ctg ctg gag cca att gct     1728
Gln Asp Gln Thr Asp Ile Glu Met Phe Glu Leu Leu Glu Pro Ile Ala
                565                 570                 575 gac ggt ttc cgt aac tat cgc gct cgt ctg gac gtt tcc acc acc gag     1776
Asp Gly Phe Arg Asn Tyr Arg Ala Arg Leu Asp Val Ser Thr Thr Glu
            580                 585                 590 tca ctg ctg atc gac aaa gca cag caa ctg acg ctg acc gcg ccg gaa     1824
Ser Leu Leu Ile Asp Lys Ala Gln Gln Leu Thr Leu Thr Ala Pro Glu
        595                 600                 605 atg act gcg ctg gtg ggc ggc atg cgt gta ctg ggt gcc aac ttc gat     1872
Met Thr Ala Leu Val Gly Gly Met Arg Val Leu Gly Ala Asn Phe Asp
610                 615                 620 ggc agc aaa aac ggc gtc ttc act gac cgc gtt ggc gta ttg agc aat     1920
Gly Ser Lys Asn Gly Val Phe Thr Asp Arg Val Gly Val Leu Ser Asn
625                 630                 635                 640 gac ttc ttc gtg aac ttg ctg gat atg cgt tac gag tgg aaa gcg acc     1968
Asp Phe Phe Val Asn Leu Leu Asp Met Arg Tyr Glu Trp Lys Ala Thr
                645                 650                 655 gac gaa tcg aaa gag ctg ttc gaa ggc cgt gac cgt gaa acc ggc gaa     2016
Asp Glu Ser Lys Glu Leu Phe Glu Gly Arg Asp Arg Glu Thr Gly Glu
            660                 665                 670 gtg aaa ttt acg gcc agc cgt gcg gat ctg gtg ttt ggt tct aac tcc     2064
Val Lys Phe Thr Ala Ser Arg Ala Asp Leu Val Phe Gly Ser Asn Ser
        675                 680                 685 gtc ctg cgt gcg gtg gcg gaa gtt tac gcc agt agc gat gcc cac gag     2112
Val Leu Arg Ala Val Ala Glu Val Tyr Ala Ser Ser Asp Ala His Glu
690                 695                 700
```

```
aag ttt gtt aaa gac ttc gtg gcg gca tgg gtg aaa gtg atg aac ctc    2160
Lys Phe Val Lys Asp Phe Val Ala Ala Trp Val Lys Val Met Asn Leu
705                 710                 715                 720 gac cgt ttc gac ctg ctg taa                                        2181
Asp Arg Phe Asp Leu Leu
725
```

<210> SEQ ID NO 36
<211> LENGTH: 726
<212> TYPE: PRT
<213> ORGANISM: Escherichia coli

<400> SEQUENCE: 36

```
Met Ser Thr Ser Asp Ile His Asn Thr Thr Ala Thr Gly Lys Cys
1               5                   10                  15

Pro Phe His Gln Gly Gly His Asp Gln Ser Ala Gly Ala Gly Thr Thr
            20                  25                  30

Thr Arg Asp Trp Trp Pro Asn Gln Leu Arg Val Asp Leu Leu Asn Gln
        35                  40                  45

His Ser Asn Arg Ser Asn Pro Leu Gly Glu Asp Phe Asp Tyr Arg Lys
    50                  55                  60

Glu Phe Ser Lys Leu Asp Tyr Tyr Gly Leu Lys Lys Asp Leu Lys Ala
65                  70                  75                  80

Leu Leu Thr Glu Ser Gln Pro Trp Trp Pro Ala Asp Trp Gly Ser Tyr
                85                  90                  95

Ala Gly Leu Phe Ile Arg Met Ala Trp His Gly Ala Gly Thr Tyr Arg
            100                 105                 110

Ser Ile Asp Gly Arg Gly Gly Ala Gly Arg Gly Gln Gln Arg Phe Ala
        115                 120                 125

Pro Leu Asn Ser Trp Pro Asp Asn Val Ser Leu Asp Lys Ala Arg Arg
    130                 135                 140

Leu Leu Trp Pro Ile Lys Gln Lys Tyr Gly Gln Lys Ile Ser Trp Ala
145                 150                 155                 160

Asp Leu Phe Ile Leu Ala Gly Asn Val Ala Leu Glu Asn Ser Gly Phe
                165                 170                 175

Arg Thr Phe Gly Phe Gly Ala Gly Arg Glu Asp Val Trp Glu Pro Asp
            180                 185                 190

Leu Asp Val Asn Trp Gly Asp Glu Lys Ala Trp Leu Thr His Arg His
        195                 200                 205

Pro Glu Ala Leu Ala Lys Ala Pro Leu Gly Ala Thr Glu Met Gly Leu
    210                 215                 220

Ile Tyr Val Asn Pro Glu Gly Pro Asp His Ser Gly Glu Pro Leu Ser
225                 230                 235                 240

Ala Ala Ala Ala Ile Arg Ala Thr Phe Gly Asn Met Gly Met Asn Asp
                245                 250                 255

Glu Glu Thr Val Ala Leu Ile Ala Gly Gly His Thr Leu Gly Lys Thr
            260                 265                 270

His Gly Ala Gly Pro Thr Ser Asn Val Gly Pro Asp Pro Glu Ala Ala
        275                 280                 285

Pro Ile Glu Glu Gln Gly Leu Gly Trp Ala Ser Thr Tyr Gly Ser Gly
    290                 295                 300

Val Gly Ala Asp Ala Ile Thr Ser Gly Leu Glu Val Val Trp Thr Gln
305                 310                 315                 320

Thr Pro Thr Gln Trp Ser Asn Tyr Phe Phe Glu Asn Leu Phe Lys Tyr
                325                 330                 335

Glu Trp Val Gln Thr Arg Ser Pro Ala Gly Ala Ile Gln Phe Glu Ala
```

```
                    340             345                 350
Val Asp Ala Pro Glu Ile Ile Pro Asp Pro Phe Asp Pro Ser Lys Lys
                355                 360                 365

Arg Lys Pro Thr Met Leu Val Thr Asp Leu Thr Leu Arg Phe Asp Pro
            370                 375                 380

Glu Phe Glu Lys Ile Ser Arg Arg Phe Leu Asn Asp Pro Gln Ala Phe
385                 390                 395                 400

Asn Glu Ala Phe Ala Arg Ala Trp Phe Lys Leu Thr His Arg Asp Met
                405                 410                 415

Gly Pro Lys Ser Arg Tyr Ile Gly Pro Glu Val Pro Lys Glu Asp Leu
            420                 425                 430

Ile Trp Gln Asp Pro Leu Pro Gln Pro Ile Tyr Asn Pro Thr Glu Gln
                435                 440                 445

Asp Ile Ile Asp Leu Lys Phe Ala Ile Ala Asp Ser Gly Leu Ser Val
            450                 455                 460

Ser Glu Leu Val Ser Val Ala Trp Ala Ser Ala Ser Thr Phe Arg Gly
465                 470                 475                 480

Gly Asp Lys Arg Gly Gly Ala Asn Gly Ala Arg Leu Ala Leu Met Pro
                485                 490                 495

Gln Arg Asp Trp Asp Val Asn Ala Ala Ala Val Arg Ala Leu Pro Val
            500                 505                 510

Leu Glu Lys Ile Gln Lys Glu Ser Gly Lys Ala Ser Leu Ala Asp Ile
                515                 520                 525

Ile Val Leu Ala Gly Val Val Gly Val Glu Lys Ala Ala Ser Ala Ala
            530                 535                 540

Gly Leu Ser Ile His Val Pro Phe Ala Pro Gly Arg Val Asp Ala Arg
545                 550                 555                 560

Gln Asp Gln Thr Asp Ile Glu Met Phe Glu Leu Leu Glu Pro Ile Ala
                565                 570                 575

Asp Gly Phe Arg Asn Tyr Arg Ala Arg Leu Asp Val Ser Thr Thr Glu
            580                 585                 590

Ser Leu Leu Ile Asp Lys Ala Gln Gln Leu Thr Leu Thr Ala Pro Glu
                595                 600                 605

Met Thr Ala Leu Val Gly Gly Met Arg Val Leu Gly Ala Asn Phe Asp
    610                 615                 620

Gly Ser Lys Asn Gly Val Phe Thr Asp Arg Val Gly Val Leu Ser Asn
625                 630                 635                 640

Asp Phe Phe Val Asn Leu Leu Asp Met Arg Tyr Glu Trp Lys Ala Thr
                645                 650                 655

Asp Glu Ser Lys Glu Leu Phe Glu Gly Arg Asp Arg Glu Thr Gly Glu
            660                 665                 670

Val Lys Phe Thr Ala Ser Arg Ala Asp Leu Val Phe Gly Ser Asn Ser
                675                 680                 685

Val Leu Arg Ala Val Ala Glu Val Tyr Ala Ser Ser Asp Ala His Glu
            690                 695                 700

Lys Phe Val Lys Asp Phe Val Ala Ala Trp Val Lys Val Met Asn Leu
705                 710                 715                 720

Asp Arg Phe Asp Leu Leu
                725
```

<210> SEQ ID NO 37
<211> LENGTH: 6329
<212> TYPE: DNA
<213> ORGANISM: Artificial Sequence
<220> FEATURE:

<223> OTHER INFORMATION: Plasmid pKD46

<400> SEQUENCE: 37

```
catcgattta ttatgacaac ttgacggcta catcattcac tttttcttca caaccggcac      60
ggaactcgct cgggctggcc ccggtgcatt ttttaaatac ccgcgagaaa tagagttgat     120
cgtcaaaacc aacattgcga ccgacggtgg cgataggcat ccgggtggtg ctcaaaagca     180
gcttcgcctg gctgatacgt tggtcctcgc gccagcttaa gacgctaatc cctaactgct     240
ggcggaaaag atgtgacaga cgcgacggcg acaagcaaac atgctgtgcg acgctggcga     300
tatcaaaatt gctgtctgcc aggtgatcgc tgatgtactg acaagcctcg cgtacccgat     360
tatccatcgg tggatggagc gactcgttaa tcgcttccat gcgccgcagt aacaattgct     420
caagcagatt tatcgccagc agctccgaat agcgcccttc ccttgcccg gcgttaatga     480
tttgcccaaa caggtcgctg aaatgcggct ggtgcgcttc atccgggcga agaaccccg     540
tattggcaaa tattgacggc cagttaagcc attcatgcca gtaggcgcgc ggacgaaagt     600
aaacccactg gtgataccat tcgcgagcct ccggatgacg accgtagtga tgaatctctc     660
ctggcgggaa cagcaaaata tcacccggtc ggcaaacaaa ttctcgtccc tgattttta     720
ccaccccctg accgcgaatg gtgagattga gaatataacc tttcattccc agcggtcggt     780
cgataaaaaa atcgagataa ccgttggcct caatcggcgt taaacccgcc accagatggg     840
cattaaacga gtatcccggc agcaggggat cattttgcgc ttcagccata cttttcatac     900
tcccgccatt cagagaagaa accaattgtc catattgcat cagacattgc cgtcactgcg     960
tcttttactg gctcttctcg ctaaccaaac cggtaacccc gcttattaaa agcattctgt    1020
aacaaagcgg gaccaaagcc atgacaaaaa cgcgtaacaa aagtgtctat aatcacggca    1080
gaaaagtcca cattgattat ttgcacggcg tcacactttg ctatgccata gcatttttat    1140
ccataagatt agcggatcct acctgacgct ttttatcgca actctctact gtttctccat    1200
acccgttttt ttgggaattc gagctctaag gaggttataa aaaatggata ttaatactga    1260
aactgagatc aagcaaaagc attcactaac cccctttcct gttttcctaa tcagcccggc    1320
atttcgcggg cgatattttc acagctattt caggagttca gccatgaacg cttattacat    1380
tcaggatcgt cttgaggctc agagctgggc gcgtcactac cagcagctcg cccgtgaaga    1440
gaaagaggca gaactggcag acgacatgga aaaaggcctg ccccagcacc tgtttgaatc    1500
gctatgcatc gatcatttgc aacgccacgg ggccagcaaa aaatccatta cccgtgcgtt    1560
tgatgacgat gttgagtttc aggagcgcat ggcagaacac atccggtaca tggttgaaac    1620
cattgctcac caccaggttg atattgattc agaggtataa aacgaatgag tactgcactc    1680
gcaacgctgg ctgggaagct ggctgaacgt gtcggcatgg attctgtcga cccacaggaa    1740
ctgatcacca ctcttcgcca gacggcattt aaaggtgatg ccagcgatgc gcagttcatc    1800
gcattactga tcgttgccaa ccagtacggc cttaatccgt ggacgaaaga aatttacgcc    1860
tttcctgata agcagaatgg catcgttccg gtggtgggcg ttgatggctg tcccgcatc    1920
atcaatgaaa accagcagtt tgatggcatg actttgagc aggacaatga atcctgtaca    1980
tgccggattt accgcaagga ccgtaatcat ccgatctgcg ttaccgaatg gatggatgaa    2040
tgccgccgcg aaccattcaa aactcgcgaa ggcagagaaa tcacgggcc gtggcagtcg    2100
catcccaaac ggatgttacg tcataaagcc atgattcagt gtgcccgtct ggccttcgga    2160
tttgctggta tctatgacaa ggatgaagcc gagcgcattg tcgaaaatac tgcatacact    2220
gcagaacgtc agccggaacg cgacatcact ccggttaacg atgaaccat gcaggagatt    2280
```

```
aacactctgc tgatcgccct ggataaaaca tgggatgacg acttattgcc gctctgttcc    2340
cagatatttc gccgcgacat tcgtgcatcg tcagaactga cacaggccga agcagtaaaa    2400
gctcttggat tcctgaaaca gaaagccgca gagcagaagg tggcagcatg acaccggaca    2460
ttatcctgca gcgtaccggg atcgatgtga gagctgtcga acaggggat gatgcgtggc     2520 acaaattacg gctcggcgtc atccgcctt cagaagttca caacgtgata gcaaaacccc     2580
gctccggaaa gaagtggcct gacatgaaaa tgtcctactt ccacaccctg cttgctgagg    2640
tttgcaccgg tgtggctccg gaagttaacg ctaaagcact ggcctgggga aaacagtacg    2700
agaacgacgc cagaaccctg tttgaattca cttccggcgt gaatgttact gaatccccga    2760
tcatctatcg cgacgaaagt atgcgtaccg cctgctctcc cgatggttta tgcagtgacg    2820
gcaacggcct tgaactgaaa tgcccgttta cctcccggga tttcatgaag ttccggctcg    2880
gtggtttcga ggccataaag tcagcttaca tggcccaggt gcagtacagc atgtgggtga    2940
cgcgaaaaaa tgcctggtac tttgccaact atgacccgcg tatgaagcgt gaaggcctgc    3000
attatgtcgt gattgagcgg gatgaaaagt acatggcgag ttttgacgag atcgtgccgg    3060
agttcatcga aaaaatggac gaggcactgg ctgaaattgg ttttgtattt ggggagcaat    3120
ggcgatgacg catcctcacg ataatatccg ggtaggcgca atcactttcg tctactccgt    3180
tacaaagcga ggctgggtat ttcccggcct ttctgttatc cgaaatccac tgaaagcaca    3240
gcggctggct gaggagataa ataataaacg aggggctgta tgcacaaagc atcttctgtt    3300
gagttaagaa cgagtatcga gatggcacat agccttgctc aaattggaat caggtttgtg    3360
ccaataccag tagaaacaga cgaagaatcc atgggtatgg acagttttcc ctttgatatg    3420
taacggtgaa cagttgttct acttttgttt gttagtcttg atgcttcact gatagataca    3480
agagccataa gaacctcaga tccttccgta tttagccagt atgttctcta gtgtggttcg    3540 ttgttttgc gtgagccatg agaacgaacc attgagatca tacttacttt gcatgtcact    3600 caaaatttt gcctcaaaac tggtgagctg aattttgca gttaaagcat cgtgtagtgt      3660
ttttcttagt ccgttacgta ggtaggaatc tgatgtaatg gttgttggta ttttgtcacc    3720 attcatttt atctggttgt tctcaagttc ggttacgaga tccatttgtc tatctagttc     3780
aacttggaaa atcaacgtat cagtcgggcg gcctcgctta tcaaccacca atttcatatt    3840
gctgtaagtg tttaaatctt tacttattgg tttcaaaacc cattggttaa gccttttaaa    3900
ctcatggtag ttattttcaa gcattaacat gaacttaaat tcatcaaggc taatctctat    3960
atttgccttg tgagttttct tttgtgttag ttcttttaat aaccactcat aaatcctcat    4020
agagtatttg ttttcaaaag acttaacatg ttccagatta tatttatga atttttttaa    4080 ctggaaaaga taaggcaata tctcttcact aaaaactaat tctaattttt cgcttgagaa    4140
cttggcatag tttgtccact ggaaaatctc aaagccttta accaaggat tcctgatttc     4200 cacagttctc gtcatcagct ctctggttgc tttagctaat acaccataag cattttccct    4260
actgatgttc atcatctgag cgtattggtt ataagtgaac gataccgtcc gttctttcct    4320
tgtagggttt tcaatcgtgg ggttgagtag tgccacacag cataaaatta gcttggtttc    4380
atgctccgtt aagtcatagc gactaatcgc tagttcattt gctttgaaaa caactaattc    4440
agacatacat ctcaattggt ctaggtgatt ttaatcacta taccaattga gatgggctag    4500
tcaatgataa ttactagtcc ttttcctttg agttgtgggt atctgtaaat tctgctagac    4560
ctttgctgga aaacttgtaa attctgctag accctctgta aattccgcta gacctttgtg    4620 tgttttttt gtttatattc aagtggttat aatttataga ataaagaaag aataaaaaaa    4680
```

```
gataaaaaga atagatccca gccctgtgta taactcacta ctttagtcag ttccgcagta    4740
ttacaaaagg atgtcgcaaa cgctgtttgc tcctctacaa aacagacctt aaaaccctaa    4800
aggcttaagt agcaccctcg caagctcggt tgcggccgca atcgggcaaa tcgctgaata    4860
ttccttttgt ctccgaccat caggcacctg agtcgctgtc tttttcgtga cattcagttc    4920
gctgcgctca cggctctggc agtgaatggg ggtaaatggc actacaggcg ccttttatgg    4980
attcatgcaa ggaaactacc cataatacaa gaaaagcccg tcacgggctt ctcagggcgt    5040
tttatggcgg gtctgctatg tggtgctatc tgacttttg ctgttcagca gttcctgccc    5100
tctgattttc cagtctgacc acttcggatt atcccgtgac aggtcattca gactggctaa    5160
tgcacccagt aaggcagcgg tatcatcaac ggggtctgac gctcagtgga acgaaaactc    5220
acgttaaggg attttggtca tgagattatc aaaaaggatc ttcacctaga tccttttaaa    5280
ttaaaaatga gttttaaat caatctaaag tatatatgag taaacttggt ctgacagtta    5340
ccaatgctta atcagtgagg cacctatctc agcgatctgt ctatttcgtt catccatagt    5400
tgcctgactc cccgtcgtgt agataactac gatacgggag ggcttaccat ctggccccag    5460
tgctgcaatg ataccgcgag acccacgctc accggctcca gatttatcag caataaacca    5520
gccagccgga agggccgagc gcagaagtgg tcctgcaact ttatccgcct ccatccagtc    5580
tattaattgt tgccgggaag ctagagtaag tagttcgcca gttaatagtt tgcgcaacgt    5640
tgttgccatt gctacaggca tcgtggtgtc acgctcgtcg tttggtatgg cttcattcag    5700
ctccggttcc caacgatcaa ggcgagttac atgatccccc atgttgtgca aaaaagcggt    5760
tagctccttc ggtcctccga tcgttgtcag aagtaagttg gccgcagtgt tatcactcat    5820
ggttatggca gcactgcata attctcttac tgtcatgcca tccgtaagat gcttttctgt    5880
gactggtgag tactcaacca agtcattctg agaatagtgt atgcggcgac cgagttgctc    5940
ttgcccggcg tcaatacggg ataataccgc gccacatagc agaactttaa aagtgctcat    6000
cattggaaaa cgttcttcgg ggcgaaaact ctcaaggatc ttaccgctgt tgagatccag    6060
ttcgatgtaa cccactcgtg cacccaactg atcttcagca tcttttactt tcaccagcgt    6120
ttctgggtga gcaaaaacag gaaggcaaaa tgccgcaaaa aagggaataa gggcgacacg    6180
gaaatgttga atactcatac tcttcctttt tcaatattat tgaagcattt atcagggtta    6240
ttgtctcatg agcggataca tatttgaatg tatttagaaa aataaacaaa tagggggttcc    6300
gcgcacattt ccccgaaaag tgccacctg                                      6329
```

<210> SEQ ID NO 38
<211> LENGTH: 25
<212> TYPE: DNA
<213> ORGANISM: Artificial Sequence
<220> FEATURE:
<223> OTHER INFORMATION: Primer

<400> SEQUENCE: 38
aacaatatgt aagatctcaa ctatc                                            25

<210> SEQ ID NO 39
<211> LENGTH: 25
<212> TYPE: DNA
<213> ORGANISM: Artificial Sequence
<220> FEATURE:
<223> OTHER INFORMATION: Primer

<400> SEQUENCE: 39
cagacatgag agatccagtg tgtag                                            25

<210> SEQ ID NO 40
<211> LENGTH: 9332
<212> TYPE: DNA
<213> ORGANISM: Artificial Sequence
<220> FEATURE:
<223> OTHER INFORMATION: Plasmid pCP20

<400> SEQUENCE: 40

| | | | | | |
|---|---|---|---|---|---|
| gagacacaac | gtggctttgt | tgaataaatc | gaacttttgc | tgagttgaag | gatcagatca | 60 |
| cgcatcttcc | cgacaacgca | gaccgttccg | tggcaaagca | aaagttcaaa | atcaccaact | 120 |
| ggtccaccta | caacaaagct | ctcatcaacc | gtggctccct | cactttctgg | ctggatgatg | 180 |
| gggcgattca | ggcctggtat | gagtcagcaa | caccttcttc | acgaggcaga | cctcagcgcc | 240 |
| acaggtgcgg | ttgctggcgc | taaccgtttt | tatcaggctc | tgggaggcag | aataaatgat | 300 |
| catatcgtca | attattacct | ccacggggag | agcctgagca | aactggcctc | aggcatttga | 360 |
| gaagcacacg | gtcacactgc | ttccggtagt | caataaaccg | gtaaaccagc | aatagacata | 420 |
| agcggctatt | taacgaccct | gccctgaacc | gacgaccggg | tcgaatttgc | tttcgaattt | 480 |
| ctgccattca | tccgcttatt | atcacttatt | caggcgtagc | aaccaggcgt | ttaagggcac | 540 |
| caataactgc | cttaaaaaaa | ttacgccccg | ccctgccact | catcgcagta | ctgttgtaat | 600 |
| tcattaagca | ttctgccgac | atggaagcca | tcacaaacgg | catgatgaac | ctgaatcgcc | 660 |
| agcggcatca | gcaccttgtc | gccttgcgta | taatatttgc | ccatggtgaa | aacgggggcg | 720 |
| aagaagttgt | ccatattggc | cacgtttaaa | tcaaaactgg | tgaaactcac | ccagggattg | 780 |
| gctgagacga | aaaacatatt | ctcaataaac | cctttaggga | aataggccag | gttttcaccg | 840 |
| taacacgcca | catcttgcga | atatatgtgt | agaaactgcc | ggaaatcgtc | gtggtattca | 900 |
| ctccagagcg | atgaaaacgt | ttcagtttgc | tcatggaaaa | cggtgtaaca | agggtgaaca | 960 |
| ctatcccata | tcaccagctc | accgtctttc | attgccatac | ggaattccgg | atgagcattc | 1020 |
| atcaggcggg | caagaatgtg | aataaaggcc | ggataaaact | tgtgcttatt | tttctttacg | 1080 |
| gtctttaaaa | aggccgtaat | atccagctga | acggtctggt | tataggtaca | ttgagcaact | 1140 |
| gactgaaatg | cctcaaaatg | ttctttacga | tgccattggg | atatatcaac | ggtggtatat | 1200 |
| ccagtgattt | ttttctccat | tttagcttcc | ttagctcctg | aaaatctcga | taactcaaaa | 1260 |
| aatacgcccg | gtagtgatct | tatttcatta | tggtgaaagt | tggaacctct | tacgtgccga | 1320 |
| tcaacgtctc | attttcgcca | aaagttggcc | cagggcttcc | cggtatcaac | agggacacca | 1380 |
| ggatttattt | attctgcgaa | gtgatcttcc | gtcacaggta | tttattcggc | gcaaagtgcg | 1440 |
| tcgggtgatg | ctgccaactt | actgatttag | tgtatgatgg | tgtttttgag | gtgctccagt | 1500 |
| ggcttctgtt | tctatcagct | gtccctcctg | ttcagctact | gacggggtgg | tgcgtaacgg | 1560 |
| caaaagcacc | gccggacatc | agcgcttgtt | tcggcgtggg | tatggtggca | ggccccgtgg | 1620 |
| ccggggggact | gttgggcgcc | tgtagtgcca | tttaccccca | ttcactgcca | gagccgtgag | 1680 |
| cgcagcgaac | tgaatgtcac | gaaaaagaca | gcgactcagg | tgcctgatgg | tcggagacaa | 1740 |
| aaggaatatt | cagcgatttg | cccgagcttg | cgagggtgct | acttaagcct | ttagggtttt | 1800 |
| aaggtctgtt | ttgtagagga | gcaaacagcg | tttgcgacat | ccttttgtaa | tactgcggaa | 1860 |
| ctgactaaag | tagtgagtta | tacacagggc | tgggatctat | tcttttttatc | ttttttttatt | 1920 |
| ctttctttat | tctataaatt | ataaccactt | gaatataaac | aaaaaaaaca | cacaaaggtc | 1980 |
| tagcggaatt | tacagagggt | ctagcagaat | ttacaagttt | tccagcaaag | gtctagcaga | 2040 |
| atttacagat | acccacaact | caaaggaaaa | ggactagtaa | ttatcattga | ctagcccatc | 2100 |

```
tcaattggta tagtgattaa aatcacctag accaattgag atgtatgtct gaattagttg    2160
ttttcaaagc aaatgaacta gcgattagtc gctatgactt aacggagcat gaaaccaagc    2220
taattttatg ctgtgtggca ctactcaacc ccacgattga aaaccctaca aggaaagaac    2280
ggacggtatc gttcacttat aaccaatacg ttcagatgat gaacatcagt agggaaaatg    2340
cttatggtgt attagctaaa gcaaccagag agctgatgac gagaactgtg gaaatcagga    2400
atcctttggt taaaggcttt gagattttcc agtggacaaa ctatgccaag ttctcaagcg    2460
aaaaattaga attagttttt agtgaagaga tattgcctta tcttttccag ttaaaaaaat    2520
tcataaaata taatctggaa catgttaagt cttttgaaaa caaatactct atgaggattt    2580
atgagtggtt attaaaagaa ctaacacaaa agaaaactca caaggcaaat atagagatta    2640
gccttgatga atttaagttc atgttaatgc ttgaaaataa ctaccatgag tttaaaaggc    2700
ttaaccaatg ggttttgaaa ccaataagta aagatttaaa cacttacagc aatatgaaat    2760
tggtggttga taagcgaggc cgcccgactg atacgttgat tttccaagtt gaactagata    2820
gacaaatgga tctcgtaacc gaacttgaga acaaccagat aaaaatgaat ggtgacaaaa    2880
taccaacaac cattacatca gattcctacc tacataacgg actaagaaaa acactacacg    2940
atgctttaac tgcaaaaatt cagctcacca gttttgaggc aaaattttg agtgacatgc     3000 aaagtaagta tgatctcaat ggttcgttct catggctcac gcaaaaacaa cgaaccacac    3060
tagagaacat actggctaaa tacggaagga tctgaggttc ttatggctct tgtatctatc    3120
agtgaagcat caagactaac aaacaaaagt agaacaactg ttcaccgtta catatcaaag    3180
ggaaaactgt ccatatgcac agatgaaaac ggtgtaaaaa agatagatac atcagagctt    3240
ttacgagttt ttggtgcatt taaagctgtt caccatgaac agatcgacaa tgtaacagat    3300
gaacagcatg taacacctaa tagaacaggt gaaaccagta aaacaaagca actagaacat    3360
gaaattgaac acctgagaca acttgttaca gctcaacagt cacacataga cagcctgaaa    3420
caggcgatgc tgcttatcga atcaaagctg ccgacaacac gggagccagt gacgcctccc    3480
gtggggaaaa aatcatggca attctggaag aaatagcgcc tgtttcgttt caggcaggtt    3540
atcagggagt gtcagcgtcc tgcggttctc cggggcgttc gggtcatgca gcccgtaatg    3600
gtgatttacc agcgtctgcc aggcatcaat tctaggcctg tctgcgcggt cgtagtacgg    3660
ctggaggcgt tttccggtct gtagctccat gttcggaatg acaaaattca gctcaagccg    3720
tcccttgtcc tggtgctcca cccacaggat gctgtactga ttttttttcga gaccgggcat    3780 cagtacacgc tcaaagctcg ccatcacttt ttcacgtcct cccggcggca gctccttctc    3840
cgcgaacgac agaacaccgg acgtgtattt cttcgcaaat ggcgtggcat cgatgagttc    3900
ccggacttct tccggattac cctgaagcac cgttgcgcct tcgcggttac gctccctccc    3960
cagcaggtaa tcaaccggac cactgccacc accttttccc ctggcatgaa atttaactat    4020
catcccgcgc cccctgttcc ctgacagcca gacgcagccg gcgcagctca tccccgatgg    4080
ccatcagtgc ggccaccacc tgaacccggt caccggaaga ccactgcccg ctgttcacct    4140
tacgggctgt ctgattcagg ttatttccga tggcggccag ctgacgcagt aacgcggtg    4200 ccagtgtcgg cagttttccg gaacgggcaa ccggctcccc caggcagacc gccgcatcc    4260 ataccgccag ttgtttaccc tcacagcgtt caagtaaccg gcatgttca tcatcagtaa     4320 cccgtattgt gagcatcctc tcgcgtttca tcggtatcat taccccatga acagaaatcc    4380
cccttacacg gaggcatcag tgactaaacg gggtctgacg ctcagtggaa cgaaaactca    4440
cgttaaggga ttttggtcat gagattatca aaaaggatct tcacctagat ccttttaaat    4500
```

```
taaaaatgaa gttttaaatc aatctaaagt atatatgagt aaacttggtc tgacagttac    4560
caatgcttaa tcagtgaggc acctatctca gcgatctgtc tatttcgttc atccatagtt    4620
gcctgactcc ccgtcgtgta gataactacg atacgggagg gcttaccatc tggccccagt    4680
gctgcaatga taccgcgaga cccacgctca ccggctccag atttatcagc aataaaccag    4740
ccagccggaa gggccgagcg cagaagtggt cctgcaactt tatccgcctc catccagtct    4800
attaattgtt gccgggaagc tagagtaagt agttcgccag ttaatagttt gcgcaacgtt    4860
gttgccattg ctgcaggcat cgtggtgtca cgctcgtcgt ttggtatggc ttcattcagc    4920
tccggttccc aacgatcaag gcgagttaca tgatccccca tgttgtgcaa aaaagcggtt    4980
agctccttcg gtcctccgat cgttgtcaga agtaagttgg ccgcagtgtt atcactcatg    5040
gttatggcag cactgcataa ttctcttact gtcatgccat ccgtaagatg cttttctgtg    5100
actggtgagt actcaaccaa gtcattctga gaatagtgta tgcggcgacc gagttgctct    5160
tgcccggcgt caacacggga taataccgcg ccacatagca gaactttaaa agtgctcatc    5220
attggaaaac gttcttcggg gcgaaaactc tcaaggatct taccgctgtt gagatccagt    5280
tcgatgtaac ccactcgtgc acccaactga tcttcagcat cttttacttt caccagcgtt    5340
tctgggtgag caaaaacagg aaggcaaaat gccgcaaaaa agggaataag ggcgacacgg    5400
aaatgttgaa tactcatact cttccttttt caatattatt gaagcattta tcagggttat    5460
tgtctcatga gcggatacat atttgaatgt atttagaaaa ataaacaaat aggggttccg    5520
cgcacatttc cccgaaaagt gccacctgac gtctaagaaa ccattattat catgacatta    5580
acctataaaa ataggcgtat cacgaggccc tttcgtcttc aagaatttta taaaccgtgg    5640
agcgggcaat actgagctga tgagcaattt ccgttgcacc agtgcccttc tgatgaagcg    5700
tcagcacgac gttcctgtcc acggtacgcc tgcggccaaa tttgattcct ttcagctttg    5760
cttcctgtcg gccctcattc gtgcgctcta ggatcctcta cgccggacgc atcgtggccg    5820
gcatcaccgg cgctgaggtc tgcctcgtga agaaggtgtt gctgactcat accaggcctg    5880
aatcgcccca tcatccagcc agaaagtgag ggagccacgg ttgatgagag ctttgttgta    5940
ggtggaccag ttggtgattt tgaacttttg ctttgccacg gaacggtctg cgttgtcggg    6000
aagatgcgtg atctgatcct tcaactcagc aaaagttcga tttattcaac aaagccgccg    6060
tcccgtcaag tcagcgtaat gctctgccag tgttacaacc aattaaccaa ttctgattag    6120
aaaaactcat cgagcatcaa atgaaactgc aatttattca tatcaggatt atcaatacca    6180
tatttttgaa aaagccgttt ctgtaatgaa ggagaaaact caccgaggca gttccatagg    6240
atggcaagat cctggtatcg gtctgcgatt ccgactcgtc caacatcaat acaacctatt    6300
aatttcccct cgtcaaaaat aaggttatca agtgagaaat caccatgagt gacgactgaa    6360
tccggtgaga atggcagaat aggaacttcg gaataggaac ttcaaagcgt ttccgaaaac    6420
gagcgcttcc gaaaatgcaa cgcgagctgc gcacatacag ctcactgttc acgtcgcacc    6480
tatatctgcg tgttgcctgt atatatatat acatgagaag aacggcatag tgcgtgttta    6540
tgcttaaatg cgtacttata tgcgtctatt tatgtaggat gaaaggtagt ctagtacctc    6600
ctgtgatatt atcccattcc atgcggggta tcgtatgctt ccttcagcac tacccttag    6660 ctgttctata tgctgccact cctcaattgg attagtctca tccttcaatg ctatcatttc    6720
ctttgatatt ggatcatatg catagtaccg agaaactagt gcgaagtagt gatcaggtat    6780
tgctgttatc tgatgagtat acgttgtcct ggccacggca gaagcacgct tatcgctcca    6840
atttcccaca acattagtca actccgttag gcccttcatt gaaagaaatg aggtcatcaa    6900
```

```
atgtcttcca atgtgagatt tgggccatt ttttatagca aagattgaat aaggcgcatt      6960
tttcttcaaa gctttattgt acgatctgac taagttatct tttaataatt ggtattcctg      7020
tttattgctt gaagaattgc cggtcctatt tactcgtttt aggactggtt cagaattcct      7080
caaaaattca tccaaatata caagtggatc gatcctaccc cttgcgctaa agaagtatat      7140
gtgcctacta acgcttgtct ttgtctctgt cactaaacac tggattatta ctcccagata      7200
cttattttgg actaatttaa atgatttcgg atcaacgttc ttaatatcgc tgaatcttcc      7260
acaattgatg aaagtagcta ggaagaggaa ttggtataaa gttttttgttt ttgtaaatct      7320 cgaagtatac tcaaacgaat ttagtatttt ctcagtgatc tcccagatgc tttcacccctc     7380 acttagaagt gctttaagca ttttttttact gtggctattt cccttatctg cttcttccga     7440
tgattcgaac tgtaattgca aactacttac aatatcagtg atatcagatt gatgttttttg    7500 tccatagtaa ggaataattg taaattccca agcaggaatc aatttcttta atgaggcttc      7560
cagaattgtt gcttttttgcg tcttgtattt aaactggagt gatttattga caatatcgaa     7620
actcagcgaa ttgcttatga tagtattata gctcatgaat gtggctctct tgattgctgt      7680
tccgttatgt gtaatcatcc aacataaata ggttagttca gcagcacata atgctatttt      7740
ctcacctgaa ggtctttcaa acctttccac aaactgacga acaagcacct taggtggtgt     7800
tttacataat atatcaaatt gtggcataca acctccttag tacatgcaac cattatcacc     7860
gccagaggta aaatagtcaa cacgcacggt gttagatatt tatcccttgc ggtgatagat     7920
ttaacgtatg agcacaaaaa agaaaccatt aacacaagag cagcttgagg acgcacgtcg     7980
ccttaaagca atttatgaaa aaagaaaaa tgaacttggc ttatcccagg aatctgtcgc      8040
agacaagatg gggatggggc agtcaggcgt tggtgcttta tttaatggca tcaatgcatt     8100
aaatgcttat aacgccgcat tgcttacaaa aattctcaaa gttagcgttg aagaatttag     8160
cccttcaatc gccagagaaa tctacgagat gtatgaagcg gttagtatgc agccgtcact     8220
tagaagtgag tatgagtacc ctgtttttttc tcatgttcag gcaggatgt tctcacctaa     8280 gcttagaacc tttaccaaag gtgatgcgga gagatgggta agcacaacca aaaaagccag     8340
tgattctgca ttctggcttg aggttgaagg taattccatg accgcaccaa caggctccaa     8400
gccaagcttt cctgacggaa tgttaattct cgttgaccct gagcaggctg ttgagccagg     8460
tgatttctgc atagccagac ttgggggtga tgagtttacc ttcaagaaac tgatcaggga     8520
tagcggtcag gtgttttttac aaccactaaa cccacagtac ccaatgatcc catgcaatga     8580
gagttgttcc gttgtgggga aagttatcgc tagtcagtgg cctgaagaga cgtttggctg     8640
atcggcaagg tgttctggtc ggcgcatagc tgataacaat tgagcaagaa tctgcatttc     8700
tttccagact tgttcaacag gccagccatt acgctcgtca tcaaaatcac tcgcatcaac     8760
caaaccgtta ttcattcgtg attgcgcctg agcgagacga aatacgcgat cgctgttaaa     8820
aggacaatta caaacaggaa tcgaatgcaa ccggcgcagg aacactgcca gcgcatcaac     8880
aatattttca cctgaatcag atattcttc taatacctgg aatgctgttt tcccggggat      8940
cgcagtggta agtaaccatg catcatcagg agtacggata aaatgcttga tggtcggaag     9000
aggcataaat tccgtcagcc agtttagtct gaccatctca tctgtaacat cattggcaac     9060
gctacctttg ccatgtttca gaaacaactc tggcgcatcg gcttcccat acaatcgata      9120 gattgtcgca cctgattgcc cgacattatc gcgagcccat ttatacccat ataaatcagc    9180
atccatgttg gaatttaatc gcggcctcga gcaagacgtt tcccgttgaa tatggctcat     9240
aacacccctt gtattactgt ttatgtaagc agacagtttt attgttcatg atgatatatt    9300
```

| | |
|---|---|
| tttatcttgt gcaatgtaac atcagagatt tt | 9332 |

```
<210> SEQ ID NO 41
<211> LENGTH: 80
<212> TYPE: DNA
<213> ORGANISM: Artificial Sequence
<220> FEATURE:
<223> OTHER INFORMATION: Primer

<400> SEQUENCE: 41
```

| | |
|---|---|
| atgtcgcaac ataacgaaaa gaacccacat cagcaccagt caccactaca cgattccagc | 60 |
| gtgtaggctg gagctgcttc | 80 |

```
<210> SEQ ID NO 42
<211> LENGTH: 82
<212> TYPE: DNA
<213> ORGANISM: Artificial Sequence
<220> FEATURE:
<223> OTHER INFORMATION: Primer

<400> SEQUENCE: 42
```

| | |
|---|---|
| ttacgccggg attttgtcaa tcttaggaat gcgtgaccac acgcggtgtg ctgtcatcag | 60 |
| attccgggga tccgtcgacc tg | 82 |

```
<210> SEQ ID NO 43
<211> LENGTH: 1424
<212> TYPE: DNA
<213> ORGANISM: Artificial Sequence
<220> FEATURE:
<223> OTHER INFORMATION: Synthetic construct

<400> SEQUENCE: 43
```

| | |
|---|---|
| ttacgccggg attttgtcaa tcttaggaat gcgtgaccac acgcggtgtg ctgtcatcag | 60 |
| attccgggga tccgtcgacc tgcagttcga agttcctatt ctctagaaag tataggaact | 120 |
| tcagagcgct tttgaagctc acgctgccgc aagcactcag ggcgcaaggg ctgctaaagg | 180 |
| aagcggaaca cgtagaaagc cagtccgcag aaacggtgct gaccccggat gaatgtcagc | 240 |
| tactgggcta tctggacaag ggaaaacgca agcgcaaaga gaaagcaggt agcttgcagt | 300 |
| gggcttacat ggcgatagct agactgggcg gttttatgga cagcaagcga accggaattg | 360 |
| ccagctgggg cgccctctgg taaggttggg aagccctgca agtaaactg gatggctttc | 420 |
| ttgccgccaa ggatctgatg gcgcagggga tcaagatctg atcaagagac aggatgagga | 480 |
| tcgtttcgca tgattgaaca agatggattg cacgcaggtt ctccggccgc ttgggtggag | 540 |
| aggctattcg gctatgactg gcacaacag acaatcggct gctctgatgc cgccgtgttc | 600 |
| cggctgtcag cgcaggggcg cccggttctt tttgtcaaga ccgacctgtc cggtgccctg | 660 |
| aatgaactgc aggacgaggc agcgcggcta tcgtggctgg ccacgacggg cgttccttgc | 720 |
| gcagctgtgc tcgacgttgt cactgaagcg ggaagggact ggctgctatt gggcgaagtg | 780 |
| ccggggcagg atctcctgtc atctcacctt gctcctgccg agaaagtatc catcatggct | 840 |
| gatgcaatgc ggcggctgca tacgcttgat ccggctacct gcccattcga ccaccaagcg | 900 |
| aaacatcgca tcgagcgagc acgtactcgg atggaagccg gtcttgtcga tcaggatgat | 960 |
| ctggacgaag agcatcaggg gctcgcgcca gccgaactgt tcgccaggct caaggcgcgc | 1020 |
| atgcccgacg gcgaggatct cgtcgtgacc catggcgatg cctgcttgcc gaatatcatg | 1080 |
| gtggaaaatg gccgcttttc tggattcatc gactgtggcc ggctgggtgt ggcggaccgc | 1140 |
| tatcaggaca tagcgttggc tacccgtgat attgctgaag agcttggcgg cgaatgggct | 1200 |

-continued

```
gaccgcttcc tcgtgcttta cggtatcgcc gctcccgatt cgcagcgcat cgccttctat   1260
cgccttcttg acgagttctt ctaataaggg gatcttgaag ttcctattcc gaagttccta   1320
ttctctagaa agtataggaa cttcgaagca gctccagcct acacgctgga atcgtgtagt   1380
ggtgactggt gctgatgtgg gttcttttcg ttatgttgcg acat                    1424

<210> SEQ ID NO 44
<211> LENGTH: 2262
<212> TYPE: DNA
<213> ORGANISM: Escherichia coli
<220> FEATURE:
<221> NAME/KEY: CDS
<222> LOCATION: (1)..(2262)

<400> SEQUENCE: 44 atg tcg caa cat aac gaa aag aac cca cat cag cac cag tca cca cta    48
Met Ser Gln His Asn Glu Lys Asn Pro His Gln His Gln Ser Pro Leu
1               5                  10                  15 cac gat tcc agc gaa gcg aaa ccg ggg atg gac tca ctg gca cct gag    96
His Asp Ser Ser Glu Ala Lys Pro Gly Met Asp Ser Leu Ala Pro Glu
            20                  25                  30 gac ggc tct cat cgt cca gcg gct gaa cca aca ccg cca ggt gca caa   144
Asp Gly Ser His Arg Pro Ala Ala Glu Pro Thr Pro Pro Gly Ala Gln
        35                  40                  45 cct acc gcc cca ggg agc ctg aaa gcc cct gat acg cgt aac gaa aaa   192
Pro Thr Ala Pro Gly Ser Leu Lys Ala Pro Asp Thr Arg Asn Glu Lys
    50                  55                  60 ctt aat tct ctg gaa gac gta cgc aaa ggc agt gaa aat tat gcg ctg   240
Leu Asn Ser Leu Glu Asp Val Arg Lys Gly Ser Glu Asn Tyr Ala Leu
65                  70                  75                  80 acc act aat cag ggc gtg cgc atc gcc gac gat caa aac tca ctg cgt   288
Thr Thr Asn Gln Gly Val Arg Ile Ala Asp Asp Gln Asn Ser Leu Arg
                85                  90                  95 gcc ggt agc cgt ggt cca acg ctg ctg gaa gat ttt att ctg cgc gag   336
Ala Gly Ser Arg Gly Pro Thr Leu Leu Glu Asp Phe Ile Leu Arg Glu
            100                 105                 110 aaa atc acc cac ttt gac cat gag cgc att ccg gaa cgt att gtt cat   384
Lys Ile Thr His Phe Asp His Glu Arg Ile Pro Glu Arg Ile Val His
        115                 120                 125 gca cgc gga tca gcc gct cac ggt tat ttc cag cca tat aaa agc tta   432
Ala Arg Gly Ser Ala Ala His Gly Tyr Phe Gln Pro Tyr Lys Ser Leu
    130                 135                 140 agc gat att acc aaa gcg gat ttc ctc tca gat ccg aac aaa atc acc   480
Ser Asp Ile Thr Lys Ala Asp Phe Leu Ser Asp Pro Asn Lys Ile Thr
145                 150                 155                 160 cca gta ttt gta cgt ttc tct acc gtt cag ggt ggt gct ggc tct gct   528
Pro Val Phe Val Arg Phe Ser Thr Val Gln Gly Gly Ala Gly Ser Ala
                165                 170                 175 gat acc gtg cgt gat atc cgt ggc ttt gcc acc aag ttc tat acc gaa   576
Asp Thr Val Arg Asp Ile Arg Gly Phe Ala Thr Lys Phe Tyr Thr Glu
            180                 185                 190 gag ggt att ttt gac ctc gtt ggc aat aac acg cca atc ttc ttt atc   624
Glu Gly Ile Phe Asp Leu Val Gly Asn Asn Thr Pro Ile Phe Phe Ile
        195                 200                 205 cag gat gcg cat aaa ttc ccc gat ttt gtt cat gcg gta aaa cca gaa   672
Gln Asp Ala His Lys Phe Pro Asp Phe Val His Ala Val Lys Pro Glu
    210                 215                 220 ccg cac tgg gca att cca caa ggg caa agt gcc cac gat act ttc tgg   720
Pro His Trp Ala Ile Pro Gln Gly Gln Ser Ala His Asp Thr Phe Trp
225                 230                 235                 240 gat tat gtt tct ctg caa cct gaa act ctg cac aac gtg atg tgg gcg   768
Asp Tyr Val Ser Leu Gln Pro Glu Thr Leu His Asn Val Met Trp Ala
```

```
                                                             -continued

Asp Tyr Val Ser Leu Gln Pro Glu Thr Leu His Asn Val Met Trp Ala
            245                 250                 255 atg tcg gat cgc ggt atc ccc cgc agt tac cgc acc atg gaa ggc ttc         816
Met Ser Asp Arg Gly Ile Pro Arg Ser Tyr Arg Thr Met Glu Gly Phe
        260                 265                 270 ggt att cac acc ttc cgc ctg att aat gcc gaa ggg aag gca acg ttt         864
Gly Ile His Thr Phe Arg Leu Ile Asn Ala Glu Gly Lys Ala Thr Phe
            275                 280                 285 gta cgt ttc cac tgg aaa cca ctg gca ggt aaa gcc tca ctc gtt tgg         912
Val Arg Phe His Trp Lys Pro Leu Ala Gly Lys Ala Ser Leu Val Trp
    290                 295                 300 gat gaa gca caa aaa ctc acc gga cgt gac ccg gac ttc cac cgc cgc         960
Asp Glu Ala Gln Lys Leu Thr Gly Arg Asp Pro Asp Phe His Arg Arg
305                 310                 315                 320 gag ttg tgg gaa gcc att gaa gca ggc gat ttt ccg gaa tac gaa ctg        1008
Glu Leu Trp Glu Ala Ile Glu Ala Gly Asp Phe Pro Glu Tyr Glu Leu
                325                 330                 335 ggc ttc cag ttg att cct gaa gaa gat gaa ttc aag ttc gac ttc gat        1056
Gly Phe Gln Leu Ile Pro Glu Glu Asp Glu Phe Lys Phe Asp Phe Asp
            340                 345                 350 ctt ctc gat cca acc aaa ctt atc ccg gaa gaa ctg gtg ccc gtt cag        1104
Leu Leu Asp Pro Thr Lys Leu Ile Pro Glu Glu Leu Val Pro Val Gln
        355                 360                 365 cgt gtc ggc aaa atg gtg ctc aat cgc aac ccg gat aac ttc ttt gct        1152
Arg Val Gly Lys Met Val Leu Asn Arg Asn Pro Asp Asn Phe Phe Ala
    370                 375                 380 gaa aac gaa cag gcg gct ttc cat cct ggg cat atc gtg ccg gga ctg        1200
Glu Asn Glu Gln Ala Ala Phe His Pro Gly His Ile Val Pro Gly Leu
385                 390                 395                 400 gac ttc acc aac gat ccg ctg ttg cag gga cgt ttg ttc tcc tat acc        1248
Asp Phe Thr Asn Asp Pro Leu Leu Gln Gly Arg Leu Phe Ser Tyr Thr
                405                 410                 415 gat aca caa atc agt cgt ctt ggt ggg ccg aat ttc cat gag att ccg        1296
Asp Thr Gln Ile Ser Arg Leu Gly Gly Pro Asn Phe His Glu Ile Pro
            420                 425                 430 att aac cgt ccg acc tgc cct tac cat aat ttc cag cgt gac ggc atg        1344
Ile Asn Arg Pro Thr Cys Pro Tyr His Asn Phe Gln Arg Asp Gly Met
        435                 440                 445 cat cgc atg ggg atc gac act aac ccg gcg aat tac gaa ccg aac tcg        1392
His Arg Met Gly Ile Asp Thr Asn Pro Ala Asn Tyr Glu Pro Asn Ser
    450                 455                 460 att aac gat aac tgg ccg cgc gaa aca ccg ccg ggg ccg aaa cgc ggc        1440
Ile Asn Asp Asn Trp Pro Arg Glu Thr Pro Pro Gly Pro Lys Arg Gly
465                 470                 475                 480 ggt ttt gaa tca tac cag gag cgc gtg gaa ggc aat aaa gtt cgc gag        1488
Gly Phe Glu Ser Tyr Gln Glu Arg Val Glu Gly Asn Lys Val Arg Glu
                485                 490                 495 cgc agc cca tcg ttt ggc gaa tat tat tcc cat ccg cgt ctg ttc tgg        1536
Arg Ser Pro Ser Phe Gly Glu Tyr Tyr Ser His Pro Arg Leu Phe Trp
            500                 505                 510 cta agt cag acg cca ttt gag cag cgc cat att gtc gat ggt ttc agt        1584
Leu Ser Gln Thr Pro Phe Glu Gln Arg His Ile Val Asp Gly Phe Ser
        515                 520                 525 ttt gag tta agc aaa gtc gtt cgt ccg tat att cgt gag cgc gtt gtt        1632
Phe Glu Leu Ser Lys Val Val Arg Pro Tyr Ile Arg Glu Arg Val Val
    530                 535                 540 gac cag ctg gcg cat att gat ctc act ctg gcc cag gcg gtg gcg aaa        1680
Asp Gln Leu Ala His Ile Asp Leu Thr Leu Ala Gln Ala Val Ala Lys
545                 550                 555                 560 aat ctc ggt atc gaa ctg act gac gac cag ctg aat atc acc cca cct        1728
```

```
Asn Leu Gly Ile Glu Leu Thr Asp Asp Gln Leu Asn Ile Thr Pro Pro
            565                 570                 575 ccg gac gtc aac ggt ctg aaa aag gat cca tcc tta agt ttg tac gcc      1776
Pro Asp Val Asn Gly Leu Lys Lys Asp Pro Ser Leu Ser Leu Tyr Ala
        580                 585                 590 att cct gac ggt gat gtg aaa ggt cgc gtg gta gcg att tta ctt aat      1824
Ile Pro Asp Gly Asp Val Lys Gly Arg Val Val Ala Ile Leu Leu Asn
    595                 600                 605 gat gaa gtg aga tcg gca gac ctt ctg gcc att ctc aag gcg ctg aag      1872
Asp Glu Val Arg Ser Ala Asp Leu Leu Ala Ile Leu Lys Ala Leu Lys
610                 615                 620 gcc aaa ggc gtt cat gcc aaa ctg ctc tac tcc cga atg ggt gaa gtg      1920
Ala Lys Gly Val His Ala Lys Leu Leu Tyr Ser Arg Met Gly Glu Val
625                 630                 635                 640 act gcg gat gac ggt acg gtg ttg cct ata gcc gct acc ttt gcc ggt      1968
Thr Ala Asp Asp Gly Thr Val Leu Pro Ile Ala Ala Thr Phe Ala Gly
                645                 650                 655 gca cct tcg ctg acg gtc gat gcg gtc att gtc cct tgc ggc aat atc      2016
Ala Pro Ser Leu Thr Val Asp Ala Val Ile Val Pro Cys Gly Asn Ile
            660                 665                 670 gcg gat atc gct gac aac ggc gat gcc aac tac tac ctg atg gaa gcc      2064
Ala Asp Ile Ala Asp Asn Gly Asp Ala Asn Tyr Tyr Leu Met Glu Ala
        675                 680                 685 tac aaa cac ctt aaa ccg att gcg ctg gcg ggt gac gcg cgc aag ttt      2112
Tyr Lys His Leu Lys Pro Ile Ala Leu Ala Gly Asp Ala Arg Lys Phe
    690                 695                 700 aaa gca aca atc aag atc gct gac cag ggt gaa gaa ggg att gtg gaa      2160
Lys Ala Thr Ile Lys Ile Ala Asp Gln Gly Glu Glu Gly Ile Val Glu
705                 710                 715                 720 gct gac agc gct gac ggt agt ttt atg gat gaa ctg cta acg ctg atg      2208
Ala Asp Ser Ala Asp Gly Ser Phe Met Asp Glu Leu Leu Thr Leu Met
                725                 730                 735 gca gca cac cgc gtg tgg tca cgc att cct aag att gac aaa att cct      2256
Ala Ala His Arg Val Trp Ser Arg Ile Pro Lys Ile Asp Lys Ile Pro
            740                 745                 750 gcc tga                                                               2262
Ala
```

<210> SEQ ID NO 45
<211> LENGTH: 753
<212> TYPE: PRT
<213> ORGANISM: Escherichia coli

<400> SEQUENCE: 45

```
Met Ser Gln His Asn Glu Lys Asn Pro His Gln His Gln Ser Pro Leu
1               5                   10                  15

His Asp Ser Ser Glu Ala Lys Pro Gly Met Asp Ser Leu Ala Pro Glu
                20                  25                  30

Asp Gly Ser His Arg Pro Ala Ala Glu Pro Thr Pro Pro Gly Ala Gln
            35                  40                  45

Pro Thr Ala Pro Gly Ser Leu Lys Ala Pro Asp Thr Arg Asn Glu Lys
        50                  55                  60

Leu Asn Ser Leu Glu Asp Val Arg Lys Gly Ser Glu Asn Tyr Ala Leu
65                  70                  75                  80

Thr Thr Asn Gln Gly Val Arg Ile Ala Asp Asp Gln Asn Ser Leu Arg
                85                  90                  95

Ala Gly Ser Arg Gly Pro Thr Leu Leu Glu Asp Phe Ile Leu Arg Glu
            100                 105                 110

Lys Ile Thr His Phe Asp His Glu Arg Ile Pro Glu Arg Ile Val His
```

```
                115                 120                 125
Ala Arg Gly Ser Ala Ala His Gly Tyr Phe Gln Pro Tyr Lys Ser Leu
    130                 135                 140

Ser Asp Ile Thr Lys Ala Asp Phe Leu Ser Asp Pro Asn Lys Ile Thr
145                 150                 155                 160

Pro Val Phe Val Arg Phe Ser Thr Val Gln Gly Ala Gly Ser Ala
                165                 170                 175

Asp Thr Val Arg Asp Ile Arg Gly Phe Ala Thr Lys Phe Tyr Thr Glu
            180                 185                 190

Glu Gly Ile Phe Asp Leu Val Gly Asn Asn Thr Pro Ile Phe Phe Ile
        195                 200                 205

Gln Asp Ala His Lys Phe Pro Asp Phe Val His Ala Val Lys Pro Glu
    210                 215                 220

Pro His Trp Ala Ile Pro Gln Gly Gln Ser Ala His Asp Thr Phe Trp
225                 230                 235                 240

Asp Tyr Val Ser Leu Gln Pro Glu Thr Leu His Asn Val Met Trp Ala
                245                 250                 255

Met Ser Asp Arg Gly Ile Pro Arg Ser Tyr Arg Thr Met Glu Gly Phe
            260                 265                 270

Gly Ile His Thr Phe Arg Leu Ile Asn Ala Glu Gly Lys Ala Thr Phe
        275                 280                 285

Val Arg Phe His Trp Lys Pro Leu Ala Gly Lys Ala Ser Leu Val Trp
    290                 295                 300

Asp Glu Ala Gln Lys Leu Thr Gly Arg Asp Pro Asp Phe His Arg Arg
305                 310                 315                 320

Glu Leu Trp Glu Ala Ile Glu Ala Gly Asp Phe Pro Glu Tyr Glu Leu
                325                 330                 335

Gly Phe Gln Leu Ile Pro Glu Glu Asp Glu Phe Lys Phe Asp Phe Asp
            340                 345                 350

Leu Leu Asp Pro Thr Lys Leu Ile Pro Glu Glu Leu Val Pro Val Gln
        355                 360                 365

Arg Val Gly Lys Met Val Leu Asn Arg Asn Pro Asp Asn Phe Phe Ala
    370                 375                 380

Glu Asn Glu Gln Ala Ala Phe His Pro Gly His Ile Val Pro Gly Leu
385                 390                 395                 400

Asp Phe Thr Asn Asp Pro Leu Leu Gln Gly Arg Leu Phe Ser Tyr Thr
                405                 410                 415

Asp Thr Gln Ile Ser Arg Leu Gly Gly Pro Asn Phe His Glu Ile Pro
            420                 425                 430

Ile Asn Arg Pro Thr Cys Pro Tyr His Asn Phe Gln Arg Asp Gly Met
        435                 440                 445

His Arg Met Gly Ile Asp Thr Asn Pro Ala Asn Tyr Glu Pro Asn Ser
    450                 455                 460

Ile Asn Asp Asn Trp Pro Arg Glu Thr Pro Gly Pro Lys Arg Gly
465                 470                 475                 480

Gly Phe Glu Ser Tyr Gln Glu Arg Val Glu Gly Asn Lys Val Arg Glu
                485                 490                 495

Arg Ser Pro Ser Phe Gly Glu Tyr Tyr Ser His Pro Arg Leu Phe Trp
            500                 505                 510

Leu Ser Gln Thr Pro Phe Glu Gln Arg His Ile Val Asp Gly Phe Ser
        515                 520                 525

Phe Glu Leu Ser Lys Val Val Arg Pro Tyr Ile Arg Glu Arg Val Val
    530                 535                 540
```

| | | | | | | | | | | | | | | |
|---|---|---|---|---|---|---|---|---|---|---|---|---|---|---|
| Asp | Gln | Leu | Ala | His | Ile | Asp | Leu | Thr | Leu | Ala | Gln | Ala | Val | Ala | Lys |
| 545 | | | | 550 | | | | | 555 | | | | | 560 | |

Asp Gln Leu Ala His Ile Asp Leu Thr Leu Ala Gln Ala Val Ala Lys
545                 550                 555                 560

Asn Leu Gly Ile Glu Leu Thr Asp Asp Gln Leu Asn Ile Thr Pro Pro
                565                 570                 575

Pro Asp Val Asn Gly Leu Lys Lys Asp Pro Ser Leu Ser Leu Tyr Ala
            580                 585                 590

Ile Pro Asp Gly Asp Val Lys Gly Arg Val Val Ala Ile Leu Leu Asn
        595                 600                 605

Asp Glu Val Arg Ser Ala Asp Leu Leu Ala Ile Leu Lys Ala Leu Lys
    610                 615                 620

Ala Lys Gly Val His Ala Lys Leu Leu Tyr Ser Arg Met Gly Glu Val
625                 630                 635                 640

Thr Ala Asp Asp Gly Thr Val Leu Pro Ile Ala Ala Thr Phe Ala Gly
                645                 650                 655

Ala Pro Ser Leu Thr Val Asp Ala Val Ile Val Pro Cys Gly Asn Ile
            660                 665                 670

Ala Asp Ile Ala Asp Asn Gly Asp Ala Asn Tyr Tyr Leu Met Glu Ala
        675                 680                 685

Tyr Lys His Leu Lys Pro Ile Ala Leu Ala Gly Asp Ala Arg Lys Phe
    690                 695                 700

Lys Ala Thr Ile Lys Ile Ala Asp Gln Gly Glu Glu Gly Ile Val Glu
705                 710                 715                 720

Ala Asp Ser Ala Asp Gly Ser Phe Met Asp Glu Leu Leu Thr Leu Met
                725                 730                 735

Ala Ala His Arg Val Trp Ser Arg Ile Pro Lys Ile Asp Lys Ile Pro
            740                 745                 750

Ala

<210> SEQ ID NO 46
<211> LENGTH: 25
<212> TYPE: DNA
<213> ORGANISM: Artificial Sequence
<220> FEATURE:
<223> OTHER INFORMATION: Primer

<400> SEQUENCE: 46
gatctgactg gtggtctata gttag                                  25

<210> SEQ ID NO 47
<211> LENGTH: 25
<212> TYPE: DNA
<213> ORGANISM: Artificial Sequence
<220> FEATURE:
<223> OTHER INFORMATION: Primer

<400> SEQUENCE: 47
gtagttatca tgatgtgtaa gtaag                                  25

<210> SEQ ID NO 48
<211> LENGTH: 963
<212> TYPE: DNA
<213> ORGANISM: Artificial Sequence
<220> FEATURE:
<223> OTHER INFORMATION: Synthetic construct

<400> SEQUENCE: 48
atgcagctgt ttgacctgag cctggaagaa ctgaaaaagt ataaaccgaa aaagaccgcc    60
cgtcctgact ctctgatttt ctggaagaaa tctctggaag aactgcgtca ggtagaagct   120
gaaccgaccc tggaaagcta cgactatcca gtaaagggcg tgaaagtgta ccgtctgact   180

```
taccagtcttt tcggtcactc taagattgaa ggtttctacg ctgtaccgga ccaaactggt      240
ccgcatccgg cgctggttcg tttccatggc tacaatgctt cttatgatgg cggtattcac      300
gacatcgtca attgggctct gcacggctac gcaactttcg gcatgctggt ccgtggccag      360
ggtggcagcg aagataccag cgtcactcca ggcggccatg cactgggttg gatgaccaaa      420
ggtattctga gcaaagacac ctactactac cgcggcgtct acctggatgc ggtacgtgct      480
ctggaagtca ttcagtcttt cccggaagtc gacgaacacc gtatcggtgt aattggtggc      540
tctcagggtg gcgccctggc catcgcggca gcggcactgt ccgatatccc gaaggtggtg      600
gtggcggatt acccgtacct gtctaacttc gaacgtgcgg ttgacgtggc tctggaacag      660
ccgtacctgg agatcaactc ttacttccgc cgtaacagcg atccgaaagt ggaggagaaa      720
gcgttcgaaa ccctgagcta cttcgatctg atcaacctgg caggctgggt gaaacagccg      780
actctgatgg ctattggtct gatcgataag atcaccccgc catccactgt cttcgcggct      840
tacaaccacc tggaaactga taagatctg aaagtatacc gttacttcgg ccacgagttt      900
atccctgcat ccagaccga gaaactgtct ttcctgcaaa agcacctgct gctgtccacc      960
taa                                                                    963
```

```
<210> SEQ ID NO 49
<211> LENGTH: 182
<212> TYPE: PRT
<213> ORGANISM: Bacillus subtilis

<400> SEQUENCE: 49
```

Arg Gly Gln Gln Ser Ser Glu Asp Thr Ser Ile Ser Leu His Gly His
1               5                   10                  15

Ala Leu Gly Trp Met Thr Lys Gly Ile Leu Asp Lys Asp Thr Tyr Tyr
            20                  25                  30

Tyr Arg Gly Val Tyr Leu Asp Ala Val Arg Ala Leu Glu Val Ile Ser
        35                  40                  45

Ser Phe Asp Glu Val Asp Glu Thr Arg Ile Gly Val Thr Gly Gly Ser
    50                  55                  60

Gln Gly Gly Gly Leu Thr Ile Ala Ala Ala Ala Leu Ser Asp Ile Pro
65                  70                  75                  80

Lys Ala Ala Val Ala Asp Tyr Pro Tyr Leu Ser Asn Phe Glu Arg Ala
                85                  90                  95

Ile Asp Val Ala Leu Glu Gln Pro Tyr Leu Glu Ile Asn Ser Phe Phe
            100                 105                 110

Arg Arg Asn Gly Ser Pro Glu Thr Glu Val Gln Ala Met Lys Thr Leu
        115                 120                 125

Ser Tyr Phe Asp Ile Met Asn Leu Ala Asp Arg Val Lys Val Pro Val
    130                 135                 140

Leu Met Ser Ile Gly Leu Ile Asp Lys Val Thr Pro Pro Ser Thr Val
145                 150                 155                 160

Phe Ala Ala Tyr Asn His Leu Glu Thr Glu Lys Glu Leu Lys Val Tyr
                165                 170                 175

Arg Tyr Phe Gly His Glu
            180

```
<210> SEQ ID NO 50
<211> LENGTH: 988
<212> TYPE: DNA
<213> ORGANISM: Artificial Sequence
<220> FEATURE:
<223> OTHER INFORMATION: PCR amplification product
```

```
<400> SEQUENCE: 50
taactgcagt aaggaggaat aggacatgcc tctggttgat atgcctctgc gtgaactgct      60
ggcttatgaa ggcatcaacc caaaacctgc tgacttcgat cagtattgga accgcgctaa     120
aaccgaaatt gaggctatcg atcctgaagt aactctggta gagtcctcct tccagtgctc     180
cttcgctaac tgctaccatt tctattatcg ttccgcgggc aacgctaaaa tccacgcgaa     240
gtacgtacag ccaaaagcgg gtgaaaaaac tccggcagtc ttcatgtttc acggctacgg     300
tggtcgttcc gctgaatggt cctctctgct gaactacgtt gctgctggtt tcagcgtctt     360
ctacatggat gttcgtggcc agggcggtac ctccgaggac ccgggtggcg tacgtggtaa     420
cacctatcgt ggtcatatca tccgtggcct ggacgcgggt ccggatgcgc tgttctaccg     480
ttccgtgttc ctggacacgg tacagctggt gcgcgctgca aaaaccctgc cgcacattga     540
caagacccgt ctgatggcca ccggctggag ccagggtggc gcactgactc tggcgtgtgc     600
agcgctggta ccggaaatca aacgtctggc gccggtctac ccgttcctgt ctgactacaa     660
acgcgtatgg cagatggacc tggctgttcg ttcctacaaa gaactggcgg actatttccg     720
ctcctatgat ccgcagcata acgccacgtg aaattttc gaacgcctgg gttatatcga      780
cgttcagcac ctggctgatc gtattcaggg cgacgttctg atgggtgtgg cctgatgga     840
caccgaatgc cgccgagca cccaattttgc ggcgtacaac aagattaaag ctaagaaaag      900
ctacgaactg tacccggact ttggtcatga gcatctgcct ggtatgaacg atcacatctt     960
ccgcttcttc acctcctaat ctagatca                                       988

<210> SEQ ID NO 51
<211> LENGTH: 951
<212> TYPE: DNA
<213> ORGANISM: Artificial Sequence
<220> FEATURE:
<223> OTHER INFORMATION: Synthetic gene - codon optimized

<400> SEQUENCE: 51
atgcctctgg ttgatatgcc tctgcgtgaa ctgctggctt atgaaggcat caacccaaaa      60
cctgctgact tcgatcagta ttggaaccgc gctaaaaccg aaattgaggc tatcgatcct     120
gaagtaactc tggtagagtc ctccttccag tgctccttcg ctaactgcta ccatttctat     180
tatcgttccg cgggcaacgc taaaatccac gcgaagtacg tacagccaaa agcgggtgaa     240
aaaactccgg cagtcttcat gtttcacggc tacggtggtc gttccgctga atggtcctct     300
ctgctgaact acgttgctgc tggtttcagc gtcttctaca tggatgttcg tggccagggc     360
ggtacctccg aggacccggg tggcgtacgt ggtaacacct atcgtggtca tatcatccgt     420
ggcctggacg cgggtccgga tgcgctgttc taccgttccg tgttcctgga cacggtacag     480
ctggtgcgcg ctgcaaaaac cctgccgcac attgacaaga cccgtctgat ggccaccggc     540
tggagccagg gtggcgcact gactctggcg tgtgcagcgc tggtaccgga aatcaaacgt     600
ctggcgccgg tctacccgtt cctgtctgac tacaaacgcg tatggcagat ggacctggct     660
gttcgttcct acaaagaact ggcggactat ttccgctcct atgatccgca gcataaacgc     720
cacggtgaaa ttttcgaacg cctgggttat atcgacgttc agcacctggc tgatcgtatt     780
cagggcgacg ttctgatggg tgtgggcctg atggacaccg aatgccgcc gagcacccaa      840
tttgcggcgt acaacaagat taaagctaag aaaagctacg aactgtaccc ggactttggt     900
catgagcatc tgcctggtat gaacgatcac atcttccgct tcttcacctc c               951
```

-continued

```
<210> SEQ ID NO 52
<211> LENGTH: 997
<212> TYPE: DNA
<213> ORGANISM: Artificial Sequence
<220> FEATURE:
<223> OTHER INFORMATION: PCR amplification product

<400> SEQUENCE: 52
taactgcagt aaggaggaat aggacatggg tctgttcgat atgccactgc aaaaactgcg      60
tgaatatacc ggtaccaacc catgtcctga ggatttcgat gaatactggg atcgcgcact     120
ggacgaaatg cgtagcgttg atcctaaaat caagatgaag aagagctcct ttcaagttcc     180
gttcgcggaa tgttacgatc tgtattttac cggcgttcgt ggtgcccgca ttcacgcgaa     240
atacattcgt ccgaaaaccg aaggcaaaca cccggcgctg attcgcttcc atggttactc     300
cagcaactct ggtgattgga acgacaagct gaactacgtt gcggctggtt ttaccgtagt     360
agcgatggac gctcgtggcc agggtggcca atctcaggac gtcggcggtg ttaatggcaa     420
caccctgaac ggtcacatca tccgtggcct ggacgatgat gcagataaca tgctgttccg     480
tcatattttc ctggacaccg cgcagctggc tggtatcgtt atgaacatgc cggaaatcga     540
tgaggaccgc gtagctgtta tgggtccgtc ccagggcggc ggtctgtccc tggcgtgtgc     600
ggctctggaa cctaaaatcc gtaaagtagt gtccgaatat ccgttcctga gcgactacaa     660
gcgtgtgtgg gatctggatc tggccaaaaa tgcgtaccaa gaaatcactg actatttccg     720
tctgttcgac ccacgccacg aacgtgagaa cgaggttttt actaaactgg ttacattga     780 cgtaaagaac ctggcgaaac gtatcaaagg tgatgttctg atgtgcgtgg gcctgatgga     840
tcaggtctgc ccgccagcca ccgtatttgc agcatacaac aacatccagt ccaagaagga     900
catcaaagtc tacccggact atggtcacga accgatgcgt ggcttcggtg acctggctat     960
gcagttcatg ctggaactgt attcttaatc tagatca                              997

<210> SEQ ID NO 53
<211> LENGTH: 960
<212> TYPE: DNA
<213> ORGANISM: Artificial Sequence
<220> FEATURE:
<223> OTHER INFORMATION: Synthetic gene - codon optimized

<400> SEQUENCE: 53
atgggtctgt tcgatatgcc actgcaaaaa ctgcgtgaat ataccggtac caacccatgt      60
cctgaggatt tcgatgaata ctgggatcgc gcactggacg aaatgcgtag cgttgatcct     120
aaaatcaaga tgaagaagag ctcctttcaa gttccgttcg cggaatgtta cgatctgtat     180
tttaccggcg ttcgtggtgc ccgcattcac gcgaaataca ttcgtccgaa accgaaggc     240 aaacacccgg cgctgattcg cttccatggt tactccagca actctggtga ttggaacgac     300
aagctgaact acgttgcggc tggttttacc gtagtagcga tggacgctcg tggccagggt     360
ggccaatctc aggacgtcgg cggtgttaat ggcaacaccc tgaacggtca catcatccgt     420
ggcctggacg atgatgcaga taacatgctg ttccgtcata ttttcctgga caccgcgcag     480
ctggctggta tcgttatgaa catgccggaa atcgatgagg accgcgtagc tgttatgggt     540
ccgtcccagg gcggcggtct gtccctggcg tgtgcggctc tggaacctaa aatccgtaaa     600
gtagtgtccg aatatccgtt cctgagcgac tacaagcgtg tgtgggatct ggatctggcc     660
aaaaatgcgt accaagaaat cactgactat ttccgtctgt tcgacccacg ccacgaacgt     720
gagaacgagg ttttttactaa actgggttac attgacgtaa agaacctggc gaaacgtatc     780
aaaggtgatg ttctgatgtg cgtgggcctg atggatcagg tctgcccgcc agcaccgta     840
```

```
tttgcagcat acaacaacat ccagtccaag aaggacatca aagtctaccc ggactatggt    900
cacgaaccga tgcgtggctt cggtgacctg gctatgcagt tcatgctgga actgtattct    960
```

<210> SEQ ID NO 54
<211> LENGTH: 320
<212> TYPE: PRT
<213> ORGANISM: Thermoanaerobacterium saccharolyticum

<400> SEQUENCE: 54

Met Gly Leu Phe Asp Met Pro Leu Gln Lys Leu Arg Glu Tyr Thr Gly
1               5                   10                  15

Thr Asn Pro Cys Pro Glu Asp Phe Asp Glu Tyr Trp Asp Arg Ala Leu
            20                  25                  30

Asp Glu Met Arg Ser Val Asp Pro Lys Ile Lys Met Lys Lys Ser Ser
        35                  40                  45

Phe Gln Val Pro Phe Ala Glu Cys Tyr Asp Leu Tyr Phe Thr Gly Val
    50                  55                  60

Arg Gly Ala Arg Ile His Ala Lys Tyr Ile Arg Pro Lys Thr Glu Gly
65                  70                  75                  80

Lys His Pro Ala Leu Ile Arg Phe His Gly Tyr Ser Ser Asn Ser Gly
                85                  90                  95

Asp Trp Asn Asp Lys Leu Asn Tyr Val Ala Ala Gly Phe Thr Val Val
            100                 105                 110

Ala Met Asp Ala Arg Gly Gln Gly Gly Gln Ser Gln Asp Val Gly Gly
        115                 120                 125

Val Asn Gly Asn Thr Leu Asn Gly His Ile Ile Arg Gly Leu Asp Asp
    130                 135                 140

Asp Ala Asp Asn Met Leu Phe Arg His Ile Phe Leu Asp Thr Ala Gln
145                 150                 155                 160

Leu Ala Gly Ile Val Met Asn Met Pro Glu Ile Asp Glu Asp Arg Val
                165                 170                 175

Ala Val Met Gly Pro Ser Gln Gly Gly Gly Leu Ser Leu Ala Cys Ala
            180                 185                 190

Ala Leu Glu Pro Lys Ile Arg Lys Val Val Ser Glu Tyr Pro Phe Leu
        195                 200                 205

Ser Asp Tyr Lys Arg Val Trp Asp Leu Asp Leu Ala Lys Asn Ala Tyr
    210                 215                 220

Gln Glu Ile Thr Asp Tyr Phe Arg Leu Phe Asp Pro Arg His Glu Arg
225                 230                 235                 240

Glu Asn Glu Val Phe Thr Lys Leu Gly Tyr Ile Asp Val Lys Asn Leu
                245                 250                 255

Ala Lys Arg Ile Lys Gly Asp Val Leu Met Cys Val Gly Leu Met Asp
            260                 265                 270

Gln Val Cys Pro Pro Ser Thr Val Phe Ala Ala Tyr Asn Asn Ile Gln
        275                 280                 285

Ser Lys Lys Asp Ile Lys Val Tyr Pro Asp Tyr Gly His Glu Pro Met
    290                 295                 300

Arg Gly Phe Gly Asp Leu Ala Met Gln Phe Met Leu Glu Leu Tyr Ser
305                 310                 315                 320

<210> SEQ ID NO 55
<211> LENGTH: 1012
<212> TYPE: DNA
<213> ORGANISM: Artificial Sequence
<220> FEATURE:
<223> OTHER INFORMATION: PCR amplification product

<400> SEQUENCE: 55

```
taactgcagt aaggaggaat aggacatggc gttcttcgac ctgcctctgg aagaactgaa    60
gaaataccgt ccagagcgtt acgaagagaa ggacttcgac gagttctggg aggaaactct   120
ggcggagagc gaaaagtttc cgctggaccc agtgttcgag cgtatggaat ctcacctgaa   180
aaccgtggag gcatatgacg ttactttttc tggttaccgt ggccagcgta tcaaaggctg   240
gctgctggtt ccgaaactgg aggaagaaaa actgccgtgc gtagttcagt acatcggtta   300
caacggtggc cgtggctttc gcacgattg gctgttctgg ccgtctatgg ctacatttg    360
cttcgtcatg gatactcgtg gtcagggttc cggctggctg aaaggcgata ctccggatta   420
tccggagggc ccggtagacc gcagtaccc tggcttcatg acgcgtggta ttctggatcc   480
gcgtacctat tactatcgcc gcgttttta cgatgcagtt cgtgccgtag aggccgcggc   540
ttctttccct caggttgacc aggagcgtat tgttatcgct ggtggctccc agggtggcgg   600
catcgccctg gcgtatctg cgctgagcaa gaaagctaag gcactgctgt gtgacgtccc   660
gttcctgtgt cacttccgtc gcgctgttca gctggtagat acccatccgt acgcggagat   720
tactaacttc ctgaaaactc accgcgacaa agaagaaatc gttttccgca ccctgtccta   780
tttcgacggc gttaacttcg cggctcgtgc aaaaattccg gcactgttct ctgttggtct   840
gatgacaac atctgccctc cttctaccgt tttcgcggca taactatt atgcgggtcc     900
gaaagaaatc cgtatctatc cgtacaacaa ccacgaaggc ggtggtagct ttcaggctgt   960
tgaacaagtg aaattcctga agaaactgtt tgagaagggc taatctagat ca          1012
```

<210> SEQ ID NO 56
<211> LENGTH: 975
<212> TYPE: DNA
<213> ORGANISM: Artificial Sequence
<220> FEATURE:
<223> OTHER INFORMATION: Synthetic gene - codon optimized

<400> SEQUENCE: 56

```
atggcgttct tcgacctgcc tctggaagaa ctgaagaaat ccgtccaga gcgttacgaa     60
gagaaggact tcgacgagtt ctgggaggaa actctggcgg agagcgaaaa gtttccgctg   120
gacccagtgt tcgagcgtat ggaatctcac ctgaaaaccg tggaggcata tgacgttact   180
ttttctggtt accgtggcca gcgtatcaaa ggctggctgc tggttccgaa actggaggaa   240
gaaaaactgc cgtgcgtagt tcagtacatc ggttacaacg gtggccgtgg ctttccgcac   300
gattggctgt tctggccgtc tatgggctac atttgcttcg tcatggatac tcgtggtcag   360
ggttccggct ggctgaaagg cgatactccg gattatccgg agggcccggt agacccgcag   420
tacccctggc tcatgacgcg tggtattctg gatccgcgta cctattacta tcgccgcgtt   480
tttaccgatg cagttcgtgc cgtagaggcc gcggcttctt tccctcaggt tgaccaggag   540
cgtattgtta tcgctggtgg ctcccagggt ggcggcatcg ccctggcggt atctgcgctg   600
agcaagaaag ctaaggcact gctgtgtgac gtcccgttcc tgtgtcactt ccgtcgcgct   660
gttcagctgg tagataccca tccgtacgcg gagattacta acttcctgaa aactcaccgc   720
gacaaagaag aaatcgtttt ccgcaccctg tcctatttcg acggcgttaa cttcgcggct   780
cgtgcaaaaa ttccggcact gttctctgtt ggtctgatga caacatctg ccctccttct   840
accgttttcg cggcatataa ctattatgcg ggtccgaaag aaatccgtat ctatccgtac   900
aacaaccacg aaggcggtgg tagctttcag gctgttgaac aagtgaaatt cctgaagaaa   960
ctgtttgaga agggc                                                    975
```

<210> SEQ ID NO 57
<211> LENGTH: 36
<212> TYPE: DNA
<213> ORGANISM: Artificial Sequence
<220> FEATURE:
<223> OTHER INFORMATION: Primer

<400> SEQUENCE: 57

```
tgatctagat tattcgcgca tagaaatggt tttctt                                    36
```

<210> SEQ ID NO 58
<211> LENGTH: 1015
<212> TYPE: DNA
<213> ORGANISM: Artificial Sequence
<220> FEATURE:
<223> OTHER INFORMATION: Synthetic construct

<400> SEQUENCE: 58

```
taactgcagt aaggaggaat aggacatggt ttacttcgat atgccactgg aagatctgcg         60
caaatacctg ccgcagcgct acgaagaaaa agactttgac gatttctgga acagacgat         120 tcacgaaacc cgtggttact tccaggagcc gatcctgaag aaagttgatt tctacctgca         180
aaacgttgaa acgttcgatg tgaccttctc tggttaccgt ggtcagaaga tcaaaggctg         240
gctgatcctg cctaaatttc gtaacggcaa actgccatgc gttgttgagt cgtaggtta         300 cggtggcggc cgtggtttcc cgtatgattg gctgctgtgg tccgctgccg gctacgctca         360
cttcatcatg ataccccgcg tcagggttc taactggatg aaaggcgaca cgccagacta         420
tgaggacaac ccgagcgatc cgcagtaccc gggttttctg accaaaggcg tgctgaaccc         480
ggaaacctac tattatcgtc gcgttttcat ggatgctttc atggcggttg aaactatctc         540
tcagctggag cagattgact cccagaccat catcctgtcc ggtgcaagcc agggtggcgg         600
tatcgctctg gccgttagcg ccctgtctag caaagtgatg gccctgctgt gcgatgtacc         660
gttcctgtgc cattataaac gcgcagtaca gattactgat tctatgccgt atgcagaaat         720
cacccgttac tgcaaaacgc acatcgacaa aattcagacc gttttttcgca ccctgtctta         780 ctttgatggc gtaaacttcg cagcccgcgc taagtgcccg gcactgttct ccgttggcct         840
gatggatgat atttgcccgc cgtctacggt attcgccgca taacactact atgcaggcga         900
gaaagatatt cgtatttacc cgtataacaa ccatgaaggc ggtggctctt ccacactct         960 ggagaaactg aagttcgtta agaaaaccat ttctatgcgc gaataatcta gatca             1015
```

<210> SEQ ID NO 59
<211> LENGTH: 981
<212> TYPE: DNA
<213> ORGANISM: Thermotoga lettingae

<400> SEQUENCE: 59

```
atggtctatt ttgatatgcc attggaagat ttgagaaaat atctgccaca gaggtacgaa         60
gaaaaggatt tcgatgattt ctggaaacaa acaatccatg aaacaagggg atattttcaa        120
gaaccaattc tcaaaaaagt ggattttat ttgcagaatt ttgagacttt tgatgtgact         180
ttctctggtt acagaggtca gaagataaaa ggatggttga tttttgccaaa attcagaaat        240 gggaaattac cctgcgtagt tgaatttgtt ggttatggag gaggaagagg atttccatat         300
gactggctgc tttggagtgc ggcaggatac gcacatttca taatggacac gagaggacaa         360
ggtagcaact ggatgaaggg tgatacacca gattatgaag ataatccttc agatccacaa         420
tatccaggct ttctgacaaa aggagtactg aacccggaaa cttattatta caggagagtt         480
```

```
tttatggatg catttatggc tgttgaaact atcagccaac ttgaacaaat agattcacaa      540
accataatat tatcaggtgc aagccagggt ggtggaatag ctttggctgt gagtgcattg      600
tcttcaaagg tcatggctct actttgtgat gttcccttc tgtgtcatta caaaagagca      660
gttcagataa cagattcaat gccctatgca gaaattacga gatattgcaa aactcacatt      720
gacaaaatcc aaacagtatt cagaacccctc tcttattttg acggcgtcaa ttttgcagct      780
cgtgcaaaat gccctgcttt gttttcggtg ggactcatgg acgacatttg cccaccttca      840 acagttttg ccgcttacaa ttattacgct ggtgagaaag atattagaat ttacccatac       900
aacaaccatg aaggcggtgg ttccttccat acactggaaa aattgaaatt tgtgaaaaaa      960
acaatttcta tgagagagtg a                                                981
```

<210> SEQ ID NO 60
<211> LENGTH: 326
<212> TYPE: PRT
<213> ORGANISM: Thermotoga lettingae
<400> SEQUENCE: 60

```
Met Val Tyr Phe Asp Met Pro Leu Glu Asp Leu Arg Lys Tyr Leu Pro
1               5                   10                  15

Gln Arg Tyr Glu Glu Lys Asp Phe Asp Asp Phe Trp Lys Gln Thr Ile
            20                  25                  30

His Glu Thr Arg Gly Tyr Phe Gln Glu Pro Ile Leu Lys Lys Val Asp
        35                  40                  45

Phe Tyr Leu Gln Asn Val Glu Thr Phe Asp Val Thr Phe Ser Gly Tyr
    50                  55                  60

Arg Gly Gln Lys Ile Lys Gly Trp Leu Ile Leu Pro Lys Phe Arg Asn
65                  70                  75                  80

Gly Lys Leu Pro Cys Val Val Glu Phe Val Gly Tyr Gly Gly Arg
                85                  90                  95

Gly Phe Pro Tyr Asp Trp Leu Leu Trp Ser Ala Ala Gly Tyr Ala His
            100                 105                 110

Phe Ile Met Asp Thr Arg Gly Gln Gly Ser Asn Trp Met Lys Gly Asp
        115                 120                 125

Thr Pro Asp Tyr Glu Asp Asn Pro Ser Asp Pro Gln Tyr Pro Gly Phe
    130                 135                 140

Leu Thr Lys Gly Val Leu Asn Pro Glu Thr Tyr Tyr Arg Arg Val
145                 150                 155                 160

Phe Met Asp Ala Phe Met Ala Val Glu Thr Ile Ser Gln Leu Glu Gln
                165                 170                 175

Ile Asp Ser Gln Thr Ile Ile Leu Ser Gly Ala Ser Gln Gly Gly Gly
            180                 185                 190

Ile Ala Leu Ala Val Ser Ala Leu Ser Ser Lys Val Met Ala Leu Leu
        195                 200                 205

Cys Asp Val Pro Phe Leu Cys His Tyr Lys Arg Ala Val Gln Ile Thr
    210                 215                 220

Asp Ser Met Pro Tyr Ala Glu Ile Thr Arg Tyr Cys Lys Thr His Ile
225                 230                 235                 240

Asp Lys Ile Gln Thr Val Phe Arg Thr Leu Ser Tyr Phe Asp Gly Val
                245                 250                 255

Asn Phe Ala Ala Arg Ala Lys Cys Pro Ala Leu Phe Ser Val Gly Leu
            260                 265                 270

Met Asp Asp Ile Cys Pro Pro Ser Thr Val Phe Ala Ala Tyr Asn Tyr
        275                 280                 285
```

Tyr Ala Gly Glu Lys Asp Ile Arg Ile Tyr Pro Tyr Asn Asn His Glu
    290                 295                 300

Gly Gly Gly Ser Phe His Thr Leu Glu Lys Leu Lys Phe Val Lys Lys
305                 310                 315                 320

Thr Ile Ser Met Arg Glu
            325

<210> SEQ ID NO 61
<211> LENGTH: 978
<212> TYPE: DNA
<213> ORGANISM: Artificial Sequence
<220> FEATURE:
<223> OTHER INFORMATION: Synthetic construct

<400> SEQUENCE: 61

```
atggcattct tcgacctgcc gctggaggaa ctgaaaaagt atcgcccgga gcgttacgaa      60
gaaaaggatt tcgatgagtt ctgggaaggc accctggccg agaacgaaaa attccctctg     120
gatccggtct tcgaacgtat ggaaagccat ctgaaaaccg tagaggctta cgacgtgacc     180
ttcagcggtt acatgggcca gcgtatcaaa ggctggctgc tggtcccgaa actggaggag     240
gagaaactgc cgtgcgttgt tcagtacatc ggctacaacg gcggtcgcgg tttcccgcac     300
gattggctgt tctggccgtc tatgggttac atctgctttg ttatggacac ccgtggccag     360
ggtagcggtt ggatgaaggg tgacaccccg gactatccgg aggacccggt agacccgcag     420
tacccaggct ttatgacccg cggcattctg gacccgcgca cttactacta ccgtcgcgtt     480
tttaccgatg ctgttcgcgc agtggaggca gccgcgtcct ttccacgcgt agaccacgaa     540
cgtatcgtaa tcgcaggcgg ctcccagggt ggcggcatcg cgctggcggt ttccgcactg     600
agcaaaaagg ccaaagcgct gctgtgcgat gtgccgttcc tgtgtcactt ccgtcgtgcg     660
gttcagctgg tagataccca cccgtacgct gagatcacca ctttctgaa gacgcatcgt      720
gataaagagg aaatcgtatt tcgtacgctg tcctatttcg atggtgtgaa ctttgcggta     780
cgtgcaaaga tcccggccct gttctctgtt ggtctgatgg acaacatttg cccgccgagc     840
actgtctttg cagcgtacaa ccactatgcg ggcccaaaag aaattcgcat ctacccatac     900
aacaaccacg aaggcggcgg ttccttccag gcaatcgaac aggtcaaatt cctgaaacgt     960
ctgttcgaga aaggttaa                                                   978
```

<210> SEQ ID NO 62
<211> LENGTH: 1012
<212> TYPE: DNA
<213> ORGANISM: Artificial Sequence
<220> FEATURE:
<223> OTHER INFORMATION: Synthetic construct

<400> SEQUENCE: 62

```
taactgcagt aaggaggaat aggacatggc attcttcgac ctgccgctgg aggaactgaa      60
aaagtatcgc ccggagcgtt acgaagaaaa ggatttcgat gagttctggg aaggcaccct     120
ggccgagaac gaaaaattcc ctctggatcc ggtcttcgaa cgtatggaaa gccatctgaa     180
aaccgtagag gcttacgacg tgaccttcag cggttacatg ggccagcgta tcaaaggctg     240
gctgctggtc ccgaaactgg aggaggagaa actgccgtgc gttgttcagt acatcggcta     300
caacggcggt cgcggttttcc gcacgattg gctgttctgg ccgtctatgg gttacatctg     360
ctttgttatg gacacccgtg gccagggtag cggttggatg aagggtgaca ccccggacta     420
tccggaggac ccggtagacc cgcagtaccc aggctttatg acccgcggca ttctggaccc     480
```

```
gcgcacttac tactaccgtc gcgtttttac cgatgctgtt cgcgcagtgg aggcagccgc      540
gtcctttcca cgcgtagacc acgaacgtat cgtaatcgca ggcggctccc agggtggcgg      600
catcgcgctg gcggtttccg cactgagcaa aaaggccaaa gcgctgctgt gcgatgtgcc      660
gttcctgtgt cacttccgtc gtgcggttca gctggtagat acccacccgt acgctgagat      720
caccaacttt ctgaagacgc atcgtgataa agaggaaatc gtatttcgta cgctgtccta      780
tttcgatggt gtgaactttg cggtacgtgc aaagatcccg gccctgttct ctgttggtct      840
gatggacaac atttgcccgc gagcactgt ctttgcagcg tacaaccact atgcgggccc      900
aaaagaaatt cgcatctacc catacaacaa ccacgaaggc ggcggttcct tccaggcaat      960
cgaacaggtc aaattcctga acgtctgtt cgagaaaggt taatctagat ca              1012

<210> SEQ ID NO 63
<211> LENGTH: 978
<212> TYPE: DNA
<213> ORGANISM: Thermotoga petrophila

<400> SEQUENCE: 63
atggcctttt tcgatttacc actcgaagaa ctgaagaaat atcgtccaga gcggtacgaa       60
gagaaagact tcgatgagtt ctgggaaggg acactcgcag agaacgaaaa gttcccctta      120
gaccccgtct tcgagaggat ggagtctcac ctcaaaacag tcgaagcgta cgatgtaact      180
ttctccggat acatgggaca gaggatcaag gggtggctcc ttgttccaaa actggaagaa      240
gaaaaacttc cctgcgttgt gcagtacata ggatacaacg gtggaagagg attccctcac      300
gactggctgt tctggccttc tatgggttac atatgtttcg tcatggatac tcgaggacag      360
ggaagcggct ggatgaaagg agatacaccg gattaccctg aggatcccgt tgaccctcag      420
tatccaggat tcatgacaag aggaatactg gatcccagaa cttactacta cagacgagtc      480
ttcacggacg ctgtcagagc cgttgaagcc gctgcttctt ttcctcgggt agatcacgaa      540
agaatcgtga tagctggagg cagtcagggt ggcggaatag cccttgcggt gagcgctctc      600
tcaaagaaag caaaggctct tctgtgcgat gtgccgtttc tgtgtcactt cagaagggca      660
gtgcagcttg tggatacgca tccatacgcg gagatcacga acttctaaa gacccacagg      720 gacaaggaag aaatcgtgtt caggactctt tcctatttcg atggagtgaa cttcgcagtc      780
agagcgaaga tccctgcgct gttttctgtg gtctcatgg acaacatttg tcctccttca      840 acggttttg ctgcctacaa tcactacgct gggccgaagg aaatcagaat ctatccgtac      900
aacaaccacg agggaggagg ctcttttccag gcaattgaac aggtgaaatt cttgaagaga      960
ctatttgaga aaggctag                                                    978

<210> SEQ ID NO 64
<211> LENGTH: 325
<212> TYPE: PRT
<213> ORGANISM: Thermotoga petrophila

<400> SEQUENCE: 64

Met Ala Phe Phe Asp Leu Pro Leu Glu Glu Leu Lys Lys Tyr Arg Pro
 1               5                  10                  15

Glu Arg Tyr Glu Glu Lys Asp Phe Asp Glu Phe Trp Glu Gly Thr Leu
             20                  25                  30

Ala Glu Asn Glu Lys Phe Pro Leu Asp Pro Val Phe Glu Arg Met Glu
         35                  40                  45

Ser His Leu Lys Thr Val Glu Ala Tyr Asp Val Thr Phe Ser Gly Tyr
     50                  55                  60
```

```
Met Gly Gln Arg Ile Lys Gly Trp Leu Leu Val Pro Lys Leu Glu Glu
 65                  70                  75                  80
Glu Lys Leu Pro Cys Val Val Gln Tyr Ile Gly Tyr Asn Gly Gly Arg
             85                  90                  95
Gly Phe Pro His Asp Trp Leu Phe Trp Pro Ser Met Gly Tyr Ile Cys
            100                 105                 110
Phe Val Met Asp Thr Arg Gly Gln Gly Ser Gly Trp Met Lys Gly Asp
        115                 120                 125
Thr Pro Asp Tyr Pro Glu Asp Pro Val Asp Pro Gln Tyr Pro Gly Phe
130                 135                 140
Met Thr Arg Gly Ile Leu Asp Pro Arg Thr Tyr Tyr Tyr Arg Arg Val
145                 150                 155                 160
Phe Thr Asp Ala Val Arg Ala Val Glu Ala Ala Ser Phe Pro Arg
                165                 170                 175
Val Asp His Glu Arg Ile Val Ile Ala Gly Gly Ser Gln Gly Gly
            180                 185                 190
Ile Ala Leu Ala Val Ser Ala Leu Ser Lys Lys Ala Lys Ala Leu Leu
        195                 200                 205
Cys Asp Val Pro Phe Leu Cys His Phe Arg Arg Ala Val Gln Leu Val
210                 215                 220
Asp Thr His Pro Tyr Ala Glu Ile Thr Asn Phe Leu Lys Thr His Arg
225                 230                 235                 240
Asp Lys Glu Glu Ile Val Phe Arg Thr Leu Ser Tyr Phe Asp Gly Val
                245                 250                 255
Asn Phe Ala Val Arg Ala Lys Ile Pro Ala Leu Phe Ser Val Gly Leu
            260                 265                 270
Met Asp Asn Ile Cys Pro Pro Ser Thr Val Phe Ala Ala Tyr Asn His
        275                 280                 285
Tyr Ala Gly Pro Lys Glu Ile Arg Ile Tyr Pro Tyr Asn Asn His Glu
290                 295                 300
Gly Gly Gly Ser Phe Gln Ala Ile Glu Gln Val Lys Phe Leu Lys Arg
305                 310                 315                 320
Leu Phe Glu Lys Gly
                325

<210> SEQ ID NO 65
<211> LENGTH: 978
<212> TYPE: DNA
<213> ORGANISM: Artificial Sequence
<220> FEATURE:
<223> OTHER INFORMATION: Synthetic construct

<400> SEQUENCE: 65
atggcgttct tgatctgcc tctggaagaa ctgaagaaat accgtccaga acgctatgaa      60
gaaaaggatt ttgatgaatt ttggaaagaa actctggctg aatctgaaaa gttcccgctg     120
gatccggttt tcgaacgtat ggaatctcac ctgaagactt tgaggtttta cgatgtgact     180
tttagcggct atcgtggcca gcgtatcaaa ggctggctgc tggtgccgaa actggaggag     240
gagaaactgc cgtgtgtcgt tcaatacatt ggttataatg gtggccgcgg tttcccgcat     300
gattggctgt tctggccgtc catgggctat atctgctttg taatggacac ccgtggccag     360
ggctccggtt ggctgaaagg tgataccccg gactacccgg aggacccggt tgatccgcag     420
tatccgggtt ttatgacccg cggtatcctg gaccctcgta cttactatta ccgtcgcgta     480
ttcaccgatg cagtgcgcgc tgttgaggcg gcagcaagct cccgcgcgt cgaccacgag     540 cgtatcgtta tcgcgggtgg ttctcaaggc ggtggcattg ccctggcggt gtccgcgctg     600
```

```
agcaagaaag cgaaagcgct gctgtgcgac gttccattcc tgtgtcactt ccgccgtgct    660
gttcagctgg ttgatactca cccatacgct gaaatcacta acttcctgaa aactcaccgt    720
gacaaggaag agattgtatt ccgtactctg tcctacttcg acggtgtgaa cttcgcggtt    780
cgtgcaaaga tcccagccct gttttctgtg ggtctgatgg ataacatctg cccgccgagc    840 acggttttg ctgcgtacaa ccactatgct ggtccaaaag aaatccgtat ctatccgtac    900
aacaatcacg agggcggtgg ttctttccag gcgattgagc aggtgaagtt cctgaaacgt    960
ctgttcgaga aaggctaa                                                  978

<210> SEQ ID NO 66
<211> LENGTH: 1012
<212> TYPE: DNA
<213> ORGANISM: Artificial Sequence
<220> FEATURE:
<223> OTHER INFORMATION: Synthetic construct

<400> SEQUENCE: 66
taactgcagt aaggaggaat aggacatggc gttctttgat ctgcctctgg aagaactgaa     60
gaaataccgt ccagaacgct atgaagaaaa ggatttgat gaattttgga agaaactct     120 ggctgaatct gaaagttcc cgctggatcc ggttttcgaa cgtatggaat ctcacctgaa    180
gactgttgag gttacgatg tgacttttag cggctatcgt ggccagcgta tcaaaggctg    240
gctgctggtg ccgaaactgg aggaggagaa actgccgtgt gtcgttcaat acattggtta    300
taatggtggc gcggtttcc cgcatgattg gctgttctgg ccgtccatgg ctatatctg     360 ctttgtaatg gacacccgtg gccagggctc cggttggctg aaaggtgata ccccggacta    420 ccggaggac ccgttgatc cgcagtatcc gggttttatg acccgcggta tcctggaccc    480
tcgtacttac tattaccgtc gcgtattcac cgatgcagtg cgcgctgttg aggcggcagc    540
aagcttcccg cgcgtcgacc acgagcgtat cgttatcgcg ggtggttctc aaggcggtgg    600
cattgccctg gcggtgtccg cgctgagcaa gaaagcgaaa gcgctgctgt gcgacgttcc    660
attcctgtgt cacttccgcc gtgctgttca gctggttgat actcacccat acgctgaaat    720
cactaacttc ctgaaaactc accgtgacaa ggaagagatt gtattccgta ctctgtccta    780
cttcgacggt gtgaacttcg cggttcgtgc aaagatccca gccctgtttt ctgtgggtct    840
gatggataac atctgcccgc cgagcacggt ttttgctgcg tacaaccact atgctggtcc    900
aaaagaaatc cgtatctatc cgtacaacaa tcacgagggc ggtggttctt tccaggcgat    960
tgagcaggtg aagttcctga acgtctgtt cgagaaaggc taatctagat ca           1012

<210> SEQ ID NO 67
<211> LENGTH: 978
<212> TYPE: DNA
<213> ORGANISM: Thermotoga sp.

<400> SEQUENCE: 67 atggccttt tcgatttacc actcgaagaa ctgaagaaat accgtccgga gcggtacgaa     60
gagaaagact tcgatgagtt ctggaaagaa acactcgcag agagcgaaaa gtttccctg    120 gaccccgtct tcgagaggat ggagtctcac ctcaaaacgg tcgaagtgta cgatgtcacc    180
ttctccggat acagaggaca gaggatcaag gggtggctcc ttgttccaaa attggaagaa    240
gaaaaacttc cctgcgttgt gcagtacata ggatacaacg gtggaagagg attccctcac    300
gactggctgt tctggccttc tatgggttac atatgtttcg tcatggatac tcgaggacag    360
ggaagcggct ggctgaaagg agatacaccg gattaccctg aggatcccgt tgaccctcag    420
```

```
tatccaggat tcatgacaag aggaatactg gatcccagaa cttactacta cagacgagtc    480
ttcacggacg ctgtcagagc cgttgaagcc gctgcttctt ttcctcgggt agatcacgaa    540
agaatcgtga tagctggagg cagtcagggt ggcggaatag cccttgcggt gagcgctctc    600
tcaaagaaag caaaggctct tctgtgcgat gtgccgtttc tgtgtcactt cagaagggca    660
gtgcagcttg tggatacgca tccatacgcg gagatcacga actttctaaa gactcacagg    720
gacaaggaag aaatcgtgtt caggactctt tcctatttcg atggagtgaa cttcgcagtc    780
agagcgaaga tccctgcgct gttttctgtg gtctcatgg acaacatttg tcctccttca    840 acggttttg ctgcctacaa tcactacgct gggccgaagg aaatcagaat ctatccgtac    900
aacaaccacg agggaggagg ctctttccag gcaattgaac aggtgaaatt cttgaagaga    960
ctatttgaga aaggctag                                                 978
```

```
<210> SEQ ID NO 68
<211> LENGTH: 325
<212> TYPE: PRT
<213> ORGANISM: Thermotoga sp.

<400> SEQUENCE: 68

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Lys Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Val Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Asp Pro Val Asp Pro Gln Tyr Pro Gly Phe
    130                 135                 140

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Arg
                165                 170                 175

Val Asp His Glu Arg Ile Val Ile Ala Gly Gly Ser Gln Gly Gly Gly
            180                 185                 190

Ile Ala Leu Ala Val Ser Ala Leu Ser Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Val Arg Ala Lys Ile Pro Ala Leu Phe Ser Val Gly Leu
            260                 265                 270
```

```
Met Asp Asn Ile Cys Pro Pro Ser Thr Val Phe Ala Ala Tyr Asn His
        275                 280                 285

Tyr Ala Gly Pro Lys Glu Ile Arg Ile Tyr Pro Tyr Asn Asn His Glu
        290                 295                 300

Gly Gly Gly Ser Phe Gln Ala Ile Glu Gln Val Lys Phe Leu Lys Arg
305                 310                 315                 320

Leu Phe Glu Lys Gly
            325

<210> SEQ ID NO 69
<211> LENGTH: 990
<212> TYPE: DNA
<213> ORGANISM: Artificial Sequence
<220> FEATURE:
<223> OTHER INFORMATION: Synthetic construct

<400> SEQUENCE: 69
atggctctgt tcgatatgcc gctggaaaaa ctgcgctctt atctgccgga tcgctatgag      60
gaggaagact ttgatctgtt ctggaaagaa accctggagg agtctcgtaa gttcccgctg     120
gatccaatct tcgaacgcgt agattacctg ctggagaacg tagaggttta cgacgtgacc     180
ttttccggct atcgtggcca gcgtatcaaa gcctggctga ttctgccggt tgttaaaaag     240
gaggagcgcc tgccgtgcat cgtcgagttc atcggctacc gcgtggtcg cggcttcccg      300 ttcgattggc tgttctggtc tagcgcgggc tatgctcact tcgttatgga tactcgcggc     360
cagggcacta gccgtgtcaa gggcgatacc ccggattact gcgatgagcc gatcaacccg     420
cagttcccgg gtttcatgac ccgtggcatc ctggacccac gcacgtacta ctatcgtcgt     480
gttttcaccg acgctgtgcg cgcagttgag accgctagca gctttccggg catcgatccg     540
gaacgtattg ctgttgttgg cacctcccag ggtggtggta tcgctctggc ggtagctgct     600
ctgtctgaaa ttccgaaagc actggttttct aacgtcccat tcctgtgcca ttttcgtcgt     660
gcggttcaga tcaccgataa tgctccgtac agcgaaatcg tgaactacct gaaagttcac     720
cgcgataaag aagagatcgt tttccgcacc ctgtcttact ttgatggcgt gaatttcgcg     780
gctcgcgcaa agattccagc gctgttttct gttgccctga tggataaaac ctgtccgccg     840
tccaccgttt cgctgcgta taaccattac gcgggtccga agaaatcaa agtttatccg       900 ttcaatgagc acgaaggcgg tgaatccttt cagcgtatgg aggagctgcg ttttatgaag     960
cgcatcctga aggcgaatt taaggcgtaa                                        990

<210> SEQ ID NO 70
<211> LENGTH: 1027
<212> TYPE: DNA
<213> ORGANISM: Artificial Sequence
<220> FEATURE:
<223> OTHER INFORMATION: Synthetic construct

<400> SEQUENCE: 70
ttactgcagc agtccggagg aataggacat ggctctgttc gatatgccgc tggaaaaact      60
gcgctcttat ctgccggatc gctatgagga ggaagacttt gatctgttct ggaaagaaac     120
cctggaggag tctcgtaagt tcccgctgga tccaatcttc gaacgcgtag attacctgct     180
ggagaacgta gaggtttacg acgtgacctt ttccggctat cgtggccagc gtatcaaagc     240
ctggctgatt ctgccggttg ttaaaaagga ggagcgcctg ccgtgcatcg tcgagttcat     300
cggctaccgc ggtggtcgcg gcttcccgtt cgattggctg ttctggtcta gcgcgggcta     360
tgctcacttc gttatggata ctcgcggcca gggcactagc cgtgtcaagg gcgataccc      420
```

```
ggattactgc gatgagccga tcaacccgca gttcccgggt tcatgaccc gtggcatcct      480 ggacccacgc acgtactact atcgtcgtgt tttcaccgac gctgtgcgcg cagttgagac      540
cgctagcagc tttccgggca tcgatccgga acgtattgct gttgttggca cctcccaggg      600
tggtggtatc gctctggcgg tagctgctct gtctgaaatt ccgaaagcac tggtttctaa      660
cgtcccattc ctgtgccatt tcgtcgtgc ggttcagatc accgataatg ctccgtacag      720
cgaaatcgtg aactacctga agttcaccg cgataaagaa gagatcgttt ccgcaccct       780 gtcttacttt gatggcgtga atttcgcggc tcgcgcaaag attccagcgc tgttttctgt      840
tgccctgatg gataaaacct gtccgccgtc accgttttc gctgcgtata accattacgc      900
gggtccgaaa gaaatcaaag tttatccgtt caatgagcac gaaggcggtg aatcctttca      960
gcgtatggag gagctgcgtt ttatgaagcg catcctgaaa ggcgaattta aggcgtaatc     1020
tagatca                                                              1027
```

<210> SEQ ID NO 71
<211> LENGTH: 990
<212> TYPE: DNA
<213> ORGANISM: Thermotoga sp.

<400> SEQUENCE: 71

```
atggcgctat ttgatatgcc tctggaaaag ttaagatcat accttcccga tagatacgag       60
gaggaagatt ttgatctgtt ctggaaagag actcttgagg agtcaagaaa attcccactg      120
gatcctattt ttgaaagagt agattatctg ctggagaacg tggaagtata cgatgtcacc      180
ttctccggtt acaggggtca agaataaag gcgtggttga ttctaccggt tgttaagaag      240
gaagaaaggc ttccctgcat cgttgaattc ataggttaca ggggaggaag aggttttccc      300
ttcgattggc tcttctggag cagtgcgggg tatgcccatt tcgtgatgga cactcgcggc      360
cagggaacca gtagagtaaa gggtgatact cctgactact gtgatgaacc cataaatcct      420
caattccccg gattcatgac gcggggaata ctggatccca ggacttacta ttacagaaga      480
gtttttaccg atgctgtaag agcagtggaa accgcttcga gtttcccggg aatagatccc      540
gaaaggatag ccgtcgtggg aacaagccag ggtgggggaa ttgcattggc ggtggcggcg      600
ctttccgaaa ttccaaaggc tcttgtatcg aatgttccgt ttctgtgtca tttcagaaga      660
gcggttcaga taacagataa cgctccttac agtgagatag tgaattattt gaaagtccac      720
agagacaaag aggaaattgt gttcagaacg cttttcgtact ttgatggagt gaactttgct      780
gcgagggcaa aaataccagc acttttctct gttgctctca tggacaaaac ctgtccacct      840
tctacagttt ttgctgctta caaccattac gctggtccaa agaaatcaa agtgtatcca      900 ttcaacgaac atgaaggtgg agaatctttc cagagaatgg aggaacttcg ctttatgaaa      960
aggattctaa aggggaatt caaagcatga                                        990
```

<210> SEQ ID NO 72
<211> LENGTH: 329
<212> TYPE: PRT
<213> ORGANISM: Thermotoga sp.

<400> SEQUENCE: 72

```
Met Ala Leu Phe Asp Met Pro Leu Glu Lys Leu Arg Ser Tyr Leu Pro
1               5                   10                  15

Asp Arg Tyr Glu Glu Asp Phe Asp Leu Phe Trp Lys Glu Thr Leu
            20                  25                  30

Glu Glu Ser Arg Lys Phe Pro Leu Asp Pro Ile Phe Glu Arg Val Asp
        35                  40                  45
```

Tyr Leu Leu Glu Asn Val Glu Val Tyr Asp Val Thr Phe Ser Gly Tyr
    50                  55                  60

Arg Gly Gln Arg Ile Lys Ala Trp Leu Ile Leu Pro Val Val Lys Lys
65                  70                  75                  80

Glu Glu Arg Leu Pro Cys Ile Val Glu Phe Ile Gly Tyr Arg Gly Gly
                85                  90                  95

Arg Gly Phe Pro Phe Asp Trp Leu Phe Trp Ser Ser Ala Gly Tyr Ala
                100                 105                 110

His Phe Val Met Asp Thr Arg Gly Gln Gly Thr Ser Arg Val Lys Gly
                115                 120                 125

Asp Thr Pro Asp Tyr Cys Asp Glu Pro Ile Asn Pro Gln Phe Pro Gly
            130                 135                 140

Phe Met Thr Arg Gly Ile Leu Asp Pro Arg Thr Tyr Tyr Tyr Arg Arg
145                 150                 155                 160

Val Phe Thr Asp Ala Val Arg Ala Val Glu Thr Ala Ser Ser Phe Pro
                165                 170                 175

Gly Ile Asp Pro Glu Arg Ile Ala Val Val Gly Thr Ser Gln Gly Gly
                180                 185                 190

Gly Ile Ala Leu Ala Val Ala Ala Leu Ser Glu Ile Pro Lys Ala Leu
            195                 200                 205

Val Ser Asn Val Pro Phe Leu Cys His Phe Arg Arg Ala Val Gln Ile
    210                 215                 220

Thr Asp Asn Ala Pro Tyr Ser Glu Ile Val Asn Tyr Leu Lys Val His
225                 230                 235                 240

Arg Asp Lys Glu Glu Ile Val Phe Arg Thr Leu Ser Tyr Phe Asp Gly
                245                 250                 255

Val Asn Phe Ala Ala Arg Ala Lys Ile Pro Ala Leu Phe Ser Val Ala
                260                 265                 270

Leu Met Asp Lys Thr Cys Pro Pro Ser Thr Val Phe Ala Ala Tyr Asn
            275                 280                 285

His Tyr Ala Gly Pro Lys Glu Ile Lys Val Tyr Pro Phe Asn Glu His
    290                 295                 300

Glu Gly Gly Glu Ser Phe Gln Arg Met Glu Glu Leu Arg Phe Met Lys
305                 310                 315                 320

Arg Ile Leu Lys Gly Glu Phe Lys Ala
                325

<210> SEQ ID NO 73
<211> LENGTH: 325
<212> TYPE: PRT
<213> ORGANISM: Thermotoga neapolitana
<220> FEATURE:
<221> NAME/KEY: MISC_FEATURE
<222> LOCATION: (277)..(277)
<223> OTHER INFORMATION: Xaa is Ala, Val, Ser, or Thr.

<400> SEQUENCE: 73

Met Ala Phe Phe Asp Met Pro Leu Glu Glu Leu Lys Lys Tyr Arg Pro
1               5                   10                  15

Glu Arg Tyr Glu Glu Lys Asp Phe Asp Glu Phe Trp Arg Glu Thr Leu
                20                  25                  30

Lys Glu Ser Glu Gly Phe Pro Leu Asp Pro Val Phe Glu Lys Val Asp
            35                  40                  45

Phe His Leu Lys Thr Val Glu Thr Tyr Asp Val Thr Phe Ser Gly Tyr
    50                  55                  60

Arg Gly Gln Arg Ile Lys Gly Trp Leu Leu Val Pro Lys Leu Ala Glu

```
                65                  70                  75                  80
Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
                100                 105                 110

Phe Val Met Asp Thr Arg Gly Gln Gly Ser Gly Trp Met Lys Gly Asp
                115                 120                 125

Thr Pro Asp Tyr Pro Glu Gly Pro Val Asp Pro Gln Tyr Pro Gly Phe
            130                 135                 140

Met Thr Arg Gly Ile Leu Asp Pro Gly Thr Tyr Tyr Arg Arg Val
145                 150                 155                 160

Phe Val Asp Ala Val Arg Ala Val Glu Ala Ala Ile Ser Phe Pro Arg
                165                 170                 175

Val Asp Ser Arg Lys Val Val Ala Gly Gly Ser Gln Gly Gly
                180                 185                 190

Ile Ala Leu Ala Val Ser Ala Leu Ser Asn Arg Val Lys Ala Leu Leu
                195                 200                 205

Cys Asp Val Pro Phe Leu Cys His Phe Arg Arg Ala Val Gln Leu Val
            210                 215                 220

Asp Thr His Pro Tyr Val Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Val Pro Ala Leu Phe Ser Val Gly Leu
            260                 265                 270

Met Asp Thr Ile Xaa Pro Pro Ser Thr Val Phe Ala Ala Tyr Asn His
            275                 280                 285

Tyr Ala Gly Pro Lys Glu Ile Arg Ile Tyr Pro Tyr Asn Asn His Glu
            290                 295                 300

Gly Gly Gly Ser Phe Gln Ala Ile Glu Gln Val Lys Phe Leu Lys Arg
305                 310                 315                 320

Leu Phe Glu Glu Gly
            325

<210> SEQ ID NO 74
<211> LENGTH: 325
<212> TYPE: PRT
<213> ORGANISM: Thermotoga maritima
<220> FEATURE:
<221> NAME/KEY: MISC_FEATURE
<222> LOCATION: (277)..(277)
<223> OTHER INFORMATION: Xaa is Ala, Val, Ser, or Thr.

<400> SEQUENCE: 74

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
                20                  25                  30

Ala Glu Ser Glu Lys Phe Pro Leu Asp Pro Val Phe Glu Arg Met Glu
            35                  40                  45

Ser His Leu Lys Thr Val Glu Ala Tyr Asp Val Thr Phe Ser Gly Tyr
        50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95
```

-continued

```
Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
        130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
                180                 185                 190

Ile Ala Leu Ala Val Ser Ala Leu Ser Lys Lys Ala Lys Ala Leu Leu
                195                 200                 205

Cys Asp Val Pro Phe Leu Cys His Phe Arg Arg Ala Val Gln Leu Val
        210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
                260                 265                 270

Met Asp Asn Ile Xaa Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
        290                 295                 300

Gly Gly Gly Ser Phe Gln Ala Val Glu Gln Val Lys Phe Leu Lys Lys
305                 310                 315                 320

Leu Phe Glu Lys Gly
                325
```

METHOD FOR PRODUCING PEROXYCARBOXYLIC ACID

CROSS-REFERENCE TO RELATED APPLICATIONS

This application claims the benefit of U.S. Provisional Application Nos. 61/102,505; 61/102,512; 61/102,514; 61/102,520; 61/102,531; and 61/102,539; each filed Oct. 3, 2008, each of which incorporated by reference herein in their entireties.

FIELD OF THE INVENTION

The following relates to the field of enzymatic peracid synthesis and in situ enzyme catalysis using multicomponent systems. Specifically, processes are provided to produce and efficaciously deliver peroxycarboxylic acids using the perhydrolysis activity of enzymes identified structurally as belonging to the CE-7 family of carbohydrate esterases, including cephalosporin acetyl hydrolases (CAHs; E.C. 3.1.1.41) and acetyl xylan esterases (AXEs; E.C. 3.1.1.72) using multi-component systems (i.e., in the present context, systems that involve the production of peroxycarboxylic acid using at least two reaction components that are separately stored prior to a desired time of reaction). At least one peroxycarboxylic acid is produced at sufficient concentrations as to be efficacious for the disinfection or sanitization of surfaces, medical instrument sterilization, food processing equipment sterilization, and suitable for use in laundry care applications such as disinfecting, bleaching, destaining, deodorizing, and sanitizing.

BACKGROUND OF THE INVENTION

Peracid compositions have been reported to be effective antimicrobial agents. Methods to clean, disinfect, and/or sanitize hard surfaces, meat products, living plant tissues, and medical devices against undesirable microbial growth have been described (e.g., U.S. Pat. No. 6,545,047; U.S. Pat. No. 6,183,807; U.S. Pat. No. 6,518,307; U.S. Pat. No. 5,683,724; and U.S. Patent Application Publication No. 2003/0026846). Peracids have also been reported to be useful in preparing bleaching compositions for laundry detergent applications (U.S. Pat. No. 3,974,082; U.S. Pat. No. 5,296,161; and U.S. Pat. No. 5,364,554).

Peroxycarboxylic acids can be prepared by the chemical reaction of a carboxylic acid alkyl ester and a peroxide reagent, such as hydrogen peroxide (see *Organic Peroxides*, Daniel Swern, ed., Vol. 1, pp 313-516; Wiley Interscience, New York, 1971). However, under slightly basic to acidic pH (from about 8 to about 4), the reaction often does not proceed rapidly enough to produce a peroxycarboxylic acid concentration that is suitable for many commercial disinfecting and/or bleaching applications.

One way to overcome the disadvantages of chemical peroxycarboxylic acid production is to use an enzyme catalyst having perhydrolysis activity. U.S. patent application Ser. No. 11/638,635 and U.S. Patent Application Publication Nos. 2008/0176783; 2008/0176299; and 2009/0005590 to DiCosimo et al, disclose enzymes structurally classified as members of the CE-7 family of carbohydrate esterases (e.g., cephalosporin C deacetylases [CAHs] and acetyl xylan esterases [AXEs]) that are characterized by significant perhydrolysis activity for converting carboxylic acid esters (in the presence of a suitable source of peroxygen, such as hydrogen peroxide) into peroxycarboxylic acids at concentrations sufficient for use as a disinfectant and/or a bleaching agent. Some members of the CE-7 family of carbohydrate esterases have been demonstrated to have perhydrolytic activity sufficient to produce 4000-5000 ppm peracetic acid from acetyl esters of alcohols, dials, and glycerols in 1 minute and up to 9000 ppm between 5 minutes and 30 minutes once the reaction components were mixed (DiCosimo et al., U.S. 2009/0005590). The enzymatic peracid generation system described by DiCosimo et al. in each of the cited patent application publications may be based on the use of multiple reaction components that remain separated until the peracid solution is needed.

It has been observed that, when using a multi-component system comprising a first enzyme catalyst/substrate component and a second component comprising an aqueous source of peroxygen, the use of one or more substrates that are insoluble or partially insoluble in water after mixing of the two components can result in at least three conditions that interfere with the ability to efficaciously produce and deliver a peroxycarboxylic acid product: first, the viscosity of the enzyme catalyst/substrate constituent can be too high to permit efficient mixing with a second constituent comprising a source of peroxygen, which decreases the rate of production of peroxycarboxylic acid; second, the viscosity of the enzyme catalyst/substrate constituent can be too high to permit certain modes of delivery of a product comprising a mixture of the enzyme catalyst/substrate constituent and the source of peroxygen, such as spraying; third, the dissolution rate of the substrate in the enzyme/substrate component after mixing with a second component comprising a source of peroxygen in aqueous solution is too low to permit a satisfactory rate of production of peroxycarboxylic acid. These problems also become evident in situations where use of a particular ratio of a component comprising an aqueous source of peroxygen to a component comprising an enzyme catalyst/substrate constituent is desired. As such, commercial uses of multi-component systems that involve the storage of the enzyme catalyst having perhydrolysis activity and substrate separately from a source of peroxygen until a desired time of reaction have remained impracticable for some applications.

The problem to be solved is to provide a method to enzymatically produce peracids when using a multi-component generation system characterized by at least one first component comprising a formulation of a carboxylic acid ester substrate and an enzyme catalyst comprising a CE-7 carbohydrate esterase having perhydrolysis activity, wherein the carboxylic acid ester substrate is (1) partially or substantially insoluble in an aqueous matrix, and/or (2) slow to dissolve into an aqueous reaction matrix and/or (3) has a viscosity that does not facilitate easy mixing for some commercial applications (e.g., use of a two compartment spray bottle designed to mix two liquid components having different viscosities and/or solubilities), and additionally characterized by at least one second component comprising an aqueous solution comprising a source of peroxygen (e.g., an aqueous formulation of hydrogen peroxide).

SUMMARY OF THE INVENTION

The problem has been solved by providing a method and a system to enzymatically produce a peracid that incorporates the use of at least one cosolvent in the first component of a two component system, wherein said first component is a substantially non-aqueous formulation of a carboxylic acid ester and at least one enzyme catalyst comprising a CE-7 carbohydrate esterase having perhydrolysis activity, wherein the addition of the at least one cosolvent improves the viscosity of the first component for delivery and mixing in a two component system, allows for the desired adjustment of the volume of the first component so as to enable mixing with the second component with a desired ratio of the two components, and improves the solubility and/or dissolution rate of the first component when combined with an aqueous second component (i.e., an aqueous formulation providing a source of peroxygen) to form an aqueous peracid formulation.

It has been discovered that the inclusion of a cosolvent comprising an organic solvent having a log P of less than about 2, wherein log P is defined as the logarithm of the partition coefficient of a substance between octanol and water, expressed as log P=log [[solute]$_{octanol}$/[solute]$_{water}$], resolves the aforementioned conditions that otherwise interfere with the ability to efficaciously produce and deliver a peroxycarboxylic acid product in a form that can be delivered by means that are conventional to or otherwise suitable in consumer, industrial, and medical contexts. The cosolvent is preferably inert and nonreactive in the formulation and miscible with the carboxylic acid ester substrate, wherein the cosolvent is not a substrate for said enzyme catalyst. The cosolvent is preferably an organic alcohol lacking an enzymatically perhydrolyzable ester group. As used herein, an "alcohol" is molecule comprising at least one hydroxyl moiety. The cosolvent also is preferably soluble at its final concentration following mixing or contacting the components of the multi-component system. However, it has been reported that biocatalysis in organic solvents having the having a log P of less than about 2 often adversely affects enzyme activity (for example, by inactivating the enzyme constituent (see, e.g., C. Laane et al., *Biotechnol. Bioeng.* 30:81-87 (1987) and Cowan, D. A. and Plant, A., *Biocatalysis in Organic Phase Systems.*, Ch. 7 in *Biocatalysis at Extreme Temperatures*, Kelly, R. W. W. and Adams, M., eds., Amer. Chem. Soc. Symposium Series, Oxford University Press, New York, N.Y., pp 86-107 (1992)). As such, the beneficial results provided by the inclusion of a cosolvent comprising an alcohol represent an unexpectedly positive outcome. These and other benefits of the present methods and systems are discussed more fully infra.

In one embodiment, a method for producing a peroxycarboxylic acid is provided comprising
(a) providing a first component comprising:
 (i) a carboxylic acid ester substrate;
 (ii) an enzyme catalyst having perhydrolysis activity, wherein said enzyme catalyst comprises an enzyme having a carbohydrate esterase family 7 (CE-7) signature motif that aligns with SEQ ID NO: 2 using CLUSTALW, said signature motif comprising;
  (1) an RGQ motif at amino acid positions aligning with 118-120 of SEQ ID NO:2;
  (2) a GXSQG motif at amino acid positions aligning with 179-183 of SEQ ID NO:2; and
  (3) an HE motif at amino acid positions aligning with 298-299 of SEQ ID NO:2;
 said enzyme comprising at least 30% amino acid identity to SEQ ID NO: 2; and
 (iii) at least one cosolvent comprising an organic solvent having a log P of less than about 2, wherein log P is defined as the logarithm of the partition coefficient of a substance between octanol and water, expressed as P=[solute]$_{octanol}$/[solute]$_{water}$ and wherein the at least one cosolvent is not a substrate for said enzyme catalyst;
wherein said first component is a substantially non-aqueous mixture of (i)-(iii);
(b) providing a second component comprising a source of peroxygen in water; and
(c) combining said first component and said second component to form an aqueous reaction mixture,
 wherein said cosolvent solubilizes the carboxylic acid ester substrate in the aqueous reaction mixture without substantial loss of perhydrolytic activity of the enzyme catalyst and whereby peroxycarboxylic acid is produced.

In another aspect, a method for disinfecting a surface comprising performing the method above, further comprising the step of applying said aqueous reaction mixture comprising peroxycarboxylic acid to a surface for disinfection or bleaching.

In another aspect, a method for treating an article of clothing is provided comprising performing the method above, further comprising the step of applying said aqueous reaction mixture comprising peroxycarboxylic acid to the article of clothing for bleaching, stain removal, odor reduction, sanitization, disinfection, or a combination thereof.

Another aspect of the invention is a multi-component system for producing a peroxycarboxylic acid comprising
(a) providing a first component comprising:
 (i) a carboxylic acid ester substrate;
 (ii) an enzyme catalyst having perhydrolysis activity, wherein said enzyme catalyst comprises an enzyme having a CE-7 signature motif that aligns with SEQ ID NO: 2 using CLUSTALW, said signature motif comprising;
  (1) an RGQ motif at amino acid positions aligning with 118-120 of SEQ ID NO: 2;
  (2) a GXSQG motif at amino add positions aligning with 179-183 of SEQ ID NO: 2; and
  (3) an HE motif at amino acid positions aligning with 298-299 of SEQ ID NO: 2;
 said enzyme comprising at least 30% amino acid identity to SEQ ID NO: 2; and
 (iii) at least one cosolvent comprising an organic solvent having a log P of less than about 2, wherein log P is defined as the logarithm of the partition coefficient of a substance between octanol and water, expressed as P=[solute]$_{octanol}$/[solute]$_{water}$ and wherein the cosolvent is not a substrate for said enzyme catalyst;
 wherein said first component is a substantially non-aqueous mixture of (i)-(iii); and
(b) providing a second component comprising a source of peroxygen in water;
 wherein said first component and said second component are combined to produce an aqueous reaction mixture comprising a peroxycarboxylic acid and wherein said cosolvent solubilizes the carboxylic acid ester substrate in the aqueous reaction mixture without substantial loss of perhydrolytic activity of the enzyme catalyst.

The design of the multi-component packaging/delivery systems for separating and combining the first and second components described herein will generally depend upon the physical form of the individual reaction components. In one embodiment, any delivery system suitable for liquid-liquid systems may be used. In another embodiment, the present two-component peracid generation system comprises a first container comprising the present first component and a second container comprising the present second component. Typical examples of containers and/or packing system may include individual bottles, individual bottles packaged together in a single kit, dual chamber dispenser bottles (such as squeeze bottles, spray bottles, and the like.), rigid or non-rigid dual chamber dispenser packets, individual packets, and dissolvable or degradable dual chamber dispenser packets, to name a few. (See U.S. Pat. Nos. 4,678,103; 4,585,150; 6,223,942; 5,954,213; 6,758,411; 5,862,949; 5,398,846; 6,995,125; and 6,391,840; U.S. Published Patent Application Nos. 2005/

0139608 and 2002/0030063; and PCT Publication Nos. WO00/61713; WO02/22467; and WO2005/035705). In one embodiment, the delivery system is a dual compartment spray bottle.

In further embodiments, the enzyme catalyst comprises an amino acid sequence selected from the group consisting of SEQ ID NO: 2, SEQ ID NO:4, SEQ ID NO:6, SEQ ID NO:8, SEQ ID NO: 10, SEQ ID NO: 12, SEQ ID NO:14, SEQ ID NO: 16, SEQ ID NO:18, SEQ ID NO:20, SEQ ID NO:22, SEQ ID NO:24, SEQ ID NO: 26, SEQ ID NO: 54, SEQ ID NO: 60, SEQ ID NO: 64, SEQ ID NO: 68, SEQ ID NO: 72, SEQ ID NO: 73, and SEQ ID NO: 74 or a substantially similar enzyme having perhydrolase activity derived by substituting, deleting or adding one or more amino acids to said amino acid sequence.

In a further embodiment, the substantially similar enzyme having perhydrolase activity is at least 30%, preferably at least 33%, more preferably at least 40%, more preferably at least 50%, even more preferably at least 60%, yet even more preferable at least 70%, yet even more preferably at least 80%, yet even more preferably at least 90%, 91%, 92%, 93%, 94%, 95%, 96%, 97%, 98%, or 99% identical to one or more amino acid sequences selected from the group consisting of SEQ ID NO: 2, SEQ ID NO:4, SEQ ID NO:6, SEQ ID NO:8, SEQ ID NO: 10, SEQ ID NO: 12, SEQ ID NO:14, SEQ ID NO: 16, SEQ ID NO:18, SEQ ID NO:20, SEQ ID NO:22, SEQ ID NO:24, SEQ ID NO: 26, SEQ ID NO: 54, SEQ ID NO: 60, SEQ ID NO: 64, SEQ ID NO: 68, SEQ ID NO: 72, SEQ ID NO: 73, and SEQ ID NO: 74.

In one aspect, the carboxylic acid ester substrate used in the present methods and multi-component systems is selected from the group consisting of:

(a) one or more esters having the structure

wherein

X is an ester group of the formula $R_6C(O)O$; $R_6$ is a C1 to C7 linear, branched or cyclic hydrocarbyl moiety, optionally substituted with a hydroxyl group or C1 to C4 alkoxy group, wherein $R_6$ optionally comprises one or more ether linkages where $R_6$ is C2 to C7;

$R_5$ is a C1 to C6 linear, branched, or cyclic hydrocarbyl moiety optionally substituted with a hydroxyl group, wherein each carbon atom in $R_5$ individually comprises no more than one hydroxyl group or no more than one ester group, and wherein $R_5$ optionally comprises one or more ether linkages;

m is 1 to the number of carbon atoms in $R_5$, said one or more esters having solubility in water of at least 5 ppm at 25° C.;

(b) one or more glycerides having the structure

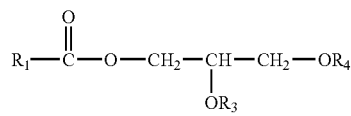

wherein $R_1$ is a C1 to C7 straight chain or branched chain alkyl optionally substituted with a hydroxyl or a C1 to C4 alkoxy group and $R_3$ and $R_4$ are individually H or $R_1C(O)$;

(c) one or more esters of the formula

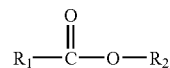

wherein $R_1$ is a C1 to C7 straight chain or branched chain alkyl optionally substituted with an hydroxyl or a C1 to C4 alkoxy group and $R_2$ is a C1 to C10 straight chain or branched chain alkyl, alkenyl, alkynyl, aryl, alkylaryl, alkylheteroaryl, heteroaryl, $(CH_2CH_2O)_n$, or $(CH_2CH(CH_3)$—$O)_nH$ and n is 1 to 10;

(d) one or more acetylated monosaccharides, acetylated disaccharides, or acetylated polysaccharides; and (e) any combination of (a) through (d);

In one embodiment, the carboxylic acid ester substrate is selected from the group consisting of: monoacetin; triacetin; monopropionin; dipropionin; tripropionin; monobutyrin; dibutyrin; tributyrin; glucose pentaacetate; xylose tetraacetate; acetylated xylan; acetylated xylan fragments; β-D-ribofuranose-1,2,3,5-tetraacetate; tri-O-acetyl-D-galactal; tri-O-acetyl-glucal; propylene glycol diacetate, ethylene glycol diacetate; monoesters or diesters of 1,2-ethanediol; 1,2-propanediol; 1,3-propanediol; 1,2-butanediol; 1,3-butanediol; 2,3-butanediol; 1,4-butanediol; 1,2-pentanediol; 2,5-pentanediol; 1,6-pentanediol; 1,2-hexanediol; 2,5-hexanediol; 1,6-hexanediol; and mixtures thereof. In another embodiment the substrate is selected from the group consisting of propylene glycol diacetate, ethylene glycol diacetate, and mixtures thereof. In further embodiment, the substrate preferably comprises triacetin.

Unless otherwise specified, disclosure of a particular embodiment applies equally to the present methods for producing peroxycarboxylic acid in a multi-component system, the present methods for disinfecting a surface, the present multi-component formulation compositions, and the present generation systems for producing peroxycarboxylic acid.

In a further aspect, the present method and systems may also be used in laundry care applications to produce a beneficial effect including, but not limited to, bleaching, destaining, deodorizing, and sanitizing.

BRIEF DESCRIPTION OF THE FIGURE

FIG. 1, sheets A-F, show the results of a CLUSTALW alignment (version 1.83) of several enzymes structurally classified as carbohydrate esterase family 7 members including SEQ ID NOs 2, 4, 6, 8, 10, 12, 14, 16, 18, 20, 22, 24, 26, 54, 60, 64, 68, 72, 73, and 74. All of the enzymes share the conserved motifs (underlined) that together form the signature motif for CE-7 carbohydrate esterases (see Vincent et al., *J. Mol. Biol.*, 330:593-606 (2003) and U.S. Patent Application Publication No. 2008/0176783 to DiCosimo et al.). An additional motif that may be used to further characterize members of the CE-7 family of enzymes is underlined and bold (i.e., the LXD motif).

BRIEF DESCRIPTION OF THE BIOLOGICAL SEQUENCES

The following sequences comply with 37 C.F.R. §§1.821-1.825 ("Requirements for patent applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the European Patent Convention (EPC) and the Patent Cooperation Treaty (PCT) Rules 5.2 and 49.5(a-bis), and Section 208 and Annex C of the Administrative Instructions. The symbols and format used for nucleotide and amino acid sequence data comply with the rules set forth in 37 C.F.R. §1.822.

SEQ ID NO: 1 is the nucleic acid sequence of the cephalosporin C deacetylase (cah) coding region from *Bacillus subtilis* ATCC® 31954™.

SEQ ID NO: 2 is the deduced amino acid sequence of the cephalosporin C deacetylase from *Bacillus subtilis* ATCC® 31954™.

SEQ ID NO: 3 is the nucleic acid sequence of the cephalosporin C deacetylase coding region from *B. subtilis* subsp. *subtilis* str. 168.

SEQ ID NO: 4 is the deduced amino acid sequence of the cephalosporin C deacetylase from *B. subtilis* subsp. *subtilis* str. 168, and is identical to the deduced amino acid sequence of the cephalosporin C deacetylase from *B. subtilis* BE1010.

SEQ ID NO: 5 is the nucleic acid sequence of the cephalosporin acetylesterase coding region from *B. subtilis* ATCC® 6633™.

SEQ ID NO: 6 is the deduced amino acid sequence of the cephalosporin acetylesterase from *B. subtilis* ATCC® 6633™.

SEQ ID NO: 7 is the nucleic acid sequence of the cephalosporin C deacetylase coding region from *B. licheniformis* ATCC® 14580™.

SEQ ID NO: 8 is the deduced amino acid sequence of the cephalosporin C deacetylase from *B. licheniformis* ATCC® 14580™.

SEQ ID NO: 9 is the nucleic acid sequence of the acetyl xylan esterase coding region from *B. pumilus* PS213.

SEQ ID NO: 10 is the deduced amino acid sequence of the acetyl xylan esterase from *B. pumilus* PS213.

SEQ ID NO: 11 is the nucleic acid sequence of the acetyl xylan esterase coding region from *Clostridium thermocellum* ATCC® 27405™.

SEQ ID NO: 12 is the deduced amino acid sequence of the acetyl xylan esterase from *Clostridium thermocellum* ATCC® 27405™.

SEQ ID NO: 13 is the nucleic acid sequence of the acetyl xylan esterase coding region from *Thermotoga neapolitana*.

SEQ ID NO: 14 is the deduced amino acid sequence of the acetyl xylan esterase from *Thermotoga neapolitana*.

SEQ ID NO: 15 is the nucleic acid sequence of the acetyl xylan esterase coding region from *Thermotoga maritima* MSB8.

SEQ ID NO: 16 is the deduced amino acid sequence of the acetyl xylan esterase from *Thermotoga maritima* MSB8.

SEQ ID NO: 17 is the nucleic acid sequence of the acetyl xylan esterase coding region from *Thermoanaerobacterium* sp. JW/SL YS485.

SEQ ID NO: 18 is the deduced amino acid sequence of the acetyl xylan esterase from *Thermoanaerobacterium* sp. JW/SL YS485.

SEQ ID NO: 19 is the nucleic acid sequence encoding the cephalosporin C deacetylase from *Bacillus* sp. NRRL B-14911 as reported in GENBANK® Accession number ZP_01168674. However, the reported sequence appears to have a 15 amino acid N-terminal addition that is likely incorrect based on sequence alignments with other cephalosporin C deacetylases and a comparison of the reported length (340 amino acids) versus the observed length of other CAH enzymes (typically 318-325 amino acids in length).

SEQ ID NO: 20 is the deduced amino acid sequence of the cephalosporin C deacetylase from *Bacillus* sp. NRRL B-14911 without the N-terminal 15 amino acids reported under GENBANK® Accession number ZP_01168674.

SEQ ID NO: 21 is the nucleic acid sequence of the cephalosporin C deacetylase coding region from *Bacillus halodurans* C-125.

SEQ ID NO: 22 is the deduced amino acid sequence of the cephalosporin C deacetylase from *Bacillus halodurans* C-125.

SEQ ID NO: 23 is the nucleic acid sequence of the cephalosporin C deacetylase coding region from *Bacillus clausii* KSM-K16.

SEQ ID NO: 24 is the deduced amino acid sequence of the cephalosporin C deacetylase from *Bacillus clausii* KSM-K16.

SEQ ID NO: 25 is the nucleic acid sequence of the *Bacillus subtilis* ATCC 29233™ cephalosporin C deacetylase (cah) gene cloned into pSW190.

SEQ ID NO: 26 is the deduced amino acid sequence of the *Bacillus subtilis* ATCC® 29233™ cephalosporin C deacetylase (CAH).

SEQ ID NOs: 27 and 28 are primers used to PCR amplify the *Thermotoga neapolitana* acetyl xylan esterase coding region (GENBANK® U58632) for construction of pSW196.

SEQ ID NO: 29 is the nucleic acid sequence of the codon-optimized version of the *Thermotoga neapolitana* acetyl xylan esterase gene in plasmid pSW196.

SEQ ID NO: 30 is the nucleic acid sequence of the kanamycin resistance gene (kan).

SEQ ID NO: 31 is the nucleic acid sequence of plasmid pKD13.

SEQ ID NOs: 32 and 33 are primers used to generate a PCR product encoding the kanamycin gene flanked by regions having homology to the katG catalase gene in *E. coli* MG1655. The product was used to disrupt the endogenous katG gene.

SEQ ID NO: 34 is the nucleic acid sequence of the PCR product encoding the kanamycin resistance gene flanked by regions having homology to the katG catalase gene in *E. coli* MG1655. The product was used to disrupt the endogenous katG gene.

SEQ ID NO: 35 is the nucleic acid sequence of the katG catalase gene in *E. coli* MG1655.

SEQ ID NO: 36 is the deduced amino acid sequence of the KatG catalase in *E. coli* MG1655.

SEQ ID NO: 37 is the nucleic acid sequence of plasmid pKD46.

SEQ ID NOs: 38 and 39 are primers used to confirm the disruption of the katG gene.

SEQ ID NO: 40 is the nucleic acid sequence of plasmid pCP20.

SEQ ID NOs: 41 and 42 are primers used to generate a PCR product encoding the kanamycin gene flanked by regions having homology to the katE catalase gene in *E. coli* MG1655. The product was used to disrupt the endogenous katE gene.

SEQ ID NO: 43 is the nucleic acid sequence of the PCR product encoding the kanamycin resistance gene flanked by regions having homology to the katE catalase gene in *E. coli* MG1655. The product was used to disrupt the endogenous katE gene.

SEQ ID NO: 44 is the nucleic acid sequence of the katE catalase gene in *E. coli* MG1655.

SEQ ID NO: 45 is the deduced amino acid sequence of the KatE catalase in *E. coli* MG1655.

SEQ ID NOs: 46 and 47 are primers used to confirm disruption of the katE gene in the single knockout strain *E. coli*

MG1655 ΔkatE, and in the double-knockout strain E. coli MG1655 ΔkatG ΔkatE, herein referred to as E. coli KLP18.

SEQ ID NO: 48 is the nucleic acid sequence of the codon optimized version of the Bacillus pumilus PS213 encoding the amino acid sequence SEQ ID NO: 10.

SEQ ID NO: 49 is the amino acid sequence of the region encompassing amino acids residues 118 through 299 of SEQ ID NO: 2.

SEQ ID NO: 50 is the nucleic acid sequence of the PCR product encoding the codon-optimized version of the Bacillus clausii KSM-K16 cephalosporin-C deacetylase coding sequence.

SEQ ID NO: 51 is the nucleic acid sequence of the codon-optimized Bacillus clausii KSM-K16 cephalosporin-C deacetylase coding sequence.

SEQ ID NO: 52 is the nucleic acid sequence of the PCR product encoding the codon-optimized version of the Thermoanaerobacterium saccharolyticum acetyl xylan esterase coding sequence.

SEQ ID NO: 53 is the nucleic acid sequence of the codon-optimized version of the Thermoanaerobacterium saccharolyticum acetyl xylan esterase coding sequence.

SEQ ID NO: 54 is the deduced amino acid sequence of the acetyl xylan esterase from Thermoanaerobacterium saccharolyticum (GENBANK® Accession No. S41858).

SEQ ID NO: 55 is the nucleic acid sequence of the PCR product encoding the codon-optimized version of the Thermotoga maritima MSB8 acetyl xylan esterase coding sequence.

SEQ ID NO: 56 is the nucleic acid sequence of the codon-optimized version of the Thermotoga maritima MSB8 acetyl xylan esterase coding sequence.

SEQ ID NO: 57 is the nucleic acid sequence of the PCR product encoding the codon-optimized version of the Thermotoga lettingae acetyl xylan esterase coding sequence.

SEQ ID NO: 58 is the nucleic acid sequence of the PCR product encoding the codon-optimized version of the Thermotoga lettingae acetyl xylan esterase coding sequence.

SEQ ID NO: 59 is the nucleic acid sequence of the acetyl xylan esterase coding region from Thermotoga lettingae.

SEQ ID NO: 60 is the deduced amino acid sequence of the acetyl xylan esterase from Thermotoga lettingae.

SEQ ID NO: 61 is the nucleic acid sequence of the PCR product encoding the codon-optimized version of the Thermotoga petrophila acetyl xylan esterase coding sequence.

SEQ ID NO: 62 is the nucleic acid sequence of the PCR product encoding a codon-optimized version of the Thermotoga petrophila acetyl xylan esterase coding sequence.

SEQ ID NO: 63 is the nucleic acid sequence of the acetyl xylan esterase coding region from Thermotoga petrophila.

SEQ ID NO: 64 is the deduced amino acid sequence of an acetyl xylan esterase from Thermotoga petrophila.

SEQ ID NO: 65 is the nucleic acid sequence of the PCR product encoding the codon-optimized version of the Thermotoga sp. RQ2 "RQ2(a)" acetyl xylan esterase coding sequence.

SEQ ID NO: 66 is the nucleic acid sequence of the PCR product encoding a codon-optimized version of the Thermotoga sp. RQ2 "RQ2(a)" acetyl xylan esterase coding sequence.

SEQ ID NO: 67 is the nucleic acid sequence of the acetyl xylan esterase coding region from Thermotoga sp. RQ2 identified herein as "RQ2(a)".

SEQ ID NO: 68 is the deduced amino acid sequence of an acetyl xylan esterase (GENBANK® Accession No. ACB09222) from Thermotoga sp. RQ2 identified herein as "RQ2(a)".

SEQ ID NO: 69 is the nucleic acid sequence of the PCR product encoding the codon-optimized version of the Thermotoga sp. RQ2 "RQ2(b)" acetyl xylan esterase coding sequence.

SEQ ID NO: 70 is the nucleic acid sequence of the PCR product encoding a codon-optimized version of the Thermotoga sp. RQ2 "RQ2(b)" acetyl xylan esterase coding sequence.

SEQ ID NO: 71 is the nucleic acid sequence of the acetyl xylan esterase coding region from Thermotoga sp. RQ2 identified herein as "RQ2(b)".

SEQ ID NO: 72 is the deduced amino acid sequence of an acetyl xylan esterase (GENBANK® Accession No. ACB08860) from Thermotoga sp. RQ2 identified herein as "RQ2(b)".

SEQ ID NO: 73 is the deduced amino acid sequence of a Thermotoga neapolitana acetyl xylan esterase variant from co-owned, co-filed, and copending U.S. patent application Ser. No. 12/572,094 (incorporated herein by reference in its entirety), where the Xaa residue at position 277 is Ala, Val, Ser, or Thr.

SEQ ID NO: 74 is the deduced amino acid sequence of a Thermotoga maritima MSB8 acetyl xylan esterase variant from co-owned, co-filed, and copending U.S. patent application Ser. No. 12/572,094, where the Xaa residue at position 277 is Ala, Val, Ser, or Thr.

DETAILED DESCRIPTION OF THE INVENTION

In certain applications for a multicomponent in situ peracid disinfectant formulation, it may be desirable for the ratio of the second component (comprising an aqueous source of peroxygen) to the first component (comprising the enzyme and the enzyme substrate) to be within a range of from 1:1 to 10:1, where from 10 parts to 1 part (by weight) of the second component is mixed with one part (by weight) of the first component to produce a peracid at a concentration efficacious for disinfection.

The stated problems have been solved by the discovery that, in multicomponent methods and systems (i.e., in the present context, methods and systems that involve the production of peroxycarboxylic acid using at least two reaction components that are separately stored prior to a desired time of reaction), substrates of perhydrolases can be efficaciously mixed with a source of peroxygen in water and satisfactorily delivered, for example, to a surface, through the inclusion of a cosolvent. As described herein, addition of an organic solvent to a catalyst composition (Component A; herein also referred to as the "first" component) and removal of an equal volume of water from the aqueous source of peroxygen (Component B; herein also referred to as the "second" component), such that the ratio of Component B to Component A is within a range of from 1:1 to 10:1, allows production of a peracid at a concentration efficacious for disinfection. The organic solvent is preferably inert and non-reactive in the formulation. The cosolvent also is preferably completely miscible with the enzyme substrate (e.g., triacetin). The cosolvent also is preferably soluble at its final concentration in the combined Components A and B after mixing. Pursuant to the present invention, the CE-7 carbohydrate esterase family of structurally-related enzymes can be used in multicomponent systems to generate concentrations of peracids with high efficiency for disinfection and/or bleaching applications, and, as described for fully infra, cosolvents comprising organic solvents can surprisingly be used to enhance the solubility of the substrate in an aqueous reaction formulation without substantial loss of perhydrolytic activity of the enzyme catalyst.

In a further aspect, the present invention includes methods and multi-component systems for use in laundry care applications wherein an article of clothing or a textile is contacted with peracids at concentrations suitable for bleaching, stain removal, odor reduction, sanitization, disinfection, or a combination thereof.

The present invention may be understood more readily by reference to the following detailed description taken in connection with the accompanying figure, the sequence listing, and examples, which form a part of this disclosure. It is to be understood that this invention is not limited to the specific products, methods, conditions or parameters described and/or shown herein, and that the terminology used herein is for the purpose of describing particular embodiments by way of example only and is not intended to be limiting of the claimed invention.

In this disclosure, a number of terms and abbreviations are used. The following definitions apply unless specifically stated otherwise.

As used herein, the articles "a", "an", and "the" preceding an element or component of the invention are intended to be nonrestrictive regarding the number of instances (i.e., occurrences) of the element or component. Therefore "a", "an" and "the" should be read to include one or at least one, and the singular word form of the element or component also includes the plural unless the number is obviously meant to be singular.

As used herein, the term "comprising" means the presence of the stated features, integers, steps, or components as referred to in the claims, but that it does not preclude the presence or addition of one or more other features, integers, steps, components or groups thereof. The term "comprising" is intended to include embodiments encompassed by the terms "consisting essentially of" and "consisting of". Similarly, the term "consisting essentially of" is intended to include embodiments encompassed by the term "consisting of".

As used herein, the term "about" modifying the quantity of an ingredient or reactant employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

Where present, all ranges are inclusive and combinable. For example, when a range of "1 to 5" is recited, the recited range should be construed as including ranges "1 to 4", "1 to 3", "1-2", "1-2 & 4-5", "1-3 & 5", and the like.

As used herein, the term "peracid" is synonymous with peroxyacid, peroxycarboxylic acid, peroxy acid, percarboxylic acid and peroxoic acid.

As used herein, the term "peracetic acid" is abbreviated as "PAA" and is synonymous with peroxyacetic acid, ethaneperoxoic acid and all other synonyms of CAS Registry Number 79-21-0.

As used herein, the terms "substrate", "suitable substrate", and "carboxylic acid ester substrate" interchangeably refer specifically to:

(a) one or more esters having the structure

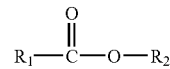

wherein

X is an ester group of the formula $R_6C(O)O$;

$R_6$ is a C1 to C7 linear, branched or cyclic hydrocarbyl moiety, optionally substituted with a hydroxyl group or C1 to C4 alkoxy group, wherein $R_6$ optionally comprises one or more ether linkages where $R_6$ is C2 to C7;

$R_5$ is a C1 to C6 linear, branched, or cyclic hydrocarbyl moiety optionally substituted with a hydroxyl group, wherein each carbon atom in $R_5$ individually comprises no more than one hydroxyl group or no more than one ester group, and wherein $R_5$ optionally comprises one or more ether linkages;

m is 1 to the number of carbon atoms in $R_5$, said one or more esters having solubility in water of at least 5 ppm at 25° C.; or (b) one or more glycerides having the structure

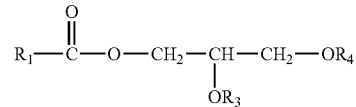

wherein $R_1$ is a C1 to C7 straight chain or branched chain alkyl optionally substituted with an hydroxyl or a C1 to C4 alkoxy group and $R_3$ and $R_4$ are individually H or $R_1C(O)$; or (c) one or more esters of the formula $$R_1-\overset{O}{\underset{\|}{C}}-O-R_2$$

wherein $R_1$ is a C1 to C7 straight chain or branched chain alkyl optionally substituted with an hydroxyl or a C1 to C4 alkoxy group and $R_2$ is a C1 to C10 straight chain or branched chain alkyl, alkenyl, alkynyl, aryl, alkylaryl, alkylheteroaryl, heteroaryl, $(CH_2CH_2O)_n$, or $(CH_2CH(CH_3)-O)_nH$ and n is 1 to 10; or (d) one or more acetylated monosaccharides, acetylated disaccharides, or acetylated polysaccharides; or (e) any combination of (a) through (d).

Examples of said carboxylic acid ester substrate may include monoacetin; triacetin; monopropionin; dipropionin; tripropionin; monobutyrin; dibutyrin; tributyrin; glucose pentaacetate; xylose tetraacetate; acetylated xylan; acetylated xylan fragments; β-D-ribofuranose-1,2,3,5-tetraacetate, tri-O-acetyl-D-galactal; tri-O-acetyl-glucal; propylene glycol diacetate; ethylene glycol diacetate; monoesters or diesters of 1,2-ethanediol; 1,2-propanediol; 1,3-propanediol; 1,2-butanediol; 1,3-butanediol; 2,3-butanediol; 1,4-butanediol; 1,2-pentanediol; 2,5-pentanediol; 1,6-pentanediol; 1,2-hexanediol; 2,5-hexanediol; 1,6-hexanediol; or any combination thereof.

As used herein, the term "monoacetin" is synonymous with glycerol monoacetate, glycerin monoacetate, and glyceryl monoacetate.

As used herein, the term "diacetin" is synonymous with glycerol diacetate; glycerin diacetate, glyceryl diacetate, and all other synonyms of CAS Registry Number 25395-31-7.

As used herein, the term "triacetin" is synonymous with glycerin triacetate; glycerol triacetate; glyceryl triacetate, 1,2,3-triacetoxypropane, 1,2,3-propanetriol triacetate and all other synonyms of CAS Registry Number 102-76-1.

As used herein, the term "monobutyrin" is synonymous with glycerol monobutyrate, glycerin monobutyrate, and glyceryl monobutyrate.

As used herein, the term "dibutyrin" is synonymous with glycerol dibutyrate and glyceryl dibutyrate.

As used herein, the term "tributyrin" is synonymous with glycerol tributyrate, 1,2,3-tributyrylglycerol, and all other synonyms of CAS Registry Number 60-01-5.

As used herein, the term "monopropionin" is synonymous with glycerol monopropionate, glycerin monopropionate, and glyceryl monopropionate.

As used herein, the term "dipropionin" is synonymous with glycerol dipropionate and glyceryl dipropionate.

As used herein, the term "tripropionin" is synonymous with glyceryl tripropionate, glycerol tripropionate, 1,2,3-tripropionylglycerol, and all other synonyms of CAS Registry Number 139-45-7.

As used herein, the term "ethyl acetate" is synonymous with acetic ether, acetoxyethane, ethyl ethanoate, acetic acid ethyl ester, ethanoic acid ethyl ester, ethyl acetic ester and all other synonyms of CAS Registry Number 141-78-6.

As used herein, the term "ethyl lactate" is synonymous with lactic acid ethyl ester and all other synonyms of CAS Registry Number 97-64-3.

As used herein, the terms "acetylated sugar" and "acetylated saccharide" refer to mono-, di- and polysaccharides comprising at least one acetyl group. Examples include, but are not limited to, glucose pentaacetate, xylose tetraacetate, acetylated xylan, acetylated xylan fragments, β-D-ribofuranose-1,2,3,5-tetraacetate, tri-O-acetyl-D-galactal, and tri-O-acetyl-glucal.

As used herein, the terms "hydrocarbyl", "hydrocarbyl group", and "hydrocarbyl moiety" is meant a straight chain, branched or cyclic arrangement of carbon atoms connected by single, double, or triple carbon to carbon bonds and/or by ether linkages, and substituted accordingly with hydrogen atoms. Such hydrocarbyl groups may be aliphatic and/or aromatic. Examples of hydrocarbyl groups include methyl, ethyl, propyl, isopropyl, butyl, isobutyl, t-butyl, cyclopropyl, cyclobutyl, pentyl, cyclopentyl, methylcyclopentyl, hexyl, cyclohexyl, benzyl, and phenyl. In a preferred embodiment, the hydrocarbyl moiety is a straight chain, branched or cyclic arrangement of carbon atoms connected by single carbon to carbon bonds and/or by ether linkages, and substituted accordingly with hydrogen atoms.

As used herein, the terms "monoesters" and "diesters" of 1,2-ethanediol, 1,2-propanediol, 1,3-propanediol, 1,2-butanediol, 1,3-butanediol, 2,3-butanediol, 1,4-butanediol, 1,2-pentanediol, 2,5-pentanedial, 1,6-pentanediol, 1,2-hexanediol, 2,5-hexanediol, 1,6-hexanediol, and mixtures thereof refer to said compounds comprising at least one ester group of the formula RC(O)O, wherein R is a C1 to C7 linear hydrocarbyl moiety. In one embodiment, the carboxylic acid ester substrate comprises propylene glycol diacetate (PGDA), ethylene glycol diacetate (EDGA) or mixtures thereof.

As used herein, the term "propylene glycol diacetate" is synonymous with 1,2-diacetoxypropane, propylene diacetate, 1,2-propanediol diacetate, and all other synonyms of CAS Registry Number 623-84-7.

As used herein, the term "ethylene glycol diacetate" is synonymous with 1,2-diacetoxyethane, ethylene diacetate, glycol diacetate, and all other synonyms of CAS Registry Number 111-55-7.

As used herein, the terms "suitable enzymatic reaction mixture", "components suitable for in situ generation of a peracid", "suitable reaction components", "suitable aqueous reaction mixture", and "reaction mixture" refer to the materials and water in which the reactants and enzyme catalyst come into contact. The components of the suitable aqueous reaction mixture are provided herein and those skilled in the art appreciate the range of component variations suitable for this process. In one embodiment, the suitable enzymatic reaction mixture produces peracid in situ upon combining the reaction components. As such, the reaction components may be provided as a multi-component system wherein the reaction components remains separated until use. The design of systems and means for separating and combining multiple active components are known in the art and generally will depend upon the physical form of the individual reaction components. For example, multiple active fluids (liquid-liquid) systems typically use multichamber dispenser bottles or two-phase systems (e.g., U.S. Patent Application Publication No. 2005/0139608; U.S. Pat. No. 5,398,846; U.S. Pat. No. 5,624,634; U.S. Pat. No. 6,391,840; E.P. Patent 0807156B1; U.S. Patent Application Publication No. 2005/0008526; and PCT Publication No. WO 00/61713) such as found in some bleaching applications wherein the desired bleaching agent is produced upon mixing the reactive fluids. Other forms of multi-component systems used to generate peracid may include, but are not limited to, those designed for one or more solid components or combinations of solid-liquid components, such as powders (e.g., U.S. Pat. No. 5,116,575), multi-layered tablets (e.g., U.S. Pat. No. 6,210,639), water dissolvable packets having multiple compartments (e.g., U.S. Pat. No. 6,995,125) and solid agglomerates that react upon the addition of water (e.g., U.S. Pat. No. 6,319,888).

In multi-component systems, active constituents are initially separated from each other in one or more respective components and then combined to form a reaction formulation. A multi-component system can face such problems as the failure of the active components to satisfactorily combine, the neutralization or reduction of the activity of one or more components, and/or the formation of a reaction formulation that is not compatible with delivery requirements. For example, in a multi-component system including at least one component comprising an enzyme and a substrate for such enzyme that is insoluble or partially insoluble in a second component comprising water, at least three conditions may arise that interfere with the ability to efficaciously produce and deliver a peroxycarboxylic acid product: first, the viscosity of the enzyme/substrate constituent can be too high to permit efficient mixing with a second constituent comprising a source of peroxygen, which decreases the rate of production of peroxycarboxylic acid; second, the viscosity of the enzyme/substrate constituent can be too high to permit certain modes of delivery of a product comprising a mixture of the enzyme/substrate constituent and the source of peroxygen, such as spraying; third, the dissolution rate of the substrate in the enzyme/substrate component after mixing with a second component comprising a source of peroxygen in aqueous solution is too low to permit a satisfactory rate of production of peroxycarboxylic acid. These problems also become evident in situations where use of a particular ratio of a component comprising an aqueous source of peroxygen to a component comprising an enzyme/substrate constituent is desired.

It is well known to those skilled in the art that organic solvents can be deleterious to the activity of enzymes, either when enzymes are suspended directly in organic solvents, or when miscible organic/aqueous single phase solvents are employed. Two literature publications that review the effects of organic solvents on enzyme activity and structure are: (a) C. Laane et al., supra and (b) D. A. Cowan and A. R. Plant, supra. Cowan and Plant note (on page 87) that the art generally recognizes that there is little or no value in using organic solvents having a log P≦2 to stabilize intracellular enzymes in an organic phase system, where log P is defined as the logarithm of the partition coefficient of a substance between octanol and water, expressed as P=[solute]$_{octanol}$/[solute]$_{water}$. Organic solvents having a log P between 2 and 4 can be used on a case-by-case basis dependent on enzyme stability, and those having a log P>4 are generally useful in organic phase systems.

Cowan and Plant further note (on page 91) that the effect of direct exposure of an enzyme dissolved in a single-phase organic-aqueous solvent depends on solvent concentration, solvent/enzyme surface group interactions, and solvent/enzyme hydration shell interactions. Because a solvent's log P must be sufficiently low so that the solvent is fully miscible with the aqueous phase to produce a single-phase, a single-phase organic-aqueous solvent containing a low log P organic solvent usually has a negative effect on enzyme stability except in low organic solvent concentration applications. Thus, organic solvents having a low log P are traditionally thought to be detrimental to enzyme stability at anything but unworkably low concentrations.

Triacetin is reported to have a log P of 0.25 (Y. M. Gunning, et al., *J. Agric. Food Chem.* 48:395-399 (2000)), similar to that of ethanol (log P–0.26) and isopropanol (log P 0.15) (Cowan and Plant); therefore the storage of enzyme powder in triacetin would be expected to result in unacceptable loss of enzyme activity, as would the use of additional cosolvents with log P<2 (e.g., cyclohexanone, log P=0.94) (Cowan and Plant); 1,2-propanediol, log P=–1.41 (Gunning, et al.); 1,3-propanediol, log P=–1.3 (S-J. Kuo, et al., *J. Am. Oil Chem. Soc.* 73:1427-1433 (1996); diethylene glycol butyl ether, log P=0.56 (N. Funasaki, et al., *J. Phys. Chem.* 88:5786-5790 (1984); triethyleneglycol, log P=–1.75 (L. Braeken, et al., *ChemPhysChem* 6:1606-1612 (2005)). Applying the above-referenced teachings of Cowan and Plant, it would be expected that the solvents listed above, having low log P values, could not suitably be included in an enzyme-containing first component of a multicomponent system without inactivation of the enzyme (either prior to or after mixing of the first component with a second component comprising a source of peroxygen in water).

However, it has surprisingly been discovered that the inclusion of a cosolvent comprising an organic solvent having a log P of less than about 2 may function to aid in the dissolution of enzyme substrate with poor solubility in water and/or may function as a diluent of Component A to enable mixing of a desired ratio of Components A and B. In other words, the cosolvent may resolve conditions (e.g., unacceptably high viscosity of an enzyme/substrate component, poor mixing of this component with a source of peroxygen in water) that otherwise interfere with the ability to efficaciously produce and deliver a peroxycarboxylic acid product in a form that can be delivered by means that are conventional to (or otherwise suitable in) consumer, industrial, and medical contexts.

In the methods and systems described herein, the cosolvent comprising an organic solvent having a log P of less than about 2, wherein log P is defined as the logarithm of the partition coefficient of a substance between octanol and water, expressed as P=[solute]$_{octanol}$/[solute]$_{water}$, solubilizes the substrate in the aqueous reaction formulation without substantial loss of perhydrolytic activity of the enzyme catalyst; wherein the cosolvent is not a substrate for said enzyme catalyst.

In some embodiments, the first component comprising the formulation of the enzyme catalyst and the carboxylic acid ester substrate optionally comprises an inorganic or organic buffer, a stabilizer, a corrosion inhibitor, a wetting agent, or combinations thereof. In some embodiments, the source of peroxygen comprises a hydrogen peroxide stabilizer.

As used herein, the term "perhydrolysis" is defined as the reaction of a selected substrate with peroxide to form a peracid. Typically, inorganic peroxide is reacted with the selected substrate in the presence of a catalyst to produce the peracid. As used herein, the term "chemical perhydrolysis" includes perhydrolysis reactions in which a substrate (i.e., a peracid precursor) is combined with a source of hydrogen peroxide wherein peracid is formed in the absence of an enzyme catalyst.

As used herein, the term "perhydrolase activity" refers to the catalyst activity per unit mass (for example, milligram) of protein, dry cell weight, or immobilized catalyst weight.

As used herein, "one unit of enzyme activity" or "one unit of activity" or "U" is defined as the amount of perhydrolase activity required for the production of 1 μmol of peracid product per minute at a specified temperature.

As used herein, the terms "enzyme catalyst" and "perhydrolase catalyst" refer to a catalyst comprising an enzyme having perhydrolysis activity and may be in the form of a whole microbial cell, permeabilized microbial cell(s), one or more cell components of a microbial cell extract, partially purified enzyme, or purified enzyme. The enzyme catalyst may also be chemically modified (e.g., by pegylation or by reaction with cross-linking reagents). The perhydrolase catalyst may also be immobilized on a soluble or insoluble support using methods well-known to those skilled in the art; see for example, *Immobilization of Enzymes and Cells*; Gordon F. Bickerstaff, Editor; Humana Press, Totowa, N.J., USA; 1997. As described herein, all of the present enzymes having perhydrolysis activity are structurally members of the carbohydrate esterase family 7 ("CE-7" family) of enzymes (see Coutinho, P. M., Henrissat, B. "Carbohydrate-active enzymes: an integrated database approach" in *Recent Advances in Carbohydrate Bioengineering*, H. J. Gilbert, G. Davies, B. Henrissat and B. Svensson eds., (1999) The Royal Society of Chemistry, Cambridge, pp. 3-12.). The CE-7 family of enzymes has been demonstrated to be particularly effective for producing peracids from a variety of carboxylic acid ester substrates when combined with a source of peroxygen (See PCT publication No. WO2007/070609 and U.S. Patent Application Publication Nos, 2008/0176299, 2008/176783, and 2009/0005590 to DiCosimo et al.; each herein incorporated by reference in their entireties).

Members of the CE-7 family include cephalosporin C deacetylases (CAHs; E.C. 3.1.1.41) and acetyl xylan esterases (AXEs; E.C. 3.1.1.72). Members of the CE-7 esterase family share a conserved signature motif (Vincent et al., supra). Perhydrolases comprising the CE-7 signature motif and/or a substantially similar structure are suitable for use in the present invention. Means to identify substantially similar biological molecules are well known in the art (e.g., sequence alignment protocols, nucleic acid hybridizations, and/or presence of a conserved signature motif). In one aspect, the enzyme catalyst in the present processes and systems comprises a substantially similar enzyme having at least 30%, preferably at least 33%, more preferably at least 40%, more preferably at least 50%, even more preferably at least 60%, yet even more preferable at least 70%, yet even more preferably at least 80%, yet even more preferably at least 90%, 91%, 92%, 93%, 94%, 95%, 96%, 97%, 98%, or 99% amino acid identity to the sequences provided herein. The nucleic acid molecules encoding the present CE-7 carbohydrate esterases are also provided herein. In further embodiments, the perhydrolase catalyst useful in the present processes and systems is encoded by a nucleic acid molecule that hybridizes under highly stringent conditions to one of the present nucleic acid molecules.

As used herein, the terms "cephalosporin C deacetylase" and "cephalosporin C acetyl hydrolase" refer to an enzyme (E.C. 3.1.1.41) that catalyzes the deacetylation of cephalosporins such as cephalosporin C and 7-aminocephalosporanic acid (Matsushima et al., (1995) Appl. Env. Microbiol. 61(6):2224-2229). As described herein, several cephalosporin C deacetylases are provided having significant perhydrolysis activity.

As used herein, "acetyl xylan esterases" refers to an enzyme (E.C. 3.1.1.72; AXEs) that catalyzes the deacetylation of acetylated xylans and other acetylated saccharides. As illustrated herein, several enzymes classified as acetyl xylan esterases are provided having significant perhydrolase activity.

As used herein, the term "Bacillus subtilis ATCC® 31954™" refers to a bacterial cell deposited to the American Type Culture Collection (ATCC®) having international depository accession number ATCC® 31954™. Bacillus subtilis ATCC® 31954™ has been reported to have an ester hydrolase ("diacetinase") activity capable of hydrolyzing glycerol esters having 2-carbon to 8-carbon acyl groups, especially diacetin (U.S. Pat. No. 4,444,886; herein incorporated by reference in its entirety). As described herein, an enzyme having significant perhydrolase activity has been isolated from B. subtilis ATCC® 31954™ and is provided as SEQ ID NO: 2. The amino acid sequence of the isolated enzyme has 100% amino acid identity to the cephalosporin C deacetylase provided by GENBANK® Accession No. BAA01729.1 (Mitsushima et al., supra).

As used herein, the term "Bacillus subtilis BE1010" refers to the strain of Bacillus subtilis as reported by Payne and Jackson (J. Bacterial. 173:2278-2282 (1991)). Bacillus subtilis BE1010 is a derivative of Bacillus subtilis subsp. subtilis strain BR151 (ATCC® 33677™) having a chromosomal deletion in the genes encoding subtilisin and neutral protease. As described herein, an enzyme having significant perhydrolase activity has been isolated from B. subtilis BE1010 and is provided as SEQ ID NO: 4. The amino acid sequence of the isolated enzyme has 100% amino acid identity to the cephalosporin C deacetylase reported in Bacillus subtilis subsp. subtilis strain 168 (Kunst et al., Nature 390:249-256 (1997)).

As used herein, the term "Bacillus subtilis ATCC® 29233™" refers to a strain of Bacillus subtilis deposited to the American Type Culture Collection (ATCC®) having international depository accession number ATCC®29233™. As described herein, an enzyme having significant perhydrolase activity has been isolated and sequenced from B. subtilis ATCC® 29233™ and is provided as SEQ ID NO: 26.

As used herein, the term "Clostridium thermocellum ATCC® 27405™" refers to a strain of Clostridium thermocellum deposited to the American Type Culture Collection (ATCC®) having international depository accession number ATCC® 27405™. The amino acid sequence of the enzyme having perhydrolase activity from C. thermocellum ATCC® 27405™ is provided as SEQ ID NO: 12.

As used herein, the term "Bacillus subtilis ATCC® 6633™" refers to a bacterial cell deposited to the American Type Culture Collection (ATCC®) having international depository accession number ATCC® 6633™. Bacillus subtilis ATCC® 6633™ has been reported to have cephalosporin acetylhydrolase activity (U.S. Pat. No. 6,465,233). The amino acid sequence of the enzyme having perhydrolase activity from B. subtilis ATCC® 6633™ is provided as SEQ ID NO: 5.

As used herein, the term "Bacillus licheniformis ATCC® 14580™" refers to a bacterial cell deposited to the American Type Culture Collection (ATCC®) having international depository accession number ATCC® 14580™. Bacillus licheniformis ATCC® 14580™ has been reported to have cephalosporin acetylhydrolase activity (GENBANK® YP_077621). The amino acid sequence of the enzyme having perhydrolase activity from B. licheniformis ATCC® 14580™ is provided as SEQ ID NO: 8.

As used herein, the term "Bacillus pumilus PS213" refers to a bacterial cell reported to have acetyl xylan esterase activity (GENBANK® AJ249957). The amino acid sequence of the enzyme having perhydrolase activity from Bacillus pumilus PS213 is provided as SEQ ID NO: 10.

As used herein, the term "Thermotoga neapolitana" refers to a strain of Thermotoga neapolitana reported to have acetyl xylan esterase activity (GENBANK® AAB70869). The amino acid sequence of the enzyme having perhydrolase activity from Thermotoga neapolitana is provided as SEQ ID NO: 14. A variant enzyme derived from SEQ ID NO: 14 has recently been reported having improved perhydrolysis activity and is provided as SEQ ID NO: 73 (See co-owned, co-filed, and copending U.S. patent application Ser. No. 12/572,094 entitled "IMPROVED PERHYDROLASES FOR ENZYMATIC PERACID GENERATION"; incorporated herein by reference in its entirety), where the Xaa residue at position 277 is Ala, Val, Ser, or Thr.

As used herein, the term "Thermotoga maritima MSB8" refers to a strain of Thermotoga maritima reported to have acetyl xylan esterase activity (GENBANK® NP_227893.1). The amino acid sequence of the enzyme having perhydrolase activity from Thermotoga maritima is provided as SEQ ID NO: 16. A variant enzyme derived from SEQ ID NO: 16 has recently been reported having improved perhydrolysis activity and is provided as SEQ ID NO: 74 (See co-owned, co-filed, and copending U.S. patent application Ser. No. 12/572, 094, where the Xaa residue at position 277 is Ala, Val, Ser, or Thr.

As used herein, the term "Bacillus clausii KSM-K16" refers to a bacterial cell reported to have cephalosporin-C deacetylase activity (GENBANK®YP_175265). The amino acid sequence of the enzyme having perhydrolase activity from Bacillus clausii KSM-K16 is provided as SEQ ID NO: 24.

As used herein, the term "Thermoanearobacterium saccharolyticum" refers to a bacterial strain reported to have acetyl xylan esterase activity (GENBANK® S41858). The amino acid sequence of the enzyme having perhydrolase activity from Thermoanearobacterium saccharolyticum is provided as SEQ ID NO: 54.

As used herein, the term "Thermotoga lettingae" refers to a bacterial cell reported to have acetyl xylan esterase activity (GENBANK® CP000812). The deduced amino acid sequence of the enzyme having perhydrolase activity from Thermotoga lettingae is provided as SEQ ID NO: 60.

As used herein, the term "Thermotoga petrophila" refers to a bacterial cell reported to have acetyl xylan esterase activity (GENBANK® CP000702). The deduced amino acid sequence of the enzyme having perhydrolase activity from Thermotoga lettingae is provided as SEQ ID NO: 64.

As used herein, the term "Thermotoga sp. RQ2" refers to a bacterial cell reported to have acetyl xylan esterase activity (GENBANK® CP000969). Two different acetyl xylan esterases have been identified from Thermotoga sp. RQ2 and are referred to herein as "RQ2(a)" (the deduced amino acid sequence provided as SEQ ID NO: 68) and "RQ2(b)" (the deduced amino acid sequence provided as SEQ ID NO: 72).

As used herein, an "isolated nucleic acid molecule" and "isolated nucleic acid fragment" will be used interchangeably and refer to a polymer of RNA or DNA that is single- or double-stranded, optionally containing synthetic, non-natural or altered nucleotide bases. An isolated nucleic acid molecule in the form of a polymer of DNA may be comprised of one or more segments of cDNA, genomic DNA or synthetic DNA.

The term "amino acid" refers to the basic chemical structural unit of a protein or polypeptide. The following abbreviations are used herein to identify specific amino acids:

| Amino Acid | Three-Letter Abbreviation | One-Letter Abbreviation |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid (or as defined herein) | Xaa | X |

As used herein, "substantially similar" refers to nucleic add molecules wherein changes in one or more nucleotide bases results in the addition, substitution, or deletion of one or more amino adds, but does not affect the functional properties (i.e., perhydrolytic activity) of the protein encoded by the DNA sequence. As used herein, "substantially similar" also refers to an enzyme having an amino acid sequence that is at least 30%, preferably at least 33%, more preferably at least 40%, more preferably at least 50%, even more preferably at least 60%, even more preferably at least 70%, even more preferably at least 80%, yet even more preferably at least 90%, 91%, 92%, 93%, 94%, 95%, 96%, 97%, 98%, or 99% identical to the sequences reported herein wherein the resulting enzyme retains the present functional properties perhydrolytic activity). "Substantially similar" may also refer to an enzyme having perhydrolytic activity encoded by nucleic acid molecules that hybridize under highly stringent conditions to the nucleic acid molecules reported herein. It is therefore understood that the invention encompasses more than the specific exemplary sequences.

For example, it is well known in the art that alterations in a gene which result in the production of a chemically equivalent amino acid at a given site, but do not affect the functional properties of the encoded protein are common. For the purposes of the present invention substitutions are defined as exchanges within one of the following five groups:

1. Small aliphatic, nonpolar or slightly polar residues: Ala, Ser, Thr (Pro, Gly);
2. Polar, negatively charged residues and their amides: Asp, Asn, Glu, Gln;
3. Polar, positively charged residues: His, Arg, Lys;
4. Large aliphatic, nonpolar residues: Met, Leu, Ile, Val (Cys); and
5. Large aromatic residues: Phe, Tyr, and Trp.

Thus, a codon for the amino acid alanine, a hydrophobic amino acid, may be substituted by a codon encoding another less hydrophobic residue (such as glycine) or a more hydrophobic residue (such as valine, leucine, or isoleucine). Similarly, changes which result in substitution of one negatively charged residue for another (such as aspartic acid for glutamic acid) or one positively charged residue for another (such as lysine for arginine) can also be expected to produce a functionally equivalent product. In many cases, nucleotide changes which result in alteration of the N-terminal and C-terminal portions of the protein molecule would also not be expected to alter the activity of the protein.

Each of the proposed modifications is well within the routine skill in the art, as is determination of retention of biological activity of the encoded products. Moreover, the skilled artisan recognizes that substantially similar sequences are encompassed by the present invention. In one embodiment, substantially similar sequences are defined by their ability to hybridize, under highly stringent conditions (0.1×SSC, 0.1% SDS, 65° C. and washed with 2×SSC, 0.1% SDS followed by 0.1×SSC, 0.1% SDS, 65° C.) with the sequences exemplified herein. In some embodiments, the present methods and systems may include enzymes having perhydrolase activity encoded by isolated nucleic acid molecules that hybridize under stringent conditions to the nucleic acid molecules reported herein. In preferred embodiments, the present methods and systems employ an enzyme having perhydrolase activity encoded by isolated nucleic acid molecule that hybridize under stringent conditions to a nucleic acid molecule having a nucleic acid sequence selected from the group consisting of SEQ ID NO: 1, SEQ ID NO:3, SEQ ID NO:5; SEQ ID NO: 7; SEQ ID NO:9, SEQ ID NO:11, SEQ ID NO:13, SEQ ID NO:15, SEQ ID NO: 17, SEQ ID NO:19, SEQ ID NO:21, SEQ ID NO:23, SEQ ID NO: 25; SEQ ID NO:29; SEQ ID NO:48, SEQ ID NO: 51, SEQ ID NO: 53, SEQ ID NO: 56, SEQ ID NO: 57, SEQ ID NO: 58, SEQ ID NO: 59, SEQ ID NO: 61, SEQ ID NO: 62, SEQ ID NO: 63, SEQ ID NO: 65, SEQ ID NO: 66, SEQ ID NO: 67, SEQ ID NO: 69, SEQ ID NO: 70, and SEQ ID NO: 71.

As used herein, a nucleic acid molecule is "hybridizable" to another nucleic acid molecule, such as a cDNA, genomic DNA, or RNA, when a single strand of the first molecule can anneal to the other molecule under appropriate conditions of temperature and solution ionic strength. Hybridization and washing conditions are well known and exemplified in Sambrook, J. and Russell, D., T. *Molecular Cloning: A Laboratory Manual*, Third Edition, Cold Spring Harbor Laboratory Press, Cold Spring Harbor (2001). The conditions of temperature and ionic strength determine the "stringency" of the hybridization. Stringency conditions can be adjusted to screen for moderately similar molecules, such as homologous sequences from distantly related organisms, to highly similar molecules, such as genes that duplicate functional enzymes from closely related organisms. Post-hybridization washes typically determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of conditions uses higher temperatures in which the washes are identical to those above except for the temperature of the final two 30 min washes in 0.2×SSC, 0.5% SDS was increased to 60° C. Another preferred set of stringent hybridization conditions is 0.1×SSC, 0.1% SDS, 65° C. and washed with 2×SSC, 0.1% SDS followed by a final wash of 0.1×SSC, 0.1% SDS, 65° C. with the sequences exemplified herein.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (Sambrook and Russell, supra). For hybridizations with shorter nucleic acids, i.e., oligonucleotides, the position of mismatches becomes more important, and the length of the oligonucleotide determines its specificity (Sambrook and Russell, supra). In one aspect, the length for a hybridizable nucleic acid is at least about 10 nucleotides. Preferably, a minimum length for a hybridizable nucleic acid is at least about 15 nucleotides in length, more preferably at least about 20 nucleotides in length, even more preferably at least 30 nucleotides in length, even more preferably at least 300 nucleotides in length, and most preferably at least 800 nucleotides in length. Furthermore, the skilled artisan will recognize that the temperature and wash solution salt concentration may be adjusted as necessary according to factors such as length of the probe.

As used herein, the term "percent identity" is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, NY (1988); *Biocomputing: Informatics and Genome Protects* (Smith, D. W., ed.) Academic Press, NY (1993); *Computer Analysis of Sequence Data, Part I* (Griffin, A. M., and Griffin, H. G., eds.) Humana Press, NJ (1994); *Sequence Analysis in Molecular Biology* (von Heinje, G., ed.) Academic Press (1987); and *Sequence Analysis Primer* (Gribskov, M. and Devereux, J., eds.) Stockton Press, NY (1991). Methods to determine identity and similarity are codified in publicly available computer programs. Sequence alignments and percent identity calculations may be performed using the Megalign program of the LASERGENE bioinformatics computing suite (DNASTAR Inc., Madison, Wis.), the AlignX program of Vector NTI v. 7.0 (Informax, Inc., Bethesda, Md.), or the EMBOSS Open Software Suite (EMBLEM; Rice et al., *Trends in Genetics* 16, (6) pp 276-277 (2000)). Multiple alignment of the sequences can be performed using the CLUSTAL method (such as CLUSTALW; for example version 1.83) of alignment (Higgins and Sharp, *CABIOS,* 5:151-153 (1989); Higgins et al., *Nucleic Acids Res.* 22:4673-4680 (1994); and Chema et al., *Nucleic Acids Res* 31 (13):3497-500 (2003)), available from the European Molecular Biology Laboratory via the European Bioinformatics Institute) with the default parameters. Suitable parameters for CLUSTALW protein alignments include GAP Existence penalty=15, GAP extension=0.2, matrix=Gonnet (e.g., Gonnet250), protein ENDGAP=−1, Protein GAPDIST=4, and KTUPLE=1, In one embodiment, a fast or slow alignment is used with the default settings wherein a slow alignment is preferred. Alternatively, the parameters using the CLUSTALW method (version 1.83) may be modified to also use KTUPLE=1, GAP PENALTY=10, GAP extension=1, matrix=BLOSUM (e.g. BLOSUM64), WINDOW=5, and TOP DIAGONALS SAVED=5.

In one aspect of the present methods and systems, suitable isolated nucleic acid molecules (isolated polynucleotides of the present invention) encode a polypeptide having an amino acid sequence that is at least about 30%, preferably at least 33%, preferably at least 40%, preferably at least 50%, preferably at least 60%, more preferably at least 70%, more preferably at least 80%, even more preferably at least 85%, even more preferably at least 90%, 91%, 92%, 93%, 94%, 95%, 96%, 97%, 98%, or 99% identical to the amino acid sequences reported herein. Suitable nucleic acid molecules of the present invention not only have the above homologies, but also typically encode a polypeptide having about 300 to about 340 amino acids, more preferably about 310 to about 330 amino acids, and most preferably about 318 to about 325 amino acids in length.

As used herein, the terms "signature motif" and "diagnostic motif" refer to conserved structures shared among a family of enzymes having a defined activity. The signature motif can be used to define and/or identify the family of structurally related enzymes having similar enzymatic activity for a defined family of substrates. The signature motif can be a single contiguous amino acid sequence or a collection of discontiguous, conserved motifs that together form the signature motif. Typically, the conserved motif(s) is represented by an amino acid sequence. As described herein, the present perhydrolases belong to the family of CE-7 carbohydrate esterases. This family of enzymes can be defined by the presence of a CE-7 "signature motif" (Vincent at al., supra).

As used herein, "codon degeneracy" refers to the nature of the genetic code permitting variation of the nucleotide sequence without affecting the amino acid sequence of an encoded polypeptide. Accordingly, the present invention relates to any nucleic acid molecule that encodes all or a substantial portion of the amino acid sequences encoding the present microbial polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

As used herein, the term "codon optimized", as it refers to genes or coding regions of nucleic acid molecules for transformation of various hosts, refers to the alteration of codons in the gene or coding regions of the nucleic acid molecules to reflect the typical codon usage of the host organism without altering the polypeptide for which the DNA codes.

As used herein, "synthetic genes" can be assembled from oligonucleotide building blocks that are chemically synthesized using procedures known to those skilled in the art. These building blocks are ligated and annealed to form gene segments that are then enzymatically assembled to construct the entire gene. "Chemically synthesized", as pertaining to a DNA sequence, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequences to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

As used herein, "gene" refers to a nucleic acid molecule that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different from that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

As used herein, "coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, RNA processing site, effector binding site and stem-bop structure.

As used herein, "promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene at different stages of development, or in response to different environmental or physiological conditions. Promoters that cause a gene to be expressed at most times are commonly referred to as "constitutive promoters". It is further recognized that since in most cases the exact boundaries of regulatory sequences have not been completely defined, DNA fragments of different lengths may have identical promoter activity.

As used herein, the "3' non-coding sequences" refer to DNA sequences located downstream of a coding sequence and include polyadenylation recognition sequences (normally limited to eukaryotes) and other sequences encoding regulatory signals capable of affecting mRNA processing or gene expression. The polyadenylation signal is usually characterized by affecting the addition of polyadenylic acid tracts (normally limited to eukaryotes) to the 3' end of the mRNA precursor.

As used herein, the term "operably linked" refers to the association of nucleic acid sequences on a single nucleic acid molecule so that the function of one is affected by the other. For example, a promoter is operably linked with a coding sequence when it is capable of affecting the expression of that coding sequence, i.e., that the coding sequence is under the transcriptional control of the promoter. Coding sequences can be operably linked to regulatory sequences in sense or anti-sense orientation.

As used herein, the term "expression" refers to the transcription and stable accumulation of sense (mRNA) or antisense RNA derived from the nucleic acid molecule described herein. Expression may also refer to translation of mRNA into a polypeptide.

As used herein, "transformation" refers to the transfer of a nucleic acid molecule into the genome of a host organism, resulting in genetically stable inheritance. In the present invention, the host cell's genome includes chromosomal and extrachromosomal (e.g., plasmid) genes. Host organisms containing the transformed nucleic acid molecules are referred to as "transgenic" or "recombinant" or "transformed" organisms.

As used herein, the terms "plasmid", "vector" and "cassette" refer to an extrachromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

As used herein, the term "sequence analysis software" refers to any computer algorithm or software program that is useful for the analysis of nucleotide or amino acid sequences. "Sequence analysis software" may be commercially available or independently developed. Typical sequence analysis software will include, but is not limited to, the GCG suite of programs (Wisconsin Package Version 9.0, Genetics Computer Group (GCG), Madison, Wis.), BLASTP, BLASTN, BLASTX (Altschul et al., *J. Mol. Biol.* 215:403-410 (1990), and DNASTAR (DNASTAR, Inc. 1228 S. Park St. Madison, Wis. 53715 USA), CLUSTALW (for example, version 1.83; Thompson et al., *Nucleic Acids Research,* 22(22):4673-4680 (1994), and the FASTA program incorporating the Smith-Waterman algorithm (W. R. Pearson, *Comput. Methods Genome Res.*, [Proc. Int. Symp.] (1994), Meeting Date 1992, 111-20. Editor(s): Suhai, Sandor. Publisher: Plenum, New York, N.Y.), Vector NTI (Informax, Bethesda, Md.) and Sequencher v. 4.05. Within the context of this application it will be understood that where sequence analysis software is used for analysis, that the results of the analysis will be based on the "default values" of the program referenced, unless otherwise specified. As used herein "default values" will mean any set of values or parameters set by the software manufacturer that originally load with the software when first initialized.

As used herein, the term "biological contaminants" refers to one or more unwanted and/or pathogenic biological entities including, but not limited to, microorganisms, spores, viruses, prions, and mixtures thereof. The process produces an efficacious concentration of at least one percarboxylic acid useful to reduce and/or eliminate the presence of the viable biological contaminants. In a preferred embodiment, the biological contaminant is a viable pathogenic microorganism.

As used herein, the term "disinfect" refers to the process of destruction of or prevention of the growth of biological contaminants. As used herein, the term "disinfectant" refers to an agent that disinfects by destroying, neutralizing, or inhibiting the growth of biological contaminants. As used herein, the term "disinfection" refers to the act or process of disinfecting. Typically, disinfectants are used to treat inanimate objects or surfaces. As used herein, the term "antiseptic" refers to a chemical agent that inhibits the growth of disease-carrying biological contaminants (such as microorganisms). In one aspect of the present methods and systems, the biological contaminants are pathogenic microorganisms.

As used herein, the term "sanitary" means of or relating to the restoration or preservation of health, typically by removing, preventing or controlling an agent that may be injurious to health. As used herein, the term "sanitize" means to make sanitary. As used herein, the term "sanitizes" refers to a sanitizing agent. As used herein the term "sanitization" refers to act or process of sanitizing.

As used herein, the term "virucide" refers to an agent that inhibits or destroys viruses, and is synonymous with "viricide". An agent that exhibits the ability to inhibit or destroy viruses is described as having "virucidal" activity. Peracids can have virucidal activity. Typical alternative virucides known in the art which may be suitable for use with the present invention include, for example, alcohols, ethers, chloroform, formaldehyde, phenols, beta propiolactone, iodine, chlorine, mercury salts, hydroxylamine, ethylene oxide, ethylene glycol, quaternary ammonium compounds, enzymes, and detergents.

As used herein, the term "biocide" refers to a chemical agent, typically broad spectrum, which inactivates or destroys microorganisms. A chemical agent that exhibits the ability to inactivate or destroy microorganisms is described as having "biocidal" activity. Peracids can have biocidal activity. Typical alternative biocides known in the art, which may be suitable for use in the present invention include, for example, chlorine, chlorine dioxide, chloroisocyanurates, hypochlorites, ozone, acrolein, amines, chlorinated phenolics, copper salts, organo-sulphur compounds, and quaternary ammonium salts.

As used herein, the phrase "minimum biocidal concentration" refers to the minimum concentration of a biocidal agent that, for a specific contact time, will produce a desired lethal, irreversible reduction in the viable population of the targeted microorganisms. The effectiveness can be measured by the $\log_{10}$ reduction in viable microorganisms after treatment. In one aspect, the targeted reduction in viable microorganisms after treatment is at least a 3-log reduction, more preferably at least a 4-log reduction, and most preferably at least a 5-log reduction. In another aspect, the minimum biocidal concentration is at least a 6-log reduction in viable microbial cells.

As used herein, the term "benefit agent" refers to something that promotes or enhances a useful advantage or favorable effect. In one embodiment, methods and systems are provided whereby a benefit agent, such as a composition comprising a peroxycarboxylic acid, is applied to an article of clothing or textile to achieve a desired benefit, such as disinfecting, sanitizing, bleaching, stain removal, deodorizing/odor reduction, and any combination thereof.

As used herein, the terms "peroxygen source" and "source of peroxygen" refer to compounds capable of providing hydrogen peroxide at a concentration of about 1 mM or more when in an aqueous solution including, but not limited to, hydrogen peroxide, hydrogen peroxide adducts (e.g., urea-hydrogen peroxide adduct (carbamide peroxide)), perborates, and percarbonates. As described herein, the concentration of the hydrogen peroxide provided by the peroxygen compound in the aqueous reaction formulation is initially at least 1 mM or more upon combining the reaction components. In one embodiment, the hydrogen peroxide concentration in the aqueous reaction formulation is at least 10 mM. In another embodiment, the hydrogen peroxide concentration in the aqueous reaction formulation is at least 100 mM. In another embodiment, the hydrogen peroxide concentration in the aqueous reaction formulation is at least 200 mM. In another embodiment, the hydrogen peroxide concentration in the aqueous reaction formulation is 500 mM or more. In yet another embodiment, the hydrogen peroxide concentration in the aqueous reaction formulation is 1000 mM or more. The molar ratio of the hydrogen peroxide to enzyme substrate, e.g. triglyceride, ($H_2O_2$:substrate) in the aqueous reaction formulation may be from about 0.002 to 20, preferably about 0.1 to 10, and most preferably about 0.5 to 5.

In some embodiments of the presently disclosed methods and systems, the enzyme catalyst comprises a perhydrolase having a structure belonging to the CE-7 carbohydrate esterase family. In other embodiments, the perhydrolase catalyst is structurally classified as a cephalosporin C deacetylase. In other embodiments, the perhydrolase catalyst is structurally classified as an acetyl xylan esterase. The terms "enzyme catalyst", "enzyme catalyst having perhydrolysis activity", and "perhydrolase catalyst" are used herein interchangeably.

In some embodiments of the present methods and systems, the perhydrolase catalyst comprises an enzyme having a CE-7 signature motif that aligns with a reference sequence SEQ ID NO: 2 using CLUSTALW, said CE-7 signature motif comprising:

i) an RGQ motif at amino acid positions 118-120 of SEQ ID NO:2;

ii) a GXSQG motif at amino acid positions 179-183 of SEQ ID NO:2; and iii) an HE motif at amino acid positions 298-299 of SEQ ID NO:2;

wherein said enzyme also comprises at least 30% amino acid identity to SEQ ID NO: 2.

In other embodiments of the present methods and systems, the signature motif additional comprises a fourth conserved motif defined as an LXD motif at amino acid residues 267-269 when aligned to reference sequence SEQ ID NO: 2 using CLUSTALW.

In additional embodiments of the present methods and systems, the perhydrolase catalyst may comprise an enzyme having perhydrolase activity selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 54, SEQ ID NO: 60, SEQ ID NO: 64, SEQ ID NO: 68, SEQ ID NO: 72, SEQ ID NO: 73, and SEQ ID NO: 74 or a substantially similar enzyme having perhydrolase activity derived by substituting, deleting or adding one or more amino acids to said amino acid sequence.

In other embodiments of the present methods and systems, substantially similar enzyme having perhydrolase activity is at least 30%, preferably at least 33%, more preferably at least 40%, more preferably at least 50%, even more preferably at least 60%, yet even more preferable at least 70%, yet even more preferably at least 80%, yet even more preferably at least 90%, 91%, 92%, 93%, 94%, 95%, 96%, 97%, 98%, or 99% identical to one or more amino acid sequences selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 54, SEQ ID NO: 60, SEQ ID NO: 64, SEQ ID NO: 68, SEQ ID NO: 72, SEQ ID NO: 73, and SEQ ID NO: 74.

In other embodiments of the present methods and systems, the perhydrolase catalyst comprises an enzyme having an amino acid sequence encoded by a nucleic acid molecule that hybridizes to a nucleic acid sequence selected from the group consisting of SEQ ID NO: 1, SEQ ID NO: 3, SEQ ID NO: 5; SEQ ID NO: 7; SEQ ID NO:9, SEQ ID NO:11, SEQ ID NO:13, SEQ ID NO: 15, SEQ ID NO: 17, SEQ ID NO:19, SEQ ID NO:21, SEQ ID NO:23, SEQ ID NO: 25; SEQ ID NO:29; SEQ ID NO:48, SEQ ID NO: 51, SEQ ID NO: 53, SEQ ID NO: 56, SEQ ID NO: 57, SEQ ID NO: 58, SEQ ID NO: 59, SEQ ID NO: 61, SEQ ID NO: 62, SEQ ID NO: 63, SEQ ID NO: 65, SEQ ID NO: 66, SEQ ID NO: 67, SEQ ID NO: 69, SEQ ID NO: 70, and SEQ ID NO: 71 under stringent hybridization conditions.

In other embodiments of the present methods and systems, the perhydrolase catalyst comprises an enzyme having an amino add sequence selected from the group consisting of SEQ ID NO: 14 and SEQ ID NO: 73 (i.e, the wild type *Thermotoga neapolitana* and *Thermotoga neapolitana* variants having an amino acid substitution at amino acid residue 277).

In other embodiments of the present methods and systems, the perhydrolase catalyst comprises an enzyme having an amino acid sequence selected from the group consisting of SEQ ID NO: 16 and SEQ ID NO: 74 (i.e, the wild type *Thermotoga maritima* and *Thermotoga maritima* variants having an amino acid substitution at amino acid residue 277).

In other embodiments of the present methods and systems, the perhydrolase catalyst comprises an enzyme having at least 30%, preferably at least 36%, amino acid identity to a contiguous signature motif defined as SEQ ID NO: 49 wherein the conserved motifs described above (i.e., RGQ, GXSQG, and HE, and optionally, LXD) are conserved.

With respect to the presently disclosed methods and systems, suitable carboxylic acid ester substrates include esters provided by the following formula:

[X]R$_5$ wherein X=an ester group of the formula R$_6$C(O)O

R$_6$=C1 to C7 linear, branched or cyclic hydrocarbyl moiety, optionally substituted with hydroxyl groups or C1 to C4 alkoxy groups, wherein R$_6$ optionally comprises one or more ether linkages for R$_6$=C2 to C7;

R$_5$=a C1 to C6 linear, branched, or cyclic hydrocarbyl moiety optionally substituted with hydroxyl groups; wherein each carbon atom in R$_5$ individually comprises no more than one hydroxyl group or no more than one ester group; wherein R$_5$ optionally comprises one or more ether linkages;

m=1 to the number of carbon atoms in R$_5$; and wherein said esters have solubility in water of at least 5 ppm at 25° C.

In other embodiments of the present methods and systems, suitable substrates also include esters of the formula:

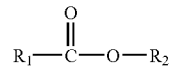

wherein R$_1$=C1 to C7 straight chain or branched chain alkyl optionally substituted with a hydroxyl or a C1 to C4 alkoxy group and R$_2$=C1 to C10 straight chain or branched chain alkyl, alkenyl, alkynyl, aryl, alkylaryl, alkylheteroaryl, heteroaryl, (CH$_2$CH$_2$—O)$_n$H or (CH$_2$CH(CH$_3$)—O)$_n$H and n=1 to 10.

In other embodiments of the present methods and systems, suitable carboxylic acid ester substrates include glycerides of the formula:

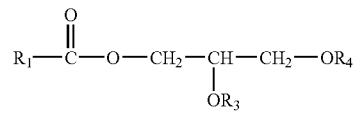

wherein R$_1$=C1 to C7 straight chain or branched chain alkyl optionally substituted with a hydroxyl or a C1 to C4 alkoxy group and R$_3$ and R$_4$ are individually H or R$_1$C(O).

In other embodiments of the present methods and systems, R$_6$ is C1 to C7 linear hydrocarbyl moiety, optionally substituted with hydroxyl groups or C1 to C4 alkoxy groups, optionally comprising one or more ether linkages. In further preferred embodiments, R$_6$ is C2 to C7 linear hydrocarbyl moiety, optionally substituted with hydroxyl groups, and/or optionally comprising one or more ether linkages.

In other embodiments of the disclosed methods and systems, suitable carboxylic acid ester substrates also include acetylated saccharides selected from the group consisting of acetylated mono-, di-, and polysaccharides. In preferred embodiments, the acetylated saccharides include acetylated mono-, di-, and polysaccharides. In other embodiments, the acetylated saccharides are selected from the group consisting of acetylated xylan, fragments of acetylated xylan, acetylated xylose (such as xylose tetraacetate), acetylated glucose (such as glucose pentaacetate), β-D-ribofuranose-1,2,3,5-tetraacetate, tri-O-acetyl-D-galactal, tri-O-acetyl-D-glucal, and acetylated cellulose. In preferred embodiments, the acetylated saccharide is selected from the group consisting of β-D-ribofuranose-1,2,3,5-tetraacetate, tri-O-acetyl-D-galactal, tri-O-acetyl-D-glucal, and acetylated cellulose. As such, acetylated carbohydrates may be suitable substrates for generating percarboxylic acids using the present methods and systems (i.e., in the presence of a peroxygen source).

In additional embodiments of the present methods and systems, the carboxylic acid ester substrate may be monoacetin; triacetin; monopropionin; dipropionin; tripropionin; monobutyrin; dibutyrin; tributyrin; glucose pentaacetate; xylose tetraacetate; acetylated xylan; acetylated xylan fragments; β-D-ribofuranose-1,2,3,5-tetraacetate; tri-O-acetyl-D-galactal; tri-O-acetyl-glucal; propylene glycol diacetate; ethylene glycol diacetate; monoesters or diesters of 1,2-ethanediol; 1,2-propanediol; 1,3-propanediol; 1,2-butanediol; 1,3-butanediol; 2,3-butanediol; 1,4-butanediol; 1,2-pentanediol; 2,5-pentanediol; 1,6-pentanediol; 1,2-hexanediol; 2,5-hexanediol; 1,6-hexanediol; and mixtures thereof. In preferred embodiments of the present methods and systems, the substrate comprises triacetin.

Preferably, the substrate used in the present methods and systems has solubility in water of less than about 100 mg/mL. In some embodiments of the present methods and systems, the percent by weight of the substrate in the aqueous reaction mixture exceeds the solubility limit of the substrate in water.

In other embodiments of the presently disclosed methods and systems, the substrate may be ethyl acetate; methyl lactate; ethyl lactate; methyl glycolate; ethyl glycolate; methyl methoxyacetate; ethyl methoxyacetate; methyl 3-hydroxybutyrate; ethyl 3-hydroxybutyrate; triethyl 2-acetyl citrate; glucose pentaacetate; gluconolactone; glycerides (mono-, di-, and triglycerides) such as monoacetin, diacetin, triacetin, monopropionin, dipropionin (glyceryl dipropionate), tripropionin (1,2,3-tripropionylglycerol), monobutyrin, dibutyrin (glyceryl dibutyrate), tributyrin (1,2,3-tributyrylglycerol); acetylated saccharides; and mixtures thereof.

In a further preferred aspect of the present methods and systems, the carboxylic acid ester substrates are selected from the group consisting of monoacetin, diacetin, triacetin, monopropionin, dipropionin, tripropionin, monobutyrin, dibutyrin, tributyrin, ethyl acetate, and ethyl lactate. In yet another aspect, the carboxylic acid ester substrates are selected from the group consisting of diacetin, triacetin, ethyl acetate, and ethyl lactate. In preferred aspects, the carboxylic acid ester is a glyceride selected from the group consisting of monoacetin, diacetin, triacetin, and mixtures thereof.

Use of Cosolvents in a Multi-Component Generation System.

The cosolvent for use in the presently disclosed methods and systems comprises an organic solvent having a log P of less than about 2. In some embodiments, the cosolvent is preferably an alcohol. The cosolvent preferably may comprise tripropylene glycol methyl ether, dipropylene glycol methyl ether, propylene glycol methyl ether, diethylene glycol butyl ether, dipropylene glycol, triethyleneglycol, 1,2-propanediol, N-ethyl-2-pyrrolidinone, isopropanol, ethanol, ethyl lactate, 1,3-propanediol, or any combination thereof. In some embodiments of the present methods and systems, the cosolvent comprises tripropylene glycol methyl ether.

In the present methods for producing peroxycarboxylic acid in a multicomponent system, the multicomponent system may comprise a first component comprising the catalyst composition comprising a cosolvent, and a second component comprising the source of peroxygen and water. The second component may comprise an optional stabilizer to extend the shelf-life of the hydrogen peroxide. The catalyst, substrate, and the cosolvent may be combined to form the first component prior to combination of the first component with the second component. Likewise, with respect to the disclosed methods for disinfecting a surface, the step of combining the catalyst composition and the source of peroxygen may comprise combining a first component comprising the catalyst composition and the cosolvent with a second component comprising the source of peroxygen and water.

In embodiments of the present methods and systems wherein the multicomponent system comprises a first component comprising the catalyst composition comprising the cosolvent, and a second component comprising the source of peroxygen and water, the first component may be combined with the second component in a ratio of about 1:1 to about 1:10 by weight. In one embodiment, the first component is combined with the second component in a ratio of about 1:9 by weight.

Within the range of a 1:1 to a 1:10 mixture of the first and second components as described above, a concentration of enzyme substrate ("activator") in the first component and a ratio of the second component to the first component are also chosen such that the substrate is soluble in the final mixture of the first component and the second component. For example, the solubility of triacetin in water is reported as 71.7 g/L (Seelig, *Chemische Serichte;* 24: 3466 (1891)), the solubility of 1,2-propanediol diacetate is reported to be 1 part in 10 parts water (Wurtz, *Annales de Chimie;* 55:443 (1859); *Justus Liebigs Annalen der Chemie;* 105:206 (1858)), and the solubility of tributyrin in water is reported to be 0.015% (volume/volume) (*Loskit, Zeitschrift fuer Physikalische Chemie, Stoechiometrie and Verwandtschaftslehre;* 134:137 (1928)). Given the wide range of solubilities for the enzyme substrates of the present invention, where the enzyme substrates are described below, the cosolvent added to the first component of the present invention may function to aid in the dissolution of an enzyme substrate with poor solubility in water, in addition to its function as a diluent in the first component to enable the mixing of a desired ratio of the first component and the second component. In one embodiment of the invention, the substrate is soluble in the resulting formulation of the first component and the second component at a concentration of at least 25% (weight/weight). In a second embodiment of the present invention, the substrate is soluble in the resulting formulation of the first component and the second component at a concentration of at least 10% (weight/weight). In a third embodiment of the present invention, the substrate is soluble in the resulting formulation of the first component and the second component at a concentration of at least 5% (weight/weight). In a fourth embodiment of the present invention, the substrate is soluble in the resulting formulation of the first component and the second component at a concentration of at least 2% (weight/weight).

In one embodiment, the cosolvent may be present in the first component in an amount of about 20% to about 80% by weight. The substrate may be present in the first component in an amount of about 10% to about 60% by weight. In some embodiments, the first component may comprise about 55% by weight substrate, about 40% by weight cosolvent, about 0.3% by weight enzyme catalyst, and about 2.5% by weight filler, and the second component may comprise about 95% by weight water, about 1.5% by weight sodium bicarbonate, and about 1% by weight of a source of peroxygen. In other instances, the first component may comprise about 55.5% by weight triacetin, about 41% by weight tripropylene glycol methyl ether, about 0.9% sodium bicarbonate, about 0.3% by weight of a spray dried enzyme powder comprising *Thermotoga neapolitana* or *Thermotoga maritima* perhydrolase or a variant derivative of *Thermotoga neapolitana* or *Thermotoga maritima* perhydrolase having one or more point mutations that improve the perhydrolysis activity, and about 2.5% by weight fumed silica, and the second component may comprise about 96% by weight water, about 0.2% by weight hydrogen peroxide stabilizer (e.g., (1-hydroxyethylidene) bisphosphonic acid)), and about 3.2% by weight of a solution comprising 30% hydrogen peroxide.

With respect to the present methods and systems, the carboxylic acid ester substrate may be used at a concentration sufficient to produce the desired concentration of peracid upon enzyme-catalyzed perhydrolysis. The carboxylic acid ester need not be completely soluble in the reaction formulation, but preferably has sufficient solubility to permit conversion of the ester by the perhydrolase catalyst to the corresponding peracid. The carboxylic add ester is present in the aqueous reaction formulation at a concentration of about 0.0005 wt % to about 40 wt % of the reaction formulation, preferably at a concentration of 0.1 wt % to 20 wt % of the aqueous reaction formulation, and more preferably at a concentration of 0.5 wt % to 10 wt % of the aqueous reaction formulation. The wt % of carboxylic acid ester may be greater than the solubility limit of the carboxylic acid ester. Not all of the added carboxylic acid ester must immediately dissolve in the aqueous reaction formulation, and after an initial mixing of all reaction components, additional continuous or discontinuous mixing is optional.

In the present methods and systems, the peroxygen source may include, but is not limited to, hydrogen peroxide, hydrogen peroxide adducts (such as urea-hydrogen peroxide adduct (carbamide peroxide)), perborate salts and percarbonate salts. The concentration of peroxygen compound in the aqueous reaction formulation may range from 0.0033 wt % to about 50 wt %, preferably from 0.033 wt % to about 40 wt %, more preferably from 0.33 wt % to about 30 wt %.

The reaction formulation of the present methods and systems may comprise from about 5 mM to about 250 mM substrate, from about 5 mM to about 250 mM of the source of peroxygen, and from about 0.0001 mg/mL to about 10 mg/mL, preferably about 0.01 mg/mL to about 2.0 mg/mL, of the enzyme catalyst. In such instances, the substrate may comprise triacetin, the source of peroxygen may comprise hydrogen peroxide, and enzyme catalyst may comprise *Thermotoga neapolitana* or *Thermotoga maritima* perhydrolase. In another embodiment, the enzyme catalyst may comprise a *Thermotoga neapolitana* or *Thermotoga maritima* variant as defined by SEQ ID NO: 73 or SEQ ID NO: 74, where the wild type cysteine at amino acid residue position 277 is substituted with alanine, valine, serine, or threonine.

Many perhydrolase catalysts (such as whole cells, permeabilized whole cells, and partially purified whole cell extracts) have been reported to have catalase activity (EC 1.11.1.6). Catalases catalyze the conversion of hydrogen peroxide into oxygen and water. In one aspect of the presently disclosed methods and systems, the perhydrolysis catalyst lacks catalase activity. In another aspect, a catalase inhibitor is added to the reaction formulation. Examples of catalase inhibitors include, but are not limited to, sodium azide and hydroxylamine sulfate. One of skill in the art can adjust the concentration of catalase inhibitor as needed. The concentration of the catalase inhibitor typically ranges from 0.1 mM to about 1 M; preferably about 1 mM to about 50 mM; more preferably from about 1 mM to about 20 mM. In one aspect, sodium azide concentration typically ranges from about 20 mM to about 60 mM while hydroxylamine sulfate is concentration is typically about 0.5 mM to about 30 mM, preferably about 10 mM.

In other embodiments of the present methods and systems, the enzyme catalyst lacks significant catalase activity or is engineered to decrease or eliminate catalase activity. The catalase activity in a host cell can be down-regulated or eliminated by disrupting expression of the gene(s) responsible for the catalase activity using well known techniques including, but not limited to, transposon mutagenesis, RNA antisense expression, targeted mutagenesis, and random mutagenesis. In some embodiments of the present methods and systems, the gene(s) encoding the endogenous catalase activity are down-regulated or disrupted (i.e., a "knocked-out"). As used herein, a "disrupted" gene is one where the activity and/or function of the protein encoded by the modified gene is no longer present. Means to disrupt a gene are well-known in the art and may include, but are not limited to, insertions, deletions, or mutations to the gene so long as the activity and/or function of the corresponding protein is no longer present. In a further preferred embodiment, the production host is an *E. coli* production host comprising a disrupted catalase gene selected from the group consisting of katG (SEQ ID NO: 35) and katE (SEQ ID NO: 44). In other embodiments, the production host is an *E. coli* strain comprising a down-regulation and/or disruption in both katg1 and katE catalase genes. An *E. coli* strain comprising a double-knockout of katG and katE is provided herein (*E. coli* strain KLP18).

The catalase negative *E. coli* strain KLP18 described herein has been demonstrated to be a superior host for large scale (10-L and greater) production of perhydrolase enzymes compared to the catalase negative strain UM2 (*E. coli* Genetic Stock Center #7156, Yale University, New Haven Conn.), as determined by growth under fermenter conditions. Although both KLP18 and UM2 are catalase-negative strains, UM2 is known to have numerous nutritional auxotrophies, and therefore requires media that is enriched with yeast extract and peptone. Even when employing enriched media for fermentation, UM2 grew poorly and to a limited maximum cell density (OD). In contrast, KLP18 had no special nutritional requirements and grew to high cell densities on mineral media alone or with additional yeast extract.

The concentration of the catalyst in the aqueous reaction formulation of the present methods and systems depends on the specific catalytic activity of the catalyst and is chosen to obtain the desired rate of reaction. The weight of catalyst in perhydrolysis reactions typically ranges from 0.0001 mg to 10 mg per mL of total reaction volume, preferably from 0.010 mg to 2.0 mg per mL. The catalyst may also be immobilized on a soluble or insoluble support using methods well-known to those skilled in the art; see for example, *Immobilization of Enzymes and Cells*; Gordon F. Bickerstaff, Editor; Humana Press, Totowa, N.J., USA; 1997. The use of immobilized catalysts permits the recovery and reuse of the catalyst in subsequent reactions. The enzyme catalyst may be in the form of whole microbial cells, permeabilized microbial cells, microbial cell extracts, partially-purified or purified enzymes, or mixtures thereof.

In one aspect of the present methods and systems, the concentration of peracid generated by the combination of chemical perhydrolysis and enzymatic perhydrolysis of the carboxylic acid ester is sufficient to provide an effective concentration of peracid for bleaching, sanitization or disinfection at a desired pH. In another aspect, the present methods and systems provide combinations of enzymes and enzyme substrates to produce the desired effective concentration of peracid, where, in the absence of added enzyme, there is a significantly lower concentration of peracid produced. Although there may in some cases be substantial chemical perhydrolysis of the enzyme substrate by direct chemical reaction of inorganic peroxide with the enzyme substrate, there may not be a sufficient concentration of peracid generated to provide an effective concentration of peracid in the desired applications, and a significant increase in total peracid concentration is achieved by the addition of an appropriate perhydrolase catalyst to the reaction formulation.

In connection with the present systems and methods, the concentration of peracid generated (e.g., peracetic acid) by the perhydrolysis of at least one carboxylic acid ester may be at least about 2 ppm, preferably at least 20 ppm, preferably at least 100 ppm, more preferably at least about 200 ppm peracid, more preferably at least 300 ppm, more preferably at least 500 ppm, more preferably at least 700 ppm, more preferably at least about 1000 ppm peracid, most preferably at least 2000 ppm peracid within 10 minutes, preferably within 5 minutes, and most preferably within 1 minute of initiating the perhydrolysis reaction. The product formulation comprising the peracid may be optionally diluted with water, or a solution predominantly comprised of water, to produce a formulation with the desired lower concentration of peracid. In one aspect of the present methods and systems, the reaction time required to produce the desired concentration of peracid is not greater than about two hours, preferably not greater than about 30 minutes, more preferably not greater than about 10 minutes, even more preferably not greater than about 5 minutes, and most preferably in about 1 minute or less. In other aspects of the present methods for disinfecting a surface, a surface, including a hard surface or inanimate object, contaminated with a biological contaminant(s) is contacted with the peracid formed in accordance with the processes described herein within about 1 minute to about 168 hours of combining said reaction components, or within about 1 minute to about 48 hours, or within about 1 minute to 2 hours of combining said reaction components, or any such time interval therein.

The temperature of the reaction is chosen to control both the reaction rate and the stability of the enzyme catalyst activity. The temperature of the reaction may range from just above the freezing point of the reaction formulation (approximately 0° C.) to about 95° C., preferably about 5° C. to about 75° C., with a more preferred range of reaction temperature of from about 5° C. to about 55° C.

The pH of the final reaction formulation containing peracid is from about 2 to about 9, preferably from about 3 to about 8, more preferably from about 5 to about 8, even more preferably about 6 to about 8, and yet even more preferably about 6.5 to about 7.5. In another embodiment, the pH of the reaction formulation is acidic (pH<7). The pH of the reaction, and of the final reaction formulation, may optionally be controlled by the addition of a suitable buffer, including, but not limited to, bicarbonate, citrate, acetate, phosphate, pyrophosphate, methylphosphonate, succinate, malate, fumarate, tartrate, or maleate. The concentration of buffer, when employed, is typically from 0.1 mM to 1.0 M, preferably from 1 mM to 300 mM, most preferably from 10 mM to 100 mM.

In another aspect of the present methods and systems, the enzymatic perhydrolysis product may contain additional components that provide desirable functionality. In a further aspect, the present methods and systems are used in laundry care applications for the treatment of an article of clothing. Examples of additional components include, but are not limited to, buffers, detergent builders, thickening agents, emulsifiers, surfactants, wetting agents, corrosion inhibitors (such as benzotriazole), enzyme stabilizers, and hydrogen peroxide stabilizers (such as metal ion chelating agents). Many of the additional components are well known in the detergent industry (such as those described in U.S. Pat. No. 5,932,532; hereby incorporated by reference). Examples of emulsifiers include, but are not limited to, polyvinyl alcohol or polyvinylpyrrolidone. Examples of thickening agents include, but are not limited to, LAPONITE® RD, corn starch, PVP, CARBOWAX®, CARBOPOL®, CABOSIL®, polysorbate 20, PVA, and lecithin. Examples of buffering systems include, but are not limited to, sodium phosphate monobasic/sodium phosphate dibasic; sulfamic acid/triethanolamine; citric acid/triethanolamine, tartaric acid/triethanolamine; succinic acid/triethanolamine; and acetic acid/triethanolamine. Examples of surfactants include, but are not limited to, (a) non-ionic surfactants such as block copolymers of ethylene oxide or propylene oxide, ethoxylated or propoxylated linear and branched primary and secondary alcohols, and aliphatic phosphine oxides; (b) cationic surfactants such as quaternary ammonium compounds, particularly quaternary ammonium compounds having a C8-C20 alkyl group bound to a nitrogen atom additionally bound to three C1-C2 alkyl groups; (c) anionic surfactants such as alkane carboxylic acids (e.g., C8-C20 fatty acids), alkyl phosphonates, alkane sulfonates (e.g., sodium dodecylsulphate "SDS") or linear or branched alkyl benzene sulfonates, alkene sulfonates; and (d) amphoteric and zwitterionic surfactants such as aminocarboxylic acids, aminodicarboxylic acids, alkylbetaines, and mixtures thereof. Additional components may include fragrances, dyes, stabilizers of hydrogen peroxide (e.g., metal chelators such as 1-hydroxyethylidene-1,1-diphosphonic acid (DEQUEST® 2010, Solutia Inc., St. Louis, Mo. and ethylenediaminetetraacetic acid (EDTA)), TURPINAL® SL (CAS#2809-21-4), DEQUEST® 0520, DEQUEST® 0531, stabilizers of enzyme activity (e.g., polyethylene glycol (PEG)), and detergent builders.

In another aspect of the present methods of disinfecting a surface, the enzymatic perhydrolysis product may be pre-mixed to generate the desired concentration of peroxycarboxylic acid prior to contacting the surface to be disinfected. In another aspect of the present methods of disinfecting a surface, the enzymatic perhydrolysis product is not pre-mixed to generate the desired concentration of peroxycarboxylic acid prior to contacting the surface (such as a hard surface or inanimate object) to be disinfected, but instead, the components of the reaction formulation that generate the desired concentration of percarboxylic acid are contacted with the surface to be disinfected, sanitized, bleached, destained, deodorized or any combination thereof, generating the desired concentration of peroxycarboxylic acid. In some embodiments, the components of the reaction formulation combine or mix at the locus. In some embodiments, the reaction components are delivered or applied to the locus and subsequently mix or combine to generate the desired concentration of peroxycarboxylic acid.

In any embodiment of the present methods of disinfecting a surface or delivering a benefit to an article of clothing or textile (stain removal, order reduction, bleaching, sanitization, and/or disinfection), the aqueous reaction formulation may be applied to the surface by spraying, pouring, sprinkling, wiping, or by any other suitable technique, of which numerous other examples will be appreciated among those skilled in the art.

In Situ Production of Peracids Using a Perhydrolase Catalyst

Cephalosporin C deacetylases (E.C. 3.1.1.41; systematic name cephalosporin C acetylhydrolases; CAHs) are enzymes having the ability to hydrolyze the acetyl ester bond on cephalosporins such as cephalosporin C, 7-aminocephalosporanic acid, and 7-(thiophene-2-acetamido)cephalosporanic acid (Abbott, B. and Fukuda, D., *Appl. Microbiol.* 30(3):413-419 (1975)). CAHs belong to a larger family of structurally related enzymes referred to as the carbohydrate esterase family seven (CE-7; see Coutinho, P. M., Henrissat, B. "Carbohydrate-active enzymes: an integrated database approach" in *Recent Advances in Carbohydrate Bioengineering*, H. J. Gilbert, G. Davies, B. Henrissat and B. Svensson eds., (1999) The Royal Society of Chemistry, Cambridge, pp. 3-12.)

The CE-7 family includes both CAHs and acetyl xylan esterases (AXEs; E.C. 3.1.1.72). CE-7 family members share a common structural motif and are quite unusual in that they typically exhibit ester hydrolysis activity for both acetylated xylooligosaccharides and cephalosporin C, suggesting that the CE-7 family represents a single class of proteins with a multifunctional deacetylase activity against a range of small substrates (Vincent et al., supra). Vincent et al. describes the structural similarity among the members of this family and defines a signature sequence motif characteristic of the CE-7 family ("the CE-7 signature motif").

Members of the CE-7 family are found in plants, fungi (e.g., *Cephalosporidium acremonium*), yeasts (e.g., *Rhodosporidium toruloides, Rhodotorula glutinis*), and bacteria such as *Thermoanaerobacterium* sp.; *Norcardia lactamdurans*, and various members of the genus *Bacillus* (Politino et al., *Appl. Environ, Microbiol.*, 63(12):4807-4811 (1997);

Sakai et al., *J. Ferment. Bioeng.* 85:53-57 (1998); Lorenz, W. and Wiegel, J., *J. Bacteriol* 179:5436-5441 (1997); Cardoza et al., *Appl. Microbiol. Biotechnol.*, 54(3):406-412 (2000); Mitsushima et al., supra, Abbott, B. and Fukuda, D., *Appl. Microbiol.* 30(3):413-419 (1975); Vincent et al., supra; Takami et al., *NAR*, 28(21):4317-4331 (2000); Rey et al., *Genome Biol.*, 5(10): article 77 (2004); Degrassi et al., *Microbiology.*, 146:1585-1591 (2000); U.S. Pat. No. 6,645,233; U.S. Pat. No. 5,281,525; U.S. Pat. No. 5,338,676; and WO 99/03984. A non-comprehensive list of CE-7 carbohydrate esterase family members having significant homology to SEQ ID NO: 2 are provided in Table 1.

TABLE 1

Examples of CE-7 Enzymes Having Significant Homology to SEQ ID NO: 2.

| Source Organism (GENBANK ® Accession No. of the CE-7 enzyme) | Nucleotide Sequence (SEQ ID NO:) | Amino Acid Sequence (SEQ ID NO:) | % Amino Acid Identity to SEQ ID NO: 2. | Reference |
|---|---|---|---|---|
| *B. subtilis* ATCC ® 31954 ™ | 1 | 2 | 100 | *B. subtilis* SHS 0133 Mitsushima et al., supra |
| *B. subtilis* subsp. *subtilis* str. 168 (NP_388200) *B. subtilis* BE1010 | 3 | 4 | 98 | Kunst et al., supra. WO99/03984 Payne and Jackson, J. Bacteriol. 173: 2278-2282 (1991)) |
| *B. subtilis* ATCC ® 6633 (YP_077621.1) | 5 | 6 | 96 | U.S. Pat. No. 6,465,233 |
| *B. subtilis* ATCC ® 29233 ™ | 25 | 26 | 96 | Abbott and Fukuda, supra |
| *B. licheniformis* ATCC ® 14580 ™ (YP_077621.1) | 7 | 8 | 77 | Rey et al., supra |
| *B. pumilus* PS213 (CAB76451.2) | 9, 48 | 10 | 76 | Degrassi et al., supra |
| *Clostridium thermocellum* ATCC ® 27405 ™ (ZP_00504991) | 11 | 12 | 57 | Copeland et al. US Dept. of Energy Joint Genome Institute (JGI-PGF) Direct Submission GENBANK ® ZP_00504991 |
| *Thermotoga neapolitana* (AAB70869.1) | 13, 29 | 14 | 42 | See GENBANK ® AAB70869.1 |
| *Thermotoga maritima* MSB8 (NP_227893.1) | 15, 56 | 16 | 42 | Nelson et al., Nature 399 (6734): 323-329 (1999) |
| *Bacillus* sp. NRRL B-14911 (ZP_01168674) | 19 | 20 | 40 | Siefert et al. J. Craig Venter Institute. Direct Submission Under GENBANK ® ZP_01168674 |
| *Thermoanaerobacterium* sp. (AAB68821.1) | 17 | 18 | 37 | Lorenz and Wiegel, supra |
| *Bacillus halodurans* C-125 (NP_244192) | 21 | 22 | 36 | Takami et al., supra |
| *Thermoanearobacterium saccharolyticum* (S41858) | 53 | 54 | 35 | Lee, Y. E. and Zeikus, J. G., J Gen Microbiol. (1993), 139 Pt 6: 1235-1243 |
| *Bacillus clausii* KSM-K16 (YP_175265) | 23, 51 | 24 | 33 | Kobayashi et al., Appl. Microbiol. Biotechnol. 43 (3), 473-481 (1995) |

TABLE 1-continued

Examples of CE-7 Enzymes Having Significant Homology to SEQ ID NO: 2.

| Source Organism (GENBANK ® Accession No. of the CE-7 enzyme) | Nucleotide Sequence (SEQ ID NO:) | Amino Acid Sequence (SEQ ID NO:) | % Amino Acid Identity to SEQ ID NO: 2. | Reference |
|---|---|---|---|---|
| *Thermotoga lettingae* (CP000812) | 57, 58, and 59 | 60 | 37 | Copeland et al. US Dept. of Energy Joint Genome Institute Direct Submission GENBANK ® CP000812 |
| *Thermotoga Petrophila* (CP000702) | 61, 62, and 63 | 64 | 41 | Copeland et al. US Dept. of Energy Joint Genome Institute Direct Submission GENBANK ® CP000702 |
| *Thermotoga* sp. RQ2 "RQ2(a)" (CP000969) | 65, 66, and 67 | 68 | 42 | Copeland et al. US Dept. of Energy Joint Genome Institute Direct Submission GENBANK ® CP000969 |
| *Thermotoga* sp. RQ2 "RQ2(b)" (CP000969) | 69, 70, and 71 | 72 | 42 | Copeland et al. US Dept. of Energy Joint Genome Institute Direct Submission GENBANK ® CP000969 |

The perhydrolases for use in the present methods and systems are preferably all members of the CE-7 carbohydrate esterase family. The enzyme catalyst may comprise *Thermotoga neapolitana* perhydrolase defined by SEQ ID NO:14. In other embodiments of the present methods and systems, the enzyme catalyst may comprise *Thermotoga maritima* perhydrolase defined by SEQ ID NO:16. As described by Vincent et al. (supra), members of the family share a common signature motif that is characteristic of this family. A CLUSTALW alignment of the present perhydrolases illustrates that all of the members belong to the CE-7 carbohydrate esterase family (FIG. 1, sheets A-F). A comparison of the overall percent amino acid identity among several of CE-7 perhydrolases is provided in Table 2.

TABLE 2

Percent Amino Acid Identity Between Perhydrolases[1]

| | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| 1 | 100 | | | | | | | | | | | | | | |
| 2 | 99 | 100 | | | | | | | | | | | | | |
| 3 | 99 | 99 | 100 | | | | | | | | | | | | |
| 4 | 96 | 96 | 97 | 100 | | | | | | | | | | | |
| 5 | 77 | 76 | 77 | 76 | 100 | | | | | | | | | | |
| 6 | 76 | 76 | 76 | 76 | 68 | 100 | | | | | | | | | |
| 7 | 57 | 57 | 57 | 56 | 56 | 56 | 100 | | | | | | | | |
| 8 | 42 | 43 | 43 | 43 | 43 | 42 | 41 | 100 | | | | | | | |
| 9 | 42 | 43 | 42 | 43 | 43 | 42 | 42 | 72 | 100 | | | | | | |
| 10 | 42 | 43 | 43 | 43 | 44 | 42 | 43 | 71 | 91 | 100 | | | | | |

TABLE 2-continued

Percent Amino Acid Identity Between Perhydrolases[1]

|    | 1  | 2  | 3  | 4  | 5  | 6  | 7  | 8  | 9  | 10 | 11  | 12  | 13  | 14  | 15  |
|----|----|----|----|----|----|----|----|----|----|----|-----|-----|-----|-----|-----|
| 11 | 41 | 43 | 43 | 43 | 45 | 42 | 43 | 71 | 97 | 91 | 100 |     |     |     |     |
| 12 | 41 | 42 | 42 | 42 | 43 | 41 | 42 | 71 | 98 | 91 | 97  | 100 |     |     |     |
| 13 | 37 | 37 | 37 | 36 | 39 | 38 | 38 | 64 | 65 | 67 | 66  | 65  | 100 |     |     |
| 14 | 34 | 36 | 35 | 36 | 35 | 36 | 33 | 36 | 32 | 34 | 34  | 33  | 36  | 100 |     |
| 15 | 33 | 34 | 33 | 33 | 32 | 34 | 32 | 30 | 30 | 32 | 31  | 31  | 32  | 34  | 100 |

[1] = Percent identity determined using blast2seq algorithm using BLOSUM62, gap open = 11, gap extension = 1, x_drop = 0, expect = 10, and wordsize = 3. Tatiana A. Tatusova, Thomas L. Madden (1999), "Blast 2 sequences - a new tool for comparing protein and nucleotide sequences", FEMS Microbiol Lett. 174: 247-250

1. *B. subtilis* ATCC® 31954™
2. *B. subtilis* BE1010
3. *B. subtilis* ATCC® 29233™
4. *B. subtilis* ATCC® 6633™
5. *B. licheniformis* 14580
6. *B. pumilus* PS213
7. *C. thermocellum* ATCC® 27405™
8. *Thermotoga* sp. RQ2(b)
9. *Thermotoga* sp. RQ2(a)
10. *T. neapolitana*
11. *T. maritima*
12. *T. petrophila*
13. *T. lettingae*
14. *T. saccharolyticum*
15. *B. clausii*

Although variation is observed in terms of overall percent amino acid identity (i.e., the *Clostridium thermocellum* ATCC® 27405™ perhydrolase; SEQ ID NO: 12 shares only 57% amino acid identity with the *Bacillus subtilis* ATCC® 31954™ perhydrolase; SEQ ID NO: 2, while the *Bacillus clausii* perhydrolase (SEQ ID NO: 24) shares only 33% identity with SEQ ID NO: 2), each of the present perhydrolase enzymes share the CE-7 signature motif. Accordingly, the perhydrolase catalyst of the present invention is an enzyme structurally classified as belonging to the CE-7 carbohydrate esterase family. Each of the present perhydrolase enzymes comprises the CE-7 signature motif.

In one embodiment of the present methods and systems, suitable perhydrolytic enzymes can be identified by the presence of the CE-7 signature motif (Vincent et al., supra). In preferred embodiments, perhydrolases comprising the CE-7 signature motif are identified using a CLUSTALW alignment against the *Bacillus subtilis* ATCC® 31954™ perhydrolase (SEQ ID NO: 2; the reference sequence used for relative amino acid position numbering). As per the amino acid residue numbering of SEQ ID NO: 2, the CE-7 signature motif comprises 3 conserved motifs defined as: a) Arg118-Gly119-Gln120; b) Gly179-Xaa180-Ser181-Gln182-Gly183; and c) His298-Glu299. Thus, the enzyme catalyst used in the present systems and methods may be comprise three sequence motifs defined as Arg118-Gly119-Gln120; Gly179-Xaa180-Ser181-Gln182-Gly183; and His298-Glu299 relative to SEQ ID NO:2. Alignments of the respective signature motifs are provided in Table 3. Typically, the Xaa at amino acid residue position 180 is glycine, alanine, proline, tryptophan, or threonine. Two of the three amino acid residues belonging to the catalytic triad are in bold. In one embodiment, the Xaa at amino acid residue position 180 is selected from the group consisting of glycine, alanine, proline, tryptophan, and threonine.

Further analysis of the conserved motifs within the CE-7 carbohydrate esterase family indicates the presence of an additional motif (LXD at amino acid positions 267-269 of SEQ ID NO: 2) that may be used to further define a perhydrolase belonging to the CE-7 carbohydrate esterase family. In a further embodiment of the present methods and systems, the signature motif defined above may include a fourth conserved motif defined as Leu267-Xaa268-Asp269 relative to reference SEQ ID NO: 2. The Xaa at amino acid residue position 268 is typically isoleucine, valine, or methionine. The fourth motif includes the aspartic acid residue that is the third member of the catalytic triad (Ser181-Asp269-His298).

Any number of well-known global alignment algorithms may be used to align two or more amino acid sequences (representing enzymes having perhydrolase activity) to determine the existence of the present signature motif (for example, CLUSTALW or Needleman and Wunsch (*J. Mol. Biol.*, 48:443-453 (1970)). The aligned sequence(s) is compared to the reference sequence (SEQ ID NO: 2). In one embodiment, a CLUSTAL alignment (e.g., CLUSTALW; for example version 1.83)) using a reference amino acid sequence (as used herein the CAH sequence (SEQ ID NO: 2) from the *Bacillus subtilis* ATCC® 31954™) is used to identify perhydrolases belonging to the CE-7 esterase family. The relative numbering of the conserved amino acid residues is based on the residue numbering of the reference amino acid sequence to account for small insertions or deletions (typically 5 amino acids or less) within the aligned sequence.

A comparison of the overall percent identity among perhydrolases exemplified herein indicates that enzymes having as little as 33% identity to SEQ ID NO: 2 (while retaining the signature motif) exhibit significant perhydrolase activity and are structurally classified as CE-7 carbohydrate esterases. In some embodiments of the present methods and systems, the present perhydrolases include enzymes comprising the present signature motif and at least 30%, preferably at least 33%, more preferably at least 40%, even more preferably at least 42%, even more preferably at least 50%, even more preferably at least 60%, even more preferably at least 70%, even more preferably at least 80%, even more preferably at least 90%, and most preferably at least 90%, 91%, 92%, 93%, 94%, 95%, 96%, 97%, 98%, or 99% amino acid identity to SEQ ID NO: 2.

Examples of CE-7 enzymes comprised of the above signature motif are provided in Table 3.

TABLE 3

Conserved motifs from several CE-7 carbohydrate esterases.

| Perhydrolase Sequence | RGQ motif[a] (Residue #s) | GXSQG motif[a] (Residue #s) | LXD motif[b] (Residue #s) | HE motif[a] (Residue #s) |
|---|---|---|---|---|
| SEQ ID NO: 2 | 118-120 | 179-183 | 267-269 | 298-299 |
| SEQ ID NO: 4 | 118-120 | 179-183 | 267-269 | 298-299 |
| SEQ ID NO: 6 | 118-120 | 179-183 | 267-269 | 298-299 |
| SEQ ID NO: 8 | 119-121 | 180-184 | 268-270 | 299-300 |
| SEQ ID NO: 10 | 118-120 | 179-183 | 267-269 | 298-299 |
| SEQ ID NO: 12 | 119-121 | 181-185 | 269-271 | 300-301 |
| SEQ ID NO: 14 | 118-120 | 186-190 | 272-274 | 303-304 |
| SEQ ID NO: 16 | 118-120 | 186-190 | 272-274 | 303-304 |
| SEQ ID NO: 18 | 117-119 | 180-184 | 270-272 | 301-302 |
| SEQ ID NO: 20 | 118-120 | 178-182 | 267-269 | 304-305 |
| SEQ ID NO: 22 | 118-119 | 181-185 | 271-273 | 302-303 |
| SEQ ID NO: 24 | 117-119 | 180-184 | 270-272 | 301-302 |
| SEQ ID NO: 26 | 118-120 | 179-183 | 267-269 | 298-299 |
| SEQ ID NO: 54 | 117-119 | 180-184 | 270-272 | 301-302 |
| SEQ ID NO: 60 | 118-120 | 186-190 | 272-274 | 303-304 |
| SEQ ID NO: 64 | 118-120 | 186-190 | 272-274 | 303-304 |
| SEQ ID NO. 68 RQ2(a) | 118-120 | 186-190 | 272-274 | 303-304 |
| SEQ ID NO. 72 RQ2(b) | 119-121 | 187-191 | 273-275 | 304-305 |
| SEQ ID NO: 73 | 118-120 | 186-190 | 272-274 | 303-304 |
| SEQ ID NO: 74 | 118-120 | 186-190 | 272-274 | 303-304 |

[a] = Conserved motifs defined by Vincent et al., supra used to define the signature motif.
[b] = an additional motif that may be useful in further defining the signature motif defined by Vincent et al., supra.

Alternatively, a contiguous signature motif (SEQ ID NO: 49) comprising the 3 conserved motifs identified by Vincent et al., supra, (RGQ, GXSQG, and HE; Amino acids residues 118-299 of SEQ ID NO: 2; an optional 4th motif, LXD, is also underlined) may also be used as a contiguous signature motif to identify CE-7 carbohydrate esterases (FIG. 1, panels A-F). As such, suitable enzymes expected to have perhydrolase activity may also be identified as having at least 30% amino acid identify, preferably at least 36%, more preferably at least 40%, even more preferably at least 50%, yet more preferably at least 60%, yet even more preferably at least 70%, yet even more preferably at least 80%, yet even more preferably at least 90%, 91%, 92%, 93%, 94%, 95%, 96%, 97%, 98%, or 99% amino acid identity to SEQ ID NO: 49 (the 4 conserved motifs found in CE-7 carbohydrate esterases are underlined).

```
                                                    (SEQ ID NO: 49)
RGQQSSEDTSISLHGHALGWMTKGILDKDTYYYRGVYLDAVRALEVISSF

DEVDETRIGVTGGSQGGGLTIAAAALSDIPKAAVADYPYLSNFERAIDVA

LEQPYLEINSFFRRNGSPETEVQAMKTLSYFDIMNLADRVKVPVLMSIGL

IDKVTPPSTVFAAYNHLETEKELKVYRYFGHE.
```

A comparison using the contiguous signature sequence against several CE-7 esterases having perhydrolase activity is provided in Table 4. BLASTP using default parameters was used.

TABLE 4

Percent Amino Acid Identity of Various CE-7 Carbohydrate Esterases having Perhydrolysis Activity Versus the Contiguous Signature Sequence (SEQ ID NO: 49).

| Perhydrolase Sequence | % Identity using BLASTP | E-score (expected) |
|---|---|---|
| SEQ ID NO: 2 | 100 | 3e-92 |
| SEQ ID NO: 4 | 98 | 6e-91 |
| SEQ ID NO: 6 | 98 | 4e-98 |
| SEQ ID NO: 8 | 78 | 1e-78 |
| SEQ ID NO: 10 | 80 | 3e-76 |
| SEQ ID NO: 12 | 63 | 2e-56 |
| SEQ ID NO: 14 | 51 | 1e-41 |
| SEQ ID NO: 16 | 50 | 6e-35 |
| SEQ ID NO: 24 | 36 | 7e-21 |
| SEQ ID NO: 26 | 99 | 2e-90 |
| SEQ ID NO: 54 | 40 | 2e-26 |
| SEQ ID NO: 60 | 40 | 3e-30 |
| SEQ ID NO: 64 | 46 | 6e-35 |
| SEQ ID NO. 68 | 46 | 6e-35 |
| SEQ ID NO. 72 | 48 | 9e-36 |

Alternatively, the percent amino acid identity to the complete length of one or more of the perhydrolases for use in the present methods and systems may also be used. Accordingly, suitable enzymes having perhydrolase activity have at least 30%, preferably at least 33%, preferably at least 40%, preferably at least 40%, more preferably at least 50%, more preferably at least 60%, more preferably at least 70%, even more preferably at least 80%, yet even more preferably at least 90%, and most preferably at least 90%, 91%, 92%, 93%, 94%, 95%, 96%, 97%, 98%, or 99% amino acid identity to SEQ ID NO: 2. In further embodiments of the present methods and systems, suitable perhydrolase catalysts comprise an amino acid sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO:20, SEQ ID NO:22, SEQ ID NO:24, SEQ ID NO: 26, SEQ ID NO: 54, SEQ ID NO: 60, SEQ ID NO: 64, SEQ ID NO: 68, SEQ ID NO: 72, SEQ ID NO: 73, and SEQ ID NO: 74. In another embodiment, the amino acid residue at position 277 of either SEQ ID NO: 73 or SEQ ID NO: 74 is selected from the group consisting of alanine, valine, serine, and threonine. In preferred embodiments, suitable enzymes having perhydrolase activity having at least 90%, at least 91%, at least 92%, at least 93%, at least 94%, at least 95%, at least 96%, at least 97%, at least 98%, or at least 99% amino acid identity to SEQ ID NO: 14 or to SEQ ID NO: 16 may be used. In further preferred embodiments, suitable enzymes having perhydrolase activity have an amino acid sequence selected from the group consisting of SEQ ID NO: 14, SEQ ID NO: 16, SEQ ID NO: 73, and SEQ ID NO: 74.

Suitable carbohydrate esterase family 7 (CE-7) enzymes having perhydrolysis activity for use in the present methods and systems may also include enzymes having one or more deletions, substitutions, and/or insertions to one of the present perhydrolase enzymes (such as SEQ ID NOs. 14 or 16). As shown in Table 2, CE-7 carbohydrates esterases having perhydrolase activity share as little as 31% overall amino acid identity. Additional enzymes having perhydrolase activity structurally classified as belonging to the CE-7 carbohydrate esterase family may have even lower percent identity, so long as the enzyme retains the conserved signature motif. As such, the numbers of deletions, substitutions, and/or insertions may vary so long as the conserved signature motifs (see Table 3) are found in their relative positions within the enzyme.

Additionally, it is well within one of skill in the art to identity suitable enzymes according to the structural similarity found within the corresponding nucleic acid sequence. Hybridization techniques can be used to identity similar gene sequences. Accordingly, suitable perhydrolase catalysts of the present invention comprise an amino acid sequence encoded by a nucleic acid molecule that hybridizes under highly stringent conditions to a nucleic acid molecule having a nucleic acid sequence selected from the group consisting of SEQ ID NO: 1, SEQ ID NO:3, SEQ ID NO:5; SEQ ID NO: 7; SEQ ID NO:9, SEQ ID NO:11, SEQ ID NO:13, SEQ ID NO:15, SEQ ID NO: 17, SEQ ID NO:19, SEQ ID NO:21, SEQ ID NO:23, SEQ ID NO: 25; SEQ ID NO:29; SEQ ID NO:48, SEQ ID NO: 51, SEQ ID NO: 53, SEQ ID NO: 56, SEQ ID NO: 57, SEQ ID NO: 58, SEQ ID NO: 59, SEQ ID NO: 61, SEQ ID NO: 62, SEQ ID NO: 63, SEQ ID NO: 65, SEQ ID NO: 66, SEQ ID NO: 67, SEQ ID NO: 69, SEQ ID NO: 70, and SEQ ID NO: 71.

Several variant CE-7 enzymes have recently been identified having enhanced perhydrolysis activity relative to the corresponding wild-type enzymes from which they were derived (see co-owned, co-filed, and copending U.S. patent application having Ser. No. 12/572,094; herein incorporated by reference). Specifically, several wild-type CE-7 enzymes from the genus *Thermotoga* were modified to produce several variants having enhanced perhydrolysis activity. Sequences of the variants are provided as SEQ ID NOs: 73 and 74 wherein the amino acid residue at position 277 of either SEQ ID NO: 73 or SEQ ID NO: 74 is selected from the group consisting of alanine, valine, serine, and threonine.

Enzymatic Multi-Component Peracid Generation Systems

The present methods and systems may be used in the production of industrially useful, efficacious concentrations of peracids in situ under aqueous reaction conditions using the perhydrolase activity of an enzyme belonging to carbohydrate esterase family 7. In some embodiments, the enzyme having perhydrolase activity is also classified structurally and functionally as a cephalosporin C deacetylase (CAH). In other embodiments, the enzyme having perhydrolase activity is classified structurally and functionally as an acetyl xylan esterase (AXE).

The peracids produced in accordance with the present methods and systems are quite reactive and may decrease in concentration over extended periods of time, depending on variables including, but are not limited to, temperature and pH. As such, it may be desirable to keep the various reaction components separated, especially for liquid formulations. In one aspect, the hydrogen peroxide source is separate from either the substrate or the perhydrolase catalyst, preferably from both. This can be accomplished using a variety of techniques including, but not limited to, the use of multi-compartment chambered dispensers (such as U.S. Pat. No. 4,585,150) and at the time of use physically combining the perhydrolase catalyst with an inorganic peroxide and the present substrates to initiate the aqueous enzymatic perhydrolysis reaction. The perhydrolase catalyst may optionally be immobilized within the body of reaction chamber or separated (such as filtered) from the reaction product comprising the peracid prior to contacting the surface and/or object targeted for treatment. The perhydrolase catalyst may be in a liquid matrix or in a solid form (such as a powder or tablet) or embedded within a solid matrix that is subsequently mixed with the substrates to initiate the enzymatic perhydrolysis reaction. In a further aspect, the perhydrolase catalyst may be contained within a dissolvable or porous pouch that may be added to the aqueous substrate matrix to initiate enzymatic perhydrolysis. In additional further aspects, a powder comprising the enzyme catalyst is suspended in the carboxylic add ester substrate (such as triacetin) and at time of use is mixed with a source of peroxygen in water. In some embodiments, a two-compartment spray bottle such as a dual-liquid fixed ratio sprayer (Model DLS100, Take 5 Corp., Rogue River, Oreg.) or a dual-liquid variable ratio sprayer (Model DLS200, Take; 5 Corp.) is utilized (U.S. Pat. No. 5,152,461 and U.S. Pat. No. 5,532,157; herein incorporated by reference). In another embodiment, a single bottle containing two separate compartments separated by a breakable seal is employed. In some embodiments, the ratio of the volume of the two separate compartments is 1:1, or 5:1 or 10:1. Examples of multi-component delivery systems may also be found in co-owned, co-filed, and copending U.S. patent application Ser. No. 12/572,107 (incorporated herein by reference in its entirety).

The presently disclosed systems for producing peroxycarboxylic add may comprise a first component comprising an enzyme catalyst (such as an enzyme powder), a carboxylic acid ester substrate (substantially free of water), and the cosolvent, and a second component comprising the source of peroxygen and water. The presence of excess water in the first component may lead to storage instability. As such, the phrase "substantially free of water" will refer to a concentration of water in the component comprising the carboxylic acid ester substrate/enzyme/cosolvent that does not adversely impact the storage stability of enzyme when present in the first component. In one embodiment, "substantially free of water" may mean less than 2000 ppm, preferably less than 1000 ppm, more preferably less than 500 ppm, and even more preferably less than 250 ppm of water in the carboxylic acid ester substrate containing component. In such embodiments, the systems may further comprise a first vessel/container for storing the first component and a second vessel/container for storing the second component. As used herein, the term "container" may be used generically to describe vessels, compartments, bottles, packets, and other packing systems suitable for holding and/or transporting the present materials. The present systems may also comprise a mixing compartment for receiving at least some of the first component from the first container and at least some of the second component from the second container, thereby permitting the formation of a formulation comprising at least some of the first component and at least some of the second component. In such instances, the systems may further comprise a nozzle for dispensing the formulation from the mixing compartment.

In other embodiments of the present systems, the system comprising a first and second vessel may further comprise a nozzle for receiving at least some of the first component from the first vessel and at least some of the second component from the second vessel, and for dispensing at least some of the first component contemporaneously with at least some of the second component. As used herein, "contemporaneously" means that during at least part of the time that at least some of the first component is dispensed, at least some of the second component is also dispensed. Thus, where some of the first component is dispensed for a total duration of one second, dispensing the second component for 1 second after dispensing the first component and for 0.1 seconds during the dispensing of the first component will be considered to have been contemporaneous with the dispensing of the first component.

Methods for Determining the Concentration of Peracid and Hydrogen Peroxide.

A variety of analytical methods may be used in the present methods to analyze the reactants and products including, but not limited to, titration, high performance liquid chromatography (HPLC), gas chromatography (GC), mass spectroscopy (MS), capillary electrophoresis (CE), the analytical procedure described by U. Karst et al., (*Anal. Chem.*, 69(17):

3623-3627 (1997)), and the 2,2'-azino-bis(3-ethylbenzothazoline)-6-sulfonate (ARTS) assay (S. Minning, et al., *Analytica Chimica Acta* 378:293-298 (1999) and WO 2004/058961 A1) as described in the present examples.

Determination of Minimum Biocidal Concentration of Peracids

The method described by J. Gabrielson, et al. (*J. Microbiol. Methods* 50: 63-73 (2002)) may be employed for determination of the Minimum Biocidal Concentration (MBC) of peracids, or of hydrogen peroxide and enzyme substrates. The assay method is based on XTT reduction inhibition, where XTT ((2,3-bis[2-methoxy-4-nitro-5-sulfophenyl]-5-[phenylamino)carbonyl]-2H-tetrazolium, inner salt, monosodium salt) is a redox dye that indicates microbial respiratory activity by a change in optical density (OD) measured at 490 nm or 450 nm. However, there are a variety of other methods available for testing the activity of disinfectants and antiseptics including, but not limited to, viable plate counts, direct microscopic counts, dry weight, turbidity measurements, absorbance, and bioluminescence (see, for example Brock, Semour S., *Disinfection, Sterilization, and Preservation*, 5$^{th}$ edition, Lippincott Williams & Wilkins, Philadelphia, Pa., USA; 2001).

Uses of Enzymatically Prepared Peracid Compositions

The enzyme catalyst-generated peroxycarboxylic acid produced according to the present method can be used in a variety of hard surface/inanimate object applications for reduction of concentrations of biological contaminants, such as decontamination of medical instruments (e.g., endoscopes), textiles (e.g., garments, carpets), food preparation surfaces, food storage and food-packaging equipment, materials used for the packaging of food products, chicken hatcheries and grow-out facilities, animal enclosures, and spent process waters that have microbial and/or virucidal activity. The enzyme-generated peroxycarboxylic acids may be used in formulations designed to inactivate prions (e.g., certain proteases) to additionally provide biocidal activity. In a preferred aspect, the present peroxycarboxylic acid compositions are particularly useful as a disinfecting agent for non-autoclavable medical instruments and food packaging equipment. As the peroxycarboxylic acid-containing formulation may be prepared using GRAS or food-grade components (enzyme, enzyme substrate, hydrogen peroxide, and buffer), the enzyme-generated peroxycarboxylic acid may also be used for decontamination of animal carcasses, meat, fruits and vegetables, or for decontamination of prepared foods. The enzyme-generated peroxycarboxylic acid may be incorporated into a product whose final form is a powder, liquid, gel, film, solid or aerosol. The enzyme-generated peroxycarboxylic acid may be diluted to a concentration that still provides an efficacious decontamination.

The compositions comprising an efficacious concentration of peroxycarboxylic acid can be used to disinfect surfaces and/or objects contaminated (or suspected of being contaminated) with biological contaminants by contacting the surface or object with the products produced by the present processes. As used herein, "contacting" refers to placing a disinfecting composition comprising an effective concentration of peroxycarboxylic acid in contact with the surface or inanimate object suspected of contamination with a biological contaminant for a period of time sufficient to clean and disinfect. Contacting includes spraying, treating, immersing, flushing, pouring on or in, mixing, combining, painting, coating, applying, affixing to and otherwise communicating a peroxycarboxylic acid solution or composition comprising an efficacious concentration of peroxycarboxylic acid, or a solution or composition that forms an efficacious concentration of peroxycarboxylic acid, with the surface or inanimate object suspected of being contaminated with a concentration of a biological contaminant. The disinfectant compositions may be combined with a cleaning composition to provide both cleaning and disinfection. Alternatively, a cleaning agent (e.g., a surfactant or detergent) may be incorporated into the formulation to provide both cleaning and disinfection in a single composition.

The compositions comprising an efficacious concentration of peroxycarboxylic acid can also contain at least one additional antimicrobial agent, combinations of prion-degrading proteases, a virucide, a sporicide, or a biocide. Combinations of these agents with the peroxycarboxylic acid produced by the claimed processes can provide for increased and/or synergistic effects when used to clean and disinfect surfaces and/or objects contaminated (or suspected of being contaminated) with biological contaminants. Suitable antimicrobial agents include carboxylic esters (e.g., p-hydroxy alkyl benzoates and alkyl cinnamates); sulfonic acids (e.g., dodecylbenzene sulfonic acid); iodo-compounds or active halogen compounds (e.g., elemental halogens, halogen oxides (e.g., NaOCl, HOC/, HOBr, $ClO_2$), iodine, interhalides (e.g., iodine monochloride, iodine dichloride, iodine trichloride, iodine tetrachloride, bromine chloride, iodine monobromide, or iodine dibromide), polyhalides, hypochlorite salts, hypochlorous acid, hypobromite salts, hypobromous acid, chloro- and bromo-hydantoins, chlorine dioxide, and sodium chlorite); organic peroxides including benzoyl peroxide, alkyl benzoyl peroxides, ozone, singlet oxygen generators, and mixtures thereof; phenolic derivatives (such as o-phenyl phenol, o-benzyl-p-chlorophenol, felt-amyl phenol and $C_1$-$C_6$ alkyl hydroxy benzoates); quaternary ammonium compounds (such as alkyldimethylbenzyl ammonium chloride, dialkyldimethyl ammonium chloride and mixtures thereof); and mixtures of such antimicrobial agents, in an amount sufficient to provide the desired degree of microbial protection. Effective amounts of antimicrobial agents include about 0.001 wt % to about 60 wt % antimicrobial agent, about 0.01 wt % to about 15 wt % antimicrobial agent, or about 0.08 wt % to about 2.5 wt % antimicrobial agent.

In one aspect, the peroxycarboxylic acids formed by the present process can be used to reduce the concentration of viable biological contaminants (such as a viable microbial population) when applied on and/or at a locus. As used herein, a "locus" comprises part or all of a target surface suitable for disinfecting or bleaching. Target surfaces include all surfaces that can potentially be contaminated with biological contaminants. Non-limiting examples include equipment surfaces found in the food or beverage industry (such as tanks, conveyors, floors, drains, coolers, freezers, equipment surfaces, walls, valves, belts, pipes, drains, joints, crevasses, combinations thereof, and the like); building surfaces (such as walls, floors and windows); non-food-industry related pipes and drains, including water treatment facilities, pools and spas, and fermentation tanks; hospital or veterinary surfaces (such as walls, floors, beds, equipment (such as endoscopes), clothing worn in hospital/veterinary or other healthcare settings, including clothing, scrubs, shoes, and other hospital or veterinary surfaces); restaurant surfaces; bathroom surfaces; toilets; clothes and shoes; surfaces of barns or stables for livestock, such as poultry, cattle, dairy cows, goats, horses and pigs; hatcheries for poultry or for shrimp; and pharmaceutical or biopharmaceutical surfaces (e.g., pharmaceutical or biopharmaceutical manufacturing equipment, pharmaceutical or biopharmaceutical ingredients, pharmaceutical or biopharmaceutical excipients). Additional hard surfaces also include food products, such as beef, poultry, pork, vegetables, fruits, seafood, combinations thereof, and the like. The locus can also include water absorbent materials such as infected linens or other textiles. The locus also includes harvested plants or plant products including seeds, corms, tubers, fruit, and vegetables, growing plants, and especially crop growing plants, including cereals, leaf vegetables and salad crops, root vegetables, legumes, berried fruits, citrus fruits and hard fruits.

Non-limiting examples of hard surface materials are metals (e.g., steel, stainless steel, chrome, titanium, iron, copper, brass, aluminum, and alloys thereof), minerals (e.g., concrete), polymers and plastics (e.g., polyolefins, such as polyethylene, polypropylene, polystyrene, poly(meth)acrylate, polyacrylonitrile, polybutadiene, poly(acrylonitrile, butadiene, styrene), poly(acrylonitrile, butadiene), acrylonitrile butadiene; polyesters such as polyethylene terephthalate; and polyamides such as nylon). Additional surfaces include brick, tile, ceramic, porcelain, wood, vinyl, linoleum, and carpet.

The peroxycarboxylic acids formed by the present process may be used to provide a benefit to a textile including, but not limited to, bleaching, destaining, sanitization, disinfection, and deodorizing. The peroxycarboxylic acids formed by the present process may be used in any number of laundry care products including, but not limited to, textile pre-wash treatments, laundry detergents, stain removers, bleaching compositions, deodorizing compositions, and rinsing agents.

Recombinant Microbial Expression

With respect to the present methods and systems, the genes and gene products of the sequences described herein may be produced in heterologous host cells, particularly in the cells of microbial hosts. Preferred heterologous host cells for expression of the genes and nucleic add molecules are microbial hosts that can be found within the fungal or bacterial families and which grow over a wide range of temperature, pH values, and solvent tolerances. For example, it is contemplated that any of bacteria, yeast, and filamentous fungi may suitably host the expression of the present nucleic acid molecules. The perhydrolase may be expressed intracellularly, extracellularly, or a combination of both intracellularly and extracellularly, where extracellular expression renders recovery of the desired protein from a fermentation product more facile than methods for recovery of protein produced by intracellular expression. Transcription, translation and the protein biosynthetic apparatus remain invariant relative to the cellular feedstock used to generate cellular biomass; functional genes will be expressed regardless. Examples of host strains include, but are not limited to, bacterial, fungal or yeast species such as *Aspergillus, Trichoderma, Saccharomyces, Pichia, Phaffia, Candida, Hansenula, Yarrowia, Kluyveromyces, Salmonella, Bacillus, Acinetobacter, Zymomonas, Agrobacterium, Erythrobacter, Chlorobium, Chromatium, Flavobacterium, Cytophaga, Rhodobacter, Rhodococcus, Streptomyces, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Alcaligenes, Synechocystis, Synechococcus, Anabaena, Thiobacillus, Methanobacterium, Klebsiella,* and *Myxococcus*. In one embodiment, bacterial host strains include *Kluyveromyces, Escherichia, Bacillus,* and *Pseudomonas*. In a preferred embodiment, the bacterial host cell is *Escherichia coli*.

Large-scale microbial growth and functional gene expression may use a wide range of simple or complex carbohydrates, organic acids and alcohols or saturated hydrocarbons, such as methane or carbon dioxide in the case of photosynthetic or chemoautotrophic hosts, the form and amount of nitrogen, phosphorous, sulfur, oxygen, carbon or any trace micronutrient including small inorganic ions. The regulation of growth rate may be affected by the addition, or not, of specific regulatory molecules to the culture and which are not typically considered nutrient or energy sources.

Vectors or cassettes useful for the transformation of suitable host cells are well known in the art. Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell and/or native to the production host, although such control regions need not be so derived.

Initiation control regions or promoters, which are useful to drive expression of the present cephalosporin C deacetylase coding region in the desired host cell are numerous and familiar to those skilled in the art. Virtually any promoter capable of driving these genes is suitable for the present invention including but not limited to CYC1, HIS3, GAL1, GAL10, ADH1, PGK, PHO5, GAPDH, ADC1, TRPS, URA3, LEU2, ENO, TPI (useful for expression in *Saccharomyces*); AOX1 (useful for expression in *Pichia*); and lac, araB, tet, trp, $IP_L$, $IP_R$, T7, tac, and trc (useful for expression in *Escherichia coli*) as well as the amy, apr, npr promoters and various phage promoters useful for expression in *Bacillus*.

Termination control regions may also be derived from various genes native to the preferred host cell. In one embodiment, the inclusion of a termination control region is optional. In another embodiment, the chimeric gene includes a termination control region derived the preferred host cell.

Industrial Production

A variety of culture methodologies may be applied to produce the present perhydrolase catalysts in accordance with the present methods and systems. For example, large-scale production of a specific gene product overexpressed from a recombinant microbial host may be produced by both batch and continuous culture methodologies.

A classical batch culturing method is a closed system where the composition of the media is set at the beginning of the culture and not subject to artificial alterations during the culturing process. Thus, at the beginning of the culturing process, the media is inoculated with the desired organism or organisms and growth or metabolic activity may occur without adding anything further to the system. Typically, however, a "batch" culture is batch with respect to the addition of carbon source, and attempts are often made to control factors such as pH and oxygen concentration. In batch systems the metabolite and biomass compositions of the system change constantly up to the time the culture is terminated. Within batch cultures cells moderate through a static lag phase to a high growth log phase and finally to a stationary phase where growth rate is diminished or halted. If untreated, cells in the stationary phase will eventually die. Cells in log phase are often responsible for the bulk of production of end product or intermediate in some systems. Stationary or post-exponential phase production can be obtained in other systems.

A variation on the standard batch system is the fed-batch system. Fed-batch culture processes are also suitable in the present invention and comprise a typical batch system except that the substrate is added in increments as the culture progresses. Fed-batch systems are useful when catabolite repression is apt to inhibit the metabolism of the cells and where it is desirable to have limited amounts of substrate in the media. Measurement of the actual substrate concentration in fed-batch systems is difficult and is estimated on the basis of the changes of measurable factors such as pH, dissolved oxygen and the partial pressure of waste gases such as $CO_2$. Batch and fed-batch culturing methods are common and well known in the art and examples may be found in Thomas D. Brock in *Biotechnology: A Textbook of Industrial Microbiology*, Second Edition, Sinauer Associates, Inc., Sunderland, Mass. (1989) and Deshpande, Mukund V., *Appl. Biochem. Biotechnol.*, 36:227-234 (1992).

Commercial production of the desired perhydrolase catalysts may also be accomplished with a continuous culture. Continuous cultures are an open system where a defined culture media is added continuously to a bioreactor and an equal amount of conditioned media is removed simultaneously for processing. Continuous cultures generally maintain the cells at a constant high liquid phase density where cells are primarily in log phase growth. Alternatively, continuous culture may be practiced with immobilized cells where carbon and nutrients are continuously added and valuable products, by-products or waste products are continuously removed from the cell mass. Cell immobilization may be performed using a wide range of solid supports composed of natural and/or synthetic materials.

Continuous or semi-continuous culture allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions, and thus the cell loss due to media being drawn off must be balanced against the cell growth rate in the culture. Methods of modulating nutrients and growth factors for continuous culture processes as well as techniques for maximizing the rate of product formation are well known in the art of industrial microbiology and a variety of methods are detailed by Brock, supra.

Fermentation media in the present invention must contain suitable carbon substrates. Suitable substrates may include, but are not limited to, monosaccharides such as glucose and fructose, disaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. Additionally, the carbon substrate may also be one-carbon substrates such as carbon dioxide, methane or methanol (for example, when the host cell is a methylotrophic microorganism). Similarly, various species of *Candida* will metabolize alanine or oleic acid (Sulter et al., *Arch. Microbiol.*, 153:485-489 (1990)). Hence, it is contemplated that the source of carbon utilized in the present invention may encompass a wide variety of carbon-containing substrates and will only be limited by the choice of organism.

Recovery of the desired perhydrolase catalysts from a batch fermentation, fed-batch fermentation, or continuous culture, may be accomplished by any of the methods that are known to those skilled in the art. For example, when the enzyme catalyst is produced intracellularly, the cell paste is separated from the culture medium by centrifugation or membrane filtration, optionally washed with water or an aqueous buffer at a desired pH, then a suspension of the cell paste in an aqueous buffer at a desired pH is homogenized to produce a cell extract containing the desired enzyme catalyst. The cell extract may optionally be filtered through an appropriate filter aid such as celite or silica to remove cell debris prior to a heat-treatment step to precipitate undesired protein from the enzyme catalyst solution. The solution containing the desired enzyme catalyst may then be separated from the precipitated cell debris and protein by membrane filtration or centrifugation, and the resulting partially-purified enzyme catalyst solution concentrated by additional membrane filtration, then optionally mixed with an appropriate carrier (for example, maltodextrin, phosphate buffer, citrate buffer, or mixtures thereof) and spray-dried to produce a solid powder comprising the desired enzyme catalyst.

Applicants specifically incorporate the entire contents of all cited references in this disclosure. Further, when an amount, concentration, or other value or parameter is given either as a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope be limited to the specific values recited when defining a range.

General Methods

The following examples are provided to demonstrate preferred aspects of the invention. It should be appreciated by those of skill in the art that the techniques disclosed in the examples which follow represent techniques discovered by the present inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the present invention.

All reagents and materials were obtained from DIFCO Laboratories (Detroit, Mich.), GIBCO/BRL (Gaithersburg, Md.), TCI America (Portland, Oreg.), Roche Diagnostics Corporation (Indianapolis, Ind.) or Sigma/Aldrich Chemical Company (St. Louis, Mo.), unless otherwise specified.

The following abbreviations in the specification correspond to units of measure, techniques, properties, or compounds as follows: "sec" or "s" means second(s), "min" means minute(s), "h" or "hr" means hour(s), "µL" means microliter(s), "mL" means milliliter(s), "L" means liter(s), "mM" means millimolar, "M" means molar, "mmol" means millimole(s), "ppm" means part(s) per million, "wt" means weight, "wt %" means weight percent, "g" means gram(s), "mg" means milligram(s), "µg" means microgram(s), "ng" means nanogram(s), "g" means gravity, "HPLC" means high performance liquid chromatography, "dd $H_2O$" means distilled and deionized water, "dcw" means dry cell weight, "ATCC" or "ATCCO" means the American Type Culture Collection (Manassas, Va.), "U" means unit(s) of perhydrolase activity, "rpm" means revolution(s) per minute, and "EDTA" means ethylenediaminetetraacetic acid.

EXAMPLE 1

Construction of a katG Catalase Disrupted *E. coli* Strain

The coding region of the kanamycin resistance gene (kan; SEQ ID NO: 30) was amplified from the plasmid pKD13 (SEQ ID NO: 31) by PCR (0.5 min at 94° C., 0.5 min at 55°

C., 1 min at 70° C., 30 cycles) using primers identified as SEQ ID NO: 32 and SEQ ID NO: 33 to generate the PCR product identified as SEQ ID NO: 34. The katG nucleic acid sequence is provided as SEQ ID NO: 35 and the corresponding amino acid sequence is SEQ ID NO: 36. *E. coli* MG1655 (ATCC® 47076™) was transformed with the temperature-sensitive plasmid pKD46 (SEQ ID NO: 37), which contains the λ-Red recombinase genes (Datsenko and Wanner, 2000, *PNAS USA* 97:6640-6645), and selected on LB-amp plates for 24 h at 30° C. MG1655/pKD46 was transformed with 50-500 ng of the PCR product by electroporation (BioRad Gene Pulser, 0.2 cm cuvette, 2.5 kV, 200 W, 25 µF), and selected on LB-kan plates for 24 h at 37° C. Several colonies were streaked onto LB-kan plates and incubated overnight at 42° C. to cure the pKD46 plasmid. Colonies were checked to confirm a phenotype of kanR/ampS. Genomic DNA was isolated from several colonies using the PUREGENE® DNA purification system (Gentra Systems, Inc., Minneapolis, Minn.), and checked by PCR to confirm disruption of the katG gene using primers identified as SEQ ID NO: 38 and SEQ ID NO: 39. Several katG-disrupted strains were transformed with the temperature-sensitive plasmid pCP20 (SEQ ID NO: 40), which contains the FLP recombinase, used to excise the kan gene, and selected on LB-amp plates for 24 h at 37° C. Several colonies were streaked onto LB plates and incubated overnight at 42° C. to cure the pCP20 plasmid. Two colonies were checked to confirm a phenotype of kanS/ampS, and called MG1655 KatG1 and MG1655 KatG2.

EXAMPLE 2

Construction of a katE Catalase Disrupted *E. coli* Strain

The kanamycin resistance gene (SEQ ID NO: 30) was amplified from the plasmid pKD13 (SEQ ID NO: 31) by PCR (0.5 min at 94° C., 0.5 min at 55° C., 1 min at 70° C., 30 cycles) using primers identified as SEQ ID NO: 41 and SEQ ID NO: 42 to generate the PCR product identified as SEQ ID NO: 43. The katE nucleic acid sequence is provided as SEQ ID NO: 44 and the corresponding amino acid sequence is SEQ ID NO: 45. *E. coli* MG1655 (ATCC® 47076™) was transformed with the temperature-sensitive plasmid pKD46 (SEQ ID NO: 37), which contains the λ-Red recombinase genes, and selected on LB-amp plates for 24 h at 30° C. MG1655/pKD46 was transformed with 50-500 ng of the PCR product by electroporation (BioRad Gene Pulser, 0.2 cm cuvette, 2.5 kV, 200 W, 25 µF), and selected on LB-kan plates for 24 h at 37° C. Several colonies were streaked onto LB-kan plates and incubated overnight at 42° C. to cure the pKD46 plasmid. Colonies were checked to confirm a phenotype of kanR/ampS. Genomic DNA was isolated from several colonies using the PUREGENE® DNA purification system, and checked by PCR to confirm disruption of the katE gene using primers identified as SEQ ID NO: 46 and SEQ ID NO: 47, Several katE-disrupted strains were transformed with the temperature-sensitive plasmid pCP20 (SEQ ID NO: 40), which contains the FLP recombinase, used to excise the kan gene, and selected on LB-amp plates for 24 h at 37° C. Several colonies were streaked onto LB plates and incubated overnight at 42° C. to cure the pCP20 plasmid. Two colonies were checked to confirm a phenotype of kanS/ampS, and named MG1655 KatE1 and MG1655 KatE2.

EXAMPLE 3

Construction of a katG Catalase and katE Catalase Disrupted *E. coli* Strain (KLP18)

The Kanamycin resistance gene (SEQ ID NO: 30) was amplified from the plasmid pKD13 (SEQ ID NO: 31) by PCR (0.5 min at 94° C., 0.5 min at 55° C., 1 min at 70° C., 30 cycles) using primers identified as SEQ ID NO: 41 and SEQ ID NO: 42 to generate the PCR product identified as SEQ ID NO: 43. *E. coli* MG1655 KatG1 was transformed with the temperature-sensitive plasmid pKD46 (SEQ ID NO: 37), which contains the λ-Red recombinase genes, and selected on LB-amp plates for 24 h at 30° C. MG1655 KatG1/pKD46 was transformed with 50-500 ng of the PCR product by electroporation (BioRad Gene Pulser, 0.2 cm cuvette, 2.5 kV, 200 W, 25 µF), and selected on LB-kan plates for 24 h at 37° C. Several colonies were streaked onto LB-kan plates and incubated overnight at 42° C. to cure the pKD46 plasmid. Colonies were checked to confirm a phenotype of kanR/ampS. Genomic DNA was isolated from several colonies using the PUREGENE® DNA purification system, and checked by PCR to confirm disruption of the katE gene using primers identified as SEQ ID NO: 46 and SEQ ID NO: 47. Several katE-disrupted strains (Δ katE) were transformed with the temperature-sensitive plasmid pCP20 (SEQ ID NO: 40), which contains the FLP recombinase, used to excise the kan gene, and selected on LB-amp plates for 24 h at 37° C. Several colonies were streaked onto LB plates and incubated overnight at 42° C. to cure the pCP20 plasmid. Two colonies were checked to confirm a phenotype of kanS/ampS, and named MG1655 KatG1KatE18.1 and MG1655 KatG1KatE23. MG1655 KatG1KatE18.1 is designated *E. coli* KLP18.

EXAMPLE 4

Cloning and Expression of Perhydrolase from *Thermotoga neapolitana*

The coding region of the gene encoding acetyl xylan esterase from *Thermotoga neapolitana* as reported in GENBANK® (Accession No. AAB70869) was synthesized using codons optimized for expression in *E. coli* (DNA 2.0, Menlo Park, Calif.). The coding region of the gene was subsequently amplified by PCR (0.5 min at 94° C., 0.5 min at 55° C., 1 min at 70° C., 30 cycles) using primers identified as SEQ ID NO: 27 and SEQ ID NO: 28. The resulting nucleic acid product (SEQ ID NO: 29) was subcloned into pTrcHis2-TOPO® to generate the plasmid identified as pSW196. The plasmid pSW196 was used to transform *E. coli* KLP18 to generate the strain KLP18/pSW196. KLP18/pSW196 was grown in LB media at 37° C. with shaking up to $OD_{600\ nm}$=0.4-0.5, at which time IPTG was added to a final concentration of 1 mM, and incubation continued for 2-3 h, Cells were harvested by centrifugation and SDS-PAGE was performed to confirm expression of the perhydrolase at 20-40% of total soluble protein.

EXAMPLE 5

Fermentation of *E. coli* KLP18 Transformants Expressing Perhydrolase

A fermentor seed culture was prepared by charging a 2-L shake flask with 0.5 L seed medium containing yeast extract (Amberex 695, 5.0 g/L), $K_2HPO_4$ (10.0 g/L), $KH_2PO_4$ (7.0 g/L), sodium citrate dihydrate (1.0 g/L), $(NH_4)_2SO_4$ (4.0 g/L), $MgSO_4$ heptahydrate (1.0 g/L) and ferric ammonium citrate (0.10 g/L). The pH of the medium was adjusted to 6.8 and the medium was sterilized in the flask. Post sterilization additions included glucose (50 wt %, 10.0 mL) and 1 mL ampicillin (25 mg/mL) stock solution. The seed medium was inoculated with a 1-mL culture of *E. coli* KLP18/pSW196 in 20% glycerol, and cultivated at 35° C. and 300 rpm. The seed culture was transferred at ca. 1-2 OD$_{550}$ to a 14 L fermentor (Braun) with 8 L of medium at 35° C. containing KH$_2$PO$_4$ (3.50 g/L), FeSO$_4$ heptahydrate (0.05 g/L), MgSO$_4$ heptahydrate (2.0 g/L), sodium citrate dihydrate (1.90 g/L), yeast extract (Amberex 695, 5.0 g/L), Biospumex153K antifoam (0.25 mL/L, Cognis Corporation), NaCl (1.0 g/L), CaCl$_2$ dihydrate (10 g/L), and NIT trace elements solution (10 mL/L). The trace elements solution contained citric acid monohydrate (10 g/L), MnSO$_4$ hydrate (2 g/L), NaCl (2 g/L), FeSO$_4$ heptahydrate (0.5 g/L), ZnSO$_4$ heptahydrate (0.2 g/L), CuSO$_4$ pentahydrate (0.02 g/L) and NaMoO$_4$ dihydrate (0.02 g/L). Post sterilization additions included glucose solution (50% w/w, 80.0 g) and ampicillin (25 mg/mL) stock solution (16.00 mL). Glucose solution (50% w/w) was used for fed batch. Glucose feed was initiated when glucose concentration decreased to 0.5 g/L, starting at 0.31 g feed/min and increasing progressively each hour to 0.36, 0.42, 0.49, 0.57, 0.66, 0.77, 0.90, 1.04, 1.21, 1.41 1.63 g/min respectively; the rate remained constant afterwards. Glucose concentration in the medium was monitored and if the concentration exceeded 0.1 g/L the feed rate was decreased or stopped temporarily. Induction was initiated between OD$_{550}$=56 and OD$_{550}$=80 with addition of 16 mL IPTG (0.5 M) for the various strains. The dissolved oxygen (DO) concentration was controlled at 25% of air saturation. The DO was controlled first by impeller agitation rate (400 to 1400 rpm) and later by aeration rate (2 to 10 slpm). The pH was controlled at 6.8. NH$_4$OH (29% w/w) and H$_2$SO$_4$ (20% w/v) were used for pH control. The head pressure was 0.5 bars. The cells were harvested by centrifugation 16 h post IPTG addition.

EXAMPLE 6

Preparation of Spray-Dried *Thermotoga neapolitana* Perhydrolase

*Thermothga neapolitana* cell paste prepared as described in Example 5 was suspended at a final concentration of 200 g wet cell weight/L in 50 mM sodium phosphate buffer at pH 7.4. The cells in the suspension were lysed in a single pass through an APV1000 homogenizer operated at 12,000 psi (~82.74 MPa) inlet pressure. The resulting lysate was heat treated at 65° C. for approximately 30 minutes, and the homogenate cooled to room temperature, and the resulting solids removed by centrifugation. The supernatant from the centrifugation was filtered using a 0.1 micron filter, and the resulting filtrate containing perhydrolase was concentrated using a 30K NMWCO filter to a final protein concentration of 34 mg protein/mL. To the protein solution was added maltodextrin to a concentration of ca. 3-fold by weight that of the concentration of protein, and the resulting solution spray-dried using an inlet temperature of 225° C. and a dryer exit temperature of 76° C. The protein concentration in the resulting powder was 20.3 wt %, and the dry solids content was 93.2 wt %.

EXAMPLE 7

Effect of Added Solvent on Peracetic Acid Production by *Thermotoga neapolitana* Perhydrolase A first mixture of 90.0 g of deionized water, 0.350 g of TURPINAL® SL ((1-hydroxy-1-phosphonoethyl)phosphonic acid, 60 wt % in water; Thermphos International, Hague, Netherlands), and 3.20 g of 30 wt % hydrogen peroxide in water was adjusted to pH 7.2 with 50% aqueous sodium hydroxide, and the final weight of the mixture adjusted to 100.0 g with deionized water. A second mixture of 55.76 g triacetin, 4.20 g of sodium bicarbonate, 2.50 g of CAB-O-SIL® M5 fumed silica (Cabot, Boston, Mass.), 0.270 g of spray-dried *Thermotoga neapolitana* perhydrolase (Example 6), and 37.43 g of one organic solvent selected from the group consisting of tripropylene glycol methyl ether (DOWANOL® TPM; Dow Chemical Corporation, Midland, Mich.), dipropylene glycol methyl ether (DOWANOL® DPM), propylene glycol methyl ether (DOWANOL® PM), diethylene glycol butyl ether (DOWANOL® DB), dipropylene glycol (DOWANOL® DPG), triethylene glycol, 1,2-propanediol, N-ethyl-2-pyrrolidinone, isopropanol, ethanol, ethyl lactate, and 1,3-propanediol was prepared. A 1.0 g aliquot of the second mixture was removed with rapid stirring (to suspend the undissolved solids) and mixed with 9.00 mL of the first mixture of hydrogen peroxide, and TURPINAL® SL in water (pH 7.2) was added thereto with stirring at 25° C.; the resulting mixture contained 255 mM triacetin, 254 mM hydrogen peroxide and 0.055 mg protein/mL of spray-dried perhydrolase. A control reaction for each solvent was also run to determine the concentration of peracetic acid produced by chemical perhydrolysis of triacetin by hydrogen peroxide in the absence of added protein.

Determination of the concentration of peracetic acid in the reaction mixtures was performed according to the method described by Karst et al, supra. Aliquots (0.040 mL) of the reaction mixture were removed at predetermined times and mixed with 0.960 mL of 5 mM phosphoric acid in water; adjustment of the pH of the diluted sample to less than pH 4 immediately terminated the reaction. The resulting solution was filtered using an ULTRAFREE® MC-filter unit (30,000 Normal Molecular Weight Limit (NMWL), Millipore Corp., Billerica, Mass.; cat #UFC3LKT 00) by centrifugation for 2 min at 12,000 rpm. An aliquot (0.100 mL) of the resulting filtrate was transferred to 1.5-mL screw cap HPLC vial (Agilent Technologies, Palo Alto, Calif.; #5182-0715) containing 0.300 mL of deionized water, then 0.100 mL of 20 mM MTS (methyl-p-tolyl-sulfide) in acetonitrile was added, the vials capped, and the contents briefly mixed prior to a 10 min incubation at ca. 25° C. in the absence of light. To each vial was then added 0.400 mL of acetonitrile and 0.100 mL of a solution of triphenylphosphine (TPP, 40 mM) in acetonitrile, the vials re-capped, and the resulting solution mixed and incubated at ca. 25° C. for 30 min in the absence of light. To each vial was then added 0.100 mL of 10 mM N,N-diethyl-m-toluamide (DEET; HPLC external standard) and the resulting solution analyzed by HPLC as described below.

HPLC Method:

Supelco Discovery C8 column (10-cm×4.0-mm, 5 μm) (cat. #569422-U) w/precolumn Supelco Supelguard Discovery C8 (Sigma-Aldrich; cat #59590-U); 10 microliter injection volume; gradient method with CH$_3$CN (Sigma-Aldrich; #270717) and deionized water at 1.0 mL/min and ambient temperature:

| Time (min:sec) | (% CH$_3$CN) |
|---|---|
| 0:00 | 40 |
| 3:00 | 40 |
| 3:10 | 100 |
| 4:00 | 100 |
| 4:10 | 40 |
| 7:00 (stop) | 40 |

The peracetic acid concentrations produced in 0.5 min, 1 min, 2 min, 5 min and 10 min for the reactions described above are listed in Table 5, below.

TABLE 5

Dependence of peracetic acid (PAA) concentration on solvent addition using triacetin (255 mM), hydrogen peroxide (254 mM) and 0.055 mg/mL of spray-dried *Thermotoga neapolitana* perhydrolase.

| Solvent | Enzyme (µg/mL) | PAA (ppm) | | | | |
|---|---|---|---|---|---|---|
| | | 0.5 min | 1 min | 2 min | 5 min | 10 min |
| DOWANOL ® PM | 0 | 39 | 54 | 52 | 81 | 137 |
| DOWANOL ® DPM | 0 | 136 | 41 | 106 | 386 | ND |
| DOWANOL ® TPM | 0 | 23 | 25 | 111 | 93 | 180 |
| DOWANOL ® DB | 0 | 107 | 102 | 105 | 157 | 218 |
| DOWANOL ® DPG | 0 | 19 | 40 | 101 | 156 | 207 |
| Triethylene glycol | 0 | 36 | 53 | 110 | 76 | 307 |
| 1,2-propanediol | 0 | 101 | 96 | 122 | 226 | 347 |
| N-ethyl-2-pyrroldinone | 0 | 37 | 49 | 60 | 77 | 133 |
| isopropanol | 0 | 70 | 13 | 147 | 150 | 242 |
| ethanol | 0 | 68 | 33 | 150 | 356 | 479 |
| ethyl lactate | 0 | 88 | 91 | 98 | 121 | 137 |
| 1,3-propanediol | 0 | 54 | 48 | 48 | 62 | 107 |
| DOWANOL ® PM | 55 | 355 | 1327 | 1632 | 3156 | 5378 |
| DOWANOL ® DPM | 55 | 846 | 972 | 1587 | 3209 | 4494 |
| DOWANOL ® TPM | 55 | 439 | 539 | 1303 | 2710 | 3740 |
| DOWANOL ® DB | 55 | 475 | 827 | 1719 | 3222 | 4863 |
| DOWANOL ® DPG | 55 | 583 | 769 | 1211 | 2784 | 4522 |
| Triethylene glycol | 55 | 325 | 834 | 1634 | 3229 | 5116 |
| 1,2-propanediol | 55 | 507 | 903 | 1428 | 2921 | 4364 |
| N-ethyl-2-pyrroldinone | 55 | 243 | 837 | 1470 | 3033 | 4839 |
| isopropanol | 55 | 326 | 656 | 1175 | 2229 | 2860 |
| ethanol | 55 | 408 | 584 | 1109 | 2235 | 2858 |
| ethyl lactate | 55 | 180 | 337 | 5736 | 1420 | 2554 |
| 1,3-propanediol | 55 | 163 | 269 | 510 | 1086 | 1657 |

To demonstrate the stability of the spray-dried enzyme in a mixture of triacetin and an organic solvent, the mixtures of triacetin, sodium bicarbonate, CAB-O-SIL® M5 (Cabot), spray-dried *Thermotoga neapolitana* perhydrolase (Example 6), and either tripropylene glycol methyl ether (DOWANOL® TPM) or 1,2-propanediol described above were stored for 24 h at ambient temperature, then a 1.0 g aliquot of each of these mixtures was removed with rapid stirring (to suspend the undissolved solids) and mixed with 9.0 mL of a freshly prepared (as described above) mixture of hydrogen peroxide and TURPINAL® SL in water (pH 7.2) with stirring at 25° C.; the resulting mixture contained 255 mM triacetin, 254 mM hydrogen peroxide and 0.055 mg protein/mL of spray-dried perhydrolase. A control reaction for each solvent was also run to determine the concentration of peracetic acid produced by chemical perhydrolysis of triacetin by hydrogen peroxide in the absence of added protein. Determination of the concentration of peracetic acid in the reaction mixtures was performed according to the method described by Karst et al. (Table 6).

TABLE 6

Stability of perhydrolase in triacetin/solvent suspension, measured in reactions containing triacetin (255 mM) and hydrogen peroxide (254 mM).

| Solvent | Enzyme (µg/mL) | PAA (ppm) | | | | |
|---|---|---|---|---|---|---|
| | | 0.5 min | 1 min | 2 min | 5 min | 10 min |
| DOWANOL ® TPM | 0 | 0 | 95 | 58 | 172 | 276 |
| 1,2-propanediol | 0 | 16 | 38 | 35 | 171 | 397 |
| DOWANOL ® TPM | 55 | 386 | 557 | 1078 | 2014 | 2717 |
| 1,2-propanediol | 55 | 566 | 768 | 1467 | 3093 | 4649 |

EXAMPLE 8

Comparison of Peracetic Acid Production by *Thermotoga neapolitana* Perhydrolase in Presence or Absence of Added Solvent A first mixture of 40.0 g of deionized water, 0.1575 g of TURPINAL® SL ((1-hydroxy-1-phosphonoethyl)phosphonic acid, 60 wt % in water; Thermphos International), and 1.44 g of 30 wt % hydrogen peroxide in water was adjusted to pH 7.2 with 50% aqueous sodium hydroxide, and the final weight of the mixture adjusted to 46.87 g with deionized water. A second mixture of 2.78 g triacetin, 0.210 g of sodium bicarbonate, 0.125 g of CAB-O-SIL® M5 (Cabot) and 0.0135 g of spray-dried *Thermotoga neapolitana* perhydrolase (Example 6) was prepared, and the first mixture of hydrogen peroxide and TURPINAL® SL in water (pH 7.2) was added to the second mixture with stirring at 25° C.; the resulting mixture contained 255 mM triacetin, 254 mM hydrogen peroxide and 0.055 mg protein/mL of spray-dried perhydrolase. Determination of the concentration of peracetic acid in the reaction mixtures was performed according to the method described by Karst et al., supra. A control reaction was also run to determine the concentration of peracetic acid produced by chemical perhydrolysis of triacetin by hydrogen peroxide in the absence of added perhydrolase.

The reaction described above was repeated, where 1.872 g of either propylene glycol monomethyl ether (DOWANOL® PM) or dipropyleneglycol monomethyl ether (DOWANOL® DPM), was substituted for an equivalent weight of water in the reaction mixture. A first mixture of 40.0 g of deionized water, 0.175 g of TURPINAL® SL, and 1.60 g of 30 wt % hydrogen peroxide in water was adjusted to pH 7.2 with 50% aqueous sodium hydroxide, and the final weight of the mixture adjusted to 50.0 g with deionized water. A second mixture of 2.78 g triacetin, 1.872 g of either propylene glycol monomethyl ether (DOWANOL® PM) or dipropyleneglycol monomethyl ether (DOWANOL® DPM), 0.210 g of sodium bicarbonate, 0.125 g of CAB-O-SIL® M5 (Cabot) and 0.0135 g of spray-dried *Thermotoga neapolitana* perhydrolase (Example 6) was prepared, and 45.0 g of the first mixture of hydrogen peroxide and TURPINAL® SL in water (pH 7.2) was added to the second mixture with stirring at 25° C.; the resulting mixture (pH 6.5) contained 255 mM triacetin, 254 mM hydrogen peroxide and 0.055 mg protein/mL of spray-dried perhydrolase. A control reaction was also run to determine the concentration of peracetic acid produced by chemical perhydrolysis of triacetin by hydrogen peroxide in the absence of added extract protein. The peracetic acid concentrations produced in 0.5 min, 1 min, 2 min, 5 min and 10 min for the three reactions described above are listed in Table 7, below.

TABLE 7

Dependence of peracetic acid (PAA) concentration on solvent addition using triacetin (255 mM), hydrogen peroxide (254 mM) and 55 µg/mL of spray-dried *Thermotoga neapolitana* perhydrolase.

| Solvent | Enzyme (µg/mL) | PAA (ppm) | | | | |
|---|---|---|---|---|---|---|
| | | 0.5 min | 1 min | 2 min | 5 min | 10 min |
| none | 0 | ND | ND | ND | ND | ND |
| DOWANOL ® PM | 0 | 89 | 90 | 205 | 318 | 498 |
| DOWANOL ® DPM | 0 | 104 | 178 | 184 | 373 | 535 |
| none | 55 | 629 | 1359 | 2020 | 4274 | 6019 |
| DOWANOL ® PM | 55 | 807 | 1390 | 2331 | 4439 | 5917 |
| DOWANOL ® DPM | 55 | 787 | 1373 | 2566 | 5122 | 6528 |

EXAMPLE 9

Use of Solvent for In Situ Peracid Generation Using a Two-Compartment Spray-Bottle Compared to Stirred Reactions A first mixture of 100 g of 0.20 M sodium citrate buffer containing 2000 ppm TURPINAL® SL ((1-hydroxy-1-phosphonoethyl)phosphonic acid, 60 wt % in water; Thermphos International), 280 g of deionized water, and 520 g of 30 wt % hydrogen peroxide in water was adjusted to pH 72 with 50% aqueous sodium hydroxide, and the final weight of the mixture adjusted to 400 g with deionized water. A second mixture was separately prepared, containing 83.4 g of triacetin, 3.75 g of CAB-O—SIL® M5 (Cabot), 0.750 g of spray-dried *Thermotoga neapolitana* perhydrolase (Example 6), and 62.1 g of a single solvent selected from: propylene glycol methyl ether (DOWANOL® PM), tripropylene glycol methyl ether (DOWANOL® TPM), diethylene glycol methyl ether (DOWANOL® DM), propylene glycol n-butyl ether (DOWANOL® PNB), propylene glycol n-propyl ether (DOWANOL® PnP), propylene glycol monomethyl ether acetate (DOWANOL® PMA), dipropylene glycol, ethanol, isopropanol, and 1,2-propanediol. In a first reaction at 25° C., 1.0 g of the first mixture was stirred with 9.0 g of the second mixture for the first 30-60 seconds of the reaction (reaction pH of 6.5-6.0), and samples were withdrawn and analyzed for peracetic acid production; the resulting reaction mixture contained 255 mM triacetin, 103 mM hydrogen peroxide and 100 μg protein/mL of spray-dried perhydrolase. Determination of the concentration of peracetic acid in the reaction mixtures (TABLE 8, below) was performed according to the method described by Karst et al., supra. A control reaction was also run to determine the concentration of peracetic acid produced by chemical perhydrolysis of triacetin by hydrogen peroxide in the absence of added perhydrolase.

The first mixture and second mixture prepared as described above were each separately charged to one of the two compartments of a two-compartment spray bottle (Custom Dual-Liquid Variable-Ratio Sprayer, Model DLS 200, manufactured by Take5 (Rogue River, Oreg.)), where the bottle was set up to spray a mixture of 9 parts by weight of the first mixture with 1 part by weight of the second mixture. The two mixtures were sprayed into a 12.5 cm diameter crystallizing dish, and the resulting reaction mixture (reaction pH of 6.5-6.0) contained 255 mM triacetin, 100 mM hydrogen peroxide and 0.100 mg protein/mL of spray-dried perhydrolase. The sprayed reaction mixture was sampled at predetermined times and analyzed for peracetic acid (TABLE 8, below) according to the method described by Karst et al., supra.

TABLE 8

Dependence of peracetic acid (PAA) concentration on solvent addition using triacetin (255 mM), hydrogen peroxide (103 mM) and 0.100 mg/mL of spray-dried *Thermotoga neapolitana* perhydrolase in stirred batch reactions and in a sprayed two-component mixture.

| Solvent | Enzyme (μg/mL) | PAA (ppm) | | | | | |
|---|---|---|---|---|---|---|---|
| | | 20 sec | 40 sec | 60 sec | 120 sec | 300 sec | 600 sec |
| DOWANOL ® PM, stirred reaction | 0 | 101 | 106 | 106 | 82 | 90 | 166 |
| DOWANOL ® PM, stirred reaction | 100 | 319 | 587 | 622 | 648 | 889 | 976 |
| DOWANOL ® PM, sprayed reaction | 100 | 375 | 454 | 515 | 671 | 873 | 994 |
| DOWANOL ® TPM, stirred reaction | 0 | 0 | 72 | 19 | 25 | 44 | 69 |
| DOWANOL ® TPM, stirred reaction | 100 | 445 | 548 | 726 | 980 | 1378 | 1560 |
| DOWANOL ® TPM, sprayed reaction | 100 | 433 | 575 | 1385 | 806 | 1089 | 1250 |
| DOWANOL ® DM, stirred reaction | 0 | 287 | 261 | 287 | 261 | 255 | 234 |
| DOWANOL ® DM, stirred reaction | 100 | 667 | 875 | 927 | 1410 | 1640 | 1876 |
| DOWANOL ® DM, sprayed reaction | 100 | 540 | 613 | 866 | 914 | 1112 | 1276 |
| DOWANOL ® PNB, stirred reaction | 0 | 76 | 70 | 40 | 58 | 0 | 11 |
| DOWANOL ® PNB, stirred reaction | 100 | 344 | 488 | 654 | 932 | 1166 | 1357 |
| DOWANOL ® PNB, sprayed reaction | 100 | 394 | 514 | 586 | 715 | 963 | 1141 |
| DOWANOL ® PnP, stirred reaction | 0 | 173 | 163 | 223 | 215 | 213 | 253 |
| DOWANOL ® PnP, stirred reaction | 100 | 611 | 716 | 857 | 1277 | 1468 | 1516 |
| DOWANOL ® PnP, sprayed reaction | 100 | 371 | 657 | 737 | 928 | 1090 | 1195 |
| DOWANOL ® PMA, stirred reaction | 0 | 0 | 0 | 14 | 0 | 128 | 166 |
| DOWANOL © PMA, stirred reaction | 100 | 335 | 510 | 756 | 1218 | 2178 | 3132 |
| DOWANOL ® PMA, sprayed reaction | 100 | 541 | 745 | 1042 | 1472 | ND | 3236 |
| dipropylene glycol, stirred reaction | 0 | 26 | 54 | 73 | 79 | 40 | 38 |

TABLE 8-continued

Dependence of peracetic acid (PAA) concentration on solvent addition using triacetin (255 mM), hydrogen peroxide (103 mM) and 0.100 mg/mL of spray-dried *Thermotoga neapolitana* perhydrolase in stirred batch reactions and in a sprayed two-component mixture.

| Solvent | Enzyme (µg/mL) | PAA (ppm) | | | | | |
|---|---|---|---|---|---|---|---|
| | | 20 sec | 40 sec | 60 sec | 120 sec | 300 sec | 600 sec |
| dipropylene glycol, stirred reaction | 100 | 318 | 539 | 708 | 1423 | 1241 | 946 |
| dipropylene glycol, sprayed reaction | 100 | 371 | 414 | 464 | 618 | 756 | 863 |
| ethanol, stirred reaction | 0 | 144 | 184 | 152 | 161 | 167 | 170 |
| ethanol, stirred reaction | 100 | 398 | 553 | 694 | 919 | 1227 | 1311 |
| ethanol, sprayed reaction | 100 | 504 | 677 | 685 | 766 | 968 | 1125 |
| isopropanol, stirred reaction | 0 | 149 | 167 | 180 | 207 | 180 | 236 |
| isopropanol, stirred reaction | 100 | 564 | 691 | 783 | 1114 | 1395 | 1533 |
| isopropanol, sprayed reaction | 100 | 621 | 767 | 882 | 1014 | 1239 | 1435 |
| 1,2-propanediol, stirred reaction | 0 | 32 | 14 | 19 | 33 | ND | 108 |
| 1,2-propanediol, stirred reaction | 100 | 427 | 665 | 921 | 1485 | 1941 | 3466 |
| 1,2-propanediol, sprayed reaction | 100 | 376 | 554 | 704 | 1376 | 1873 | 2517 |
| cyclohexanone, stirred reaction | 0 | 136 | 133 | 153 | 138 | 152 | 114 |
| cyclohexanone, stirred reaction | 100 | 97 | 153 | 185 | 351 | 329 | 459 |
| cyclohexanone, sprayed reaction | 100 | 128 | 196 | 338 | 368 | 416 | 489 |

EXAMPLE 10

Peroxycarboxylic Acid Production Using *Thermotoga maritima* Perhydrolase as an Enzyme Catalyst Cloning and expression of perhydrolase from *Thermotoga maritima* is accomplished in accordance with the methods described in preceding Examples 1-4. Fermentation of bacterial transformants expressing *Thermotoga maritima* perhydrolase is performed in accordance with preceding Example 5, and preparation of spray-dried *Thermotoga maritima* perhydrolase is accomplished using methods described in Example 6. Additional information regarding techniques for cloning, expressing, and preparation of *Thermotoga maritima* perhydrolase is available in Published U.S. Patent Application No. 2009/0005590; herein incorporated by reference.

A comparison of peracetic acid production by *Thermotoga maritima* perhydrolase in the presence and absence of added solvent is performed. A first mixture of 40.0 g of deionized water, 0.1575 g of TURPINAL® SL ((1-hydroxy-1-phosphonoethyl)phosphonic acid, 60 wt % in water; Thermphos International), and 1.44 g of 30 wt % hydrogen peroxide in water is adjusted to pH 7.2 with 50% aqueous sodium hydroxide, and the final weight of the mixture adjusted to 46.87 g with deionized water. A second mixture of 2.78 g triacetin, 0.210 g of sodium bicarbonate, 0.125 g of CAB-O-SIL® M5 (Cabot) and 0.0135 g of spray-dried *Thermotoga maritima* perhydrolase is prepared, and the first mixture of hydrogen peroxide and TURPINAL® SL in water (pH 7.2) is added to the second mixture with stirring at 25° C.; the resulting mixture containing 255 mM triacetin, 254 mM hydrogen peroxide and 0.055 mg protein/mL of spray-dried perhydrolase. Determination of the concentration of peracetic acid in the reaction mixtures is performed according to the method described by Karst et al., supra. A control reaction is also run to determine the concentration of peracetic acid produced by chemical perhydrolysis of triacetin by hydrogen peroxide in the absence of added perhydrolase.

The reaction described above is repeated, where 1.872 g of either propylene glycol monomethyl ether (DOWANOL® PM) or dipropyleneglycol monomethyl ether (DOWANOL® DPM), is substituted for an equivalent weight of water in the reaction mixture. A first mixture of 40.0 g of deionized water, 0.175 g of TURPINAL® SL, and 1.60 g of 30 wt % hydrogen peroxide in water is adjusted to pH 7.2 with 50% aqueous sodium hydroxide, and the final weight of the mixture adjusted to 50.0 g with deionized water. A second mixture of 2.78 g triacetin, 1.872 g of either propylene glycol monomethyl ether (DOWANOL® PM) or dipropyleneglycol monomethyl ether (DOWANOL® DPM), 0.210 g of sodium bicarbonate, 0.125 g of CAB-O-SIL® M5 (Cabot) and 0.0135 g of spray-dried *Thermotoga maritima* perhydrolase is prepared, and 45.0 g of the first mixture of hydrogen peroxide and TURPINAL® SL in water (pH 7.2) is added to the second mixture with stirring at 25° C.; the resulting mixture (pH 6.5) contained 255 mM triacetin, 254 mM hydrogen peroxide and 0.055 mg protein/mL of spray-dried perhydrolase. A control reaction is also run to determine the concentration of peracetic acid produced by chemical perhydrolysis of triacetin by hydrogen peroxide in the absence of added extract protein. The peracetic acid concentrations produced in 0.5 min, 1 min, 2 min, 5 min and 10 min for the three reactions described above are measured and recorded.

EXAMPLE 11

Use of Solvent for In Situ Peracid Generation Using Two-Compartment Spray Device Compared to Stirred Reaction and Using *Thermotoga maritima* Perhydrolase A first mixture of 100 g of 0.20 M sodium citrate buffer containing 2000 ppm TURPINAL® SL ((1-hydroxy-1-phosphonoethyl)phosphonic acid, 60 wt % in water; Thermphos International), 280 g of deionized water, and 5.20 g of 30 wt % hydrogen peroxide in water is adjusted to pH 7.2 with 50% aqueous sodium hydroxide, and the final weight of the mixture adjusted to 400 g with deionized water. A second mixture is separately prepared, containing 83.4 g of triacetin, 3.75 g of CAB-O-SIL® M5 (Cabot), 0.750 g of spray-dried *Thermotoga maritima* perhydrolase (Example 10), and 62.1 g of a single solvent selected from: propylene glycol methyl ether (DOWANOL® PM), tripropylene glycol methyl ether (DOWANOL® TPM), diethylene glycol methyl ether (DOWANOL® DM), propylene glycol n-butyl ether (DOWANOL® PNB), propylene glycol n-propyl ether (DOWANOL® PnP), propylene glycol monomethyl ether acetate (DOWANOL® PMA), dipropylene glycol, ethanol, isopropanol, and 1,2-propanediol. In a first reaction at 25° C., 1.0 g of the first mixture is stirred with 9.0 g of the second mixture for the first 30-60 seconds of the reaction (reaction pH of 6.5-6.0), and samples are withdrawn and analyzed for peracetic acid production; the resulting reaction mixture containing 255 mM triacetin, 103 mM hydrogen peroxide and 100 µg protein/mL of spray-dried perhydrolase. Determination of the concentration of peracetic acid in the reaction mixtures is performed according to the method described by Karst et al., supra. A control reaction is also run to determine the concentration of peracetic acid produced by chemical perhydrolysis of triacetin by hydrogen peroxide in the absence of added perhydrolase.

The first mixture and second mixture prepared as described above are each separately charged to one of the two compartments of a two-compartment spray bottle (Custom Dual-Liquid Variable-Ratio Sprayer, Model DLS 200, manufactured by Take5 (Rogue River, Oreg.)), where the bottle is set up to spray a mixture of 9 parts by weight of the first mixture with 1 part by weight of the second mixture. The two mixtures are sprayed into a 12.5 cm diameter crystallizing dish, and the resulting reaction mixture (reaction pH of 6.5-6.0) containing 255 mM triacetin, 100 mM hydrogen peroxide and 0.100 mg protein/mL of spray-dried perhydrolase. The sprayed reaction mixture is sampled at predetermined times and analyzed for peracetic acid according to the method described by Karst et al., supra.

EXAMPLE 12

Exemplary Two-Component System

One example of a two-component in situ peracid disinfectant formulation is described below.

|  | mol/L | grams |
|---|---|---|
| Component A |  |  |
| triacetin | 0.100 | 21.82 |
| *T. neapolitana* perhydrolase/excipient |  | 0.20 |
| sodium bicarbonate | 0.050 | 4.20 |

-continued

|  | mol/L | grams |
|---|---|---|
| Component B |  |  |
| $H_2O_2$ (30 wt %): | 0.100 | 11.33 |
| TURPINAL ® SL (60 wt %, 0.1% final) |  | 1.67 |
| water (deionized) |  | 960.78 |
| Total weight (grams) |  | 1000.00 |

For the two-component in situ peracid disinfectant formulation described above, Component A comprises ca. 2.6 wt % of the combined weight of Components A and B, and the weight ratio of Component B to Component A is ca. 38:1. In certain applications for a two-component in situ peracid disinfectant formulation, it may be desirable for the ratio of Component B to Component A to be within a range of from 1:1 to 10:1, where from 10 parts to 1 part (by weight) of Component B is mixed with one part (by weight) of Component A to produce a peracid at a concentration efficacious for disinfection. For example, in a first application a two-compartment spray bottle such as a dual-liquid fixed ratio sprayer (Model DLS100, Take5) or a dual-liquid variable ratio sprayer (Model DLS200, Take5) is utilized, where a maximum ratio of Component B to Component A of 10:1 is employed. In a second application, a single bottle containing two separate compartments separated by a breakable seal is employed, where the ratio of the volume of the two separate compartments is 1:1, or 5:1 or 10:1. In each of these applications, the two-component formulation cannot be mixed at the desired ratio of Component A to Component B to provide the desired concentration of reactants and final concentration of products.

EXAMPLE 13

Perhydrolysis of Propylene Glycol Diacetate or Ethylene Glycol Diacetate Using *Bacillus subtilis* ATCC® 31954™ Perhydrolase A homogenate of a transformant expressing wild-type perhydrolase from *Bacillus subtilis* ATCC® 31954™ (KLP18/pSW194) was prepared from a suspension of cell paste (20 wt % wet cell weight) in 0.05 M potassium phosphate buffer (pH 7.0) containing dithiothreitol (1 mM). The crude homogenate was centrifuged to remove cellular debris, producing a clarified cell extract that was heat-treated at 65° C. for 30 min. The resulting mixture was centrifuged, and the heat-treated supernatant concentrated on a 30K MWCO (molecular weight cutoff) membrane to a concentration of 32 mg/mL total dissolved solids; a SDS-PAGE of the clarified, heat-treated cell extract indicated that the perhydrolase was at least 85-90% pure. To this concentrate was then added 2.06 grams of $NaH_2PO_4$ and 1.17 grams $Na_2HPO_4$ per gram of solids was added to this concentrate to produce an approximate 3:1 ratio (wt/wt) of phosphate buffer to heat-treated cell extract protein. This solution was diluted by 30 wt % with deionized water, then spray-dried (180° C. inlet temperature, 70° C. exit temperature) using a Buchi B-290 laboratory spray dryer); the resulting spray-dried powder contained 25.5 wt % protein (Bradford protein assay) and was 94.3 wt % dry solids.

Reactions (10 mL total volume) were run at 23° C. in 50 mM sodium bicarbonate buffer (initial pH 7.2) containing propylene glycol diacetate (PGDA) or ethylene glycol diacetate (EGDA), hydrogen peroxide (100 mM) and 123 µg/mL of a heat-treated extract protein from the spray-dried *E. coli*

KLP18/pSW194 (expressing *Bacillus subtilis* ATCC® 31954™ wild-type perhydrolase) (prepared as described above). A control reaction for each reaction condition was run to determine the concentration of peracetic acid produced by chemical perhydrolysis of triacetin by hydrogen peroxide in the absence of added heat-treated extract protein. The reactions were sampled at 1, 5, and 30 minutes and the samples analyzed for peracetic acid using the Karst derivatization protocol (Karst et al., supra); aliquots (0.040 mL) of the reaction mixture were removed and mixed with 0.960 mL of 5 mM phosphoric acid in water; adjustment of the pH of the diluted sample to less than pH 4 immediately terminated the reaction. The resulting solution was filtered using an ULTRAFREE® MC-filter unit (30,000 Normal Molecular Weight Limit (NMWL), Millipore cat #UFC3LKT 00) by centrifugation for 2 min at 12,000 rpm. An aliquot (0.100 mL) of the resulting filtrate was transferred to 1.5-mL screw cap HPLC vial (Agilent Technologies, Palo Alto, Calif.; #5182-0715) containing 0.300 mL of deionized water, then 0.100 mL of 20 mM MTS (methyl-p-tolyl-sulfide) in acetonitrile was added, the vials capped, and the contents briefly mixed prior to a 10 min incubation at ca. 25° C. in the absence of light. To each vial was then added 0.400 mL of acetonitrile and 0.100 mL of a solution of triphenylphosphine (TPP, 40 mM) in acetonitrile, the vials re-capped, and the resulting solution mixed and incubated at ca. 25° C. for 30 min in the absence of light. To each vial was then added 0.100 mL of 10 mM N,N-diethyl-m-toluamide (DEET; HPLC external standard) and the resulting solution analyzed by HPLC. The peracetic acid concentrations produced in 1 min, 5 min and 30 min are listed in Table 9.

TABLE 9

Peracetic acid (PAA) concentration produced in reactions utilizing propylene glycol diacetate (PGDA) or ethylene glycol diacetate (EGDA) and hydrogen peroxide (100 mM) in sodium bicarbonate buffer (50 mM, initial pH 7.2) at 23° C. using 123 µg/mL of heat-treated extract protein from *E. coli* KLP18/pSW194 (*Bacillus subtilis* ATCC ® 31954 ™ perhydrolase).

| perhydrolase (50 µg/mL) | substrate (100 mM) | PAA, 1 min (ppm) | PAA, 5 min (ppm) | PAA, 30 min (ppm) |
|---|---|---|---|---|
| no enzyme (control) | PGDA | 0 | 64 | 241 |
| *B. subtilis* ATCC ® 31954 | PGDA | 666 | 781 | 815 |
| no enzyme (control) | EGDA | 0 | 18 | 141 |
| *B. subtilis* ATCC ® 31954 | EGDA | 747 | 931 | 963 |

EXAMPLE 14

Perhydrolysis of Propylene Glycol Diacetate or Ethylene Glycol Diacetate Using *T. maritima* and *T. neapolitana* Wild-Type and Variant Perhydrolases Cell extracts of transformants expressing *Thermotoga neapolitana* wild-type perhydrolase (KLP18/pSW196), *Thermotoga neapolitana* C277S variant perhydrolase (KLP18/pSW196/C277S), *Thermotoga neapolitana* C277T variant perhydrolase (KLP18/pSW196/C277T), *Thermotoga maritima* wild-type perhydrolase (KLP18/pSW228), *Thermotoga maritima* C277S variant perhydrolase (KLP18/pSW228/C277S), and *Thermotoga maritima* C277T variant perhydrolase (KLP18/pSW228/C277T) were each prepared by passing a suspension of cell paste (20 wt % wet cell weight) in 0.05 M potassium phosphate buffer (pH 7.0) containing dithiothreitol (1 mM) twice through a French press having a working pressure of 16,000 psi (~110 MPa). The lysed cells were centrifuged for 30 minutes at 12,000×g, producing a clarified cell extract that was assayed for total soluble protein (Bradford assay). The supernatant was heated at 75° C. for 20 minutes, followed by quenching in an ice bath for 2 minutes. Precipitated protein was removed by centrifugation for 10 minutes at 11,000×g. SDS-PAGE of the resulting heat-treated extract protein supernatant indicated that the CE-7 enzyme comprised approximately 85-90% of the total protein in the preparation. The heat-treated extract protein supernatant was frozen in dry ice and stored at −80° C. until use.

A first set of reactions (10 mL total volume) were run at 20° C. in 10 mM sodium bicarbonate buffer (initial pH 8.1) containing propylene glycol diacetate (PGDA) or ethylene glycol diacetate (EGDA) (100 mM), hydrogen peroxide (100 mM) and 25 µg/mL of heat-treated extract protein from one of *E. coli* KLP18/pSW196 (*Thermotoga neapolitana* wild-type perhydrolase), *E. coli* KLP18/pSW196/C277S (*Thermotoga neapolitana* C277S variant perhydrolase), *E. coli* KLP18/pSW196/C277T (*Thermotoga neapolitana* C277T variant perhydrolase), *E. coli* KLP18/pSW228 (*Thermotoga maritima* wild-type perhydrolase), *E. coli* KLP18/pSW228/C277S (*Thermotoga maritima* C277S variant perhydrolase), and *E. coli* KLP18/pSW228/C277T (*Thermotoga maritima* C277T variant perhydrolase) (prepared as described above). A control reaction for each reaction condition was run to determine the concentration of peracetic acid produced by chemical perhydrolysis of triacetin by hydrogen peroxide in the absence of added extract protein. The reactions were sampled at 1, 5, and 30 minutes and the samples analyzed for peracetic acid using the Karst derivatization protocol (Karst et al., supra) and HPLC analytical method (supra). The peracetic acid concentrations produced in 1 min, 5 min and 30 min are listed in Table 10.

TABLE 10

Peracetic acid (PAA) concentration produced utilizing *T. maritima* and *T. neapolitana* wild-type and variant perhydrolases in reactions at 20° C. in sodium bicarbonate buffer (10 mM, initial pH 8.1) containing propylene glycol diacetate (PGDA) (100 mM) or ethylene glycol diacetate (EGDA) (100 mM), hydrogen peroxide (100 mM) and 25 µg/mL of heat-treated extract protein.

| perhydrolase | substrate | substrate conc. (mM) | $H_2O_2$ (mM) | PAA, 1 min (ppm) | PAA, 5 min (ppm) | PAA, 30 min (ppm) |
|---|---|---|---|---|---|---|
| no enzyme (control) | PGDA | 100 | 100 | 0 | 15 | 165 |
| *T. maritima* WT | PGDA | 100 | 100 | 534 | 1104 | 1695 |
| *T. maritima* C277S | PGDA | 100 | 100 | 647 | 1320 | 1864 |
| *T. maritima* C277T | PGDA | 100 | 100 | 656 | 1174 | 1418 |
| *T. neapolitana* WT | PGDA | 100 | 100 | 513 | 1052 | 1946 |
| *T. neapolitana* C277S | PGDA | 100 | 100 | 875 | 1327 | 1707 |
| *T. neapolitana* C277T | PGDA | 100 | 100 | 724 | 1325 | 1864 |

TABLE 10-continued

Peracetic acid (PAA) concentration produced utilizing T. maritima and T. neapolitana wild-type and variant perhydrolases in reactions at 20° C. in sodium bicarbonate buffer (10 mM, initial pH 8.1) containing propylene glycol diacetate (PGDA) (100 mM) or ethylene glycol diacetate (EGDA) (100 mM), hydrogen peroxide (100 mM) and 25 μg/mL of heat-treated extract protein.

| perhydrolase | substrate | substrate conc. (mM) | $H_2O_2$ (mM) | PAA, 1 min (ppm) | PAA, 5 min (ppm) | PAA, 30 min (ppm) |
|---|---|---|---|---|---|---|
| no enzyme (control) | EGDA | 100 | 100 | 0 | 70 | 229 |
| T. maritima WT | EGDA | 100 | 100 | 765 | 1182 | 1595 |
| T. maritima C277S | EGDA | 100 | 100 | 725 | 1240 | 1724 |
| T. maritima C277T | EGDA | 100 | 100 | 802 | 1218 | 1734 |
| T. neapolitana WT | EGDA | 100 | 100 | 603 | 1132 | 1643 |
| T. neapolitana C277S | EGDA | 100 | 100 | 680 | 1305 | 1698 |
| T. neapolitana C277T | EGDA | 100 | 100 | 688 | 1164 | 1261 |

A second set of reactions (10 mL total volume) were run at 20° C. in 10 mM sodium bicarbonate buffer (initial pH 8.1) containing propylene glycol diacetate (PGDA) or ethylene glycol diacetate (EGDA) (2 mM), hydrogen peroxide (10 mM) and 10 μg/mL of heat-treated extract protein from one of E. coli KLP18/pSW196 (Thermotoga neapolitana wild-type perhydrolase), E. coli KLP18/pSW196/C2775 (Thermotoga neapolitana C277S variant perhydrolase), E. coli KLP18/pSW196/C277T (Thermotoga neapolitana C277T variant perhydrolase), E. coli KLP18/pSW228 (Thermotoga maritima wild-type perhydrolase), E. coli KLP18/pSW228/C277S (Thermotoga maritima C277S variant perhydrolase), and E. coli KLP18/pSW228/C277T (Thermotoga maritima C277T variant perhydrolase) (prepared as described above). A control reaction for each reaction condition was run to determine the concentration of peracetic acid produced by chemical perhydrolysis of triacetin by hydrogen peroxide in the absence of added extract protein. The reactions were sampled at 5 minutes and the samples analyzed for peracetic acid using the Karst derivatization protocol (Karst et al., supra) and HPLC analytical method (supra). The peracetic acid concentrations produced in 5 min are listed in Table 11.

TABLE 11

Peracetic acid (PAA) concentration produced utilizing T. maritima and T. neapolitana wild-type and variant perhydrolases in reactions at 20° C. in sodium bicarbonate buffer (10 mM, initial pH 8.1) containing propylene glycol diacetate (PGDA) (2 mM) or ethylene glycol diacetate (EGDA) (2 mM), hydrogen peroxide (10 mM) and 10 μg/mL of heat-treated extract protein.

| perhydrolase | substrate | substrate conc. (mM) | $H_2O_2$ (mM) | PAA, 5 min (ppm) |
|---|---|---|---|---|
| no enzyme (control) | PGDA | 2 | 10 | 3.6 |
| T. maritima WT | PGDA | 2 | 10 | 5.0 |
| T. maritima C277S | PGDA | 2 | 10 | 7.2 |
| T. maritima C277T | PGDA | 2 | 10 | 7.9 |
| T. neapolitana WT | PGDA | 2 | 10 | 5.7 |
| T. neapolitana C277S | PGDA | 2 | 10 | 7.9 |
| T. neapolitana C277T | PGDA | 2 | 10 | 3.9 |
| no enzyme (control) | EGDA | 2 | 10 | 3.3 |
| T. maritima WT | EGDA | 2 | 10 | 9.9 |
| T. maritima C277S | EGDA | 2 | 10 | 13.6 |
| T. maritima C277T | EGDA | 2 | 10 | 22.9 |
| T. neapolitana WT | EGDA | 2 | 10 | 6.6 |
| T. neapolitana C277S | EGDA | 2 | 10 | 18.4 |
| T. neapolitana C277T | EGDA | 2 | 10 | 20.2 |

EXAMPLE 15

Expression of Thermotoga neapolitana Acetyl Xylan Esterase Variants in E. coli KLP18

Plasmids comprising aetyl xylan esterase mutations as described in co-owned, co-filed, and cocpending U.S. patent application Ser. No. 12/572,094 were prepared from wild type Thermotoga neapolitana perhydrolase (SEQ ID NO: 14) by substituting at amino acid residue position 277 an Ala, Val, Ser, or Thr (SEQ ID NO: 73). The plasmids were used to transform E. coli KLP18 (Example 3). Transformants were plated onto LB-ampicillin (100 μg/mL) plates and incubated overnight at 37° C. Cells were harvested from a plate using 2.5 mL LB media supplemented with 20% (v/v) glycerol, and 1.0 mL aliquots of the resulting cell suspension frozen at −80° C. One mL of the thawed cell suspension was transferred to a 1-L APPLIKON® Bioreactor (Applikon® Biotechnology, Foster City, Calif.) with 0.7 L medium containing $KH_2PO_4$ (5.0 g/L), $FeSO_4$ heptahydrate (0.05 g/L), $MgSO_4$ heptahydrate (1.0 g/L), sodium citrate dihydrate (1.90 g/L), yeast extract (Amberex 695, 5.0 g/L), Biospumex 153K antifoam (0.25 mL/L, Cognis Corporation), NaCl (1.0 g/L), $CaCl_2$ dihydrate (0.1 g/L), and NIT trace elements solution (10 mL/L). The trace elements solution contained citric acid monohydrate (10 g/L), $MnSO_4$ hydrate (2 g/L), NaCl (2 g/L), $FeSO_4$ heptahydrate (0.5 g/L), $ZnSO_4$ heptahydrate (0.2 g/L), $CuSO_4$ pentahydrate (0.02 g/L) and $NaMoO_4$ dihydrate (0.02 g/L). Post sterilization additions included glucose solution (50% w/w, 6.5 g) and ampicillin (25 mg/mL) stock solution (2.8 mL). Glucose solution (50% w/w) was also used for fed batch. Glucose feed was initiated 40 min after glucose concentration decreased below 0.5 g/L, starting at 0.03 g feed/min and increasing progressively each hour to 0.04, 0.04, 0.05, 0.06, 0.07, 0.08, 0.09, 0.12, and 0.14 g/min respectively; the rate remaining constant afterwards. Glucose concentration in the medium was monitored, and if the concentration exceeded 0.1 g/L the feed rate was decreased or stopped temporarily. Induction was initiated at $OD_{550}$=50 with addition of 0.8 mL IPTG (0.05 M). The dissolved oxygen (DO) concentration was controlled at 25% of air saturation, first by agitation (400-1000 rpm), and following by aeration (0.5-2 slpm). The temperature was controlled at 37° C., and the pH was controlled at 6.8; $NH_4OH$ (29% w/w) and $H_2SO_4$ (20% w/v) were used for pH control. The cells were harvested by centrifugation (5,000×g for 15 minutes) at 20 h post IPTG addition. A cell culture of E. coli KLP18/pSW196 (Thermotoga neapolitana wild-type perhydrolase) was grown as described in Example 2.

EXAMPLE 16

Preparation of Cell Lysates Containing Semi-Purified Wild Type *T. neapolitana* Acetyl Xylan Esterase or *T. neapolitana* Variant Acetyl Xylan Esterases A cell culture of *E. coli* KLP18/pSW196 (*Thermotoga neapolitana* wild-type perhydrolase) was grown as described in Example 5. The resulting cell paste was resuspended (20% w/v) in 50 mM phosphate buffer pH 7.0 supplemented with 1.0 mM DTT. Resuspended cells were passed through a French pressure cell twice to ensure >95% cell lysis. Lysed cells were centrifuged for 30 minutes at 12,000×g, and the supernatant was heated at 75° C. for 20 minutes, followed by quenching in an ice bath for 2 minutes. Precipitated protein was removed by centrifugation for 10 minutes at 11,000×g. SOS-PAGE indicated that the CE-7 enzyme comprised approximately 85-90% of the total protein in the heat-treated extract supernatant.

Cell cultures of *E. coli* KLP18/pSW196/C277S (*Thermotoga neapolitana* C277S variant perhydrolase), *E. coli* KLP18/pSW196/C277V (*Thermotoga neapolitana* C277V variant perhydrolase), *E. coli* KLP18/pSW196/C277A (*Thermotoga neapolitana* C277A variant perhydrolase), and *E. coli* KLP18/pSW196/C277T (*Thermotoga neapolitana* C277T variant perhydrolase) were each grown as described in Example 15. The resulting cell pastes were resuspended (20% w/v) in 50 mM phosphate buffer pH 7.0 supplemented with 1.0 mM DTT. Resuspended cells were passed through a French pressure cell twice to ensure >95% cell lysis. Lysed cells were centrifuged for 30 minutes at 12,000×g, and the supernatant was heated at 75° C. for 20 minutes, followed by quenching in an ice bath for 2 minutes. Precipitated protein was removed by centrifugation for 10 minutes at 11,000×g. SDS-PAGE indicated that the CE-7 enzyme comprised approximately 85-90% of the total protein in the heat-treated extract supernatant.

EXAMPLE 17

Specific Activity and Perhydrolysis/Hydrolysis Ratio of *T. neapolitana* Acetyl Xylan Wild-Type Esterase and C277 Esterase Variants Reactions (40 mL total volume) were run at 25° C. in phosphate buffer (50 mM, pH 7.2) containing triacetin (100 mM), hydrogen peroxide (100 mM) and one of the following acetyl xylan esterase variants: *T. neapolitana* C277S variant perhydrolase (0.010 mg/mL of heat-treated extract total protein from *E. coli* KLP18/pSW196/C277S), *T. neapolitana* C277T variant perhydrolase (0.010 mg/mL of heat-treated extract total protein from *E. coli* KLP18/pSW196/C277T), *T. neapolitana* C277A variant perhydrolase (0.0125 mg/mL of heat-treated extract total protein from E, coil KLP18/pSW196/C277A), and *T. neapolitana* C277V variant perhydrolase (0.0125 mg/mL of heat-treated extract total protein from *E. coli* KLP18/pSW196/C277V) (prepared as described in Example 16). Reactions were stirred for only the first 30 seconds of reaction to initially mix the reactants and enzyme.

A reaction was also run under identical conditions to that described immediately above using 0.050 mg/mL of heat-treated extract total protein isolated from *E. coli* KLP18/pSW196 (expressing *Thermotoga neapolitana* wild-type acetyl xylan esterase (Example 1)), where the heat-treated extract supernatant was prepared according to the procedure of Example 16.

Two samples from each of the reaction mixtures described above were simultaneously withdrawn after the first minute of each reaction, and every two minutes thereafter for fifteen minutes, where one of the two samples was analyzed for peracetic acid, and the second sample was analyzed for total acetic acid produced from both enzymatic hydrolysis of triacetin and from subsequent conversion of peracetic acid in sample to acetic acid by reaction with methyl-p-tolyl sulfide (MTS, see below).

Measurement of the rate of peracetic acid production in the reaction mixture was performed using a modification of the method described by Karst et al., supra. A sample (0.040 mL) of the reaction mixture was removed at a predetermined time and immediately mixed with 0.960 mL of 5 mM phosphoric acid in water to terminate the reaction by adjusting the pH of the diluted sample to less than pH 4. The resulting solution was filtered using an ULTRAFREE® MC-filter unit (30,000 Normal Molecular Weight Limit (NMWL), Millipore Corp., Billerica, Mass.; cat #UFC3LKT 00) by centrifugation for 2 min at 12,000 rpm. An aliquot (0.100 mL) of the resulting filtrate was transferred to a 1.5-mL screw cap HPLC vial (Agilent Technologies, Palo Alto, Calif.; #5182-0715) containing 0.300 mL of deionized water, then 0.100 mL of 20 mM MTS (methyl-p-tolyl sulfide) in acetonitrile was added, the vial capped, and the contents briefly mixed prior to a 10 min incubation at ca. 25° C. in the absence of light. To the vial was then added 0.400 mL of acetonitrile and 0.100 mL of a solution of triphenylphosphine (TPP, 40 mM) in acetonitrile, the vial re-capped, and the resulting solution mixed and incubated at ca. 25° C. for 30 min in the absence of light. To the vial was then added 0.100 mL of 10 mM N,N-diethyl-m-toluamide (DEET; HPLC external standard) and the resulting solution analyzed by HPLC for MTSO (methyl-p-tolyl sulfoxide), the stoichiometric oxidation product produced by reaction of MTS with peracetic acid. A control reaction was run in the absence of added extract protein or triacetin to determine the rate of oxidation of MTS in the assay mixture by hydrogen peroxide, for correction of the rate of peracetic acid production for background MTS oxidation. HPLC method: Supelco Discovery C8 column (10-cm×4.0-mm, 5 μm) (catalog #569422-U) with Supelco Supelguard Discovery C8 precolumn (Sigma-Aldrich; catalog #59590-U); 10 microliter injection volume; gradient method with $CH_3CN$ (Sigma-Aldrich; catalog #270717) and deionized water at 1.0 mL/min and ambient temperature (Table 4).

TABLE 12

| HPLC Gradient for analysis of peracetic acid. | |
|---|---|
| Time (min:sec) | (% $CH_3CN$) |
| 0:00 | 40 |
| 3:00 | 40 |
| 3:10 | 100 |

TABLE 12-continued

HPLC Gradient for analysis of peracetic acid.

| Time (min:sec) | (% CH$_3$CN) |
|---|---|
| 4:00 | 100 |
| 4:10 | 40 |
| 7:00 (stop) | 40 |

For determination of the rate of perhydrolase-catalyzed acetic acid production in the reaction, a sample (0.900 mL) of the reaction mixture was removed at a predetermined time and immediately added to a 1.5 mL-microcentrifuge tube containing 0.040 mL of 0.75 M H$_3$PO$_4$, and the resulting solution briefly mixed to terminate the reaction at pH 3.0-4.0. To the tube was then added 0.020 mL of a solution of 10 mg/mL of *Aspergillus niger* catalase (Sigma-Aldrich; C3515) in 50 mM phosphate buffer pH (7.2), and the resulting solution mixed and allowed to react for 15 minutes at ambient temperature to disproportionate unreacted hydrogen peroxide to water and oxygen. To the tube was then added 0.040 mL of 0.75 M H$_3$PO$_4$ and the resulting solution mixed and filtered using an ULTRAFREE® MC-filter unit (30,000 Normal Molecular Weight Limit (NMWL), Millipore Corp., cat #UFC3LKT 00) by centrifugation for 2 min at 12,000 rpm. An aliquot (0.100 mL) of the resulting filtrate was mixed with 0.150 mL of 20 mM MTS (methyl-p-tolyl sulfide) in acetonitrile, and the resulting solution was incubated for 10 min at ca. 25° C. in the absence of light. The concentration of acetic acid in the sample produced by both enzymatic hydrolysis of triacetin and conversion of peracetic acid to acetic acid by reaction with MTS was determined using a gas chromatograph (GC) equipped with a flame ionization detector (FID) and a DB-FFAP column (length, 15 m; ID, 0.530 mm; film thickness, 1.00 µm); a fresh injection port liner was employed for each rate determination (total of eight sample analyses) to avoid build up of phosphoric add in the injection port liner over time.

The *Thermotoga neapolitana* acetyl xylan esterase variants had a significantly-higher specific activity for perhydrolysis of triacetin than the wild-type esterase (Table 13). The perhydrolysis/hydrolysis ratios for the *T. neapolitana* acetyl xylan esterase variants were determined by dividing the rate of PAA production (perhydrolysis rate) by the rate of hydrolysis of triacetin to acetic acid (hydrolysis rate) (calculated from the rate of total acetic acid production in the assay method from both PAA and acetic acid, and corrected for the rate of peracetic acid production); the P/H ratio of the *T. neapolitana* acetyl xylan esterase variants were ca. equal to or greater than the P/H ratio for the *T. neapolitana* wild-type acetyl xylan esterase (Table 13).

TABLE 13

| Thermotoga neapolitana perhydrolase | enzyme concen. (µg/mL) | perhydrolysis rate (mM/min) | hydrolysis rate (mM/min) | P/H ratio | specific activity (U/mg protein) |
|---|---|---|---|---|---|
| wild type | 50 | 3.61 | 1.22 | 3.0 | 72 |
| C277S | 10 | 4.40 | 1.61 | 2.7 | 440 |
| C277T | 10 | 4.24 | 0.81 | 5.2 | 424 |
| C277A | 12.5 | 4.14 | 1.43 | 2.9 | 331 |
| C277V | 12.5 | 3.70 | 0.88 | 4.2 | 296 |

EXAMPLE 18

Expression of *Thermotoga maritima* Acetyl Xylan Esterase Variants in *E. coli* KLP18

Plasmids comprising acetyl xylan esterase mutations as described in co-owned, co-filed, and copending U.S. patent application Ser. No. 12/572,094 were prepared from wild type *Thermotoga martima* (SEQ ID NO: 16) by substituting at amino acid residue position 277 an Ala, Val, Ser, or Thr (SEQ ID NO: 74). The plasmids were used to transform *E. coli* KLP18 (Example 3). Transformants were grown in LB media at 37° C. with shaking up to OD$_{600\ nm}$=0.4-0.5, at which time IPTG was added to a final concentration of 1 mM, and incubation continued for 2-3 h. Cells were harvested by centrifugation and SOS-PAGE was performed to confirm expression of the acetyl xylan esterase at 20-40% of total soluble protein.

EXAMPLE 19

Preparation of Cell Lysates Containing Semi-Purified *T. maritime* Acetyl Xylan Esterase Variants Cell cultures (prepared as described in Example 16) were grown using a fermentation protocol similar to that described in Example 15 at a 1-L scale (Applikon). Cells were harvested by centrifugation at 5,000×g for 15 minutes then resuspended (20% w/v) in 50 mM phosphate buffer pH 7.0 supplemented with 1.0 mM DTT. Resuspended cells were passed through a French pressure cell twice to ensure >95% cell lysis. Lysed cells were centrifuged for 30 minutes at 12,000×g, and the supernatant was heated at 75° C. for 20 minutes, followed by quenching in an ice bath for 2 minutes. Precipitated protein was removed by centrifugation for 10 minutes at 11,000×g. SDS-PAGE indicated that the CE-7 enzyme comprised approximately 85-90% of the total protein in the preparation.

EXAMPLE 20

Specific Activity and Perhydrolysis/Hydrolysis Ratio of *T. maritima* Acetyl Xylan Wild-type Esterase and C277 Esterase Variants Reactions (40 mL total volume) were run at 25° C. in phosphate buffer (50 mM, pH 7.2) containing triacetin (100 mM), hydrogen peroxide (100 mM) and one of the following acetyl xylan esterase variants: *T. maritima* C277S variant perhydrolase (0.010 mg/mL of heat-treated extract total protein from *E. coli* KLP18/pSW228/C277S), *T. maritima* C277T variant perhydrolase (0.010 mg/mL of heat-treated extract total protein from *E. coli* KLP18/pSW228/C277T), *T. maritima* C277A variant perhydrolase (0.0125 mg/mL of heat-treated extract total protein from *E. coli* KLP18/pSW228/C277A), and *T. maritima* C277V variant perhydrolase (0.0125 mg/mL of heat-treated extract total protein from *E. coli* KLP18/pSW228/C277V) (prepared as described in Example 19). Reactions were stirred for only the first 30 seconds of reaction to initially mix the reactants and enzyme.

A reaction was also run under identical conditions to that described immediately above using 0.050 mg/mL of heat-treated extract total protein isolated from *E. coli* KLP18/pSW228 (expressing *Thermotoga maritima* wild-type acetyl xylan esterase), where the heat-treated extract supernatant was prepared according to the procedure of Example 19.

Two samples from each of the reaction mixtures described above were simultaneously withdrawn after the first minute of each reaction, and every two minutes thereafter for fifteen minutes, where one of the two samples was analyzed for peracetic acid using a modification of the method described by Karst et al., supra, and the second sample was analyzed for total acetic acid produced from both enzymatic hydrolysis of triacetin and from subsequent conversion of peracetic acid in sample to acetic acid by reaction with methyl-p-tolyl sulfide (MTS).

The *Thermotoga maritima* acetyl xylan esterase variants had a significantly-higher specific activity for perhydrolysis of triacetin than the wild-type esterase (Table 14). The perhydrolysis/hydrolysis ratios for the *T. maritima* acetyl xylan esterase variants were determined by dividing the rate of PAA production (perhydrolysis rate) by the rate of hydrolysis of triacetin to acetic acid (hydrolysis rate) (calculated from the rate of total acetic acid production in the assay method from both PAA and acetic acid, and corrected for the rate of peracetic acid production); the P/H ratio of the *T. maritima* acetyl xylan esterase variants were ca. equal to or greater than the P/H ratio for the *T. neapolitana* wild-type acetyl xylan esterase (Table 14).

TABLE 14

| *Thermotoga maritima* perhydrolase | enzyme concen. (μg/mL) | perhydrolysis rate (mM/min) | hydrolysis rate (mM/min) | P/H ratio | specific activity (U/mg protein) |
|---|---|---|---|---|---|
| wild type | 50 | 3.06 | 0.47 | 6.5 | 61 |
| C277S | 10 | 7.77 | 0.48 | 16 | 777 |
| C277T | 10 | 6.93 | 1.05 | 6.6 | 693 |
| C277A | 10 | 4.27 | 0.088 | 48 | 427 |
| C277V | 10 | 4.25 | 0.062 | 68 | 425 |

EXAMPLE 21

Peracetic Acid Production Using Perhydrolases

Reactions (100 mL total volume) containing triacetin (2 mM), hydrogen peroxide (10 mM) and from 0.1 μg/mL to 2.0 μg/mL heat-treated cell extract protein (prepared as described above, where the heat-treatment was performed at 85° C. for 20 min) were run in 10 mM sodium bicarbonate buffer (initial pH 8.1) at 20° C. Determination of the concentration of peracetic acid in the reaction mixtures was performed according to the method described by Karst et al., supra. The peracetic acid concentrations produced in 1 min, 5 min, 20 min, 40 min and 60 min are listed in Table 15.

TABLE 15

Dependence of peracetic acid (PAA) concentration on perhydrolase concentration in reactions containing triacetin (2 mM) and hydrogen peroxide (10 mM) in sodium bicarbonate buffer (10 mM, initial pH 8.1) at 20° C., using heat-treated extract protein from *E. coli* KLP18/pSW228 (*Thermotoga maritima* wild-type perhydrolase) or *E. coli* KLP18/pSW228/C277S (*Thermotoga maritima* C277S variant perhydrolase) (duplicate reactions).

| *Thermotoga maritima* perhydrolase | triacetin (mM) | enzyme concen. (μg/mL) | PAA, 1 min (ppm) | PAA, 5 min (ppm) | PAA, 20 min (ppm) | PAA, 40 min (ppm) | PAA, 60 min (ppm) |
|---|---|---|---|---|---|---|---|
| no enzyme | 2 | 0 | 0 | 0 | 1 | 1 | 3 |
| wild type | 2 | 0.2 | 0 | 2 | 7 | 13 | 19 |
| wild type | 2 | 0.2 | 0 | 1 | 5 | 11 | 15 |
| wild type | 2 | 0.5 | 0 | 2 | 12 | 19 | 25 |
| wild type | 2 | 0.5 | 0 | 2 | 12 | 21 | 26 |
| wild type | 2 | 1.0 | 0 | 5 | 20 | 29 | 31 |
| wild type | 2 | 1.0 | 0 | 5 | 19 | 30 | 31 |
| wild type | 2 | 2.0 | 1 | 11 | 24 | 24 | 20 |
| wild type | 2 | 2.0 | 1 | 11 | 29 | 29 | 21 |
| C277S | 2 | 0.2 | 0 | 4 | 18 | 18 | 18 |
| C277S | 2 | 0.2 | 0 | 4 | 18 | 17 | 18 |
| C277S | 2 | 0.5 | 1 | 12 | 39 | 54 | 64 |
| C277S | 2 | 0.5 | 1 | 10 | 34 | 52 | 64 |
| C277S | 2 | 1.0 | 18 | 26 | 59 | 69 | 63 |
| C277S | 2 | 1.0 | 18 | 25 | 60 | 70 | 64 |
| C277S | 2 | 2.0 | 9 | 38 | 66 | 60 | 48 |
| C277S | 2 | 2.0 | 9 | 34 | 69 | 61 | 49 |

EXAMPLE 22
Peracetic Acid Production Using Perhydrolases

Reactions (100 mL total volume) containing triacetin (20 mM), hydrogen peroxide (10 mM) and from 0.1 µg/mL to 2.0 µg/mL heat-treated cell extract protein (prepared as described above, where the heat-treatment was performed at 85° C. for 20 min) were run in 10 mM sodium bicarbonate buffer (initial pH 8.1) at 20° C. Determination of the concentration of peracetic acid in the reaction mixtures was performed according to the method described by Karst et al., supra. The peracetic acid concentrations produced in 1 min, 5 min, 20 min, 40 min and 60 min are listed in Table 16.

mM), hydrogen peroxide (100 mM) and from 10 µg/mL to 50 µg/mL of heat-treated *T. neapolitana* or *T. maritima* wild-type or C277 variant perhydrolases (as heat-treated cell extract protein prepared as described above, where the heat-treatment was performed at 75° C. for 20 min). Reactions were stirred for only the first 30 seconds of reaction to initially mix the reactants and enzyme. Determination of the concentration of peracetic acid in the reaction mixtures was performed according to the method described by Karst et al., supra. The peracetic acid concentrations produced in 1 min, 5 min, and 30 min are listed in Table 17.

TABLE 16

Dependence of peracetic acid (PAA) concentration on perhydrolase concentration in reactions containing triacetin (20 mM) and hydrogen peroxide (10 mM) in sodium bicarbonate buffer (10 mM, initial pH 8.1) at 20° C., using heat-treated extract protein from *E. coli* KLP18/pSW228 (*Thermotoga maritima* wild-type perhydrolase) or *E. coli* KLP18/pSW228/C277S (*Thermotoga maritima* C277S variant perhydrolase) (duplicate reactions).

| *Thermotoga maritima* perhydrolase | triacetin (mM) | enzyme concen. (µg/mL) | PAA, 1 min (ppm) | PAA, 5 min (ppm) | PAA, 20 min (ppm) | PAA, 40 min (ppm) | PAA, 60 min (ppm) |
|---|---|---|---|---|---|---|---|
| no enzyme | 20 | 0 | 2 | 3 | 3 | 7 | 9 |
| wild-type | 20 | 0.2 | 3 | 10 | 15 | 27 | 35 |
| wild-type | 20 | 0.2 | 4 | 9 | 19 | 32 | 41 |
| wild-type | 20 | 0.5 | 3 | 9 | 21 | 39 | 52 |
| wild-type | 20 | 0.5 | 3 | 8 | 22 | 39 | 54 |
| wild-type | 20 | 1.0 | 4 | 13 | 35 | 62 | 82 |
| wild-type | 20 | 1.0 | 4 | 12 | 37 | 67 | |
| wild-type | 20 | 2.0 | 9 | 20 | 52 | 91 | 122 |
| wild-type | 20 | 2.0 | 10 | 20 | 52 | 87 | 114 |
| C277S | 20 | 0.2 | 7 | 16 | 67 | 109 | 148 |
| C277S | 20 | 0.2 | 9 | 24 | 67 | 112 | 144 |
| C277S | 20 | 0.5 | 16 | 43 | 140 | 202 | 260 |
| C277S | 20 | 0.5 | 17 | 48 | 148 | 228 | 272 |
| C277S | 20 | 1.0 | 24 | 75 | 230 | 289 | 353 |
| C277S | 20 | 1.0 | 26 | 97 | 232 | 297 | 372 |
| C277S | 20 | 2.0 | 32 | 130 | 318 | 402 | 443 |
| C277S | 20 | 2.0 | 37 | 135 | 323 | 401 | 430 |

EXAMPLE 23
Peracetic Acid Production Using Perhydrolases

Reactions (40 mL total volume) were run at 25° C. in phosphate buffer (50 mM, pH 7.2) containing triacetin (100

TABLE 17

Peracetic acid (PAA) production in reactions containing triacetin (100 mM) and hydrogen peroxide (100 mM) in phosphate buffer (50 mM, pH 7.2) at 25° C., using heat-treated *T. neapolitana* or *T. maritima* wild-type or C277 variant perhydrolases.

| perhydrolase | triacetin (mM) | $H_2O_2$ (mM) | enzyme concen. (µg/mL) | PAA, 1 min (ppm) | PAA, 5 min (ppm) | PAA, 30 min (ppm) |
|---|---|---|---|---|---|---|
| no enzyme | 100 | 100 | 0 | 63 | 54 | 80 |
| *T. maritima* wild-type | 100 | 100 | 50 | 529 | 1790 | 3785 |
| *T. maritima* C277S | 100 | 100 | 10 | 979 | 3241 | 4635 |
| *T. maritima* C277T | 100 | 100 | 10 | 933 | 2882 | 3527 |
| *T. maritima* C277A | 100 | 100 | 10 | 442 | 2018 | 2485 |
| *T. maritima* C277V | 100 | 100 | 10 | 577 | 1931 | 2278 |
| *T. neapolitana* wild-type | 100 | 100 | 50 | 514 | 1837 | 3850 |
| *T. neapolitana* C277S | 100 | 100 | 10 | 606 | 2237 | 4609 |
| *T. neapolitana* C277T | 100 | 100 | 10 | 634 | 2198 | 3918 |
| *T. neapolitana* C277A | 100 | 100 | 12.5 | 516 | 2041 | 3735 |
| *T. neapolitana* C277V | 100 | 100 | 12.5 | 451 | 1813 | 2758 |

EXAMPLE 24

Peracetic Acid Production Using Perhydrolases

Reactions (10 mL total volume) were run at 25° C. in sodium bicarbonate buffer (1 mM, initial pH 6.0) containing triacetin (100 mM or 150 mM), hydrogen peroxide (100 mM, 250 mM or 420 mM) and heat-treated *T. neapolitana* or *T. maritima* wild-type, C277S or C277T variant perhydrolases. Reactions run using 420 mM hydrogen peroxide additionally contained 500 ppm TURPINAL® SL. Reactions were stirred for only the first 30 seconds of reaction to initially mix the reactants and enzyme. Determination of the concentration of peracetic acid in the reaction mixtures was performed according to the method described by Karst et al., supra. The peracetic acid concentrations produced in 1 min, 5 min, and 30 min are listed in Table 18.

TABLE 18

Peracetic acid (PAA) production in reactions containing triacetin and hydrogen peroxide in bicarbonate buffer (1 mM at pH 6.0 or 100 mM at pH 8.1) or in deionized water (pH 5.0) at 25° C. using heat-treated *T. maritima* wild-type, C277S or C277T variant perhydrolases.

| *Thermotoga maritima* perhydrolase | triacetin (mM) | $H_2O_2$ (mM) | $NaHCO_3$ buffer (mM) | enzyme concen. (µg/mL) | PAA, 1 min (ppm) | PAA, 5 min (ppm) | PAA, 30 min (ppm) |
|---|---|---|---|---|---|---|---|
| no enzyme | 100 | 100 | 1.0 | 0 | 28 | 78 | 141 |
| wild-type | 100 | 100 | 1.0 | 75 | 434 | 494 | 608 |
| wild-type | 100 | 100 | 1.0 | 100 | 449 | 667 | 643 |
| C277S | 100 | 100 | 1.0 | 15 | 989 | 1554 | 1476 |
| C277S | 100 | 100 | 1.0 | 20 | 1301 | 2139 | 2131 |
| C277T | 100 | 100 | 1.0 | 15 | 1062 | 1513 | 1393 |
| C277T | 100 | 100 | 1.0 | 20 | 996 | 1430 | 1516 |
| no enzyme | 100 | 250 | 0 | 0 | 13 | 71 | 71 |
| wild-type | 100 | 250 | 0 | 75 | 512 | 535 | 533 |
| wild-type | 100 | 250 | 0 | 100 | 576 | 668 | 654 |
| C277S | 100 | 250 | 0 | 15 | 653 | 671 | 675 |
| C277S | 100 | 250 | 0 | 20 | 943 | 927 | 903 |
| C277T | 100 | 250 | 0 | 15 | 717 | 711 | 765 |
| C277T | 100 | 250 | 0 | 20 | 730 | 755 | 743 |
| no enzyme | 150 | 420 | 100 | 0 | 417 | 810 | 848 |
| wild-type | 150 | 420 | 100 | 500 | 6303 | 8627 | 9237 |
| C277S | 150 | 420 | 100 | 100 | 7822 | 10349 | 10197 |

What is claimed is:

1. A method for producing a peroxycarboxylic acid comprising
   (a) providing a first component comprising:
      (i) a carboxylic acid ester substrate;
      (ii) an enzyme catalyst having perhydrolysis activity, wherein said enzyme catalyst comprises an enzyme having a carbohydrate esterase family 7 (CE-7) signature motif that aligns with SEQ ID NO: 2 using CLUSTALW, said signature motif comprising:
         (1) an RGQ motif at amino acid positions aligning with 118-120 of SEQ ID NO:2;
         (2) a GXSQG motif at amino acid positions aligning with 179-183 of SEQ ID NO:2; and
         (3) an HE motif at amino acid positions aligning with 298-299 of SEQ ID NO:2;
      said enzyme comprising at least 90% amino acid identity to SEQ ID NO: 2, 14, 16, 73 or 74; and
      (iii) at least one cosolvent comprising an organic solvent having a log P of less than about 2, wherein log P is defined as the logarithm of the partition coefficient of a substance between octanol and water, expressed as P=[solute]$_{octanol}$/[solute]$_{water}$ and wherein the at least one cosolvent is not a substrate for said enzyme catalyst;
   wherein said first component is a substantially non-aqueous formulation of (i)-(iii);
   (b) providing a second component comprising a source of peroxygen in water; and
   (c) combining said first component and said second component to form an aqueous reaction formulation,
   wherein said cosolvent solubilizes the carboxylic acid ester substrate in the aqueous reaction formulation without substantial loss of perhydrolytic activity of the enzyme catalyst and whereby peroxycarboxylic acid is produced.

2. A method for disinfecting a surface comprising the step of applying the aqueous reaction formulation formed in step (c) of claim 1 to said surface.

3. A method for treating an article of clothing or textile comprising the step of applying the aqueous reaction formulation formed in step (c) of claim 1 to the article of clothing or textile for bleaching, stain removal, odor reduction, sanitization, disinfection, or a combination thereof.

4. The method according to claim 1, 2 or 3 wherein said aqueous reaction formulation is applied to said surface or said article of clothing by spraying.

5. The method according to claim 1, 2 or 3 wherein said first component is combined with said second component at a ratio of about 1:1 to about 1:10 by weight.

6. The method according to claim 1, 2 or 3 wherein said cosolvent is present in said first component in an amount of about 20% to about 80% by weight.

7. The method according to claim 1, 2 or 3 wherein said substrate is present in said first component in an amount of about 10% to about 60% by weight of that component.

8. The method according to claim 1, 2 or 3 wherein said first component comprises about 55% by weight carboxylic acid ester substrate, about 40% by weight cosolvent, about 0.3% by weight enzyme catalyst, and about 2.5% by weight filler, and wherein said second component comprises about 95% by weight water, about 1.5% by weight sodium bicarbonate, and about 1% by weight of a source of peroxygen.

9. The method according to claim 8 wherein said first component comprises about 55.5% by weight triacetin, about 41% by weight tripropylene glycol methyl ether, about 0.3% by weight of a spray dried enzyme powder comprising *Thermotoga neapolitana* or *Thermotoga maritima* perhydrolase or a variant derivative of *Thermotoga neapolitana* or *Thermotoga maritima* perhydrolase having one or more point mutations that improve the perhydrolysis activity, and about 2.5% by weight fumed silica, and wherein said second component comprises about 96% by weight water, about 0.2% by weight hydrogen peroxide stabilizer, and about 3.2% by weight of a solution comprising 30% hydrogen peroxide.

10. The method according to claim 1 or 2 wherein, upon combining said first component and said second component to form an aqueous reaction formulation, the initial concentration of said carboxylic acid ester substrate is about 100 mM, the initial concentration of said source of peroxygen is about 100 mM, and the initial concentration of said enzyme catalyst is about 0.1 mg/mL.

11. The method according to claim 1 or 3 wherein, upon combining said first component and said second component to form an aqueous reaction formulation, the initial concentration of said carboxylic acid ester substrate is about 10 mM, the initial concentration of said source of peroxygen is about 10 mM, and the initial concentration of said enzyme catalyst is about 0.01 mg/mL.

12. The method according to claim 7 wherein said carboxylic acid ester substrate comprises triacetin, said source of peroxygen comprises hydrogen peroxide, and said enzyme catalyst comprises an amino acid sequence selected from the group consisting of SEQ ID NO: 16 and SEQ ID NO: 74.

13. The method according to claim 1, 2 or 3 wherein said carboxylic acid ester substrate has solubility in water of less than about 100 mg/mL.

14. The method according to claim 1, 2 or 3 wherein said enzyme further comprises an LXD motif at amino acid positions aligning with 179-183 of SEQ ID NO:2.

15. The method according to claim 1, 2 or 3 wherein said enzyme catalyst comprises an amino acid sequence selected from the group consisting of SEQ ID NO: 14 and SEQ ID NO: 73.

16. The method according to claim 1, 2 or 3 wherein said cosolvent comprises tripropylene glycol methyl ether, dipropylene glycol methyl ether, propylene glycol methyl ether, diethylene glycol butyl ether, dipropylene glycol, triethyleneglycol, 1,2-propanediol, N-ethyl-2-pyrroldinone, isopropanol, ethanol, ethyl lactate, 1,3-propanediol, or any combination thereof.

17. The method according to claim 16 wherein said cosolvent comprises tripropylene glycol methyl ether.

18. The method according to claim 1, 2 or 3 wherein said peroxycarboxylic acid is a $C_3$-$C_{10}$ peroxycarboxylic acid.

19. The method according to claim 1, 2 or 3 wherein said peroxycarboxylic acid comprises peracetic acid, perpropionic acid, perbutyric acid, perlactic acid, perglycolic acid, permethoxyacetic acid, per-β-hydroxybutyric acid, or any combination thereof.

20. The method according to claim 1, 2 or 3 wherein enzyme catalyst is provided in the form of a microbial cell, a permeabilized microbial cell, a microbial cell extract, a partially purified enzyme, or a purified enzyme.

21. The method of claim 20 wherein the enzyme catalyst is immobilized in or on a soluble or an insoluble support.

22. The method according to claim 1, 2 or 3 wherein the enzyme catalyst lacks catalase activity.

* * * * *